United States Patent
England et al.

(10) Patent No.: US 10,053,433 B2
(45) Date of Patent: Aug. 21, 2018

(54) ANDROGEN RECEPTOR ANTAGONISTS

(71) Applicant: THE REGENTS OF THE UNIVERSITY OF CALIFORNIA, Oakland, CA (US)

(72) Inventors: Pamela M. England, San Francisco, CA (US); Robert J. Fletterick, San Francisco, CA (US); Kristopher Kuchenbecker, San Francisco, CA (US); Felipe de Jesus Cortez, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/382,942

(22) Filed: Dec. 19, 2016

(65) Prior Publication Data

US 2017/0101384 A1 Apr. 13, 2017

Related U.S. Application Data

(63) Continuation of application No. PCT/US2015/036793, filed on Jun. 19, 2015.

(60) Provisional application No. 62/015,221, filed on Jun. 20, 2014.

(51) Int. Cl.

| | | |
|---|---|---|
| *C07D 213/74* | (2006.01) | |
| *C07D 239/42* | (2006.01) | |
| *C07D 241/26* | (2006.01) | |
| *A61K 31/44* | (2006.01) | |
| *A61K 31/495* | (2006.01) | |
| *C07D 257/08* | (2006.01) | |
| *C07K 14/72* | (2006.01) | |
| *C07D 213/84* | (2006.01) | |
| *C07D 237/24* | (2006.01) | |
| *C07D 253/07* | (2006.01) | |

(52) U.S. Cl.
CPC ......... *C07D 257/08* (2013.01); *C07D 213/74* (2013.01); *C07D 213/84* (2013.01); *C07D 237/24* (2013.01); *C07D 239/42* (2013.01); *C07D 241/26* (2013.01); *C07D 253/07* (2013.01); *C07K 14/721* (2013.01)

(58) Field of Classification Search
None
See application file for complete search history.

(56) References Cited

U.S. PATENT DOCUMENTS

| | | |
|---|---|---|
| 4,636,505 A | 1/1987 | Tucker |
| 7,709,517 B2 | 5/2010 | Sawyers et al. |
| 8,110,594 B2 | 2/2012 | Jung et al. |
| 8,445,507 B2 | 5/2013 | Jung et al. |
| 8,802,689 B2 | 8/2014 | Jung et al. |
| 9,388,159 B2 | 7/2016 | Jung et al. |
| 2001/0012839 A1 | 8/2001 | Miller et al. |
| 2005/0209320 A1 | 9/2005 | Miller et al. |
| 2008/0057068 A1 | 3/2008 | Dalton et al. |
| 2010/0185419 A1 | 7/2010 | Singh et al. |
| 2017/0014399 A1 | 1/2017 | Jung et al. |

FOREIGN PATENT DOCUMENTS

| | | |
|---|---|---|
| WO | WO-02/076177 A2 | 10/2002 |
| WO | WO-02/076177 A3 | 10/2002 |
| WO | WO-2006/124118 A1 | 11/2006 |

OTHER PUBLICATIONS

Blackledge, G.R. (1996). "Clinical progress with a new antiandrogen, Casodex (bicalutamide)," *Eur Urol* 29 Suppl 2:96-104.
Clegg, N.J. et al. (Mar. 15, 2012, e-published Jan. 20, 2012). "ARN-509: a novel antiandrogen for prostate cancer treatment," *Cancer Res* 72(6):1494-1503.
Feldman, B.J. et al. (Oct. 2001). "The development of androgen-independent prostate cancer," *Nat Rev Cancer* 1(1):34-45.
Hara, T. et al. (Jan. 1, 2003). "Novel mutations of androgen receptor: a possible mechanism of bicalutamide withdrawal syndrome," *Cancer Res* 63(1):149-153.
International Search Report dated Dec. 4, 2015, for PCT Application No. PT/US2015/036793, filed Dec. 4, 2015, 5 pages.
Tran, C. et al. (May 8, 2009, e-published Apr. 9, 2009). "Development of a second-generation antiandrogen for treatment of advanced prostate cancer," *Science* 324(5928):787-790.
Tucker, H. et al. (Apr. 1988). "Resolution of the nonsteroidal antiandrogen 4'-cyano-3-[(4-fluorophenyhsulfonyl]-2-hydroxy-2-methyl-3'-(trifluoromethyl)-propionanilide and the determination of the absolute configuration of the active enantiomer," *J Med Chem* 31(4):885-887.
Tucker, H. et al. (May 1988). "Nonsteroidal antiandrogens. Synthesis and structure-activity relationships of 3-substituted derivatives of 2-hydroxpropionanilides," *J Med Chem* 31(5):954-959.
Written Opinion dated Dec. 4, 2015, for PCT Application No. PT/US2015/036793, filed Dec. 4, 2015, 6 pages.
Yin, D. et al. (Jan. 2003). "Key structural features of nonsteroidal ligands for binding and activation of the androgen receptor," *Mol Pharmacol* 63(1):211-223.

*Primary Examiner* — Zinna Northington Davis
(74) *Attorney, Agent, or Firm* — Anson M. Nomura; Mintz, Levin, Cohn, Ferris, Glovsky and Popeo, P.C.

(57) ABSTRACT

Disclosed herein are compositions and methods for modulating the androgen receptor.

19 Claims, 19 Drawing Sheets

SEQUENCE LISTING

```
<160> NUMBER OF SEQ ID NOS: 1

<210> SEQ ID NO 1
<211> LENGTH: 919
<212> TYPE: PRT
<213> ORGANISM: Homo sapiens
```

```
<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala
            35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gly Glu Asp Gly Ser Pro Gln
                85                  90                  95

Ala His Arg Arg Gly Pro Thr Gly Tyr Leu Val Leu Asp Glu Glu Gln
                100                 105                 110

Gln Pro Ser Gln Pro Gln Ser Ala Leu Glu Cys His Pro Glu Arg Gly
            115                 120                 125

Cys Val Pro Glu Pro Gly Ala Ala Val Ala Ala Ser Lys Gly Leu Pro
    130                 135                 140

Gln Gln Leu Pro Ala Pro Pro Asp Glu Asp Asp Ser Ala Ala Pro Ser
145                 150                 155                 160

Thr Leu Ser Leu Leu Gly Pro Thr Phe Pro Gly Leu Ser Ser Cys Ser
                165                 170                 175

Ala Asp Leu Lys Asp Ile Leu Ser Glu Ala Ser Thr Met Gln Leu Leu
                180                 185                 190

Gln Gln Gln Gln Gln Glu Ala Val Ser Glu Gly Ser Ser Ser Gly Arg
            195                 200                 205

Ala Arg Glu Ala Ser Gly Ala Pro Thr Ser Ser Lys Asp Asn Tyr Leu
    210                 215                 220

Gly Gly Thr Ser Thr Ile Ser Asp Asn Ala Lys Glu Leu Cys Lys Ala
225                 230                 235                 240

Val Ser Val Ser Met Gly Leu Gly Val Glu Ala Leu Glu His Leu Ser
                245                 250                 255

Pro Gly Glu Gln Leu Arg Gly Asp Cys Met Tyr Ala Pro Leu Leu Gly
                260                 265                 270

Val Pro Pro Ala Val Arg Pro Thr Pro Cys Ala Pro Leu Ala Glu Cys
            275                 280                 285

Lys Gly Ser Leu Leu Asp Asp Ser Ala Gly Lys Ser Thr Glu Asp Thr
290                 295                 300

Ala Glu Tyr Ser Pro Phe Lys Gly Gly Tyr Thr Lys Gly Leu Glu Gly
305                 310                 315                 320

Glu Ser Leu Gly Cys Ser Gly Ser Ala Ala Gly Ser Ser Gly Thr
                325                 330                 335

Leu Glu Leu Pro Ser Thr Leu Ser Leu Tyr Lys Ser Gly Ala Leu Asp
                340                 345                 350

Glu Ala Ala Ala Tyr Gln Ser Arg Asp Tyr Tyr Asn Phe Pro Leu Ala
            355                 360                 365

Leu Ala Gly Pro Pro Pro Pro Pro Pro Pro His Pro His Ala Arg
    370                 375                 380

Ile Lys Leu Glu Asn Pro Leu Asp Tyr Gly Ser Ala Trp Ala Ala Ala
385                 390                 395                 400

Ala Ala Gln Cys Arg Tyr Gly Asp Leu Ala Ser Leu His Gly Ala Gly
                405                 410                 415
```

```
Ala Ala Gly Pro Gly Ser Gly Ser Pro Ser Ala Ala Ser Ser Ser
            420                 425             430

Trp His Thr Leu Phe Thr Ala Glu Glu Gly Gln Leu Tyr Gly Pro Cys
        435                 440             445

Gly Gly Gly Gly Gly Gly Gly Gly Gly Gly Gly Gly Gly Gly Gly
    450                 455             460

Gly Gly Gly Gly Gly Gly Gly Glu Ala Gly Ala Val Ala Pro Tyr
465             470             475                 480

Gly Tyr Thr Arg Pro Pro Gln Gly Leu Ala Gly Gln Glu Ser Asp Phe
                485             490             495

Thr Ala Pro Asp Val Trp Tyr Pro Gly Gly Met Val Ser Arg Val Pro
            500                 505             510

Tyr Pro Ser Pro Thr Cys Val Lys Ser Glu Met Gly Pro Trp Met Asp
        515                 520             525

Ser Tyr Ser Gly Pro Tyr Gly Asp Met Arg Leu Glu Thr Ala Arg Asp
    530                 535             540

His Val Leu Pro Ile Asp Tyr Tyr Phe Pro Pro Gln Lys Thr Cys Leu
545             550             555                 560

Ile Cys Gly Asp Glu Ala Ser Gly Cys His Tyr Gly Ala Leu Thr Cys
                565             570             575

Gly Ser Cys Lys Val Phe Phe Lys Arg Ala Ala Glu Gly Lys Gln Lys
            580                 585             590

Tyr Leu Cys Ala Ser Arg Asn Asp Cys Thr Ile Asp Lys Phe Arg Arg
        595                 600             605

Lys Asn Cys Pro Ser Cys Arg Leu Arg Lys Cys Tyr Glu Ala Gly Met
    610                 615             620

Thr Leu Gly Ala Arg Lys Leu Lys Lys Leu Gly Asn Leu Lys Leu Gln
625             630             635                 640

Glu Glu Gly Glu Ala Ser Ser Thr Thr Ser Pro Thr Glu Glu Thr Thr
                645             650             655

Gln Lys Leu Thr Val Ser His Ile Glu Gly Tyr Glu Cys Gln Pro Ile
            660                 665             670

Phe Leu Asn Val Leu Glu Ala Ile Glu Pro Gly Val Val Cys Ala Gly
        675                 680             685

His Asp Asn Asn Gln Pro Asp Ser Phe Ala Ala Leu Leu Ser Ser Leu
    690                 695             700

Asn Glu Leu Gly Glu Arg Gln Leu Val His Val Val Lys Trp Ala Lys
705             710             715                 720

Ala Leu Pro Gly Phe Arg Asn Leu His Val Asp Asp Gln Met Ala Val
                725             730             735

Ile Gln Tyr Ser Trp Met Gly Leu Met Val Phe Ala Met Gly Trp Arg
            740                 745             750

Ser Phe Thr Asn Val Asn Ser Arg Met Leu Tyr Phe Ala Pro Asp Leu
        755                 760             765

Val Phe Asn Glu Tyr Arg Met His Lys Ser Arg Met Tyr Ser Gln Cys
    770                 775             780

Val Arg Met Arg His Leu Ser Gln Glu Phe Gly Trp Leu Gln Ile Thr
785             790             795                 800

Pro Gln Glu Phe Leu Cys Met Lys Ala Leu Leu Leu Phe Ser Ile Ile
                805             810             815

Pro Val Asp Gly Leu Lys Asn Gln Lys Phe Phe Asp Glu Leu Arg Met
            820                 825             830
```

```
Asn Tyr Ile Lys Glu Leu Asp Arg Ile Ile Ala Cys Lys Arg Lys Asn
        835             840             845

Pro Thr Ser Cys Ser Arg Phe Tyr Gln Leu Thr Lys Leu Leu Asp
    850             855             860

Ser Val Gln Pro Ile Ala Arg Glu Leu His Gln Phe Thr Phe Asp Leu
865             870             875             880

Leu Ile Lys Ser His Met Val Ser Val Asp Phe Pro Glu Met Met Ala
                885             890             895

Glu Ile Ile Ser Val Gln Val Pro Lys Ile Leu Ser Gly Lys Val Lys
            900             905             910

Pro Ile Tyr Phe His Thr Gln
        915
```

ANDROGEN RECEPTOR ANTAGONISTS

CROSS-REFERENCES TO RELATED APPLICATIONS

This application is a continuation of International Patent Application No. PCT/US2015/036793, filed Jun. 19, 2015, which claims the benefit of U.S. Provisional Patent Application No. 62/015,221 filed on Jun. 20, 2014, all of which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48536-553C01US_ST25.TXT, created on Dec. 15, 2016, 8,258 bytes, machine format IBM-PC, MS Windows operating system, is hereby incorporated by reference.

BACKGROUND

Androgen receptor (AR) is a member of the nuclear hormone receptor family activated by androgens, such as dihydrotestosterone (DHT). AR is a prime therapeutic target for treating prostate cancer. Several compounds have been developed as chemotherapy for prostate cancer. However, these compounds bind AR with affinities comparable to or less than the endogenous hormone and over time patients develop resistance to these drugs. Higher affinity and/or slower off-rate ligands (e.g. covalent ligands) are needed to provide more effective therapies.

Androgen receptor competitive antagonists (antiandrogens) are drugs used to treat hormonal-based syndromes and prostate cancer. Current drugs for prostate cancer include flutamide, bicalutamide, nilutamide, enzalutamide and ARN-509. Each of these inhibitors binds to the hormone-binding pocket (HBP) of the androgen receptor. This is the same site that the natural physiological steroids testosterone (TES) and dihydrotestosterone (DHT) situate to produce an active conformation of the receptor that changes the cell's transcription program and cell fate. The drugs work by competing with the natural hormones for binding to the pocket and, as a result, lessening activation of the receptor. Of all these ligands, the steroids DHT and testosterone bind tightest to the receptor. Tighter binding and/or slower off-rate drugs are desirable, along with the additional characteristic that they encourage degradation of the receptor by components resident in cells and/or prevent formation of AR variants resistant to chemotherapy.

Disclosed herein are solutions to these and other problems in the art.

BRIEF SUMMARY

In an aspect is provided a compound having the formula:

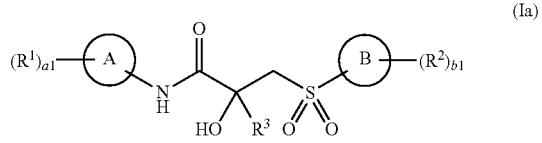

(Ia)

wherein Ring A is a heteroaryl; Ring B is a phenyl or heteroaryl; $R^1$ is independently a halogen, $-CX^a{}_3$, $-CN$, $-SO_2Cl$, $-SO_{n1}R^{10}$, $-SO_{v1}NR^7R^8$, $-NHNH_2$, $-ONR^7R^8$, $-NHC=(O)$ $NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^a{}_3$, $-OCHX^a{}_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; E is an electrophilic moiety; $R^2$ is independently a halogen, $-CX^b{}_3$, $-CN$, $-SO_2Cl$, $-SO_{n2}R^{14}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^b{}_3$, $-OCHX^b{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^3$ is independently an unsubstituted alkyl; $R^7$, $R^8$, $R^9$, $R^{10}$, $R^{11}$, $R^{12}$, $R^{13}$, and $R^{14}$ are independently hydrogen, halogen, $-CX^c{}_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCX^c{}_3$, $-OCHX^c{}_2$, $-CF_3$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; a1 is independently an integer from 0 to 4; b1 is independently an integer from 0 to 5; m1, m2, v1, and v2 are independently 1 or 2; n1 and n2 are independently an integer from 0 to 4; $X^a$, $X^b$, and $X^c$ are independently $-Cl$, $-Br$, $-I$, or $-F$.

In another aspect is provided a pharmaceutical composition including a compound as described herein, or a pharmaceutically acceptable salt thereof, and a pharmaceutically acceptable excipient.

In another aspect is provided an androgen receptor protein covalently bound to a compound (e.g., a compound as described herein).

In another aspect is provided a human androgen receptor protein covalently bound to a compound as described herein, wherein the compound is covalently bound to Cys784 of the human androgen receptor protein.

In another aspect is provided a method of treating cancer in a subject in need thereof, including administering to the subject a compound as described herein, or a pharmaceutically acceptable salt thereof.

In another aspect is provided a method of inhibiting androgen receptor activity in a subject in need thereof, including administering to the subject a compound as described herein, or a pharmaceutically acceptable salt thereof.

DETAILED DESCRIPTION

Figure 1:
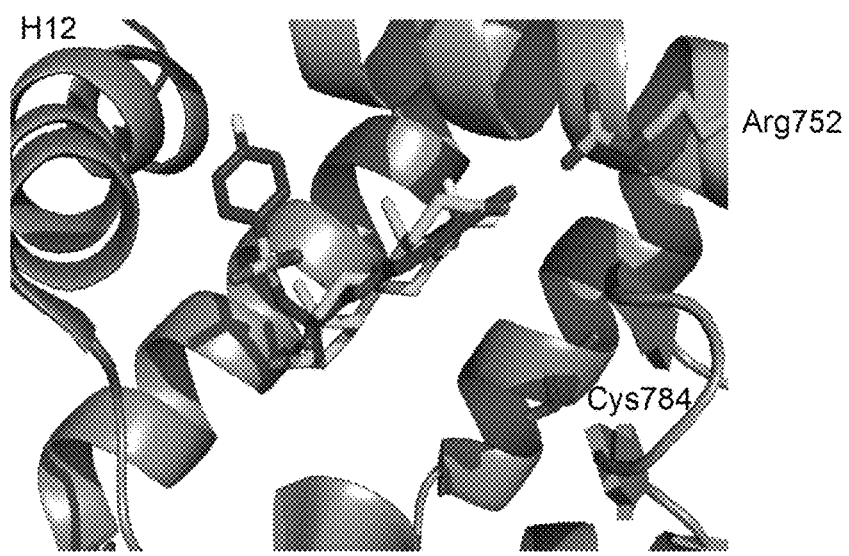
FIG. 1. Ligand binding domain of AR. $Arg^{752}$ thought to be important to ligand binding; Increased affinity of ARN-509 compared to RD162 contrary to decreased point charge on —CN; $Cys^{784}$ could contribute to binding affinity through nucleophilic attack on —CN; Crystal structures of wildtype AR bound to DHT (light gray sticks) and AR mutant W741L bound to CDX (dark gray sticks).
Figure 2:
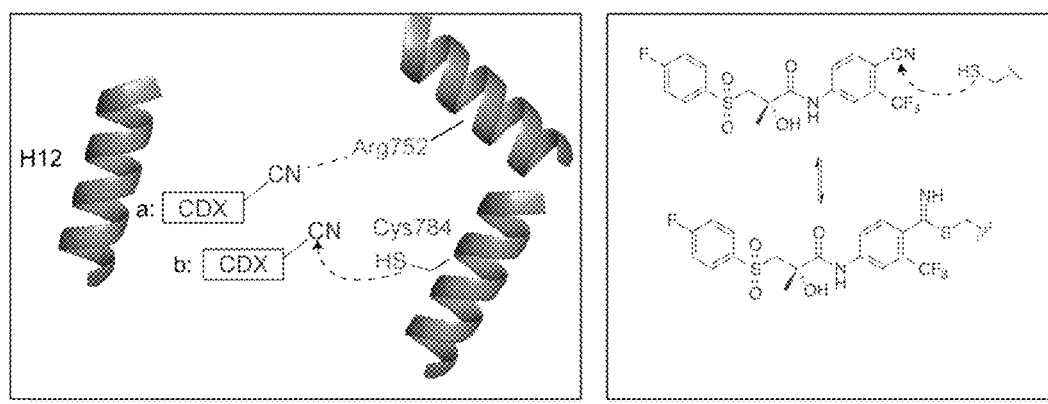
FIG. 2. Proposed Mechanism of Action. Current mechanism of action: based on crystal structure of CDX bound to mutant AR (W741L), $Arg^{752}$ forms polar interaction with CN group; proposed mechanism of action: CDX sits deeper in the pocket, CN group forms reversible covalent bond with $Cys^{784}$. Addition of nitrogen in the A-ring increases the electrophilicity of the —CN group.
Figure 3:
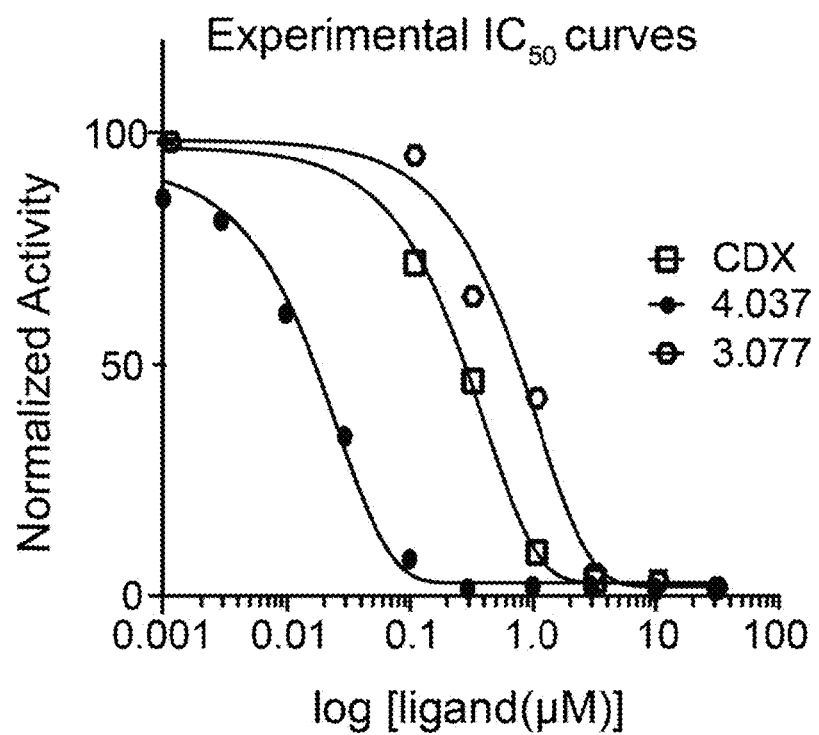
FIG. 3. Androgen receptor activity in the presence of different compounds.
Figure 4:
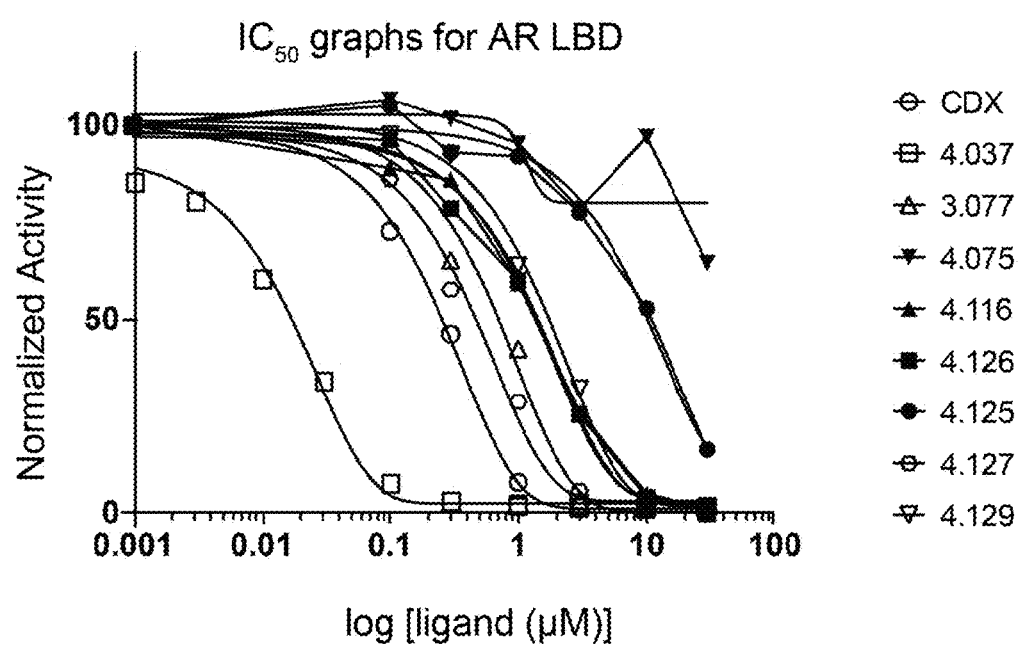
FIG. 4. IC50 of compounds with ligand binding domain of androgen receptor.
Figure 5:
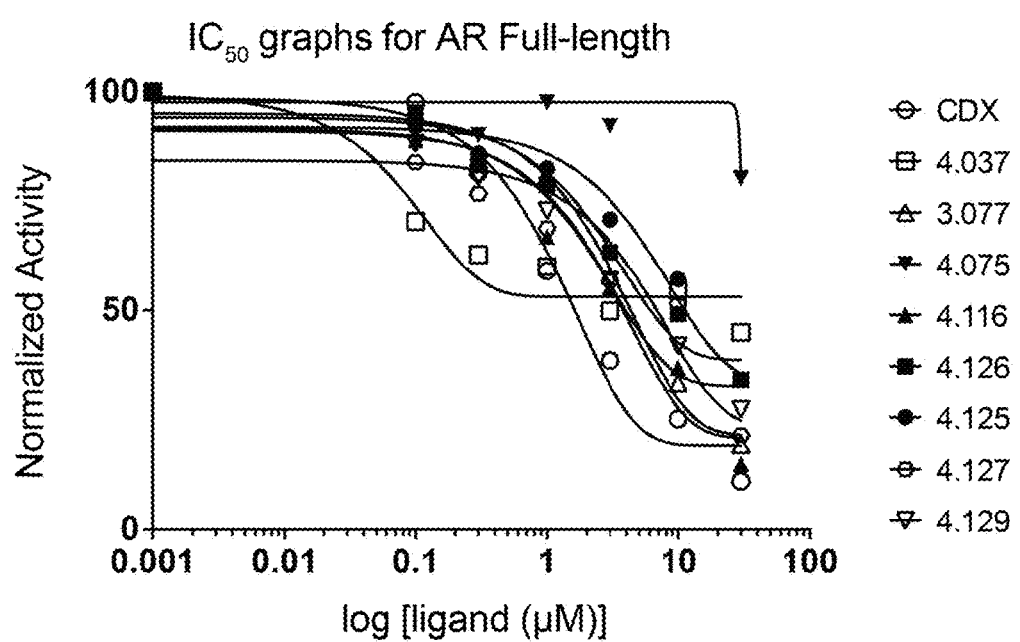
FIG. 5. IC50 of compounds with full length androgen receptor.
Figure 6:
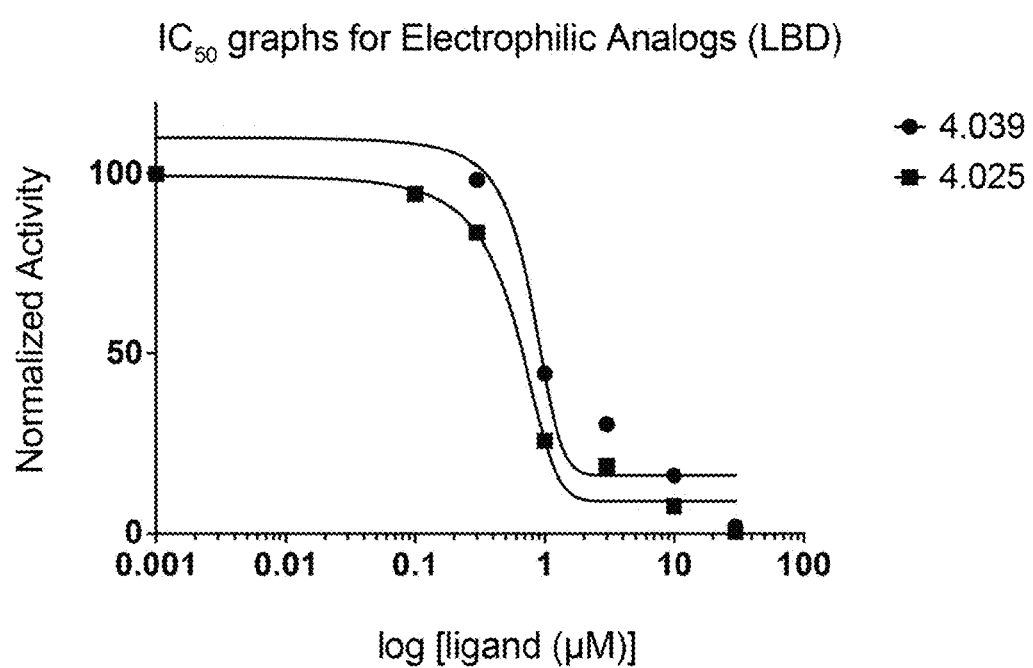
FIG. 6. IC50 of select compounds with ligand binding domain of androgen receptor.
Figure 7:
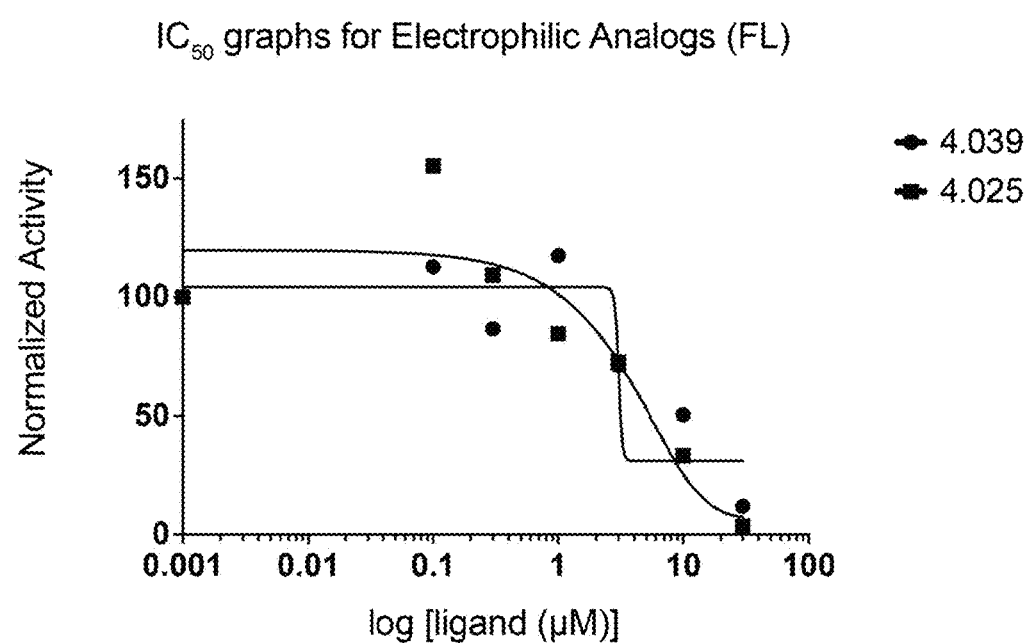
FIG. 7. IC50 of select compounds with full length androgen receptor.
Figure 8A:
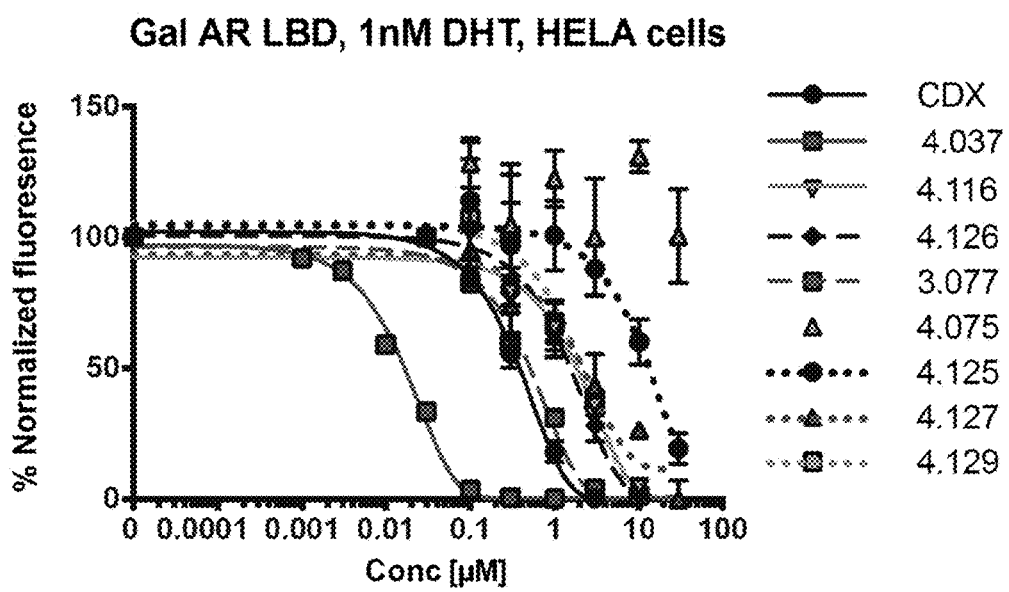
FIG. 8A-8D. AR ligand binding domain (LBD) data.
Figure 8B:
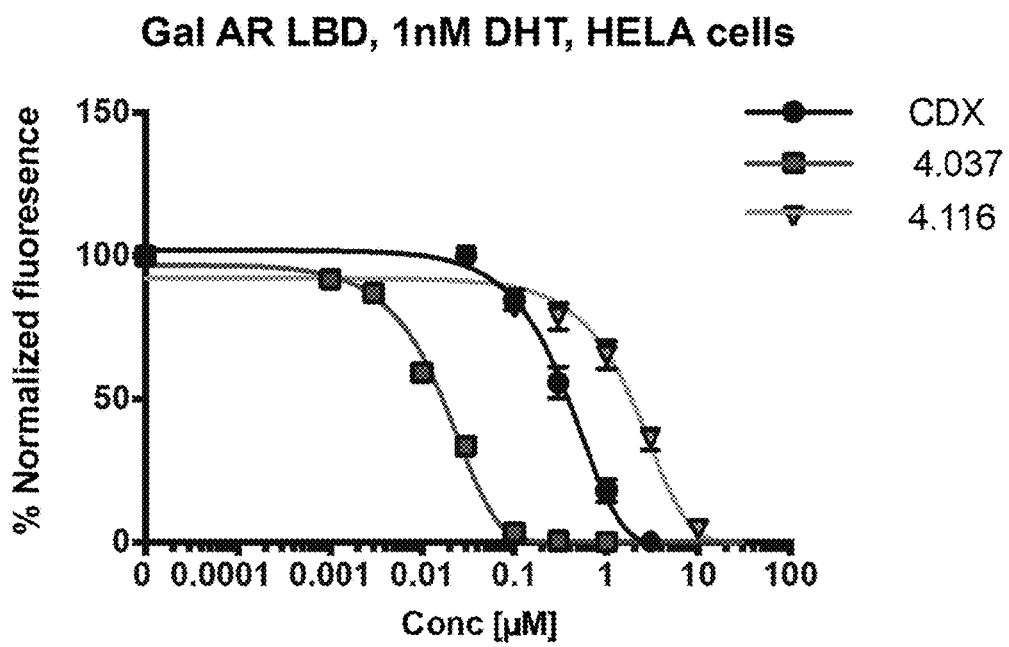
Figure 8C:
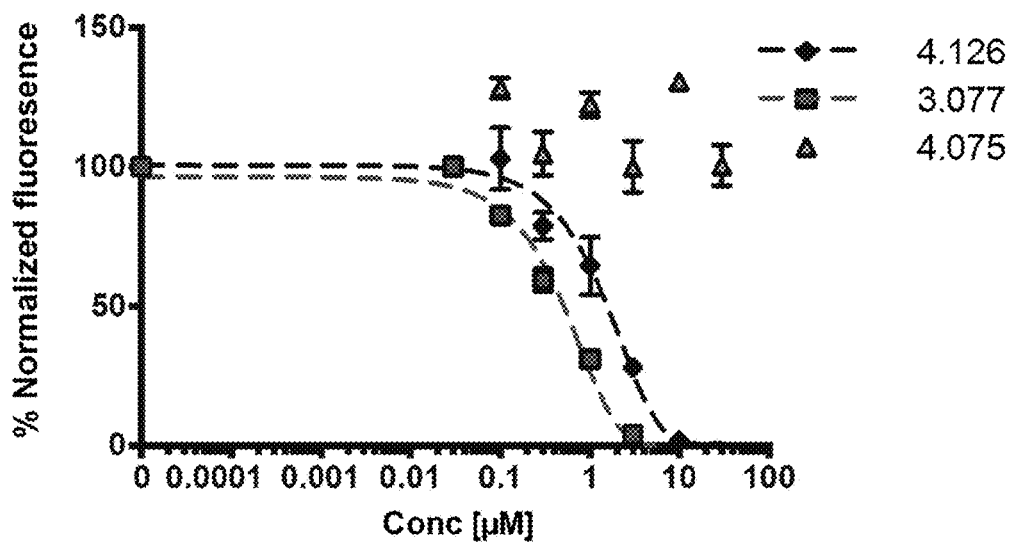
Figure 8D:
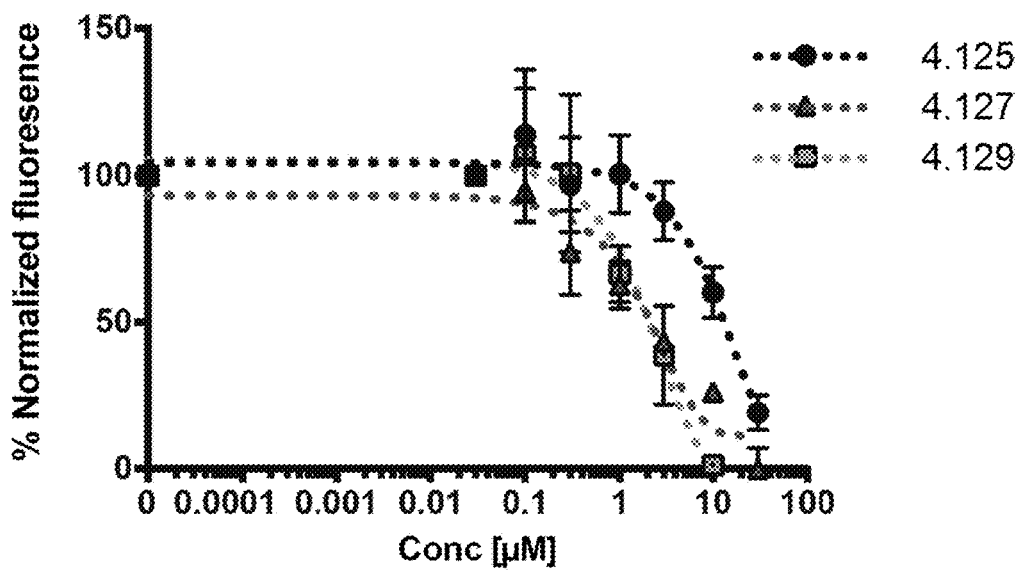
Figure 9:
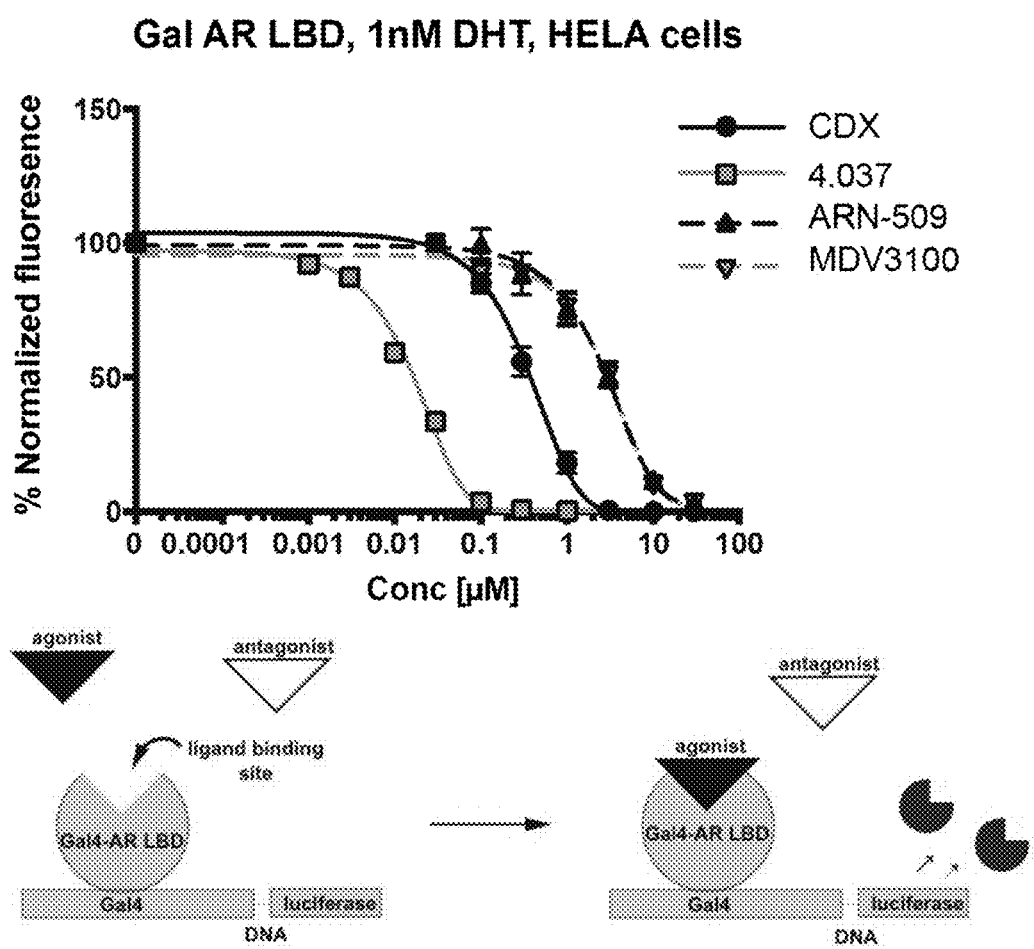
FIG. 9. AR ligand binding domain (LBD) data comparison to known compounds (4.037=N-CDX).
Figure 10A:
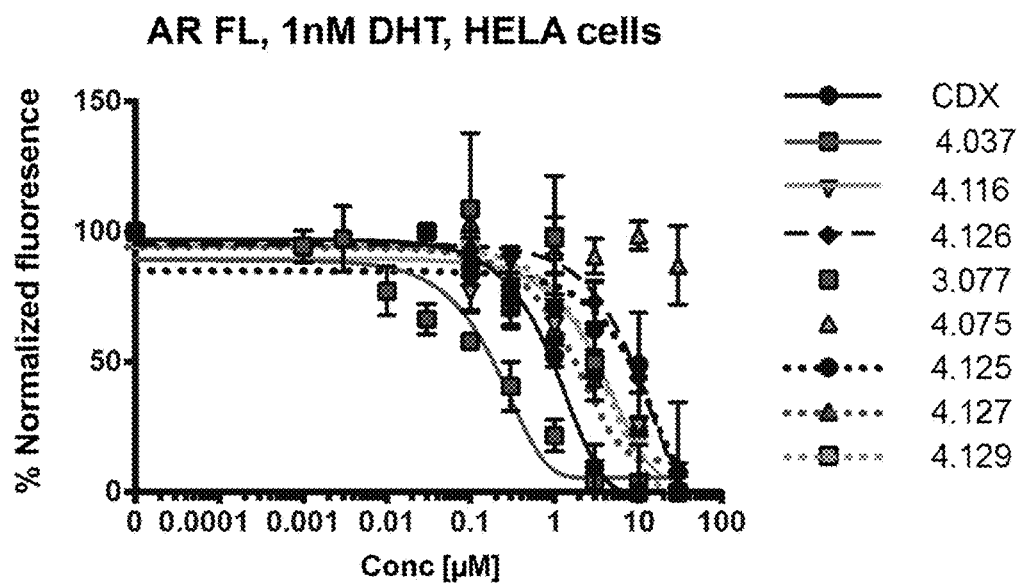
FIG. 10A-D. AR full length data (4.037=N-CDX).
Figure 10B:
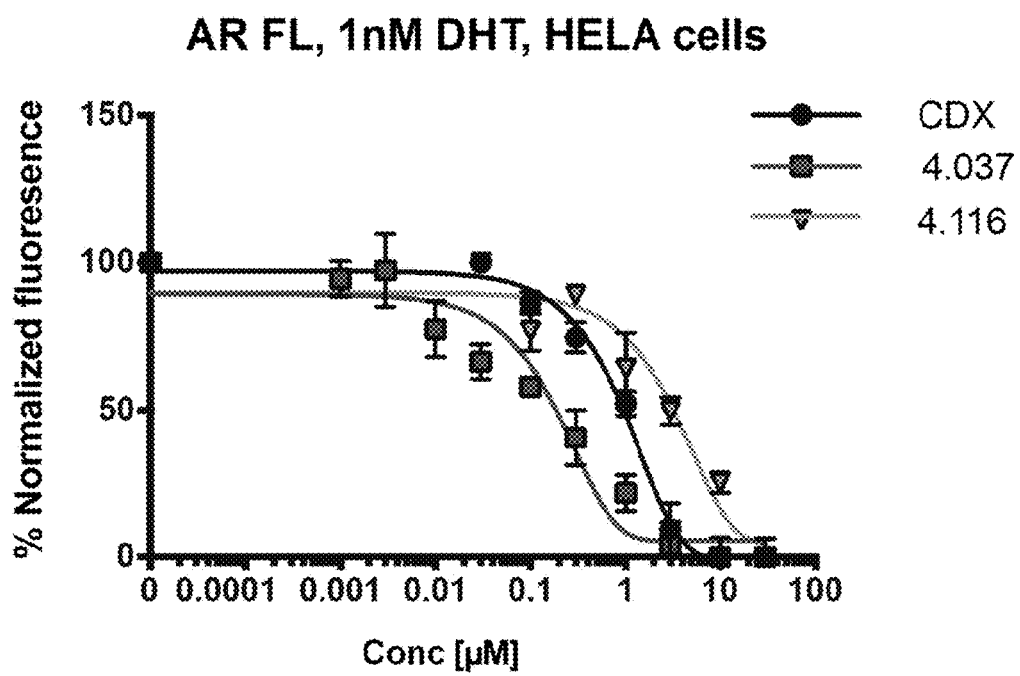
Figure 10C:
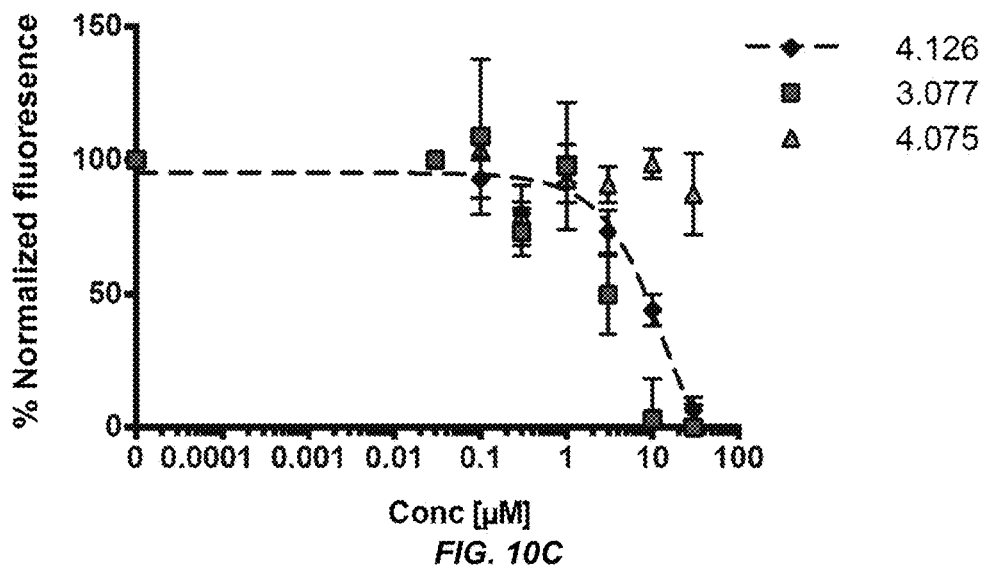
Figure 10D:
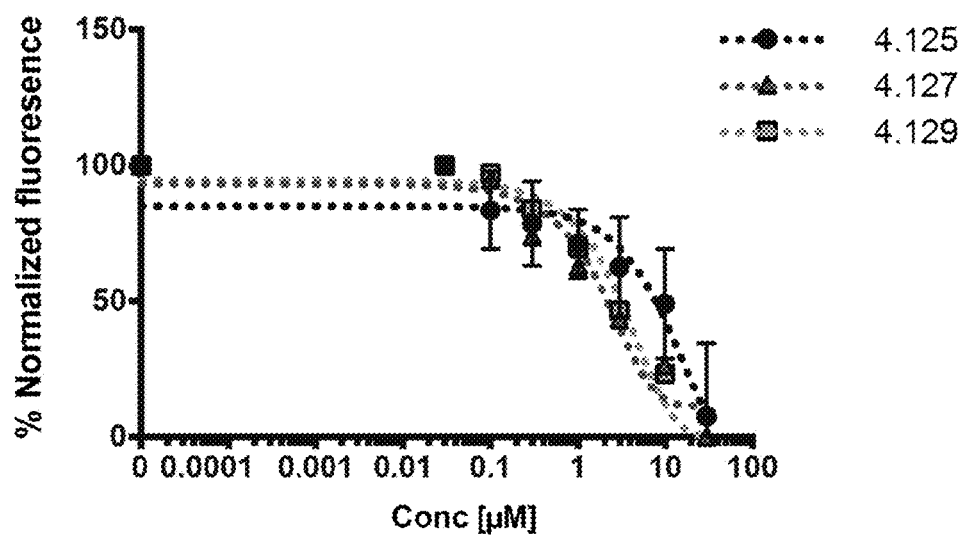
Figure 11:
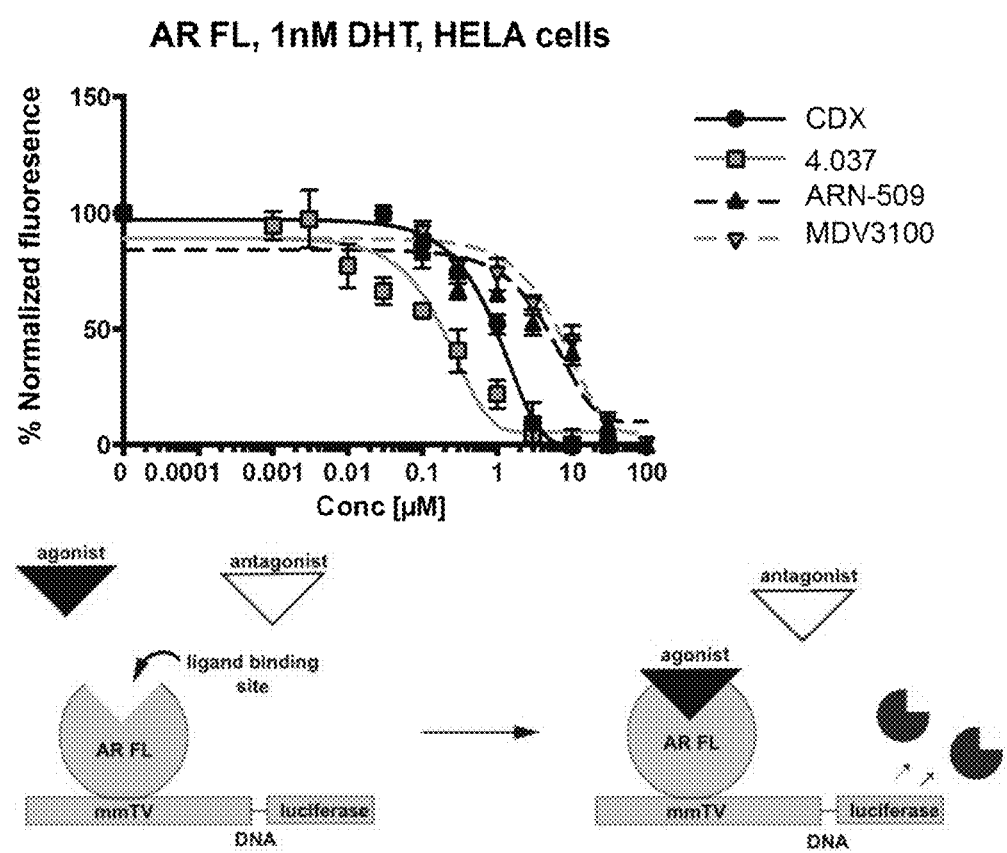
FIG. 11. AR full length data comparison to known compounds (4.037=N-CDX).
Figure 12:
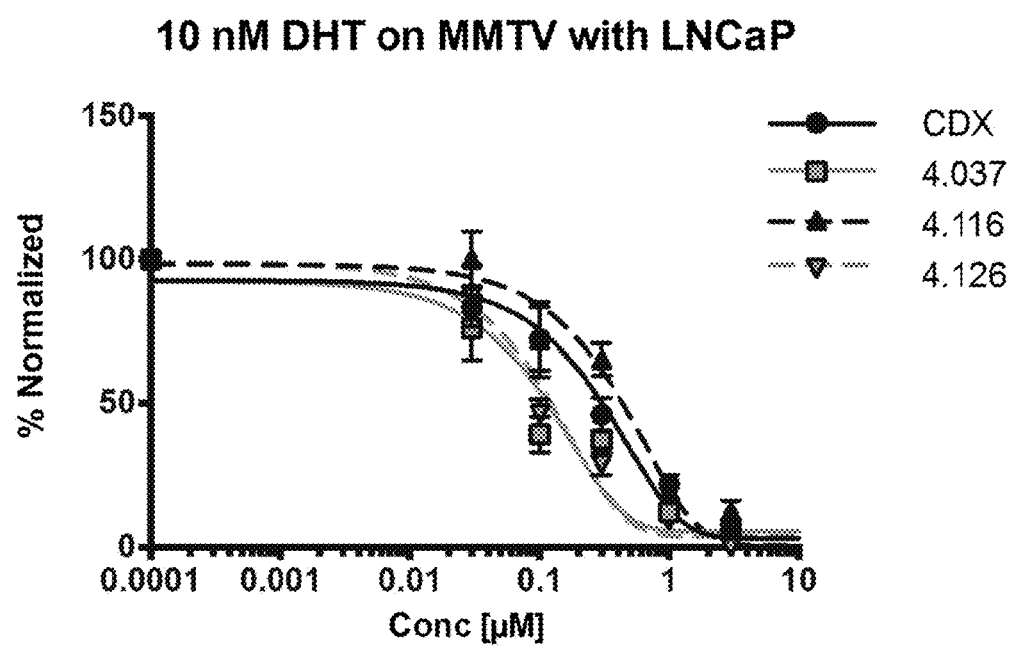
FIG. 12. AR activity in LNCap transformed with MMTV data (4.037=N-CDX).
Figure 13:
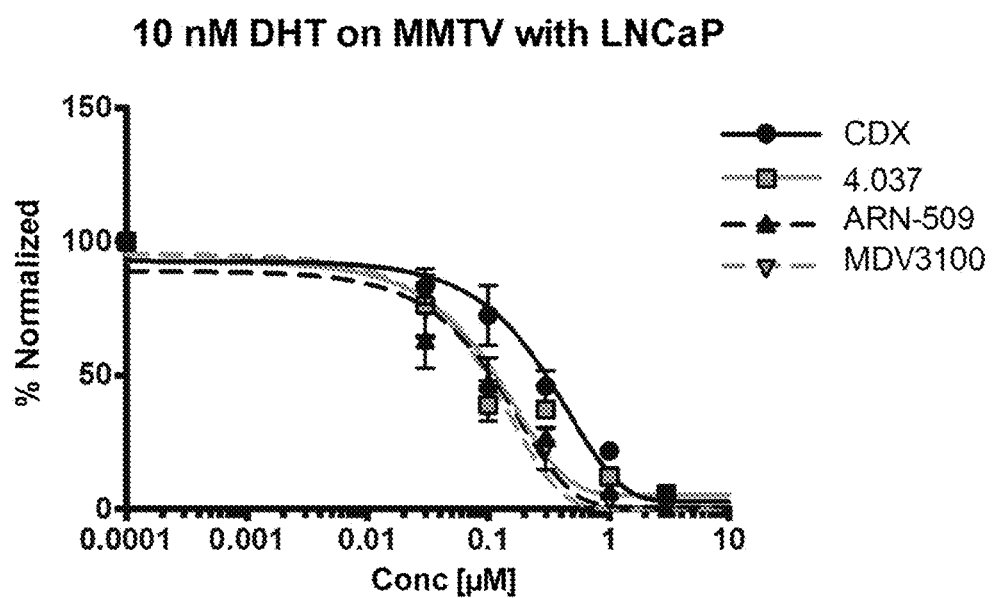
FIG. 13. AR activity in LNCap transformed with MMTV data comparison to known compounds (4.037=N-CDX).
Figure 14:
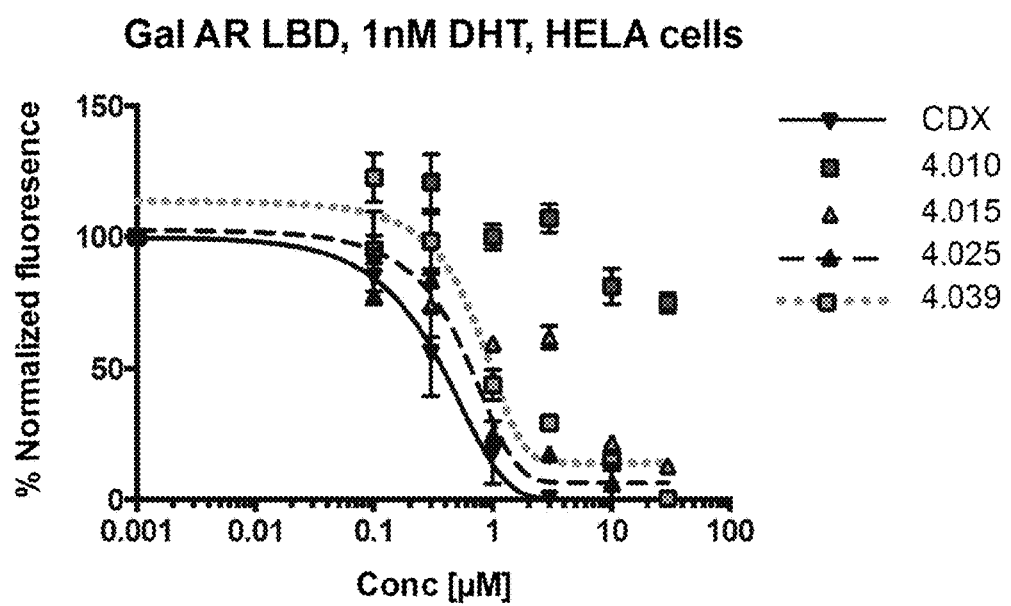
FIG. 14. Covalent bond forming compounds with AR ligand binding domain (LBD) data (4.037=N-CDX).
Figure 15:
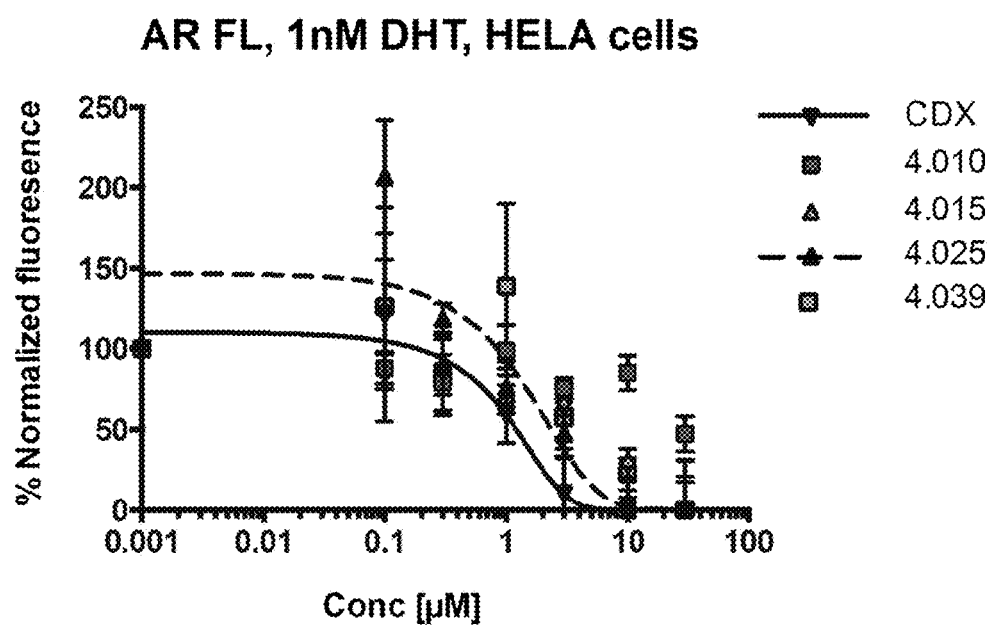
FIG. 15. Covalent bond forming compounds with AR full length data (4.037=N-CDX).
Figure 16:
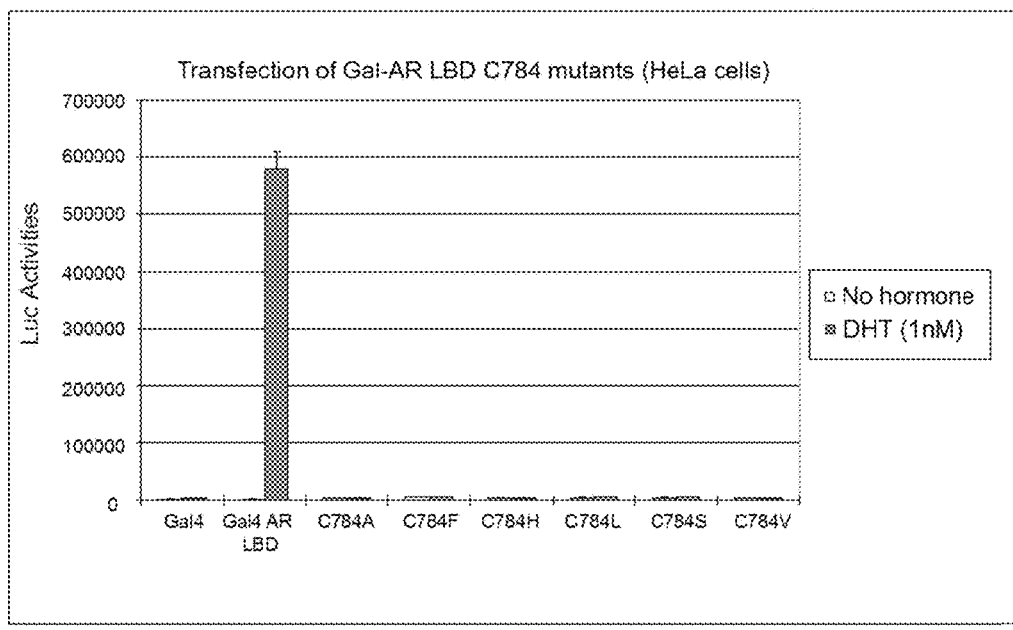
FIG. 16. Transfection of Gal-AR LBD C784 mutants.
Figure 17:
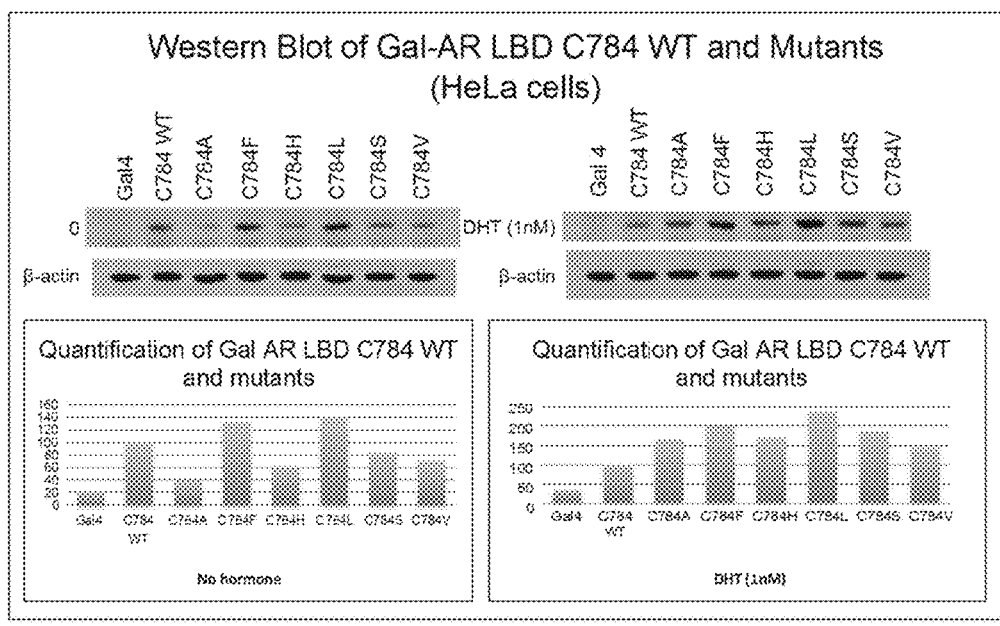
FIG. 17. Western blot of Gal-AR LBD WT and C784 mutants.
Figure 18:
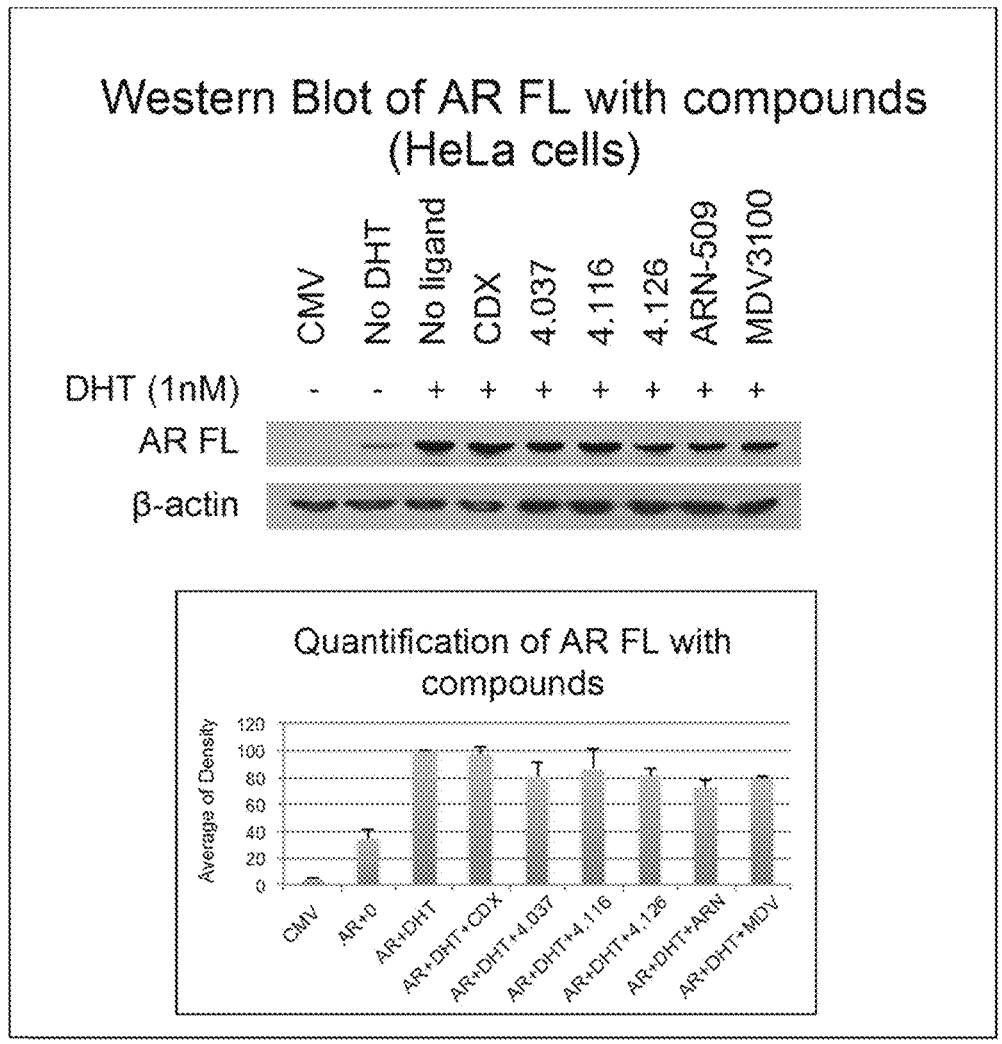
FIG. 18. Western blot of AR full length and compounds.

The mainstay of current prostate cancer therapies are drugs that directly inhibit androgen receptor (AR) function by competitively inhibiting the binding of hormones (TES, DHT) to the receptor (e.g. Casodex, Flutamide, MDV3100, ARN-509). However, tumor cells become resistant to many antiandrogens within a few years of treatment and the progression of prostate cancer subsequently resumes. We hypothesize that the limited efficacy of some current antiandrogens is due in part to the fact that they bind AR with affinities weaker than or, at best, comparable to native hormones. This allows endogenous ligands to competitively activate the receptor, and selective pressure to drive escape mechanisms. In embodiments, provided herein are new antiandrogens that bind tightly to AR.

In embodiments, described herein are significantly more potent antiandrogens than previously characterized, which can be designed based on the existing drug bicalutamide by taking into account the chemical reactivity of the AR thiol side chain of $Cys^{784}$ and the ability to improve the electrophilicity of bicalutamide. In embodiments, a compound more potent than bicalutamide is produced by replacing the CH atoms of the A ring with a nitrogen (N) atom, as described in more detail below. In embodiments, this change results in a compound that binds more tightly (e.g. 24-Fold more tightly) than bicaluatmide in cellular transcription assays.

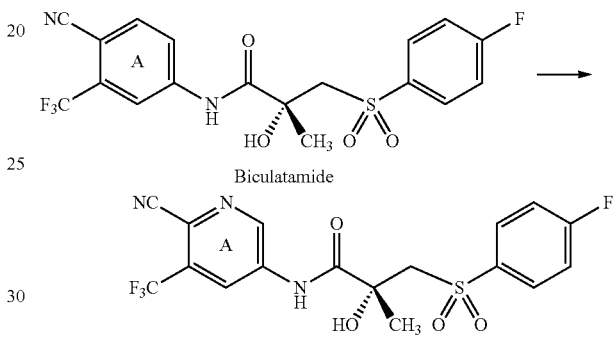

In embodiment, the compounds provided here bind tight and with a slow off-rate and thereby outcompete binding of natural steroids to the androgen receptor. In embodiments, tighter binding and/or slower off-rates can be achieved by capitalizing on the reactivity of a resident amino acid ($Cys^{784}$) in the AR receptor HBP with reactive electrophiles. In embodiments, this cysteine residue permits tighter binding to receptor antagonists containing reactive electrophiles, such as aryl-cyano groups.

In embodiments, provided herein is a recognition and improvement of a chemical reaction occurring within the hormone-binding pocket, involving the formation of a covalent bond between electrophilic moiety (e.g., aryl-cyano) containing inhibitors and a cysteine residue in the receptor hormone binding pocket. In embodiments, nucleophilic attack of a thiol ($Cys^{784}$) on an electrophilic group (e.g., aryl-cyano) on the antagonist permits the design of tighter binding and specific compounds that more effectively discourage the binding of natural steroids.

Described herein are the recognition and improvement of a chemical reaction occurring within the hormone-binding pocket, involving the formation of a covalent bond between electrophilic moiety (e.g, aryl-cyano) containing inhibitors and a cysteine residue in the receptor hormone binding pocket. Specifically, nucleophilic attack of a thiol ($Cys^{784}$) on an electrophilic group (e.g., aryl-cyano) on the antagonist permits the design of tighter binding and specific compounds that more effectively discourage the binding of natural steroids.

A. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and $CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —WC(O)$_2$—. As described above, heteroalkyl groups, as used herein, include those groups that are attached to the remainder of the molecule through a heteroatom, such as —C(O)R', —C(O)NR', —NR'R", —OR', —SW, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-Fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-Fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-Furyl, 3-Furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C($O)_2$R', —NR—C(NR'R"R'")=NR'"', —NR—C(NR'R")=NR", —S(O)R', —S($O)_2$R', —S($O)_2$NR'R", —NRSO$_2$R', NR'NR"R'", —ONR'R", NR'C=(O)NR"NR'"R", —CN, —$NO_2$, in a number ranging from zero to (2m'+1), where m' is the total number of carbon atoms in such radical. R, R', R", R'", and R" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR' R'') NR''', —S(O)R', —S(O)$_2$R', —S(O)$_2$NR'R'', —NRSO$_2$R', NR'NR''R''', —ONR'R'', NR'C=(O)NR''NR'''R'', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C''R''R''')$_d$—, where s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, heteroaryl, substituted with at least one substituent selected from:
(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with androgen receptor activity. Certain methods described herein may treat diseases associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism) by inhibiting androgen receptor activity. Certain methods described herein may treat diseases associated with androgen receptor activity by inhibiting ligand binding to androgen receptor. For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with androgen receptor activity may be treated with an agent (e.g. compound as described herein) effective for decreasing the level of androgen receptor activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is an androgen receptor antagonist. In embodiments, a modulator is a hormone receptor antagonist. In embodiments, a modulator is an androgen receptor inhibitor. In embodiments, a modulator is an androgen receptor covalent modifier.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Gurin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivatives, maytansinoids and maytansinoid analogs (e.g. mertansine), methotrexate, mitomycin C, taxoids, *vinca* alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of androgen receptor activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is prostate cancer. In embodiments, the disease is hormone sensitive prostate cancer. In embodiments, the disease is hormone refractory (insensitive) prostate cancer.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

Example of Amino Acid Classification
Small/Aliphatic residues: Gly, Ala, Val, Leu, Ile
Cyclic Imino Acid: Pro
Hydroxyl-containing Residues: Ser, Thr
Acidic Residues: Asp, Glu
Amide Residues: Asn, Gln
Basic Residues: Lys, Arg
Imidazole Residue: His
Aromatic Residues: Phe, Tyr, Trp
Sulfur-containing Residues: Met, Cys In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. For example, a selected residue in a selected protein corresponds to Cys784 of human androgen receptor when the selected residue occupies the same essential spatial or other structural relationship as Cys 784 in human androgen receptor. In some embodiments, where a selected protein is aligned for maximum homology with the human androgen receptor protein, the position in the aligned selected protein aligning with Cys784 is said to correspond to Cys784. Instead of a primary sequence alignment, a three dimensional structural alignment can also be used, e.g., where the structure of the selected protein is aligned for maximum correspondence with the human androgen receptor protein and the overall structures compared. In this case, an amino acid that occupies the same essential position as Cys784 in the structural model is said to correspond to the Cys784 residue.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer or aberrant androgen receptor activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

A "drug-resistant androgen receptor" is a modified (relative to wildtype) androgen receptor that is inhibited less effectively by the drug than a wildtype androgen receptor. A "drug-resistant human androgen receptor" is a modified (relative to wildtype) human androgen receptor that is inhibited less effectively by the drug than a wildtype human androgen receptor.

The term "androgen receptor" or "AR" or "NR3C4" refers to a nuclear receptor activated by binding of the androgenic hormone testosterone or dihydrotestosterone. The term "androgen receptor" may refer to the nucleotide sequence or protein sequence of human androgen receptor (e.g., Entrez 367, Uniprot P10275, RefSeq NM_000044, or RefSeq NP_000035). The term "androgen receptor" includes both the wild-type form of the nucleotide sequences or proteins as well as any mutants thereof. In some embodiments, "androgen receptor" is wild-type androgen receptor. In some embodiments, "androgen receptor" is one or more mutant forms. The term "androgen receptor" XYZ refers to a nucleotide sequence or protein of a mutant androgen receptor wherein the Y numbered amino acid of androgen receptor that normally has an X amino acid in the wildtype, instead has a Z amino acid in the mutant. In embodiments, an androgen receptor is the human androgen receptor. In embodiments, the androgen receptor has the nucleotide sequence corresponding to reference number GI:349501065. In embodiments, the androgen receptor has the nucleotide sequence corresponding to RefSeq NM_000044.3. In embodiments, the androgen receptor has the protein sequence corresponding to reference number GI:21322252. In embodiments, the androgen receptor has the nucleotide sequence corresponding to RefSeq NP_000035.2. In embodiments, the androgen receptor has the following amino acid sequence:

MEVQLGLGRVYPRPPSKTYRGAFQNLFQSVREVIQNPGPRHPEAASAAPP

GASLLLLQQQQQQQQQQQQQQQQQQQQQQETSPRQQQQQQGEDGSPQAHRR

GPTGYLVLDEEQQPSQPQSALECHPERGCVPEPGAAVAASKGLPQQLPAP

PDEDDSAAPSTLSLLGPTFPGLSSCSADLKDILSEASTMQLLQQQQQEAV

SEGSSSGRAREASGAPTSSKDNYLGGTSTISDNAKELCKAVSVSMGLGVE

ALEHLSPGEQLRGDCMYAPLLGVPPAVRPTPCAPLAECKGSLLDDSAGKS

TEDTAEYSPFKGGYTKGLEGESLGCSGSAAAGSSGTLELPSTLSLYKSGA

LDEAAAYQSRDYYNFPLALAGPPPPPPPPHPHARIKLENPLDYGSAWAAA

AAQCRYGDLASLHGAGAAGPGSGSPSAAASSSWHTLFTAEEGQLYGPCGG

GGGGGGGGGGGGGGGGGGGGGEAGAVAPYGYTRPPQGLAGQESDFTAPD

VWYPGGMVSRVPYPSPTCVKSEMGPWMDSYSGPYGDMRLETARDHVLPID

YYFPPQKTCLICGDEASGCHYGALTCGSCKVFFKRAAEGKQKYLCASRND

CTIDKFRRKNCPSCRLRKCYEAGMTLGARKLKKLGNLKLQEEGEASSTTS

PTEETTQKLTVSHIEGYECQPIFLNVLEAIEPGVVCAGHDNNQPDSFAAL

LSSLNELGERQLVHVVKWAKALPGFRNLHVDDQMAVIQYSWMGLMVFAMG

WRSFTNVNSRMLYFAPDLVFNEYRMHKSRMYSQCVRMRHLSQEFGWLQIT

PQEFLCMKALLLFSIIPVDGLKNQKFFDELRMNYIKELDRIIACKRKNPT

SCSRRFYQLTKLLDSVQPIARELHQFTFDLLIKSHMVSVDFPEMMAEIIS

VQVPKILSGKVKPIYFHTQ

In embodiments, the androgen receptor is a mutant androgen receptor. In embodiments, the mutant androgen receptor is associated with a disease that is not associated with wildtype androgen receptor. In embodiments, the androgen receptor includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above.

The term "electrophilic moiety" is used in accordance with its plain ordinary chemical meaning and refers to a monovalent chemical group that is electrophilic. In embodiments an electrophilic moiety is a monovalent chemical group capable of forming a covalent bond (e.g., reversible or irreversible) with a Cys, Asp, Glu, Tyr, Ser, or Lys sidechain of a nuclear receptor (e.g., androgen receptor). In embodiments an electrophilic moiety is a monovalent chemical group capable of forming a covalent bond (e.g., reversible or irreversible) with a Cys residue. In embodiments an electrophilic moiety is a monovalent chemical group capable of forming a covalent bond (e.g., reversible or irreversible) with an androgen receptor Cys residue.

B. COMPOUNDS

In an aspect is provided a compound, or a pharmaceutically acceptable salt thereof, having the formula:

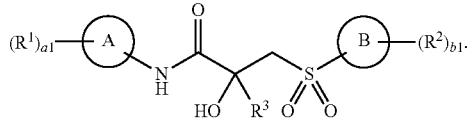

Ring A is a heteroaryl; Ring B is a phenyl or heteroaryl; $R^1$ is independently a hydrogen, halogen, —$CX^a_3$, —CN, —$SO_2Cl$, —$SO_{n1}R^{10}$, —$SO_{v1}NR^7R^8$, —$NHNH_2$, —$ONR^7R^8$, —NHC=(O)$NHNH_2$, —NHC=(O)$NR^7R^8$, —$N(O)_{m1}$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)$—$OR^9$, —$NR^7OR^9$, —$OCX^a_3$, —$OCHX^a_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. E is an electrophilic moiety. $R^2$ is independently a hydrogen, halogen, —$CX^b_3$, —CN, —$SO_2Cl$, —$SO_{n2}R^{14}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}C$=(O)$R^{13}$, —$NR^{11}C(O)$—$OR^{13}$, —$NR^{11}OR^{13}$, —$OCX^b_3$, —$OCHX^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^3$ is independently an unsubstituted alkyl. $R^7$, $R^8$, $R^9$, $R^{10}$, $R^{11}$, $R^{12}$, $R^{13}$, and $R^{14}$ are independently hydrogen, halogen, —$CX^c_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^c_3$, —$OCHX^c_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. The symbol a1 is independently an integer from 0 to 4. The symbol b1 is independently an integer from 0 to 5. The symbols m1, m2, v1, and v2 are independently 1 or 2. The symbols n1 and n2 are independently an integer from 0 to 4. The symbols $X^a$, $X^b$, and $X^c$ are independently —Cl, —Br, —I, or —F.

In embodiments, the compound has the formula

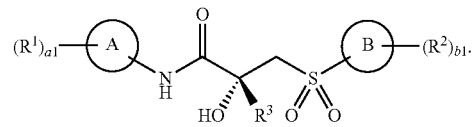

Ring A, Ring B, $R^1$, $R^2$, $R^3$, a1, and b1 are as described herein, including in embodiments (e.g., as for formula I and embodiments thereof).

In embodiments, the compound has the formula

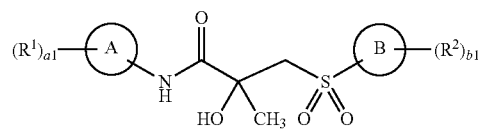

Ring A, Ring B, $R^1$, $R^2$, a1, and b1 are as described herein, including in embodiments (e.g., as for formula I and embodiments thereof).

In embodiments, the compound has the formula

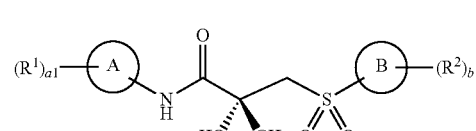

Ring A, Ring B, $R^1$, $R^2$, a1, and b1 are as described herein, including in embodiments (e.g., as for formula I, Ia, Ib, and embodiments thereof).

In embodiments, Ring A is a 6 membered heteroaryl. Ring A may be

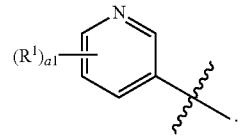

Ring A may be

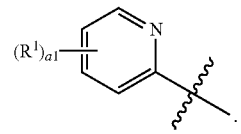

Ring A may be

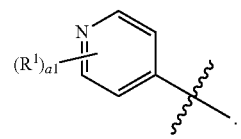

Ring A may be

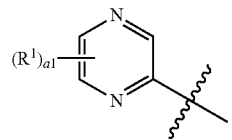

with a1 an integer from 0 to 3. Ring A may be

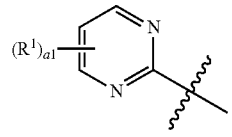

with a1 an integer from 0 to 3. Ring A may be

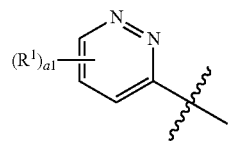

with a1 an integer from 0 to 3. Ring A may be

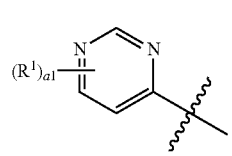

with a1 an integer from 0 to 3. Ring A may be

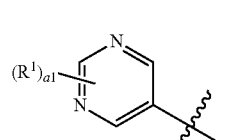

with a1 an integer from 0 to 3. Ring A may be

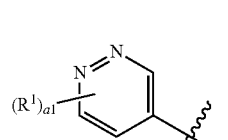

with a1 an integer from 0 to 3. Ring A may be

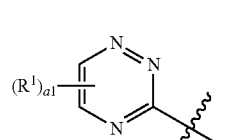

with a1 an integer from 0 to 3. Ring A may be with a1 an integer from 0 to 2. Ring A may be

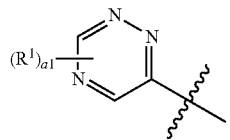

with a1 an integer from 0 to 2. Ring A may be

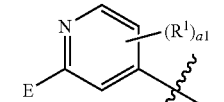

with a1 an integer from 0 to 1.
Ring A may be

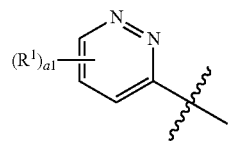

with a1 an integer from 0 to 3. Ring A may be

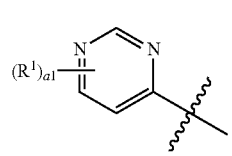

with a1 an integer from 0 to 3. Ring A may be

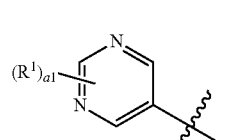

with a1 an integer from 0 to 3. Ring A may be

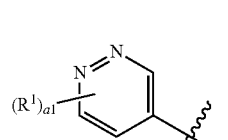

with a1 an integer from 0 to 3. Ring A may be

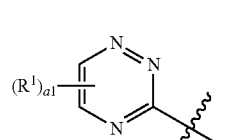

with a1 an integer from 0 to 3. Ring A may be

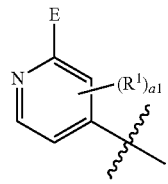

with a1 an integer from 0 to 3. Ring A may be

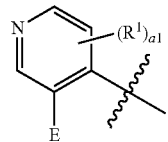

with a1 an integer from 0 to 3. Ring A may be

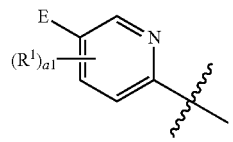

with a1 an integer from 0 to 3. Ring A may be

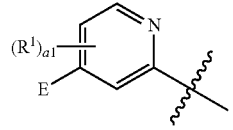

with a1 an integer from 0 to 3. Ring A may be

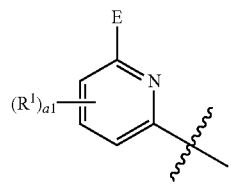

with a1 an integer from 0 to 3. Ring A may be

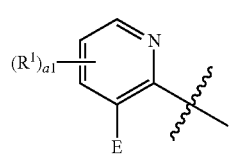

with a1 an integer from 0 to 3. Ring A may be

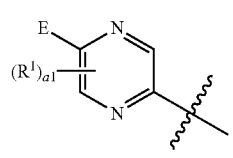

with a1 an integer from 0 to 2. Ring A may be

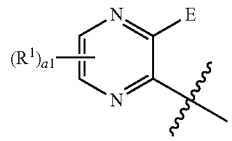

with a1 an integer from 0 to 2. Ring A may be

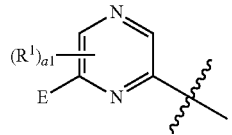

with a1 an integer from 0 to 2. Ring A may be

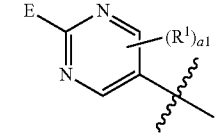

with a1 an integer from 0 to 2. Ring A may be

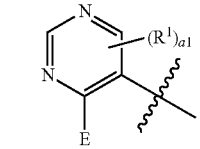

with a1 an integer from 0 to 2. Ring A may be

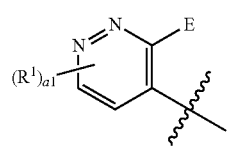

with a1 an integer from 0 to 2. Ring A may be

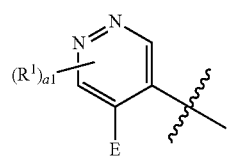

with a1 an integer from 0 to 2. Ring A may be

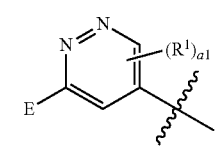

with a1 an integer from 0 to 2. Ring A may be

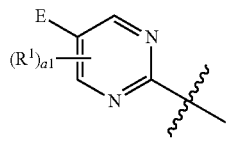

with a1 an integer from 0 to 2. Ring A may be

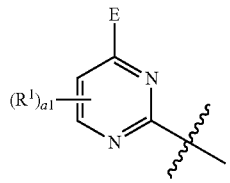

with a1 an integer from 0 to 2. Ring A may be

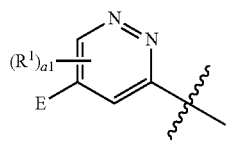

with a1 an integer from 0 to 2. Ring A may be

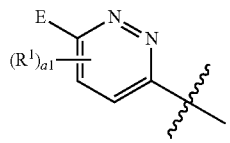

with a1 an integer from 0 to 2. Ring A may be

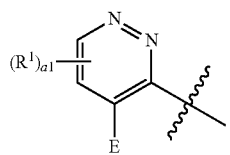

with a1 an integer from 0 to 2. Ring A may be

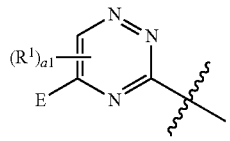

with a1 an integer from 0 to 1. Ring A may be

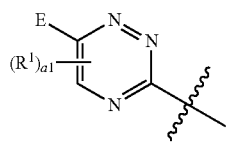

with a1 an integer from 0 to 1. Ring A may be

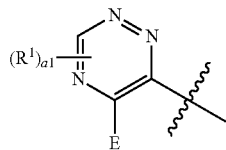

with a1 an integer from 0 to 1. Ring A may be

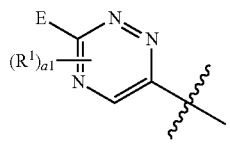

with a1 an integer from 0 to 1. Ring A may be

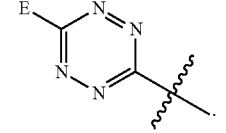

Ring A may be

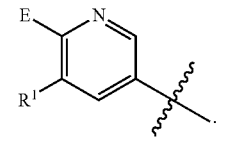

Ring A may be a 6 membered heteroaryl. Ring A may be pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. In embodiments, Ring A is a pyridinyl. In embodiments, Ring A is a pyrimidinyl.

In embodiments, Ring A does not include a heteroatom ortho to the bond to the remainder of the compound including Ring B. In embodiments, Ring A does not include a nitrogen atom ortho to the bond to the remainder of the compound including Ring B. In embodiments, Ring A is a 6 membered heteroaryl. In embodiments, Ring A is not

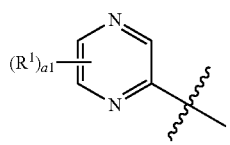

with a1 an integer from 0 to 3. In embodiments, Ring A is not

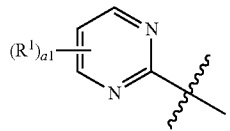

with a1 an integer from 0 to 3. In embodiments, Ring A is not

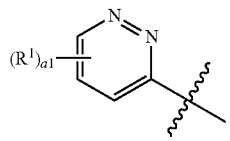

with a1 an integer from 0 to 3. In embodiments, Ring A is not

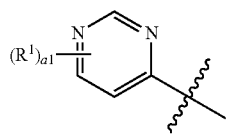

with a1 an integer from 0 to 4. In embodiments, Ring A is not

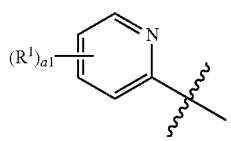

with a1 an integer from 0 to 4. In embodiments, Ring A is not

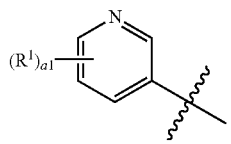

with a1 an integer from 0 to 4. In embodiments, Ring A is not

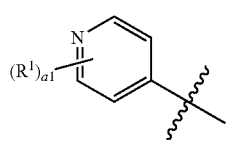

with a1 an integer from 0 to 4. In embodiments, Ring A is not

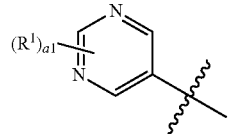

with a1 an integer from 0 to 3. In embodiments, Ring A is not

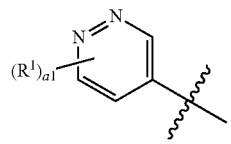

with a1 an integer from 0 to 3. In embodiments, Ring A is not

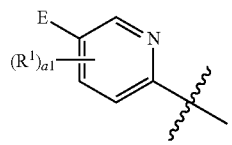

with a1 an integer from 0 to 3. In embodiments, Ring A is not

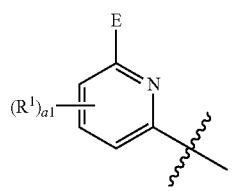

with a1 an integer from 0 to 3. In embodiments, Ring A is not

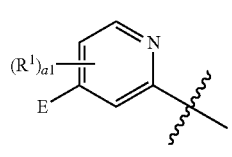

with a1 an integer from 0 to 3. In embodiments, Ring A is not

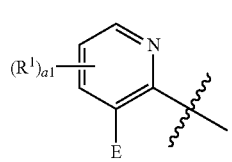

with a1 an integer from 0 to 3.

In embodiments, Ring A is not

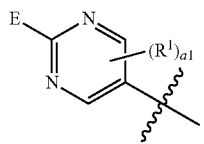

with a1 an integer from 0 to 2. In embodiments, Ring A is not

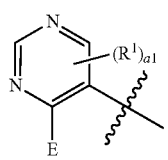

with a1 an integer from 0 to 2. In embodiments, Ring A is not

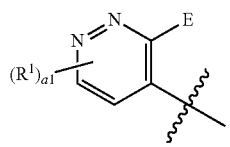

with a1 an integer from 0 to 2. In embodiments, Ring A is not

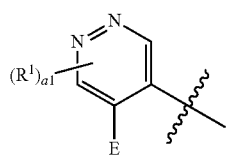

with a1 an integer from 0 to 2. In embodiments, Ring A is not

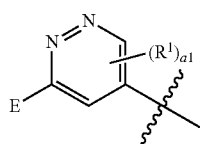

with a1 an integer from 0 to 2. In embodiments, Ring A is not

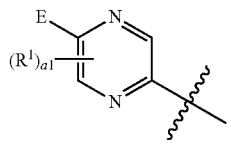

with a1 an integer from 0 to 2. In embodiments, Ring A is not

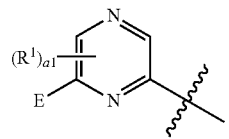

with a1 an integer from 0 to 2. In embodiments, Ring A is not

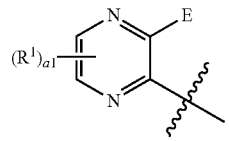

with a1 an integer from 0 to 2. In embodiments, Ring A is not

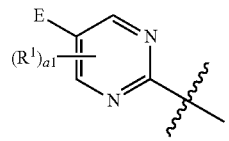

with a1 an integer from 0 to 2. In embodiments, Ring A is not

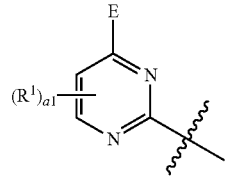

with a1 an integer from 0 to 2. In embodiments, Ring A is not

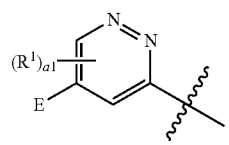

with a1 an integer from 0 to 2. In embodiments, Ring A is not

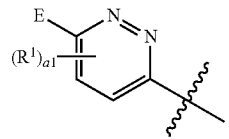

with a1 an integer from 0 to 2. In embodiments, Ring A is not

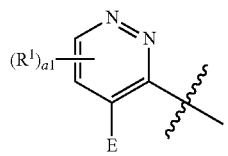

with a1 an integer from 0 to 2. In embodiments, Ring A is not

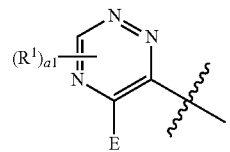

with a1 an integer from 0 to 1. In embodiments, Ring A is not with a1 an integer from 0 to 2. In embodiments, Ring A is not

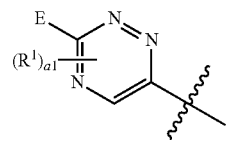

with a1 an integer from 0 to 1. In embodiments, Ring A is not with a1 an integer from 0 to 2. In embodiments, Ring A is not with a1 an integer from 0 to 1. In embodiments, Ring A is not

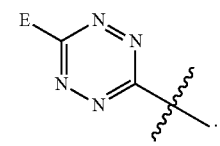

with a1 an integer from 0 to 1. In embodiments, Ring A is not

In embodiments, each $R^1$ is independently a halogen, $-CX^a{}_3$, $-CN$, $-SO_2Cl$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^a{}_3$, $-OCHX^a{}_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. E is an electrophilic moiety. Each $R^1$ may independently be $-Cl$, $-F$, $-Br$, $-I$, $-CX^a{}_3$, $-CN$, $-NHNH_2$, $-ONH_2$, $-NHC=(O)NHNH_2$, $-NHC=(O)NH_2$, $-NO_2$, $-NH_2$, $-C(O)H$, $-C(O)CH_3$, $-C(O)-OH$, $-C(O)-OCH_3$, $-C(O)NH_2$, $-OH$, $-NHC=(O)H$, $-NHC=(O)CH_3$, $-NHC(O)-OH$, $-NHC(O)OCH_3$, $-NHOH$, $-NHOCH_3$. $-OCX^a{}_3$, $-OCHX^a{}_2$, substituted or unsubstituted $C_1$-$C_5$ alkyl, substituted or unsubstituted 2 to 5 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. Each $R^1$ may independently be E. Each $R^1$ may independently be an optionally different E. Each $R^1$ may independently be a $-Cl$, $-F$, $-Br$, $-I$, $-CN$, $-CX^a{}_3$, $-NO_2$, $-OCX^a{}_3$, or $-OCHX^a{}_2$. Each $R^1$ may independently be $-Cl$. Each $R^1$ may independently be $-F$. Each $R^1$ may independently be $-Br$. Each $R^1$ may independently be $-I$. Each $R^1$ may independently be $-CX^a{}_3$. Each $R^1$ may independently be $-CF_3$. Each $R^1$ may independently be $-CN$. Each $R^1$ may independently be $-NHNH_2$. Each $R^1$ may independently be $-ONH_2$. Each $R^1$ may independently be $NHC=(O)NHNH_2$. Each $R^1$ may independently be NHC═(O)NH$_2$. Each R$^1$ may independently be —NO$_2$. Each R$^1$ may independently be —NH$_2$. Each R$^1$ may independently be —C(O)H. Each R$^1$ may independently be —C(O)CH$_3$. Each R$^1$ may independently be —C(O)—OH. Each R$^1$ may independently be —C(O)—OCH$_3$. Each R$^1$ may independently be —C(O)NH$_2$. Each R$^1$ may independently be OH. Each R$^1$ may independently be —NHC═(O)H. Each R$^1$ may independently be —NHC═(O)CH$_3$. Each R$^1$ may independently be —NHC(O)—OH. Each R$^1$ may independently be —NHC(O)OCH$_3$. Each R$^1$ may independently be —NHOH. Each R$^1$ may independently be —NHOCH$_3$. Each R$^1$ may independently be —OCX$^a$$_3$. Each R$^1$ may independently be —OCHX$^a$$_2$. Each R$^1$ may independently be substituted or unsubstituted C$_1$-C$_5$ alkyl, substituted or unsubstituted 2 to 5 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. Each R$^1$ may independently be unsubstituted C$_1$-C$_5$ alkyl, unsubstituted 2 to 5 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. Each R$^1$ may independently be substituted C$_1$-C$_5$ alkyl. Each R$^1$ may independently be unsubstituted C$_1$-C$_5$ alkyl. Each R$^1$ may independently be substituted 2 to 5 membered heteroalkyl. Each R$^1$ may independently be unsubstituted 2 to 5 membered heteroalkyl. Each R$^1$ may independently be substituted C$_3$-C$_6$ cycloalkyl. Each R$^1$ may independently be unsubstituted C$_3$-C$_6$ cycloalkyl. Each R$^1$ may independently be substituted 3 to 6 membered heterocycloalkyl. Each R$^1$ may independently be unsubstituted 3 to 6 membered heterocycloalkyl. Each R$^1$ may independently be substituted phenyl. Each R$^1$ may independently be unsubstituted phenyl. Each R$^1$ may independently be substituted 5 to 6 membered heteroaryl. Each R$^1$ may independently be unsubstituted 5 to 6 membered heteroaryl. In embodiments, two adjacent R$^1$ substituents may be joined to form a substituted or unsubstituted cycloalkyl, substituted or unsubstituted heterocycloalkyl, substituted or unsubstituted aryl, or substituted or unsubstituted heteroaryl. In embodiments, two adjacent R$^1$ substituents may be joined to form a substituted or unsubstituted C$_3$-C$_6$ cycloalkyl, substituted or unsubstituted 4 to 6 membered heterocycloalkyl, substituted or unsubstituted phenyl, or substituted or unsubstituted 5 to 6 membered heteroaryl. Two adjacent R$^1$ substituents may be joined to form a substituted or unsubstituted C$_3$-C$_6$ cycloalkyl. Two adjacent R$^1$ substituents may be joined to form a substituted or unsubstituted 4 to 6 membered heterocycloalkyl. Two adjacent R$^1$ substituents may be joined to form a substituted or unsubstituted phenyl. Two adjacent R$^1$ substituents may be joined to form a substituted or unsubstituted 5 to 6 membered heteroaryl. Two adjacent R$^1$ substituents may be joined to form an unsubstituted C$_3$-C$_6$ cycloalkyl. Two adjacent R$^1$ substituents may be joined to form an unsubstituted 4 to 6 membered heterocycloalkyl. Two adjacent R$^1$ substituents may be joined to form an unsubstituted phenyl. Two adjacent R$^1$ substituents may be joined to form an unsubstituted 5 to 6 membered heteroaryl.

In some embodiments, E includes a substituted or unsubstituted vinyl sulfone moiety, substituted or unsubstituted vinyl sulfonamide moiety, substituted or unsubstituted fluoro(C$_1$-C$_4$)alkylketone moiety, substituted or unsubstituted chloro(C$_1$-C$_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted dialdehyde moiety, substituted or unsubstituted nitrogen mustard moiety, substituted or unsubstituted propargyl moiety, substituted or unsubstituted propargylamide moiety, —CN, —NO$_2$,

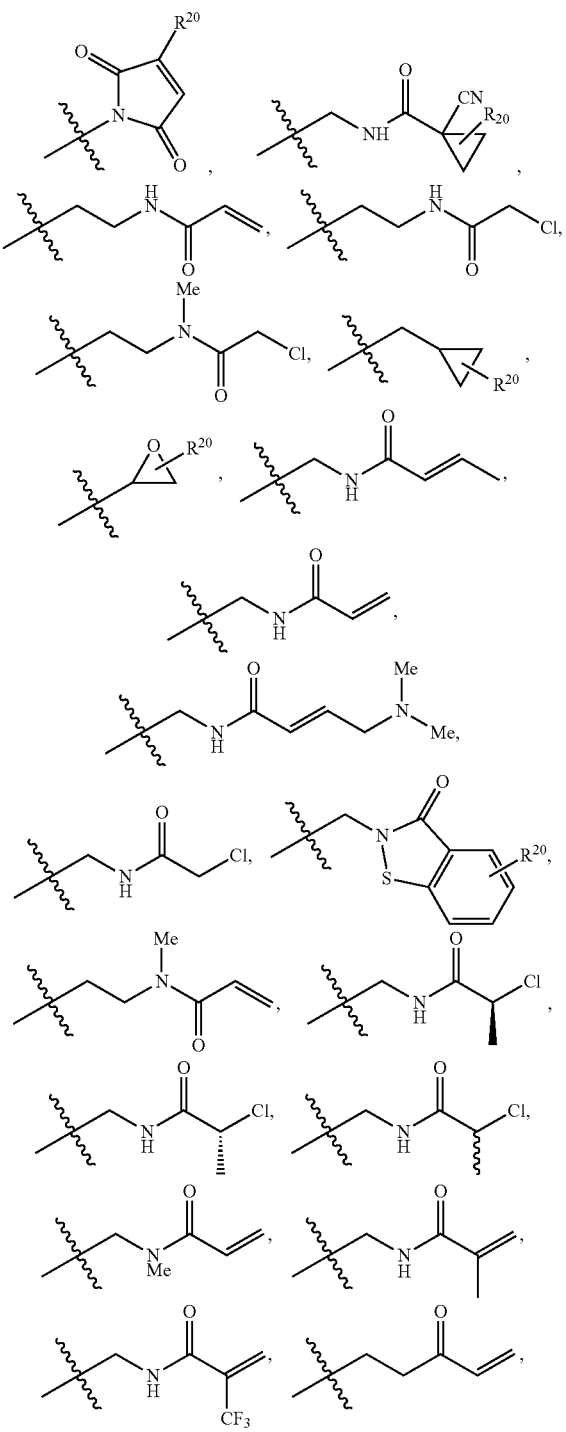

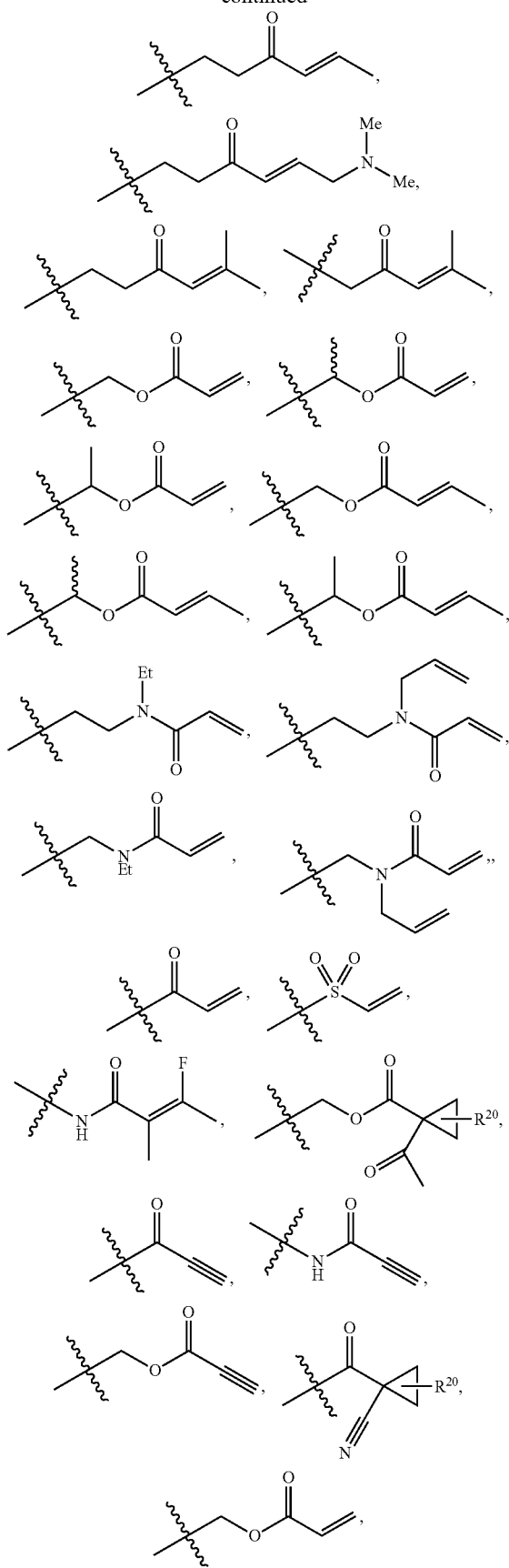
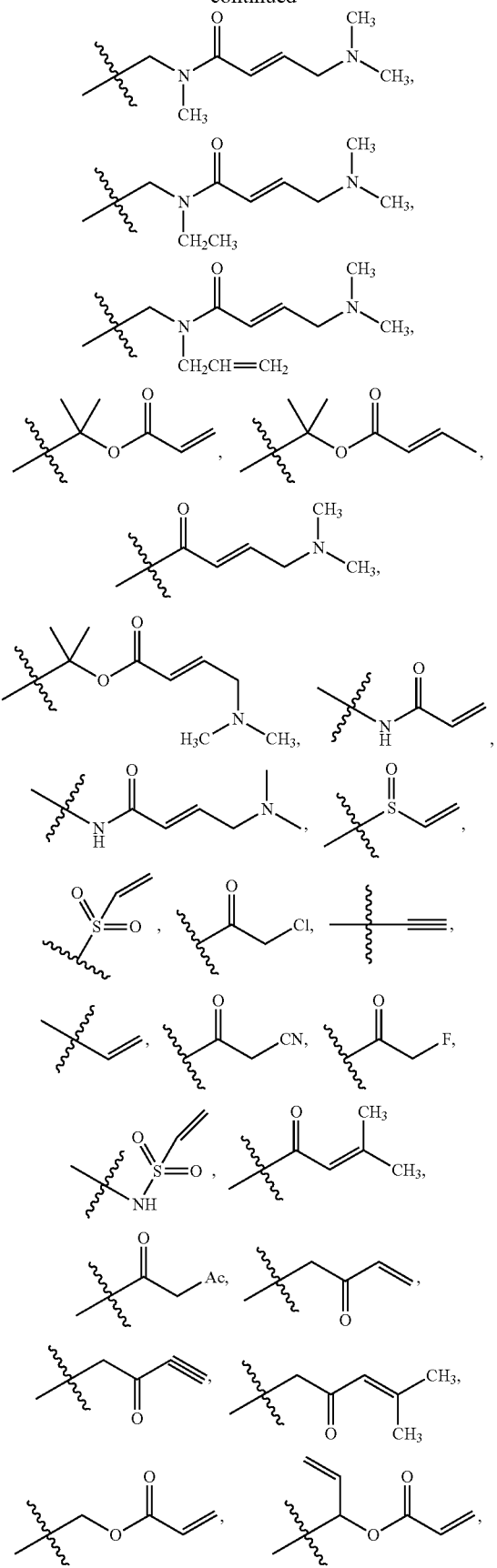

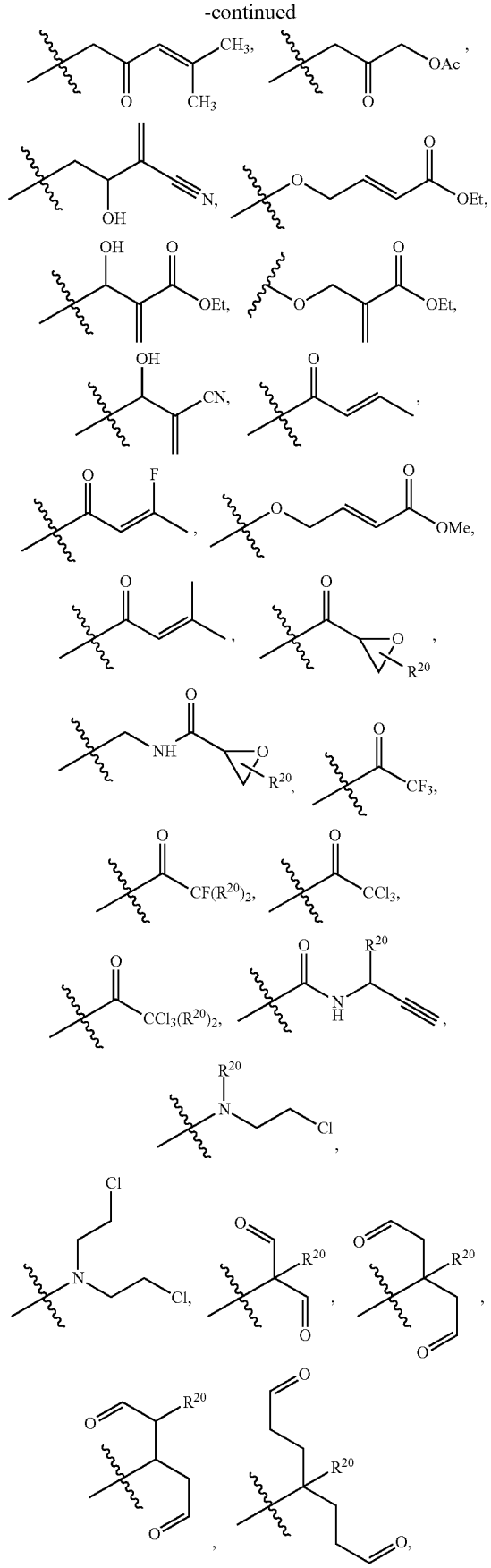
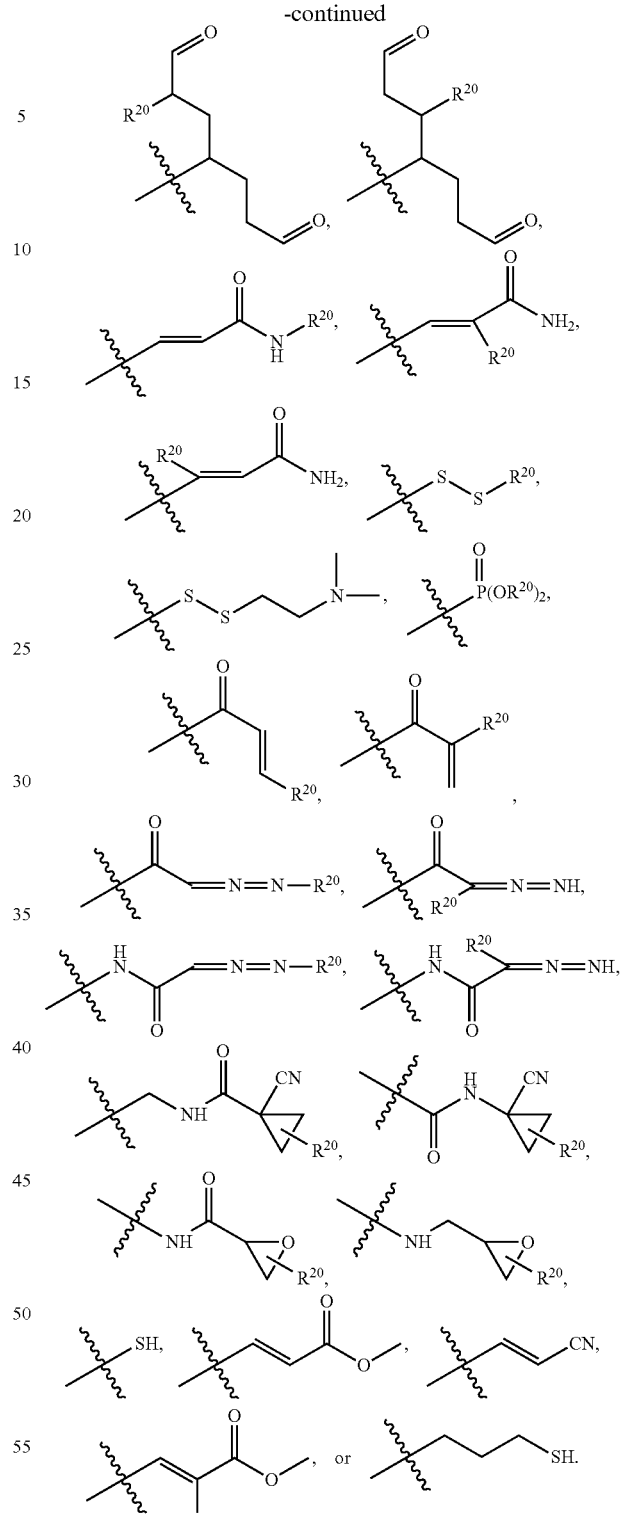

In some embodiments, E is a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro ($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted dialdehyde moiety, substituted or unsubstituted nitrogen mustard moiety, substituted or unsubstituted propargyl moiety, substituted or unsubstituted propargylamide moiety, —CN, —NO$_2$,

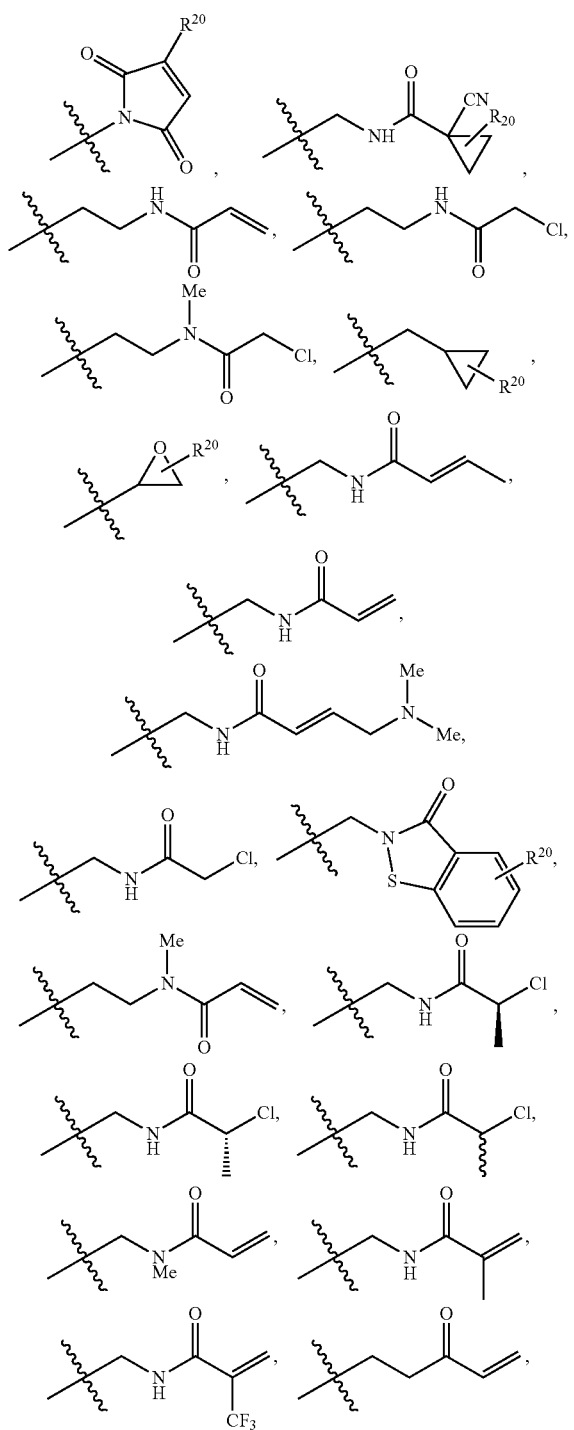

-continued

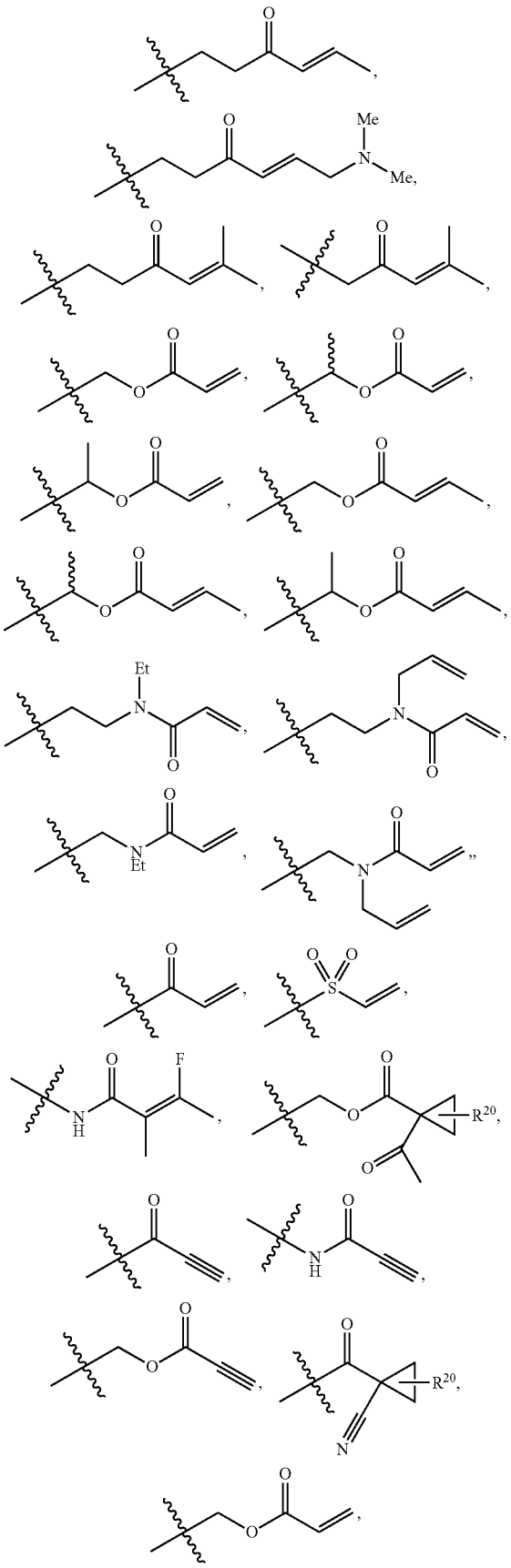

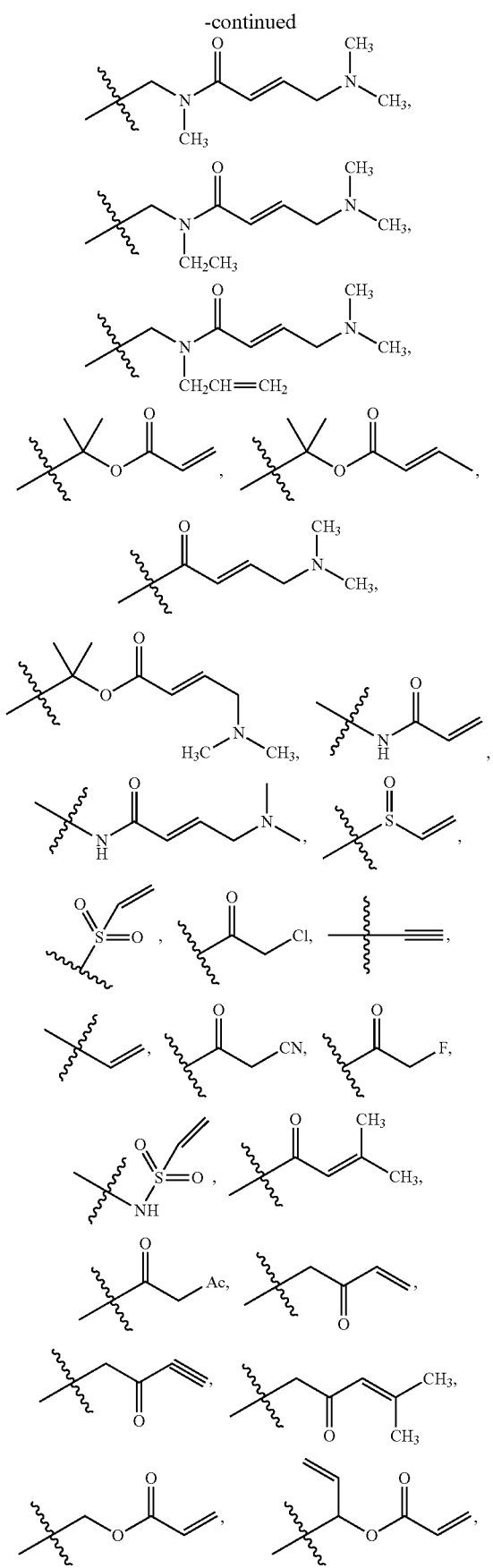
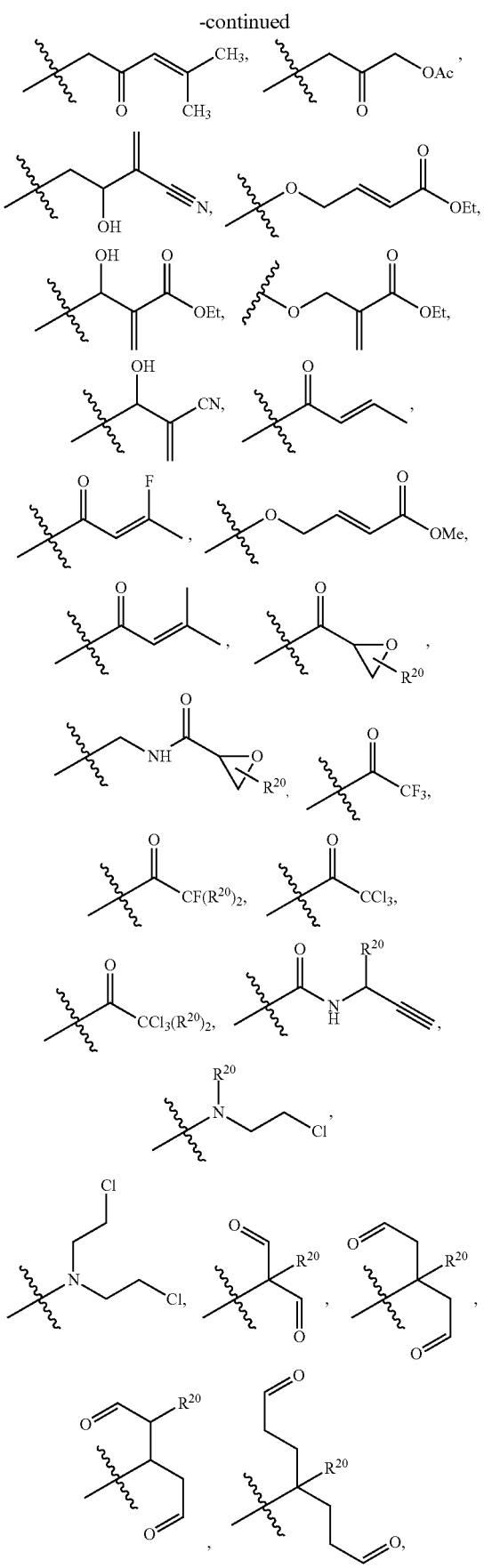

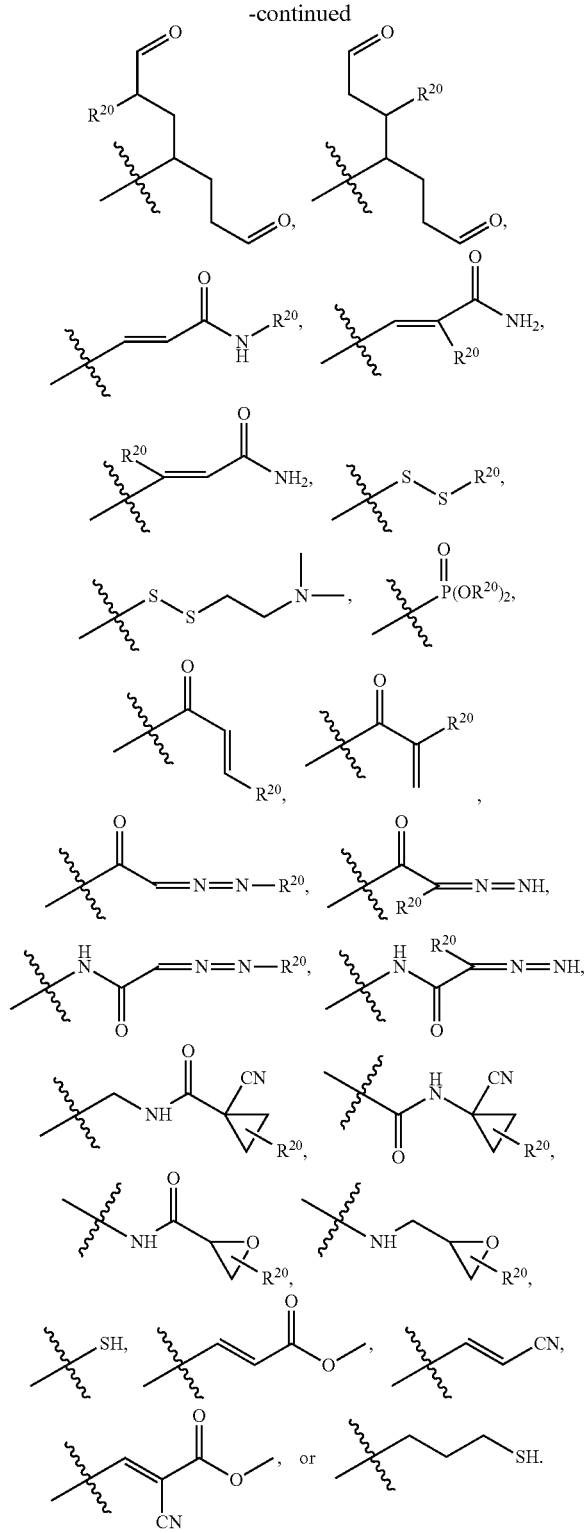

unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted dialdehyde moiety, unsubstituted nitrogen mustard moiety, unsubstituted propargyl moiety, or unsubstituted propargylamide moiety. In some embodiments, E is a cyano, an unsubstituted vinyl sulfone moiety, unsubstituted vinyl sulfonamide moiety, unsubstituted fluoro($C_1$-$C_4$)alkylketone moiety, unsubstituted chloro($C_1$-$C_4$)alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted dialdehyde moiety, unsubstituted nitrogen mustard moiety, unsubstituted propargyl moiety, or unsubstituted propargylamide moiety.

E may be —CN. E may be —$NO_2$. E may be

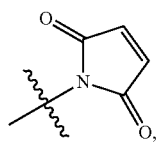

E may be —CCH. E may be —$CH_2$CCH. E may be —CHCH$_2$. E may be

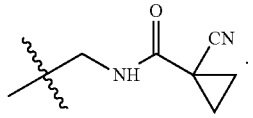

E may be

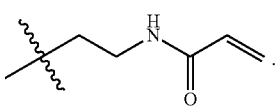 [SMILES: *CCNC(=O)C=C]

E may be

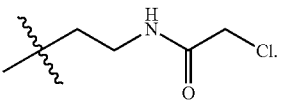 [SMILES: *CCNC(=O)CCl]

E may be

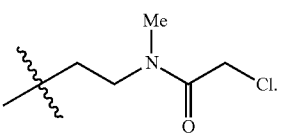 [SMILES: *CCN(C)C(=O)CCl]

E may be
E may be
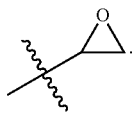 [SMILES: *C1CO1]
E may be
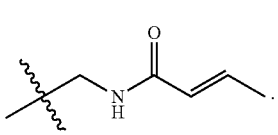 [SMILES: *CNC(=O)/C=C/C]
E may be
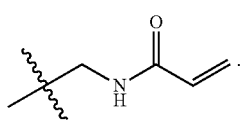 [SMILES: *CNC(=O)C=C]
E may be
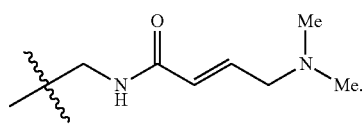 [SMILES: *CNC(=O)/C=C/CN(C)C]
E may be
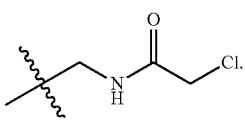 [SMILES: *CNC(=O)CCl]
E may be
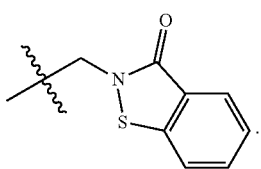 [SMILES: *Cn1sc2ccccc2c1=O]
E may be
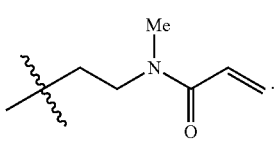 [SMILES: *CCN(C)C(=O)C=C]
E may be
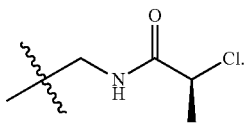 [SMILES: *CNC(=O)[C@H](C)Cl]
E may be
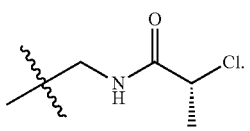
E may be
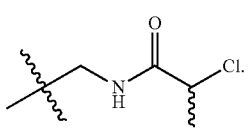
E may be
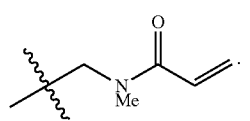 [SMILES: *CN(C)C(=O)C=C]
E may be
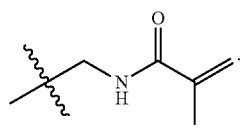 [SMILES: *CNC(=O)C(=C)C]
E may be
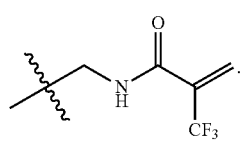
E may be
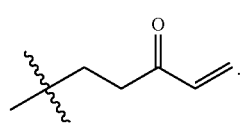 [SMILES: *CCC(=O)C=C]

E may be
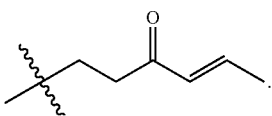 [SMILES: *CCC(=O)/C=C/C]
E may be
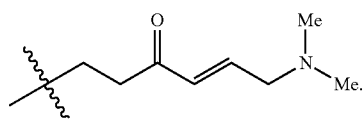 [SMILES: *CCC(=O)/C=C/CN(C)C]
E may be
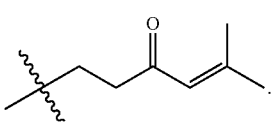 [SMILES: *CCC(=O)C=C(C)C]
E may be
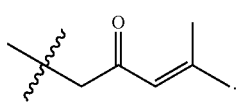 [SMILES: *CC(=O)C=C(C)C]
E may be
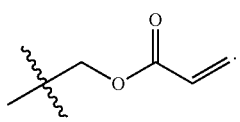 [SMILES: *COC(=O)C=C]
E may be
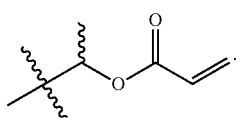 [SMILES: *C(C)OC(=O)C=C]
E may be
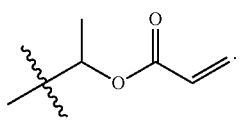 [SMILES: *C(C)OC(=O)C=C]
E may be
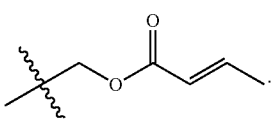 [SMILES: *COC(=O)/C=C/C]
E may be
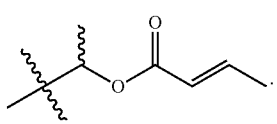 [SMILES: *C(C)OC(=O)/C=C/C]
E may be
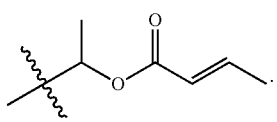 [SMILES: *C(C)OC(=O)/C=C/C]
E may be
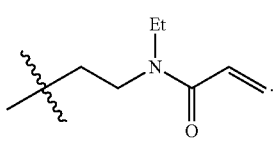 [SMILES: *CCN(CC)C(=O)C=C]
E may be
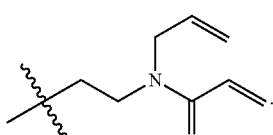
E may be
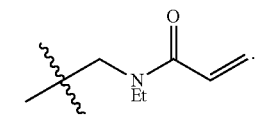
E may be
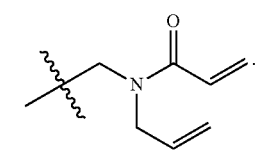 [SMILES: *CN(CC=C)C(=O)C=C]
E may be
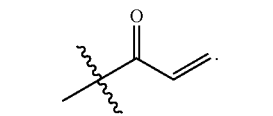 [SMILES: *C(=O)C=C]

E may be
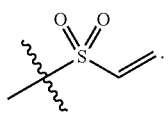
E may be
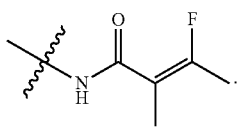 [SMILES: *NC(=O)/C(C)=C(/C)F]
E may be
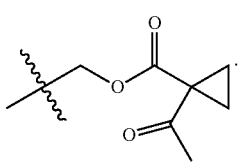 [SMILES: *COC(=O)C1(C(C)=O)CC1]
E may be
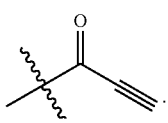 [SMILES: *C(=O)C#C]
E may be
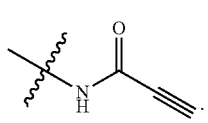 [SMILES: *NC(=O)C#C]
E may be
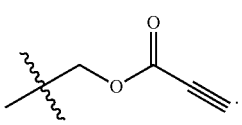 [SMILES: *COC(=O)C#C]
E may be
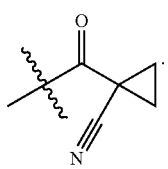 [SMILES: *C(=O)C1(C#N)CC1]
E may be
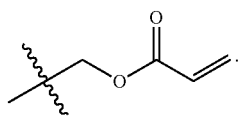 [SMILES: *COC(=O)C=C]
E may be
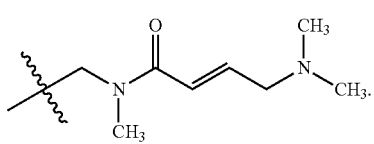 [SMILES: *CN(C)C(=O)/C=C/CN(C)C]
E may be
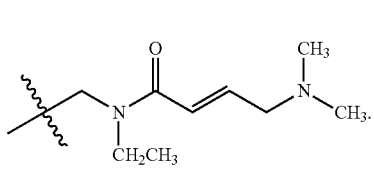 [SMILES: *CN(CC)C(=O)/C=C/CN(C)C]
E may be
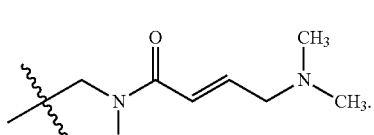
E may be
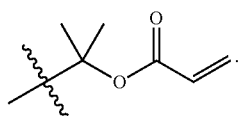 [SMILES: *C(C)(C)OC(=O)C=C]
E may be
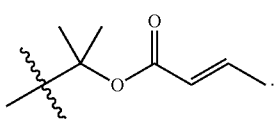 [SMILES: *C(C)(C)OC(=O)/C=C/C]
E may be
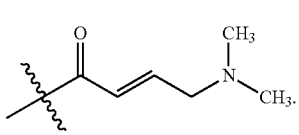 [SMILES: *C(=O)/C=C/CN(C)C]

E may be
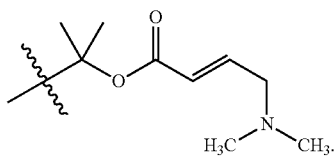 [SMILES: *C(C)(C)OC(=O)/C=C/CN(C)C]
E may be
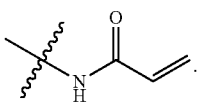 [SMILES: *NC(=O)C=C]
E may be
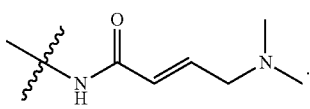 [SMILES: *NC(=O)/C=C/CN(C)C]
E may be
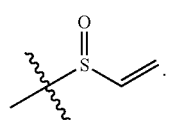 [SMILES: *S(=O)C=C]
E may be
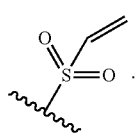 [SMILES: *S(=O)(=O)C=C]
E may be
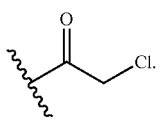
E may be
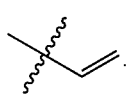
E may be
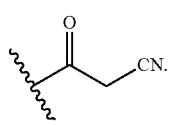 [SMILES: *C(=O)CC#N]
E may be
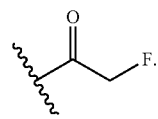 [SMILES: *C(=O)CF]
E may be
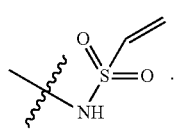 [SMILES: *NS(=O)(=O)C=C]
E may be
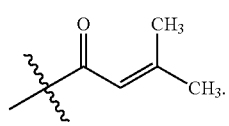
E may be
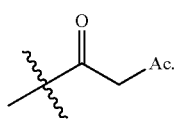
E may be
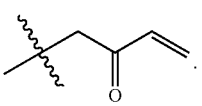 [SMILES: *CC(=O)C=C]
E may be
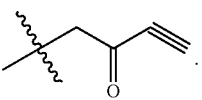
E may be
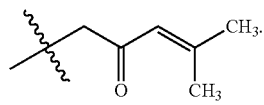
E may be
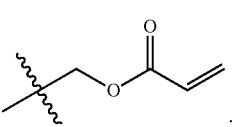 [SMILES: *COC(=O)C=C]

E may be
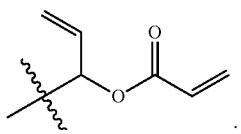 [SMILES: *C(C=C)OC(=O)C=C]
E may be
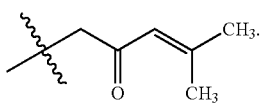 [SMILES: *CC(=O)C=C(C)C]
E may be
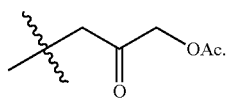 [SMILES: *CC(=O)COC(C)=O]
E may be
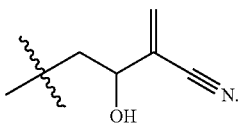 [SMILES: *CC(O)C(=C)C#N]
E may be
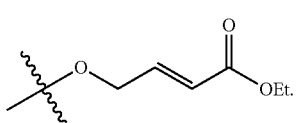 [SMILES: *OC/C=C/C(=O)OCC]
E may be
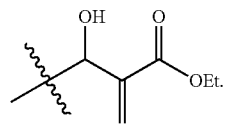 [SMILES: *C(O)C(=C)C(=O)OCC]
E may be
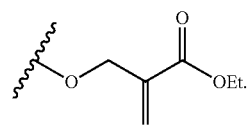 [SMILES: *OCC(=C)C(=O)OCC]
E may be
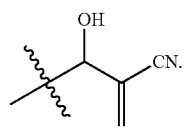 [SMILES: *C(O)C(=C)C#N]
E may be
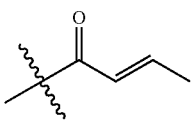
E may be
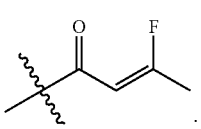 [SMILES: *C(=O)/C=C(/C)F]
E may be
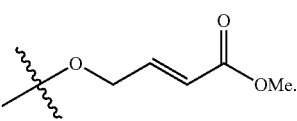 [SMILES: *OC/C=C/C(=O)OC]
E may be
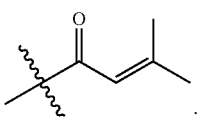
E may be
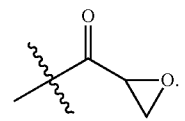 [SMILES: *C(=O)C1CO1]
E may be
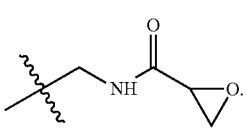 [SMILES: *CNC(=O)C1CO1]

E may be
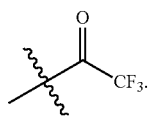
E may be
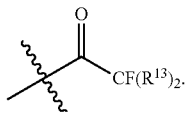
E may be
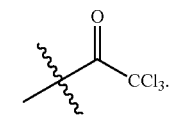
E may be
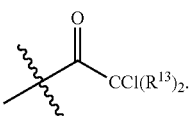
E may be
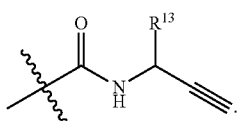
E may be
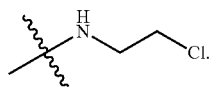 [SMILES: *NCCCl]
E may be
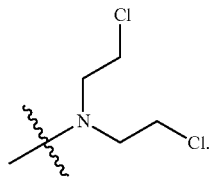 [SMILES: *N(CCCl)CCCl]
E may be
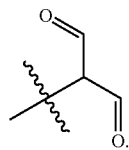 [SMILES: *C(C=O)C=O]
E may be
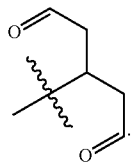 [SMILES: *C(CC=O)CC=O]
E may be
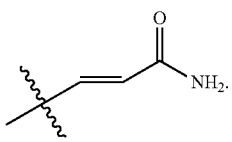
E may be
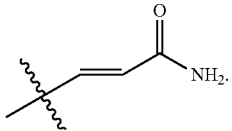 [SMILES: */C=C/C(N)=O]
E may be
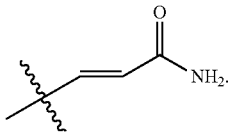 [SMILES: */C=C/C(N)=O]
E may be
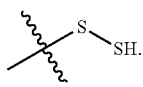

E may be
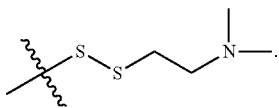
E may be
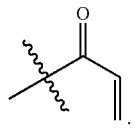 [SMILES: *C(=O)C=C]
E may be
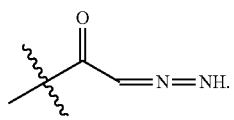
E may be
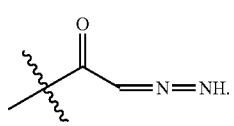
E may be
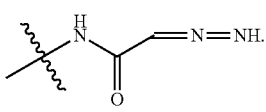
E may be
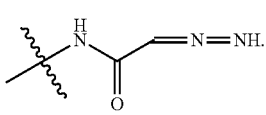
E may be
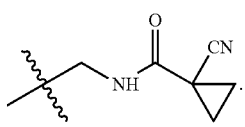 [SMILES: *CNC(=O)C1(C#N)CC1]
E may be
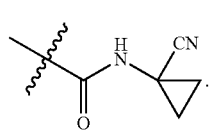 [SMILES: *C(=O)NC1(C#N)CC1]
E may be
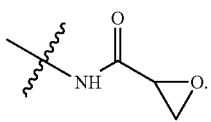 [SMILES: *NC(=O)C1CO1]
E may be
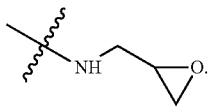 [SMILES: *NCC1CO1]
E may be
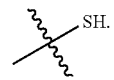
E may be
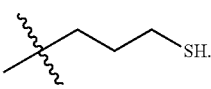 [SMILES: *CCCS]
E may be
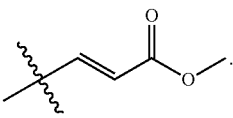 [SMILES: */C=C/C(=O)OC]
E may be
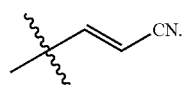 [SMILES: */C=C/C#N]
E may be
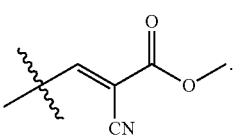 [SMILES: */C=C(\C#N)C(=O)OC]
E may be
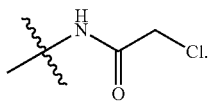 [SMILES: *NC(=O)CCl]

E may be

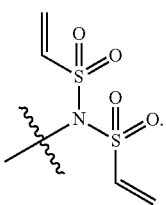 [SMILES: *N(S(=O)(=O)C=C)S(=O)(=O)C=C]

In embodiments, E is:

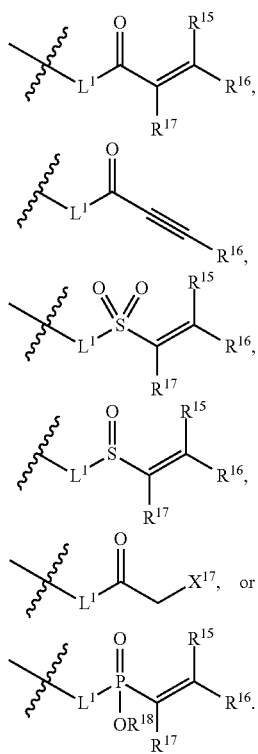

$R^{15}$ is independently hydrogen, halogen, $CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —NHC=(O)NHNR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, —OCX$^{15}_3$, —OCHX$^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{16}$ is independently hydrogen, halogen, $CX^{16}_3$, —$CHX^{16}_2$, —$CH_2X^{16}$, —CN, —$SO_{n16}R^{16D}$, —$SO_{v16}NR^{16A}R^{16B}$, —NHNR$^{16A}$R$^{16B}$, —ONR$^{16A}$R$^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —OR$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}_3$, —OCHX$^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{17}$ is independently hydrogen, halogen, $CX^{17}_3$, —$CHX^{17}_2$, —$CH_2X^{17}$, —CN, —$SO_{n17}R^{17D}$, —$SO_{v17}NR^{17A}R^{17B}$, —NHNR$^{17A}$R$^{17B}$, —ONR$^{17A}$R$^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, —OCX$^{17}_3$, —OCHX$^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{18}$ is independently hydrogen, —$CX^{18}_3$, —$CHX^{18}_2$, —$CH_2X^{18}$, —C(O)R$^{18C}$, —C(O)OR$^{18C}$, —C(O)NR$^{18A}$R$^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

Each $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl. Each X, $X^{15}$, $X^{16}$, $X^{17}$ and $X^{18}$ is independently —F, —Cl, —Br, or —I. The symbols n15, n16, n17, v15, v16, and v17, are independently and integer from 0 to 4. The symbols m15, m16, and m17 are independently and integer between 1 and 2.

$L^1$ is a bond, —O—, —C(O)—, —S—, —SO—, —S(O)$_2$—, —N(R$^{96}$)—, —NR$^{96}$C(O)—, —C(O)NR$^{96}$—, —SO$_2$NR$^{96}$—, —NR$^{96}$SO$_2$—, —OC(O)NR$^{96}$—, —NR$^{96}$C(O)O—, —NR$^{96}$C(O)NR$^{96}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is a bond, —O—, —C(O)—, —S—, —SO—, —S(O)$_2$—, —N(H)—, —NHC(O)—, —C(O)NH—, —SO$_2$NH—, —NHSO$_2$—, —OC(O)NH—, —NHC(O)O—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^1$ is a bond. In embodiments, $L^1$ is —NH—. In embodiments, $L^1$ is —N(CH$_3$)—. In embodiments, $L^1$ is

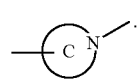

Ring C is a substituted or unsubstituted heterocycloalkylene or substituted or unsubstituted heteroarylene. In embodiments, Ring C is an $R^{19}$-substituted or unsubstituted heterocycloalkylene or $R^{19}$-substituted or unsubstituted heteroarylene. In embodiments, Ring C is an unsubstituted heterocycloalkylene. In embodiments, Ring C is an unsubstituted heteroarylene.

In embodiments, Ring C is substituted heterocycloalkylene. In embodiments, Ring C is substituted heteroarylene. In embodiments, Ring C is an $R^{19}$-substituted heterocycloalkylene. In embodiments, Ring C is an $R^{19}$-substituted heteroarylene. In embodiments, Ring C is an $R^{19}$-substituted 5 to 7 membered heterocycloalkylene. In embodiments, Ring C is an $R^{19}$-substituted 5 to 6 membered heteroarylene. In embodiments, Ring C is an unsubstituted 5 to 7 membered heterocycloalkylene. In embodiments, Ring C is an unsubstituted 5 to 6 membered heteroarylene.

In embodiments, $R^{19}$ is independently hydrogen, oxo, halogen, $-CX^{19}_3$, $-CHX^{19}_2$, $-OCH_2X^{19}$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{19}_3$, $-OCHX^{19}_2$, $R^{90}$-substituted or unsubstituted alkyl, $R^{90}$-substituted or unsubstituted heteroalkyl, $R^{90}$-substituted or unsubstituted cycloalkyl, $R^{90}$-substituted or unsubstituted heterocycloalkyl, $R^{90}$-substituted or unsubstituted aryl, or $R^{90}$-substituted or unsubstituted heteroaryl. $X^{19}$ is halogen. In embodiments, $X^{19}$ is F.

$R^{90}$ is independently oxo, halogen, $-CX^{90}_3$, $-CHX^{90}_2$, $-OCH_2X^{90}$, $-OCHX^{90}_2$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{90}_3$, $-OCHX^{90}_2$, $R^{91}$-substituted or unsubstituted alkyl, $R^{91}$-substituted or unsubstituted heteroalkyl, $R^{91}$-substituted or unsubstituted cycloalkyl, $R^{91}$-substituted or unsubstituted heterocycloalkyl, $R^{91}$-substituted or unsubstituted aryl, or $R^{91}$-substituted or unsubstituted heteroaryl. $X^{90}$ is halogen. In embodiments, $X^{90}$ is F.

$R^{91}$ is independently oxo, halogen, $-CX^{91}_3$, $-CHX^{91}_2$, $-OCH_2X^{91}$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{91}_3$, $-OCHX^{91}_2$, $R^{92}$-substituted or unsubstituted alkyl, $R^{92}$-substituted or unsubstituted heteroalkyl, $R^{92}$-substituted or unsubstituted cycloalkyl, $R^{92}$-substituted or unsubstituted heterocycloalkyl, $R^{92}$-substituted or unsubstituted aryl, or $R^{92}$-substituted or unsubstituted heteroaryl. $X^{91}$ is halogen. In embodiments, $X^{91}$ is F.

In embodiments, E is:

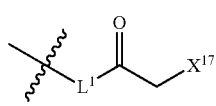

and $X^{17}$ is $-Cl$. In embodiments, E is:

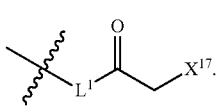

In embodiments, $X^{17}$ is $-Cl$.

In embodiments, E is:

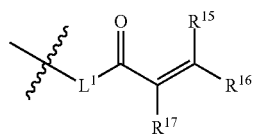

and $R^{15}$, $R^{16}$, and $R^{17}$ are independently hydrogen. In embodiments, E is:

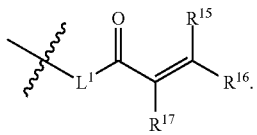

In embodiments, $R^{15}$, $R^{16}$, and $R^{17}$ are independently hydrogen.

In embodiments, E is:

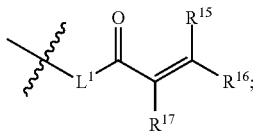

$R^{15}$ is independently hydrogen; $R^{16}$ is independently hydrogen or $-CH_2NR^{16A}R^{16B}$; $R^{17}$ is independently hydrogen; and $R^{16A}$ and $R^{16B}$ are independently hydrogen or unsubstituted alkyl. In embodiments, E is:

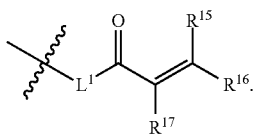

In embodiments, $R^{15}$ is independently hydrogen. In embodiments, $R^{16}$ is independently hydrogen or $-CH_2NR^{16A}R^{16B}$. In embodiments, $R^{17}$ is independently hydrogen. In embodiments, $R^{16A}$ and $R^{16B}$ are independently hydrogen or unsubstituted alkyl. In embodiments, $R^{16A}$ and $R^{16B}$ are independently unsubstituted methyl.

In embodiments, E is:

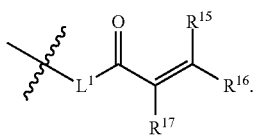

In embodiments, E is:

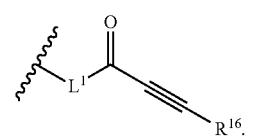

In embodiments, E is:

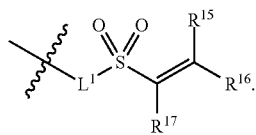

In embodiments, E is:

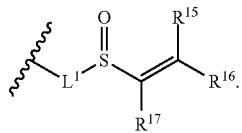

In embodiments, E is:

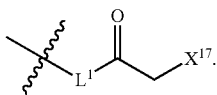

In embodiments, E is:

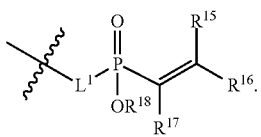

X may independently be —F. X may independently be —Cl. X may independently be —Br. X may independently be —I. $X^{15}$ may independently be —F. $X^{15}$ may independently be —Cl. $X^{15}$ may independently be —Br. $X^{15}$ may independently be —I. $X^{16}$ may independently be —F. $X^{16}$ may independently be —Cl. $X^{16}$ may independently be —Br. $X^{16}$ may independently be —I. $X^{17}$ may independently be —F. $X^{17}$ may independently be —Cl. $X^{17}$ may independently be —Br. $X^{17}$ may independently be —I. $X^{18}$ may independently be —F. $X^{18}$ may independently be —Cl. $X^{18}$ may independently be —Br. $X^{18}$ may independently be —I. n15 may independently be 0. n15 may independently be 1. n15 may independently be 2. n15 may independently be 3. n15 may independently be 4. n16 may independently be 0. n16 may independently be 1. n16 may independently be 2. n16 may independently be 3. n16 may independently be 4. n17 may independently be 0. n17 may independently be 1. n17 may independently be 2. n17 may independently be 3. n17 may independently be 4. v15 may independently be 0. v15 may independently be 1. v15 may independently be 2. v15 may independently be 3. v15 may independently be 4. v16 may independently be 0. v16 may independently be 1. v16 may independently be 2. v16 may independently be 3. v16 may independently be 4. m15 may independently be 1. m15 may independently be 2. m16 may independently be 1. m16 may independently be 2. m17 may independently be 1. m17 may independently be 2.

In embodiments, $R^{15}$ is hydrogen. In embodiments, $R^{15}$ is halogen. In embodiments, $R^{15}$ is $CX^{15}_3$. In embodiments, $R^{15}$ is —$CHX^{15}_2$. In embodiments, $R^{15}$ is —$CH_2X^{15}$. In embodiments, $R^{15}$ is —CN, —$SOR_{n15}R^{15D}$. In embodiments, $R^{15}$ is —$SO_{v15}NR^{15A}R^{15B}$. In embodiments, $R^{15}$ is —$NHNR^{15A}R^{15B}$. In embodiments, $R^{15}$ is —$ONR^{15A}R^{15B}$. In embodiments, $R^{15}$ is —NHC=(O)NHNR$^{15A}R^{15B}$. In embodiments, $R^{15}$ is —NHC(O)NR$^{15A}R^{15B}$. In embodiments, $R^{15}$ is —$N(O)_{m15}$. In embodiments, $R^{15}$ is —$NR^{15A}R^{15B}$. In embodiments, $R^{15}$ is —$C(O)R^{15C}$. In embodiments, $R^{15}$ is —C(O)—$OR^{15C}$. In embodiments, $R^{15}$ is —C(O)NR$^{15A}R^{15B}$. In embodiments, R is —$OR^{15D}$. In embodiments, $R^{15}$ is —$NR^{15A}SO_2R^{15D}$. In embodiments, $R^{15}$ is —$NR^{15A}C(O)R^{15C}$. In embodiments, $R^{15}$ is —$NR^{15A}C(O)OR^{15C}$. In embodiments, $R^{15}$ is —$NR^{15A}OR^{15C}$. In embodiments, $R^{15}$ is —$OCX^{15}_3$. In embodiments, $R^{15}$ is —$OCHX^{15}_2$. In embodiments, $R^{15}$ is substituted or unsubstituted alkyl. In embodiments, $R^{15}$ is substituted or unsubstituted heteroalkyl. In embodiments, $R^{15}$ is substituted or unsubstituted cycloalkyl. In embodiments, $R^{15}$ is substituted or unsubstituted heterocycloalkyl. In embodiments, $R^{15}$ is substituted or unsubstituted aryl. In embodiments, $R^{15}$ is substituted or unsubstituted heteroaryl. In embodiments, $R^{15}$ is substituted alkyl. In embodiments, $R^{15}$ is substituted heteroalkyl. In embodiments, $R^{15}$ is substituted cycloalkyl. In embodiments, $R^{15}$ is substituted heterocycloalkyl. In embodiments, $R^{15}$ is substituted aryl. In embodiments, $R^{15}$ is substituted heteroaryl. In embodiments, $R^{15}$ is unsubstituted alkyl. In embodiments, $R^{15}$ is unsubstituted heteroalkyl. In embodiments, $R^{15}$ is unsubstituted cycloalkyl. In embodiments, $R^{15}$ is unsubstituted heterocycloalkyl. In embodiments, $R^{15}$ is unsubstituted aryl. In embodiments, $R^{15}$ is unsubstituted heteroaryl. In embodiments, $R^{15}$ is unsubstituted methyl. In embodiments, $R^{15}$ is unsubstituted ethyl. In embodiments, $R^{15}$ is unsubstituted propyl. In embodiments, $R^{15}$ is unsubstituted isopropyl. In embodiments, $R^{15}$ is unsubstituted butyl. In embodiments, $R^{15}$ is unsubstituted tert-butyl.

In embodiments, $R^{15A}$ is unsubstituted hydrogen. In embodiments, $R^{15A}$ is —$CX_3$. In embodiments, $R^{15A}$ is —CN. In embodiments, $R^{15A}$ is —COOH. In embodiments, $R^{15A}$ is —$CONH_2$. In embodiments, $R^{15A}$ is —$CHX_2$. In embodiments, $R^{15A}$ is —$CH_2X$. In embodiments, $R^{15A}$ is unsubstituted methyl. In embodiments, $R^{15A}$ is unsubstituted ethyl. In embodiments, $R^{15A}$ is unsubstituted propyl. In embodiments, $R^{15A}$ is unsubstituted isopropyl. In embodiments, $R^{15A}$ is unsubstituted butyl. In embodiments, $R^{15A}$ is unsubstituted tert-butyl.

In embodiments, $R^{15B}$ is unsubstituted hydrogen. In embodiments, $R^{15B}$ is —$CX_3$. In embodiments, $R^{15B}$ is —CN. In embodiments, $R^{15B}$ is —COOH. In embodiments, $R^{15B}$ is —$CONH_2$. In embodiments, $R^{15B}$ is —$CHX_2$. In embodiments, $R^{15B}$ is —$CH_2X$. In embodiments, $R^{15B}$ is unsubstituted methyl. In embodiments, $R^{15B}$ is unsubstituted ethyl. In embodiments, $R^{15B}$ is unsubstituted propyl. In embodiments, $R^{15B}$ is unsubstituted isopropyl. In embodiments, $R^{15B}$ is unsubstituted butyl. In embodiments, $R^{15B}$ is unsubstituted tert-butyl.

In embodiments, $R^{15C}$ is unsubstituted hydrogen. In embodiments, $R^{15C}$ is —$CX_3$. In embodiments, $R^{15C}$ is —CN. In embodiments, $R^{15C}$ is —COOH. In embodiments, $R^{15C}$ is —$CONH_2$. In embodiments, $R^{15C}$ is —$CHX_2$. In embodiments, $R^{15C}$ is —$CH_2X$. In embodiments, $R^{15C}$ is unsubstituted methyl. In embodiments, $R^{15C}$ is unsubstituted ethyl. In embodiments, $R^{15C}$ is unsubstituted propyl. In embodiments, $R^{15C}$ is unsubstituted isopropyl. In embodiments, $R^{15C}$ is unsubstituted butyl. In embodiments, $R^{15C}$ is unsubstituted tert-butyl.

In embodiments, $R^{15D}$ is unsubstituted hydrogen. In embodiments, $R^{15D}$ is —$CX_3$. In embodiments, $R^{15D}$ is —CN. In embodiments, $R^{15D}$ is —COOH. In embodiments, $R^{15D}$ is —CONH$_2$. In embodiments, $R^{15D}$ is —CHX$_2$. In embodiments, $R^{15D}$ is —CH$_2$X. In embodiments, $R^{15D}$ is unsubstituted methyl. In embodiments, $R^{15D}$ is unsubstituted ethyl. In embodiments, $R^{15D}$ is unsubstituted propyl. In embodiments, $R^{15D}$ is unsubstituted isopropyl. In embodiments, $R^{15D}$ is unsubstituted butyl. In embodiments, $R^{15D}$ is unsubstituted tert-butyl.

In embodiments, $R^{16}$ is hydrogen. In embodiments, $R^{16}$ is halogen. In embodiments, $R^{16}$ is CX$^{16}_3$. In embodiments, $R^{16}$ is —CHX$^{16}_2$. In embodiments, $R^{16}$ is —CH$_2$X$^{16}$. In embodiments, $R^{16}$ is —CN, —SO$_{n15}$R$^{16D}$. In embodiments, $R^{16}$ is —SO$_{v15}$NR$^{16A}$R$^{16B}$. In embodiments, $R^{16}$ is —NHNR$^{16A}$R$^{16B}$. In embodiments, $R^{16}$ is —ONR$^{16A}$R$^{16B}$. In embodiments, $R^{16}$ is —NHC=(O)NHNR$^{16A}$R$^{16B}$. In embodiments, $R^{16}$ is —NHC(O)NR$^{16A}$R$^{16B}$. In embodiments, $R^{16}$ is —N(O)$_{m15}$. In embodiments, $R^{16}$ is —NR$^{16A}$R$^{16B}$. In embodiments, $R^{16}$ is —C(O)R$^{16C}$. In embodiments, $R^{16}$ is —C(O)—OR$^{16C}$. In embodiments, $R^{16}$ is —C(O)NR$^{16A}$R$^{16B}$. In embodiments, $R^{16}$ is —OR$^{16D}$. In embodiments, $R^{16}$ is —NR$^{16A}$SO$_2$R$^{16D}$. In embodiments, $R^{16}$ is —NR$^{16A}$C(O)R$^{16C}$. In embodiments, $R^{16}$ is —NR$^{16A}$C(O)OR$^{16C}$. In embodiments, $R^{16}$ is —NR$^{16A}$OR$^{16C}$. In embodiments, $R^{16}$ is —OCX$^{16}_3$. In embodiments, $R^{16}$ is —OCHX$^{16}_2$. In embodiments, $R^{16}$ is substituted or unsubstituted alkyl. In embodiments, $R^{16}$ is substituted or unsubstituted heteroalkyl. In embodiments, $R^{16}$ is substituted or unsubstituted cycloalkyl. In embodiments, $R^{16}$ is substituted or unsubstituted heterocycloalkyl. In embodiments, $R^{16}$ is substituted or unsubstituted aryl. In embodiments, $R^{16}$ is substituted or unsubstituted heteroaryl. In embodiments, $R^{16}$ is substituted alkyl. In embodiments, $R^{16}$ is substituted heteroalkyl. In embodiments, $R^{16}$ is substituted cycloalkyl. In embodiments, $R^{16}$ is substituted heterocycloalkyl. In embodiments, $R^{16}$ is substituted aryl. In embodiments, $R^{16}$ is substituted heteroaryl. In embodiments, $R^{16}$ is unsubstituted alkyl. In embodiments, $R^{16}$ is unsubstituted heteroalkyl. In embodiments, $R^{16}$ is unsubstituted cycloalkyl. In embodiments, $R^{16}$ is unsubstituted heterocycloalkyl. In embodiments, $R^{16}$ is unsubstituted aryl. In embodiments, $R^{16}$ is unsubstituted heteroaryl. In embodiments, $R^{16}$ is unsubstituted methyl. In embodiments, $R^{16}$ is unsubstituted ethyl. In embodiments, $R^{16}$ is unsubstituted propyl. In embodiments, $R^{16}$ is unsubstituted isopropyl. In embodiments, $R^{16}$ is unsubstituted butyl. In embodiments, $R^{16}$ is unsubstituted tert-butyl.

In embodiments, $R^{16A}$ is unsubstituted hydrogen. In embodiments, $R^{16A}$ is —CX$_3$. In embodiments, $R^{16A}$ is —CN. In embodiments, $R^{16A}$ is —COOH. In embodiments, $R^{16A}$ is —CONH$_2$. In embodiments, $R^{16A}$ is —CHX$_2$. In embodiments, $R^{16A}$ is —CH$_2$X. In embodiments, $R^{16A}$ is unsubstituted methyl. In embodiments, $R^{16A}$ is unsubstituted ethyl. In embodiments, $R^{16A}$ is unsubstituted propyl. In embodiments, $R^{16A}$ is unsubstituted isopropyl. In embodiments, $R^{16A}$ is unsubstituted butyl. In embodiments, $R^{16A}$ is unsubstituted tert-butyl.

In embodiments, $R^{16B}$ is unsubstituted hydrogen. In embodiments, $R^{16B}$ is —CX$_3$. In embodiments, $R^{16B}$ is —CN. In embodiments, $R^{16B}$ is —COOH. In embodiments, $R^{16B}$ is —CONH$_2$. In embodiments, $R^{16B}$ is —CHX$_2$. In embodiments, $R^{16B}$ is —CH$_2$X. In embodiments, $R^{16B}$ is unsubstituted methyl. In embodiments, $R^{16B}$ is unsubstituted ethyl. In embodiments, $R^{16B}$ is unsubstituted propyl. In embodiments, $R^{16B}$ is unsubstituted isopropyl. In embodiments, $R^{16B}$ is unsubstituted butyl. In embodiments, $R^{16B}$ is unsubstituted tert-butyl.

In embodiments, $R^{16C}$ is unsubstituted hydrogen. In embodiments, $R^{16C}$ is —CX$_3$. In embodiments, $R^{16C}$ is —CN. In embodiments, $R^{16C}$ is —COOH. In embodiments, $R^{16C}$ is —CONH$_2$. In embodiments, $R^{16C}$ is —CHX$_2$. In embodiments, $R^{16C}$ is —CH$_2$X. In embodiments, $R^{16C}$ is unsubstituted methyl. In embodiments, $R^{16C}$ is unsubstituted ethyl. In embodiments, $R^{16C}$ is unsubstituted propyl. In embodiments, $R^{16C}$ is unsubstituted isopropyl. In embodiments, $R^{16C}$ is unsubstituted butyl. In embodiments, $R^{16C}$ is unsubstituted tert-butyl.

In embodiments, $R^{16D}$ is unsubstituted hydrogen. In embodiments, $R^{16D}$ is —CX$_3$. In embodiments, $R^{16D}$ is —CN. In embodiments, $R^{16D}$ is —COOH. In embodiments, $R^{16D}$ is —CONH$_2$. In embodiments, $R^{16D}$ is —CHX$_2$. In embodiments, $R^{16D}$ is —CH$_2$X. In embodiments, $R^{16D}$ is unsubstituted methyl. In embodiments, $R^{16D}$ is unsubstituted ethyl. In embodiments, $R^{16D}$ is unsubstituted propyl. In embodiments, $R^{16D}$ is unsubstituted isopropyl. In embodiments, $R^{16D}$ is unsubstituted butyl. In embodiments, $R^{16D}$ is unsubstituted tert-butyl.

In embodiments, $R^{17}$ is hydrogen. In embodiments, $R^{17}$ is halogen. In embodiments, $R^{17}$ is CX$^{17}_3$. In embodiments, $R^{17}$ is —CHX$^{17}_2$. In embodiments, $R^{17}$ is —CH$_2$X$^{17}$. In embodiments, $R^{17}$ is —CN, —SO$_{n15}$R$^{17D}$. In embodiments, $R^{17}$ is —SO$_{v15}$NR$^{17A}$R$^{17B}$. In embodiments, $R^{17}$ is —NHNR$^{17A}$R$^{17B}$. In embodiments, $R^{17}$ is —ONR$^{17A}$R$^{17B}$. In embodiments, $R^{17}$ is —NHC=(O)NHNR$^{17A}$R$^{17B}$. In embodiments, $R^{17}$ is —NHC(O)NR$^{17A}$R$^{17B}$. In embodiments, $R^{17}$ is —N(O)$_{m15}$. In embodiments, $R^{17}$ is —NR$^{17A}$R$^{17B}$. In embodiments, $R^{17}$ is —C(O)R$^{17C}$. In embodiments, $R^{17}$ is —C(O)—OR$^{17C}$. In embodiments, $R^{17}$ is —C(O)NR$^{17A}$R$^{17B}$. In embodiments, $R^{17}$ is —OR$^{17D}$. In embodiments, $R^{17}$ is —NR$^{17A}$SO$_2$R$^{17D}$. In embodiments, $R^{17}$ is —NR$^{17A}$C(O)R$^{17C}$. In embodiments, $R^{17}$ is —NR$^{17A}$C(O)OR$^{17C}$. In embodiments, $R^{17}$ is —NR$^{17A}$OR$^{17C}$. In embodiments, $R^{17}$ is —OCX$^{17}_3$. In embodiments, $R^{17}$ is —OCHX$^{17}_2$. In embodiments, $R^{17}$ is substituted or unsubstituted alkyl. In embodiments, $R^{17}$ is substituted or unsubstituted heteroalkyl. In embodiments, $R^{17}$ is substituted or unsubstituted cycloalkyl. In embodiments, $R^{17}$ is substituted or unsubstituted heterocycloalkyl. In embodiments, $R^{17}$ is substituted or unsubstituted aryl. In embodiments, $R^{17}$ is substituted or unsubstituted heteroaryl. In embodiments, $R^{17}$ is substituted alkyl. In embodiments, $R^{17}$ is substituted heteroalkyl. In embodiments, $R^{17}$ is substituted cycloalkyl. In embodiments, $R^{17}$ is substituted heterocycloalkyl. In embodiments, $R^{17}$ is substituted aryl. In embodiments, $R^{17}$ is substituted heteroaryl. In embodiments, $R^{17}$ is unsubstituted alkyl. In embodiments, $R^{17}$ is unsubstituted heteroalkyl. In embodiments, $R^{17}$ is unsubstituted cycloalkyl. In embodiments, $R^{17}$ is unsubstituted heterocycloalkyl. In embodiments, $R^{17}$ is unsubstituted aryl. In embodiments, $R^{17}$ is unsubstituted heteroaryl. In embodiments, $R^{17}$ is unsubstituted methyl. In embodiments, $R^{17}$ is unsubstituted ethyl. In embodiments, $R^{17}$ is unsubstituted propyl. In embodiments, $R^{17}$ is unsubstituted isopropyl. In embodiments, $R^{17}$ is unsubstituted butyl. In embodiments, $R^{17}$ is unsubstituted tert-butyl.

In embodiments, $R^{17A}$ is unsubstituted hydrogen. In embodiments, $R^{17A}$ is —CX$_3$. In embodiments, $R^{17A}$ is —CN. In embodiments, $R^{17A}$ is —COOH. In embodiments, $R^{17A}$ is —CONH$_2$. In embodiments, $R^{17A}$ is —CHX$_2$. In embodiments, $R^{17A}$ is —CH$_2$X. In embodiments, $R^{17A}$ is unsubstituted methyl. In embodiments, $R^{17A}$ is unsubstituted ethyl. In embodiments, $R^{17A}$ is unsubstituted propyl. In embodiments, $R^{17A}$ is unsubstituted isopropyl. In embodiments, $R^{17A}$ is unsubstituted butyl. In embodiments, $R^{17A}$ is unsubstituted tert-butyl.

In embodiments, $R^{17B}$ is unsubstituted hydrogen. In embodiments, $R^{17B}$ is —$CX_3$. In embodiments, $R^{17B}$ is —CN. In embodiments, $R^{17B}$ is —COOH. In embodiments, $R^{17B}$ is —$CONH_2$. In embodiments, $R^{17B}$ is —$CHX_2$. In embodiments, $R^{17B}$ is —$CH_2X$. In embodiments, $R^{17B}$ is unsubstituted methyl. In embodiments, $R^{17B}$ is unsubstituted ethyl. In embodiments, $R^{17B}$ is unsubstituted propyl. In embodiments, $R^{17B}$ is unsubstituted isopropyl. In embodiments, $R^{17B}$ is unsubstituted butyl. In embodiments, $R^{17B}$ is unsubstituted tert-butyl.

In embodiments, $R^{17C}$ is unsubstituted hydrogen. In embodiments, $R^{17C}$ is —$CX_3$. In embodiments, $R^{17C}$ is —CN. In embodiments, $R^{17C}$ is —COOH. In embodiments, $R^{17C}$ is —$CONH_2$. In embodiments, $R^{17C}$ is —$CHX_2$. In embodiments, $R^{17C}$ is —$CH_2X$. In embodiments, $R^{17C}$ is unsubstituted methyl. In embodiments, $R^{17C}$ is unsubstituted ethyl. In embodiments, $R^{17C}$ is unsubstituted propyl. In embodiments, $R^{17C}$ is unsubstituted isopropyl. In embodiments, $R^{17C}$ is unsubstituted butyl. In embodiments, $R^{17C}$ is unsubstituted tert-butyl.

In embodiments, $R^{17D}$ is unsubstituted hydrogen. In embodiments, $R^{17D}$ is —$CX_3$. In embodiments, $R^{17D}$ is —CN. In embodiments, $R^{17D}$ is —COOH. In embodiments, $R^{17D}$ is —$CONH_2$. In embodiments, $R^{17D}$ is —$CHX_2$. In embodiments, $R^{17D}$ is —$CH_2X$. In embodiments, $R^{17D}$ is unsubstituted methyl. In embodiments, $R^{17D}$ is unsubstituted ethyl. In embodiments, $R^{17D}$ is unsubstituted propyl. In embodiments, $R^{17D}$ is unsubstituted isopropyl. In embodiments, $R^{17D}$ is unsubstituted butyl. In embodiments, $R^{17D}$ is unsubstituted tert-butyl.

In embodiments, $R^{18}$ is hydrogen. In embodiments, $R^{18}$ is halogen. In embodiments, $R^{18}$ is $CX^{18}_3$. In embodiments, $R^{18}$ is —$CHX^{18}_2$. In embodiments, $R^{18}$ is —$CH_2X^{18}$. In embodiments, $R^{18}$ is —CN, —$SO_{n15}R^{18D}$. In embodiments, $R^{18}$ is —$SO_{v15}NR^{18A}R^{18B}$. In embodiments, $R^{18}$ is —$NHNR^{18A}R^{18B}$. In embodiments, $R^{18}$ is —$ONR^{18A}R^{18B}$. In embodiments, $R^{18}$ is —NHC=(O)$NHNR^{18A}R^{18B}$. In embodiments, $R^{18}$ is —$NHC(O)NR^{18A}R^{18B}$. In embodiments, $R^{18}$ is —$N(O)_{m15}$. In embodiments, $R^{18}$ is —$NR^{18A}R^{18B}$. In embodiments, $R^{18}$ is —$C(O)R^{18C}$. In embodiments, $R^{18}$ is —C(O)—$OR^{18C}$. In embodiments, $R^{18}$ is —$C(O)NR^{18A}R^{18B}$. In embodiments, $R^{18}$ is —$OR^{18D}$. In embodiments, $R^{18}$ is —$NR^{18A}SO_2R^{18D}$. In embodiments, $R^{18}$ is —$NR^{18A}C(O)R^{18C}$. In embodiments, $R^{18}$ is —$NR^{18A}C(O)OR^{18C}$. In embodiments, $R^{18}$ is —$NR^{18A}OR^{18C}$. In embodiments, $R^{18}$ is —$OCX^{18}_3$. In embodiments, $R^{18}$ is —$OCHX^{18}_2$. In embodiments, $R^{18}$ is substituted or unsubstituted alkyl. In embodiments, $R^{18}$ is substituted or unsubstituted heteroalkyl. In embodiments, $R^{18}$ is substituted or unsubstituted cycloalkyl. In embodiments, $R^{18}$ is substituted or unsubstituted heterocycloalkyl. In embodiments, $R^{18}$ is substituted or unsubstituted aryl. In embodiments, $R^{18}$ is substituted or unsubstituted heteroaryl. In embodiments, $R^{18}$ is substituted alkyl. In embodiments, $R^{18}$ is substituted heteroalkyl. In embodiments, $R^{18}$ is substituted cycloalkyl. In embodiments, $R^{18}$ is substituted heterocycloalkyl. In embodiments, $R^{18}$ is substituted aryl. In embodiments, $R^{18}$ is substituted heteroaryl. In embodiments, $R^{18}$ is unsubstituted alkyl. In embodiments, $R^{18}$ is unsubstituted heteroalkyl. In embodiments, $R^{18}$ is unsubstituted cycloalkyl. In embodiments, $R^{18}$ is unsubstituted heterocycloalkyl. In embodiments, $R^{18}$ is unsubstituted aryl. In embodiments, $R^{18}$ is unsubstituted heteroaryl. In embodiments, $R^{18}$ is unsubstituted methyl. In embodiments, $R^{18}$ is unsubstituted ethyl. In embodiments, $R^{18}$ is unsubstituted propyl. In embodiments, $R^{18}$ is unsubstituted isopropyl. In embodiments, $R^{18}$ is unsubstituted butyl. In embodiments, $R^{18}$ is unsubstituted tert-butyl.

In embodiments, $R^{18A}$ is unsubstituted hydrogen. In embodiments, $R^{18A}$ is —$CX_3$. In embodiments, $R^{18A}$ is —CN. In embodiments, $R^{18A}$ is —COOH. In embodiments, $R^{18A}$ is —$CONH_2$. In embodiments, $R^{18A}$ is —$CHX_2$. In embodiments, $R^{18A}$ is —$CH_2X$. In embodiments, $R^{18A}$ is unsubstituted methyl. In embodiments, $R^{18A}$ is unsubstituted ethyl. In embodiments, $R^{18A}$ is unsubstituted propyl. In embodiments, $R^{18A}$ is unsubstituted isopropyl. In embodiments, $R^{18A}$ is unsubstituted butyl. In embodiments, $R^{18A}$ is unsubstituted tert-butyl.

In embodiments, $R^{18B}$ is unsubstituted hydrogen. In embodiments, $R^{18B}$ is —$CX_3$. In embodiments, $R^{18B}$ is —CN. In embodiments, $R^{18B}$ is —COOH. In embodiments, $R^{18B}$ is —$CONH_2$. In embodiments, $R^{18B}$ is —$CHX_2$. In embodiments, $R^{18B}$ is —$CH_2X$. In embodiments, $R^{18B}$ is unsubstituted methyl. In embodiments, $R^{18B}$ is unsubstituted ethyl. In embodiments, $R^{18B}$ is unsubstituted propyl. In embodiments, $R^{18B}$ is unsubstituted isopropyl. In embodiments, $R^{18B}$ is unsubstituted butyl. In embodiments, $R^{18B}$ is unsubstituted tert-butyl.

In embodiments, $R^{18C}$ is unsubstituted hydrogen. In embodiments, $R^{18C}$ is —$CX_3$. In embodiments, $R^{18C}$ is —CN. In embodiments, $R^{18C}$ is —COOH. In embodiments, $R^{18C}$ is —$CONH_2$. In embodiments, $R^{18C}$ is —$CHX_2$. In embodiments, $R^{18C}$ is —$CH_2X$. In embodiments, $R^{18C}$ is unsubstituted methyl. In embodiments, $R^{18C}$ is unsubstituted ethyl. In embodiments, $R^{18C}$ is unsubstituted propyl. In embodiments, $R^{18C}$ is unsubstituted isopropyl. In embodiments, $R^{18C}$ is unsubstituted butyl. In embodiments, $R^{18C}$ is unsubstituted tert-butyl.

In embodiments, $R^{18D}$ is unsubstituted hydrogen. In embodiments, $R^{18D}$ is —$CX_3$. In embodiments, $R^{18D}$ is —CN. In embodiments, $R^{18D}$ is —COOH. In embodiments, $R^{18D}$ is —$CONH_2$. In embodiments, $R^{18D}$ is —$CHX_2$. In embodiments, $R^{18D}$ is —$CH_2X$. In embodiments, $R^{18D}$ is unsubstituted methyl. In embodiments, $R^{18D}$ is unsubstituted ethyl. In embodiments, $R^{18D}$ is unsubstituted propyl. In embodiments, $R^{18D}$ is unsubstituted isopropyl. In embodiments, $R^{18D}$ is unsubstituted butyl. In embodiments, $R^{18D}$ is unsubstituted tert-butyl.

Ring B may be phenyl. Ring B may be heteroaryl. Ring B may be a 6 membered heteroaryl. Ring B may be pyridinyl. Ring B may be pyrazinyl. Ring B may be pyrimidinyl. Ring B may be pyridazinyl. Ring B may be triazinyl. Ring B may be 1,2,3-triazinyl. Ring B may be 1, 2, 4, triazinyl. Ring B may be 1,3,5-triazinyl.

Ring B may be a 5 membered heteroaryl. In embodiments, Ring B is a pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl.

In embodiments, $R^2$ is independently a halogen, —$CX^b_3$, —CN, —$SO_2Cl$, —$SO_{n2}R^{14}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —$C(O)R^{13}$, —C(O)—$OR^{13}$, —$C(O)NR^{11}R^{12}$, —$OR^{14}$, —$NR^{11}SO_2R^{14}$, —NR$^{11}$C=(O)R$^{13}$, —NR$^{11}$C(O)—OR$^{13}$, —NR$^{11}$OR$^{13}$, —OCX$^b_3$, —OCHX$^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, R$^2$ is independently a halogen, —CX$^b_3$, —C(O)NHCH$_3$, substituted or unsubstituted C$_1$-C$_5$ alkyl, substituted or unsubstituted 2 to 5 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. Each R$^2$ may independently be —Cl, —F, —Br, —I, —CX$^b_3$, —C(O)NHCH$_3$, —CN, —NHNH$_2$, —ONH$_2$, —NHC=(O)NHNH$_2$, —NHC=(O)NH$_2$, —NO$_2$, —NH$_2$, —C(O)H, —C(O)CH$_3$, —C(O)—OH, —C(O)—OCH$_3$, —C(O)NH$_2$, —OH, —NHC=(O)H, —NHC=(O)CH$_3$, —NHC(O)—OH, —NHC(O)OCH$_3$, —NHOH, —NHOCH$_3$. —OCX$^b_3$, —OCHX$^b_2$, substituted or unsubstituted C$_1$-C$_5$ alkyl, substituted or unsubstituted 2 to 5 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

Each R$^2$ may independently be a —C(O)NHCH$_3$, —Cl, —F, —Br, —I, —CX$^b_3$, —NO$_2$, —OCX$^b_3$, or —OCHX$^b_2$. Each R$^2$ may independently be —C(O)NHCH$_3$. Each R$^2$ may independently be —Cl. Each R$^2$ may independently be —F. Each R$^2$ may independently be —Br. Each R$^2$ may independently be —I. Each R$^2$ may independently be —CX$^b_3$. Each R$^2$ may independently be —CN. Each R$^2$ may independently be —NHNH$_2$. Each R$^2$ may independently be —ONH$_2$. Each R$^2$ may independently be —NHC=(O)NHNH$_2$. Each R$^2$ may independently be —NHC=(O)NH$_2$. Each R$^2$ may independently be —NO$_2$. Each R$^2$ may independently be —NH$_2$. Each R$^2$ may independently be —C(O)H. Each R$^2$ may independently be —C(O)CH$_3$. Each R$^2$ may independently be —C(O)OH. Each R$^2$ may independently be —C(O)OCH$_3$. Each R$^2$ may independently be —C(O)NH$_2$. Each R$^2$ may independently be —OH. Each R$^2$ may independently be —NHC=(O)H. Each R$^2$ may independently be —NHC=(O)CH$_3$. Each R$^2$ may independently be —NHC(O)OH. Each R$^2$ may independently be —NHC(O)OCH$_3$. Each R$^2$ may independently be —NHOH. Each R$^2$ may independently be —NHOCH$_3$. Each R$^2$ may independently be —OCX$^b_3$. Each R$^2$ may independently be —OCHX$^b_2$. Each R$^2$ may independently be substituted or unsubstituted C$_1$-C$_5$ alkyl, substituted or unsubstituted 2 to 5 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. Each R$^2$ may independently be unsubstituted C$_1$-C$_5$ alkyl, unsubstituted 2 to 5 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. Each R$^2$ may independently be substituted C$_1$-C$_5$ alkyl. Each R$^2$ may independently be unsubstituted C$_1$-C$_5$ alkyl. Each R$^2$ may independently be substituted 2 to 5 membered heteroalkyl. Each R$^2$ may independently be unsubstituted 2 to 5 membered heteroalkyl. Each R$^2$ may independently be substituted C$_3$-C$_6$ cycloalkyl. Each R$^2$ may independently be unsubstituted C$_3$-C$_6$ cycloalkyl. Each R$^2$ may independently be substituted 3 to 6 membered heterocycloalkyl. Each R$^2$ may independently be unsubstituted 3 to 6 membered heterocycloalkyl. Each R$^2$ may independently be substituted phenyl. Each R$^2$ may independently be unsubstituted phenyl. Each R$^2$ may independently be substituted 5 to 6 membered heteroaryl. Each R$^2$ may independently be unsubstituted 5 to 6 membered heteroaryl.

In embodiments, two adjacent R$^2$ substituents may be joined to form a substituted or unsubstituted cycloalkyl, substituted or unsubstituted heterocycloalkyl, substituted or unsubstituted aryl, or substituted or unsubstituted heteroaryl. In embodiments, two adjacent R$^2$ substituents may be joined to form a substituted or unsubstituted C$_3$-C$_6$ cycloalkyl, substituted or unsubstituted 4 to 6 membered heterocycloalkyl, substituted or unsubstituted phenyl, or substituted or unsubstituted 5 to 6 membered heteroaryl. Two adjacent R$^2$ substituents may be joined to form a substituted or unsubstituted C$_3$-C$_6$ cycloalkyl. Two adjacent R$^2$ substituents may be joined to form a substituted or unsubstituted 4 to 6 membered heterocycloalkyl. Two adjacent R$^2$ substituents may be joined to form a substituted or unsubstituted phenyl. Two adjacent R$^2$ substituents may be joined to form a substituted or unsubstituted 5 to 6 membered heteroaryl. Two adjacent R$^2$ substituents may be joined to form an unsubstituted C$_3$-C$_6$ cycloalkyl. Two adjacent R$^2$ substituents may be joined to form an unsubstituted 4 to 6 membered heterocycloalkyl. Two adjacent R$^2$ substituents may be joined to form an unsubstituted phenyl. Two adjacent R$^2$ substituents may be joined to form an unsubstituted 5 to 6 membered heteroaryl.

In embodiments, R$^2$ is independently —C(O)NR$^{11}$R$^{12}$, halogen, substituted or unsubstituted alkyl, or substituted or unsubstituted heteroalkyl. In embodiments, R$^2$ is independently —C(O)NR$^{11}$R$^{12}$, halogen, substituted or unsubstituted C$_1$-C$_8$ alkyl, or substituted or unsubstituted 2 to 8 membered heteroalkyl. In embodiments, R$^2$ is independently —C(O)NR$^{11}$R$^{12}$ halogen, substituted or unsubstituted C$_1$-C$_5$ alkyl, or substituted or unsubstituted 2 to 5 membered heteroalkyl. In embodiments, R$^2$ is independently —C(O)NHR$^{11}$, halogen, substituted or unsubstituted C$_1$-C$_5$ alkyl, or substituted or unsubstituted 2 to 5 membered heteroalkyl. In embodiments, R$^2$ is independently —C(O)NHR$^{11}$, halogen, unsubstituted C$_1$-C$_5$ alkyl, or unsubstituted 2 to 5 membered heteroalkyl. In embodiments, R$^2$ is independently —C(O)NHR$^{11}$, halogen, substituted C$_1$-C$_5$ alkyl, or substituted 2 to 5 membered heteroalkyl. In embodiments, R$^2$ is independently —C(O)NHR$^{11}$. In embodiments, R$^2$ is independently halogen. In embodiments, R$^2$ is independently substituted or unsubstituted C$_1$-C$_5$ alkyl. In embodiments, R$^2$ is independently substituted or unsubstituted 2 to 5 membered heteroalkyl.

In embodiments, R$^2$ is independently —C(O)NHR$^{11}$. In embodiments, R$^{11}$ is independently substituted or unsubstituted alkyl, substituted or unsubstituted heteroalkyl, substituted or unsubstituted cycloalkyl, or substituted or unsubstituted heterocycloalkyl. In embodiments, R$^{11}$ is independently substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl. In embodiments, R$^{11}$ is independently substituted or unsubstituted C$_1$-C$_5$ alkyl, substituted or unsubstituted 2 to 5 membered heteroalkyl, substituted or unsubstituted C$_3$-C$_5$ cycloalkyl, substituted or unsubstituted 3 to 5 membered heterocycloalkyl. In embodiments, R$^{11}$ is independently substituted or unsubstituted C$_1$-C$_5$ alkyl or substituted or unsubstituted 2 to 5 membered heteroalkyl. In embodiments, R$^{11}$ is independently substituted or unsubstituted $C_1$-$C_5$ alkyl. In embodiments, $R^{11}$ is independently substituted or unsubstituted $C_1$-$C_4$ alkyl. In embodiments, $R^{11}$ is independently substituted or unsubstituted $C_1$-$C_3$ alkyl. In embodiments, $R^{11}$ is independently unsubstituted $C_1$-$C_5$ alkyl, unsubstituted 2 to 5 membered heteroalkyl, unsubstituted $C_3$-$C_5$ cycloalkyl, or unsubstituted 3 to 5 membered heterocycloalkyl. In embodiments, $R^{11}$ is independently unsubstituted $C_1$-$C_5$ alkyl or unsubstituted 2 to 5 membered heteroalkyl. In embodiments, $R^{11}$ is independently unsubstituted $C_1$-$C_5$ alkyl. In embodiments, $R^{11}$ is independently unsubstituted $C_1$-$C_4$ alkyl. In embodiments, $R^{11}$ is independently unsubstituted $C_1$-$C_3$ alkyl. In embodiments, $R^{11}$ is independently substituted $C_1$-$C_5$ alkyl, substituted 2 to 5 membered heteroalkyl, substituted $C_3$-$C_5$ cycloalkyl, or substituted 3 to 5 membered heterocycloalkyl. In embodiments, $R^{11}$ is independently substituted $C_1$-$C_5$ alkyl or substituted 2 to 5 membered heteroalkyl. In embodiments, $R^{11}$ is independently substituted $C_1$-$C_5$ alkyl. In embodiments, $R^{11}$ is independently substituted $C_1$-$C_4$ alkyl. In embodiments, $R^{11}$ is independently substituted $C_1$-$C_3$ alkyl.

In embodiments, the compound is

[Chemical structure diagram]

wherein $R^1$, Ring A, and a1 are as described herein, including in embodiments. In embodiments, the compound is

[Chemical structure diagram]

wherein $R^1$, Ring A, and a1 are as described herein, including in embodiments. $R^{2.1}$ and $R^{2.2}$ are each an independent $R^2$. In embodiments, $R^{2.1}$ is as described herein for $R^2$ including embodiments. In embodiments, $R^{2.2}$ is as described herein for $R^2$ including embodiments.

In embodiments, $R^{2.1}$ is independently —C(O)NR$^{11}$R$^{12}$, halogen, substituted or unsubstituted alkyl, or substituted or unsubstituted heteroalkyl. In embodiments, $R^{2.1}$ is independently —C(O)NR$^{11}$R$^{12}$, halogen, substituted or unsubstituted $C_1$-$C_8$ alkyl, or substituted or unsubstituted 2 to 8 membered heteroalkyl. In embodiments, $R^{2.1}$ is independently —C(O)NR$^{11}$R$^{12}$, halogen, substituted or unsubstituted $C_1$-$C_5$ alkyl, or substituted or unsubstituted 2 to 5 membered heteroalkyl. In embodiments, $R^{2.1}$ is independently —C(O)NHR$^{11}$, halogen, substituted or unsubstituted $C_1$-$C_5$ alkyl, or substituted or unsubstituted 2 to 5 membered heteroalkyl. In embodiments, $R^{2.1}$ is independently —C(O)NHR$^{11}$, halogen, unsubstituted $C_1$-$C_5$ alkyl, or unsubstituted 2 to 5 membered heteroalkyl. In embodiments, $R^{2.1}$ is independently —C(O)NHR$^{11}$, halogen, substituted $C_1$-$C_5$ alkyl, or substituted 2 to 5 membered heteroalkyl. In embodiments, $R^{2.1}$ is independently —C(O)NHR$^{11}$. In embodiments, $R^2$ is independently halogen. In embodiments, $R^{2.1}$ is independently substituted or unsubstituted $C_1$-$C_5$ alkyl. In embodiments, $R^{2.1}$ is independently substituted or unsubstituted 2 to 5 membered heteroalkyl. In embodiments, $R^{2.1}$ is independently hydrogen. In embodiments, $R^{2.1}$ is independently —F. In embodiments, $R^{2.1}$ is independently —Cl. In embodiments, $R^{2.1}$ is independently —Br. In embodiments, $R^{2.1}$ is independently —I.

In embodiments, $R^{2.2}$ is independently —C(O)NR$^{11}$R$^{12}$, halogen, substituted or unsubstituted alkyl, or substituted or unsubstituted heteroalkyl. In embodiments, $R^{2.2}$ is independently —C(O)NR$^{11}$R$^{12}$, halogen, substituted or unsubstituted $C_1$-$C_8$ alkyl, or substituted or unsubstituted 2 to 8 membered heteroalkyl. In embodiments, $R^{2.2}$ is independently —C(O)NR$^{11}$R$^{12}$, halogen, substituted or unsubstituted $C_1$-$C_5$ alkyl, or substituted or unsubstituted 2 to 5 membered heteroalkyl. In embodiments, $R^{2.2}$ is independently —C(O)NHR$^{11}$, halogen, substituted or unsubstituted $C_1$-$C_5$ alkyl, or substituted or unsubstituted 2 to 5 membered heteroalkyl. In embodiments, $R^{2.2}$ is independently —C(O)NHR$^{11}$, halogen, unsubstituted $C_1$-$C_5$ alkyl, or unsubstituted 2 to 5 membered heteroalkyl. In embodiments, $R^{2.2}$ is independently —C(O)NHR$^{11}$, halogen, substituted $C_1$-$C_5$ alkyl, or substituted 2 to 5 membered heteroalkyl. In embodiments, $R^{2.2}$ is independently —C(O)NHR$^{11}$. In embodiments, $R^2$ is independently halogen. In embodiments, $R^{2.2}$ is independently substituted or unsubstituted $C_1$-$C_5$ alkyl. In embodiments, $R^{2.2}$ is independently substituted or unsubstituted 2 to 5 membered heteroalkyl. In embodiments, $R^{2.2}$ is independently hydrogen. In embodiments, $R^{2.2}$ is independently —F. In embodiments, $R^{2.2}$ is independently —Cl. In embodiments, $R^{2.2}$ is independently —Br. In embodiments, $R^{2.2}$ is independently —I.

In embodiments, $R^{21}$ is independently —C(O)NHR$^{11}$. In embodiments, $R^{2.2}$ is independently —C(O)NHR$^{11}$. In embodiments, $R^{11}$ is independently substituted or unsubstituted alkyl, substituted or unsubstituted heteroalkyl, substituted or unsubstituted cycloalkyl, or substituted or unsubstituted heterocycloalkyl. In embodiments, $R^{11}$ is independently substituted or unsubstituted $C_3$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl. In embodiments, $R^{11}$ is independently substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 3 to 5 membered heterocycloalkyl. In embodiments, $R^{11}$ is independently substituted or unsubstituted $C_1$-$C_5$ alkyl or substituted or unsubstituted 2 to 5 membered heteroalkyl. In embodiments, $R^{11}$ is independently substituted or unsubstituted $C_1$-$C_5$ alkyl. In embodiments, $R^{11}$ is independently substituted or unsubstituted $C_1$-$C_4$ alkyl. In embodiments, $R^{11}$ is independently substituted or unsubstituted $C_1$-$C_3$ alkyl. In embodiments, $R^{11}$ is independently unsubstituted $C_1$-$C_5$ alkyl, unsubstituted 2 to 5 membered heteroalkyl, unsubstituted $C_3$-$C_5$ cycloalkyl, or unsubstituted 3 to 5 membered heterocycloalkyl. In embodiments, $R^{11}$ is independently unsubstituted $C_1$-$C_5$ alkyl or unsubstituted 2 to 5 membered heteroalkyl. In embodiments, $R^{11}$ is independently unsubstituted $C_1$-$C_5$ alkyl. In embodiments, $R^{11}$ is independently unsubstituted $C_1$-$C_4$ alkyl. In embodiments, $R^{11}$ is independently unsubstituted $C_1$-$C_3$ alkyl. In embodiments, $R^{11}$ is independently substituted $C_1$-$C_5$ alkyl, substituted 2 to 5 membered heteroalkyl, substituted $C_3$-$C_5$ cycloalkyl, or substituted 3 to 5 membered heterocycloalkyl. In embodiments, $R^{11}$ is independently substituted $C_1$-$C_5$ alkyl or substituted 2 to 5 membered heteroalkyl. In embodiments, $R^{11}$ is independently substituted $C_1$-$C_5$ alkyl. In embodiments, $R^{11}$ is independently substituted $C_1$-$C_4$ alkyl. In embodiments, $R^{11}$ is independently substituted $C_1$-$C_3$ alkyl.

In embodiments, $R^{2.1}$ is independently hydrogen and $R^{2.2}$ is independently —C(O)NHR$^{11}$ and $R^{11}$ is independently unsubstituted $C_1$-$C_5$ alkyl. In embodiments, $R^{2.1}$ is independently hydrogen and $R^{2.2}$ is independently unsubstituted $C_1$-$C_5$ alkyl. In embodiments, $R^{2.1}$ is independently hydrogen and $R^{2.2}$ is independently unsubstituted $C_1$-$C_3$ haloalkyl. In embodiments, $R^{2.1}$ is independently hydrogen and $R^{2.2}$ is independently halogen. In embodiments, $R^{2.1}$ is independently hydrogen and $R^{2.2}$ is independently —F. In embodiments, $R^{2.1}$ is independently hydrogen and $R^{2.2}$ is independently $C_1$ haloalkyl. In embodiments, $R^{2.1}$ is independently hydrogen and $R^{2.2}$ is independently methyl. In embodiments, $R^{2.1}$ is independently hydrogen and $R^{2.2}$ is independently —CF$_3$. In embodiments, $R^{2.1}$ is independently hydrogen and $R^{2.2}$ is independently —CHF$_2$. In embodiments, $R^{2.1}$ is independently hydrogen and $R^{2.2}$ is independently —CH$_2$F.

In embodiments, $R^{2.1}$ is independently halogen and $R^{2.2}$ is independently —C(O)NHR$^{11}$ and $R^{11}$ is independently unsubstituted $C_1$-$C_5$ alkyl. In embodiments, $R^{2.1}$ is independently halogen and $R^{2.2}$ is independently unsubstituted $C_1$-$C_5$ alkyl. In embodiments, $R^{2.1}$ is independently halogen and $R^{2.2}$ is independently unsubstituted $C_1$-$C_3$ haloalkyl. In embodiments, $R^{2.1}$ is independently halogen and $R^{2.2}$ is independently halogen. In embodiments, $R^{2.1}$ is independently halogen and $R^{2.2}$ is independently —F. In embodiments, $R^{2.1}$ is independently halogen and $R^{2.2}$ is independently $C_1$ haloalkyl. In embodiments, $R^{2.1}$ is independently halogen and $R^{2.2}$ is independently methyl. In embodiments, $R^{2.1}$ is independently halogen and $R^{2.2}$ is independently —CF$_3$. In embodiments, $R^{2.1}$ is independently halogen and $R^{2.2}$ is independently —CHF$_2$. In embodiments, $R^{2.1}$ is independently halogen and $R^{2.2}$ is independently —CH$_2$F.

In embodiments, $R^{2.1}$ is independently —F and $R^{2.2}$ is independently —C(O)NHR$^{11}$ and $R^{11}$ is independently unsubstituted $C_1$-$C_5$ alkyl. In embodiments, $R^{2.1}$ is independently —F and $R^{2.2}$ is independently unsubstituted $C_1$-$C_5$ alkyl. In embodiments, $R^{2.1}$ is independently —F and $R^{2.2}$ is independently unsubstituted $C_1$-$C_3$ haloalkyl. In embodiments, $R^{2.1}$ is independently —F and $R^{2.2}$ is independently halogen. In embodiments, $R^{2.1}$ is independently —F and $R^{2.2}$ is independently —F. In embodiments, $R^{2.1}$ is independently —F and $R^{2.2}$ is independently $C_1$ haloalkyl. In embodiments, $R^{2.1}$ is independently —F and $R^{2.2}$ is independently methyl. In embodiments, $R^{2.1}$ is independently —F and $R^{2.2}$ is independently —CF$_3$. In embodiments, $R^{2.1}$ is independently —F and $R^{2.2}$ is independently —CHF$_2$. In embodiments, $R^{2.1}$ is independently —F and $R^{2.2}$ is independently —CH$_2$F.

In embodiments, the compound is

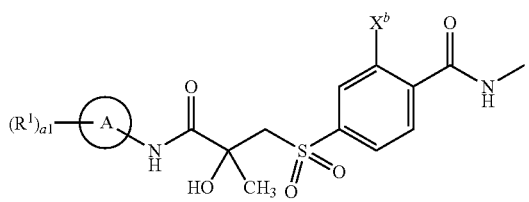

wherein $R^1$, $X^b$, Ring A, and a1 are as described herein, including in embodiments. In embodiments, the compound is

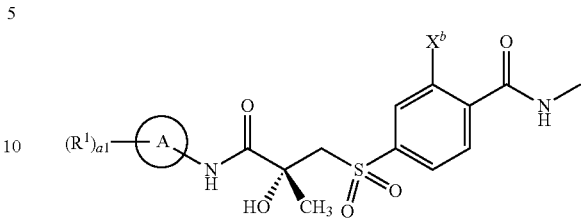

wherein $R^1$, $X^b$, Ring A, and a1 are as described herein, including in embodiments. In embodiments, the compound is

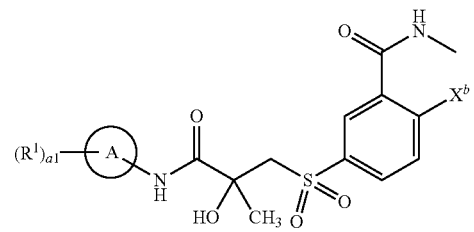

wherein $R^1$, $X^b$, Ring A, and a1 are as described herein, including in embodiments. In embodiments, the compound is

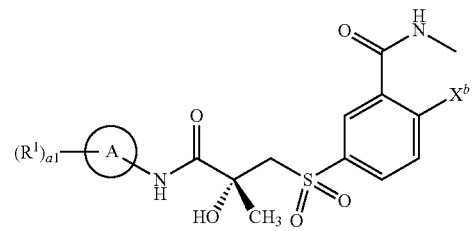

wherein $R^1$, $X^b$, Ring A, and a1 are as described herein, including in embodiments. In embodiments, $X^b$ is —F.

$R^3$ may be an unsubstituted $C_1$-$C_{10}$ alkyl. $R^3$ may be an unsubstituted $C_1$-$C_8$ alkyl. $R^3$ may be an unsubstituted $C_1$-$C_6$ alkyl. $R^3$ may be an unsubstituted $C_1$-$C_5$ alkyl. $R^3$ may be an unsubstituted $C_1$-$C_4$ alkyl. $R^3$ may be an unsubstituted $C_1$-$C_3$ alkyl. $R^3$ may be an unsubstituted $C_1$-$C_2$ alkyl. $R^3$ may be an unsubstituted methyl. $R^3$ may be an unsubstituted ethyl. $R^3$ may be an unsubstituted propyl. $R^3$ may be an unsubstituted butyl. $R^3$ may be an unsubstituted pentyl. $R^3$ may be an unsubstituted $C_1$-$C_5$ alkenyl.

Each $R^7$, $R^8$, $R^9$, $R^{10}$, $R^{11}$, $R^{12}$, $R^{13}$, and $R^{14}$ may independently be hydrogen, halogen, —CX$^c_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCX$^c_3$, —OCHX$^c_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl.

Each $R^7$ and $R^8$ substituents bonded to the same nitrogen atom may be joined to form a substituted or unsubstituted heterocycloalkyl or substituted or unsubstituted heteroaryl. Each $R^7$ and $R^8$ substituents bonded to the same nitrogen atom may be joined to form an unsubstituted heterocycloalkyl or unsubstituted heteroaryl. Each $R^7$ and $R^8$ substituents bonded to the same nitrogen atom may be joined to form a substituted or unsubstituted 4 to 6 membered heterocycloalkyl or 5 to 6 membered heteroaryl. Each $R^7$ and $R^8$ substituents bonded to the same nitrogen atom may be joined to form an unsubstituted 4 to 6 membered heterocycloalkyl or unsubstituted 5 to 6 membered heteroaryl.

Each $R^{11}$ and $R^{12}$ substituents bonded to the same nitrogen atom may be joined to form a substituted or unsubstituted heterocycloalkyl or substituted or unsubstituted heteroaryl. Each $R^{11}$ and $R^{12}$ substituents bonded to the same nitrogen atom may be joined to form an unsubstituted heterocycloalkyl or unsubstituted heteroaryl. Each $R^{11}$ and $R^{12}$ substituents bonded to the same nitrogen atom may be joined to form a substituted or unsubstituted 4 to 6 membered heterocycloalkyl or substituted or unsubstituted 5 to 6 membered heteroaryl. Each $R^{11}$ and $R^{12}$ substituents bonded to the same nitrogen atom may be joined to form an unsubstituted 4 to 6 membered heterocycloalkyl or unsubstituted 5 to 6 membered heteroaryl.

The symbol a1 may be 0. The symbol a1 may be 1. The symbol a1 may be 2. The symbol a1 may be 3. The symbol a1 may be 4.

The symbol b1 may be 0. The symbol b1 may be 1. The symbol b1 may be 2. The symbol b1 may be 3. The symbol b1 may be 4. The symbol b1 may be 5.

The symbols m1 may be 1. The symbols m1 may be 2. The symbols m2 may be 1. The symbols m2 may be 2.

The symbols v1 may be 1. The symbols v1 may be 2. The symbols v2 may be 1. The symbols v2 may be 2.

The symbol n1 may be 0. The symbol n1 may be 1. The symbol n1 may be 2. The symbol n1 may be 3. The symbol n1 may be 4.

The symbol n2 may be 0. The symbol n2 may be 1. The symbol n2 may be 2. The symbol n2 may be 3. The symbol n2 may be 4.

The symbol $X^a$ may be —Cl. The symbol $X^a$ may be —Br. The symbol $X^a$ may be —I. The symbol $X^a$ may be —F.

The symbol $X^b$ may be —Cl. The symbol $X^b$ may be —Br. The symbol $X^b$ may be —I. The symbol $X^b$ may be —F.

The symbol $X^c$ may be —Cl. The symbol $X^c$ may be —Br. The symbol $X^c$ may be —I. The symbol $X^c$ may be —F.

In embodiments, the compound is

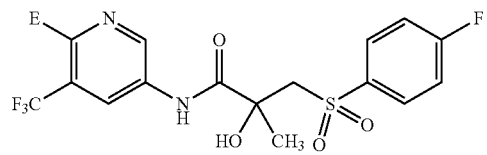

wherein E is as described herein, including in embodiments. In embodiments, the compound is

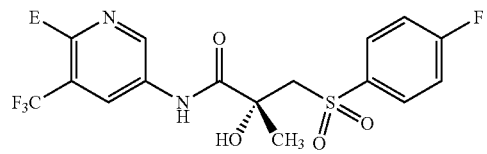

wherein E is as described herein, including in embodiments. In embodiments, the compound is

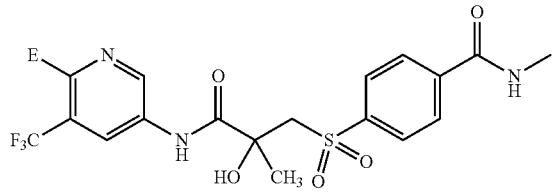

wherein E is as described herein, including in embodiments. In embodiments, the compound is

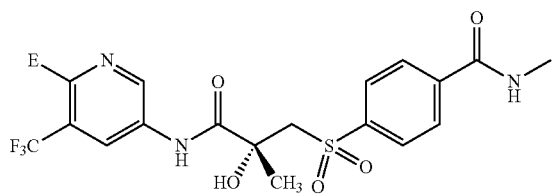

wherein E is as described herein, including in embodiments.
In embodiments, the compound is

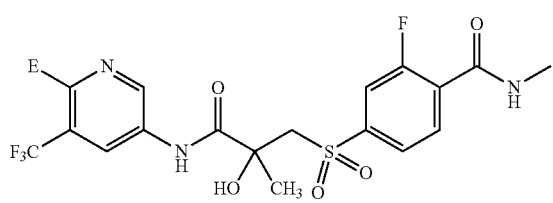

wherein E is as described herein, including in embodiments. In embodiments, the compound is

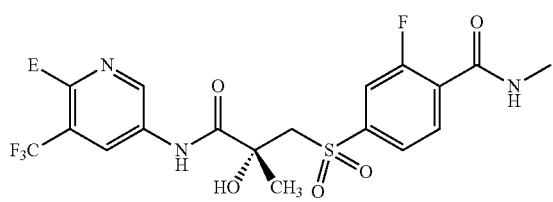

wherein E is as described herein, including in embodiments.
In embodiments, the compound is

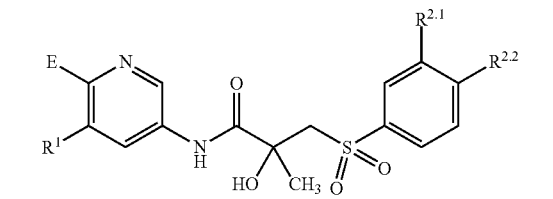

wherein E, R¹, R$^{2.1}$, and R$^{2.2}$ are as described herein, including in embodiments. R² and R$^{2.2}$ are embodiments of R². In embodiments, the compound is

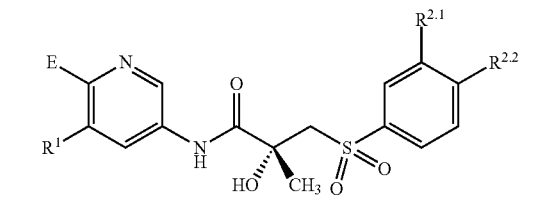

wherein E, R¹, R$^{2.1}$, and R$^{2.2}$ are as described herein, including in embodiments.

In embodiments, the compound is

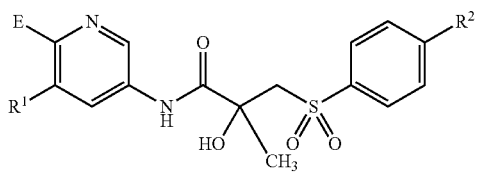

wherein E, R¹, and R² are as described herein, including in embodiments. In embodiments, the compound is

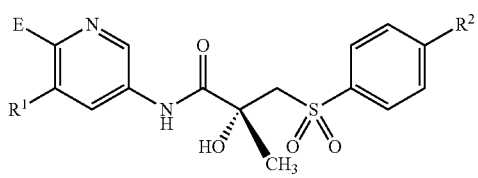

wherein E, R¹, and R² are as described herein, including in embodiments. R¹ may be —CF$_3$, —CCl$_3$, —F, —Cl, —Br, —I, —CH$_3$, —CH$_2$F, —CH$_2$Cl, —CHF$_2$, or —CHCl$_2$. R² may be —CF$_3$, —CCl$_3$, —F, —Cl, —Br, —I, —CH$_3$, —CH$_2$F, —CH$_2$Cl, —CHF$_2$, —CHCl$_2$, —CONHCH$_3$, —CONHCH$_2$CH$_3$, —CONHCH$_2$CH$_2$CH$_3$, —CONHCHCH$_3$CH$_3$, —CONHC(CH$_3$)$_3$, —CONHCF$_3$, —CONHCH$_2$F, or —CONHCHF$_2$. In embodiments, E is —CN. E may be —CHCH$_2$. E may be —CCH.

In embodiments, the compound is

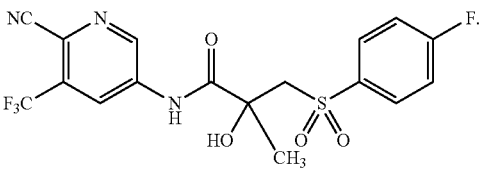 [SMILES: CC(O)(CS(=O)(=O)c1ccc(F)cc1)C(=O)Nc1cnc(C#N)c(C(F)(F)F)c1]

In embodiments, the compound is

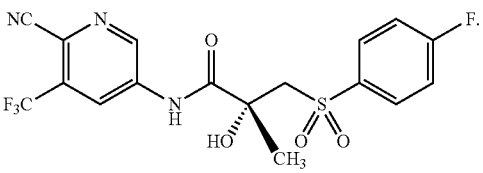

In embodiments, the compound is

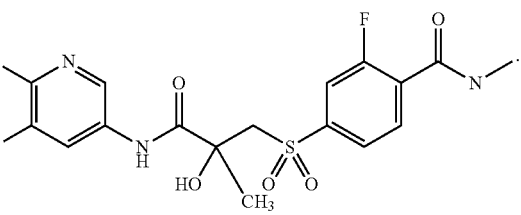

In embodiments, the compound is

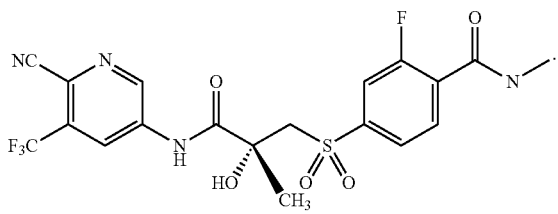 [SMILES: CNC(=O)c1ccc(S(=O)(=O)C[C@](C)(O)C(=O)Nc2cnc(C#N)c(C(F)(F)F)c2)cc1F]

In embodiments, the compound is

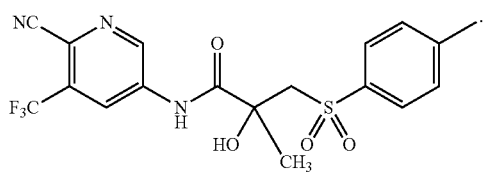 [SMILES: Cc1ccc(S(=O)(=O)CC(C)(O)C(=O)Nc2cnc(C#N)c(C(F)(F)F)c2)cc1]

In embodiments, the compound is

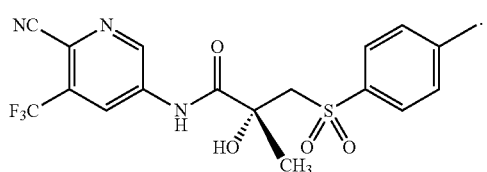

The compound may be

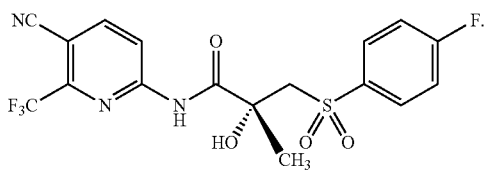 [SMILES: C[C@](O)(CS(=O)(=O)c1ccc(F)cc1)C(=O)Nc1ccc(C#N)c(C(F)(F)F)n1]

The compound may be

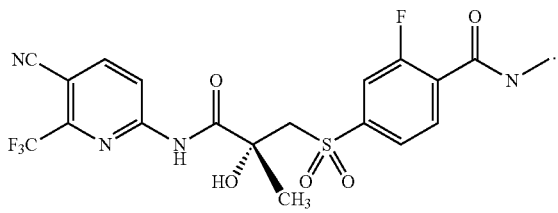 [SMILES: CNC(=O)c1ccc(S(=O)(=O)C[C@](C)(O)C(=O)Nc2ccc(C#N)c(C(F)(F)F)n2)cc1F]

The compound may be

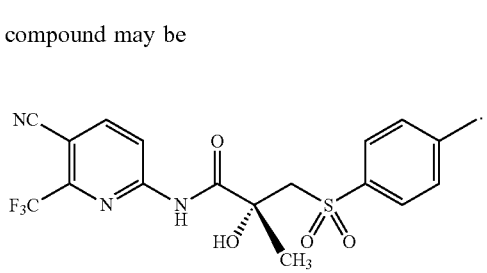

The compound may be

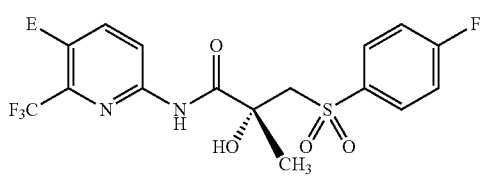

wherein E is as described herein, including in embodiments. The compound may be

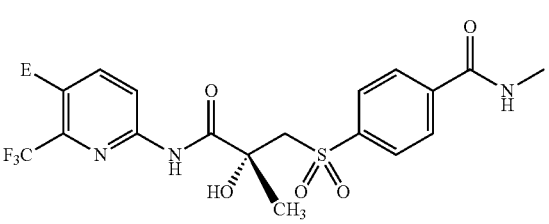

wherein E is as described herein, including in embodiments. The compound may be

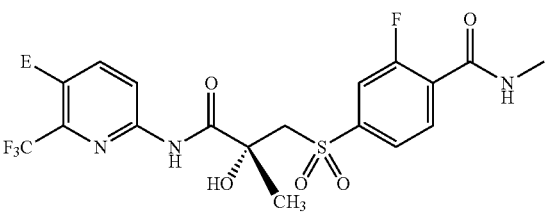

wherein E is as described herein, including in embodiments. The compound may be

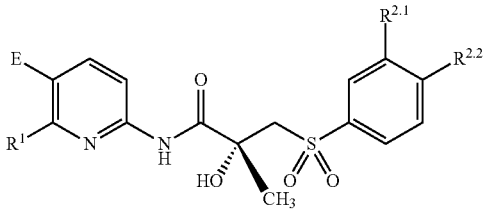

wherein E, $R^1$, $R^{2.1}$, and $R^{2.2}$ are as described herein, including in embodiments. The compound may be

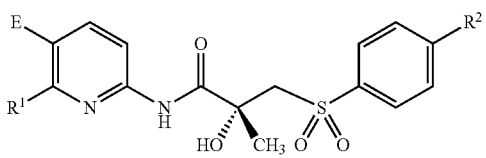

wherein E, $R^1$, and $R^2$ are as described herein, including in embodiments. The compound may be

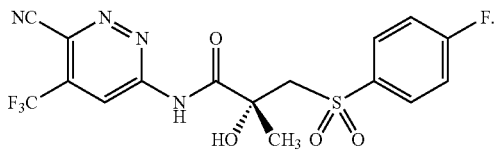 [SMILES: C[C@](O)(CS(=O)(=O)c1ccc(F)cc1)C(=O)Nc1cc(C(F)(F)F)c(C#N)nn1]

The compound may be

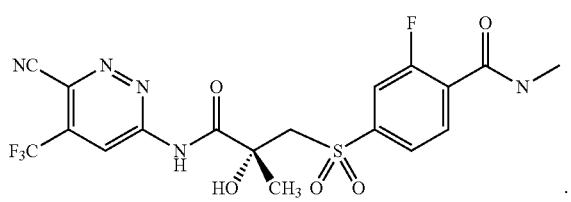 [SMILES: CNC(=O)c1ccc(S(=O)(=O)C[C@](C)(O)C(=O)Nc2cc(C(F)(F)F)c(C#N)nn2)cc1F]

The compound may be

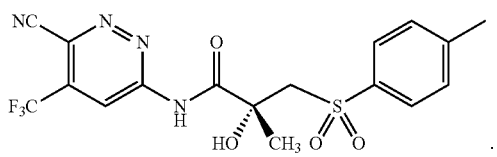

The compound may be

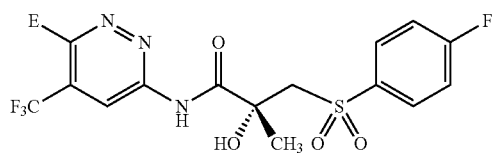

wherein E is as described herein, including in embodiments. The compound may be

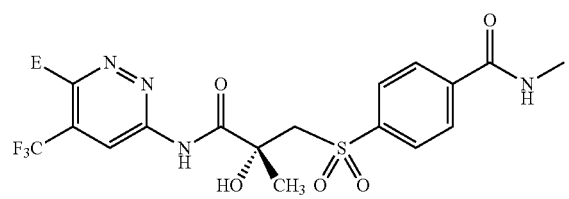

wherein E is as described herein, including in embodiments. The compound may be

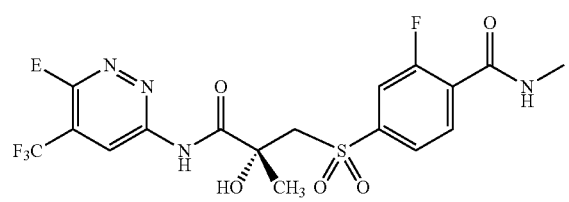

wherein E is as described herein, including in embodiments. The compound may be

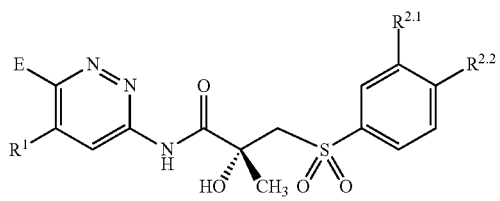

wherein E, $R^1$, $R^{2.1}$, and $R^{2.2}$ are as described herein, including in embodiments. The compound may be

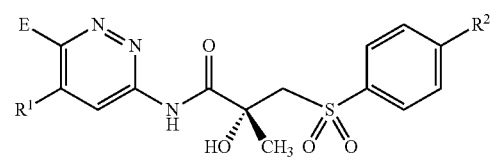

wherein E, $R^1$, and $R^2$ are as described herein, including in embodiments. The compound may be

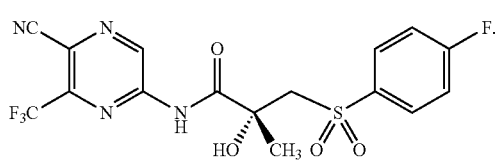

The compound may be

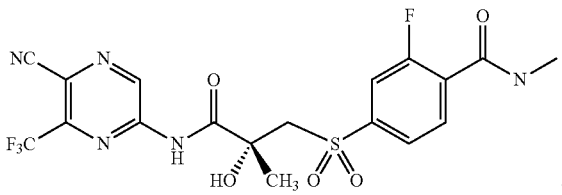

The compound may be

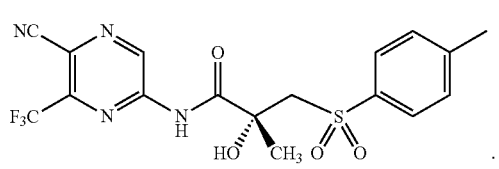 [SMILES: C[C@](O)(CS(=O)(=O)c1ccc(F)cc1)C(=O)Nc1cnc(C#N)c(C(F)(F)F)n1]

The compound may be

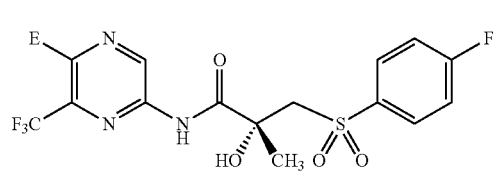

wherein E is as described herein, including in embodiments. The compound may be

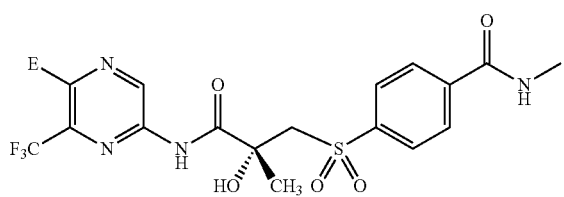

wherein E is as described herein, including in embodiments. The compound may be

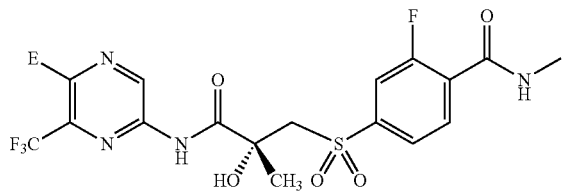

wherein E is as described herein, including in embodiments. The compound may be

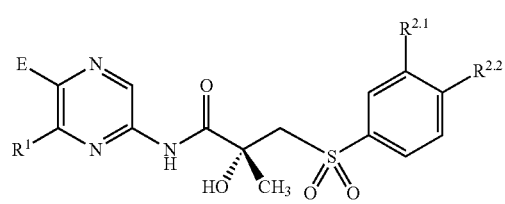

wherein E, R¹, R²·¹, and R²·² are as described herein, including in embodiments. The compound may be

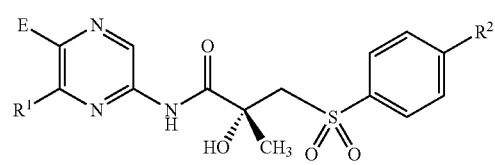

wherein E, R¹, and R² are as described herein, including in embodiments. The compound may be

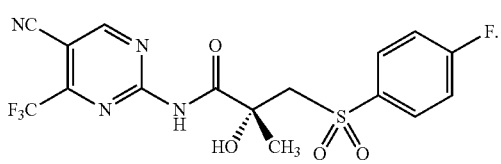 [SMILES: C[C@](O)(CS(=O)(=O)c1ccc(F)cc1)C(=O)Nc1ncc(C#N)c(C(F)(F)F)n1]

The compound may be

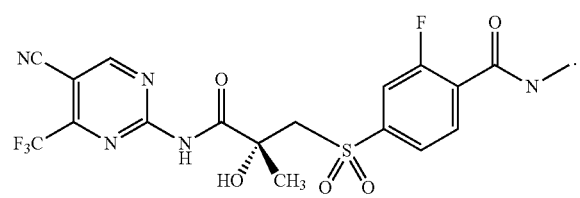 [SMILES: CNC(=O)c1ccc(S(=O)(=O)C[C@](C)(O)C(=O)Nc2ncc(C#N)c(C(F)(F)F)n2)cc1F]

The compound may be

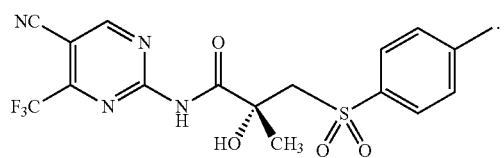

The compound may be

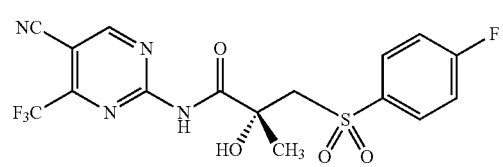

wherein E is as described herein, including in embodiments. The compound may be

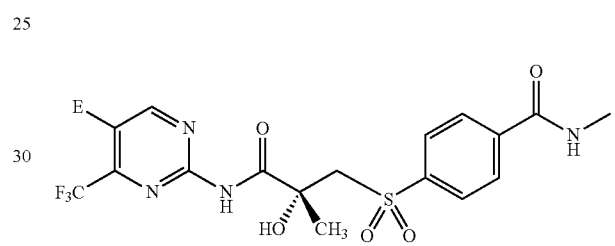

wherein E is as described herein, including in embodiments. The compound may be

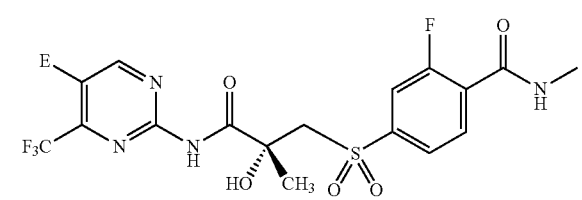

wherein E is as described herein, including in embodiments. The compound may be

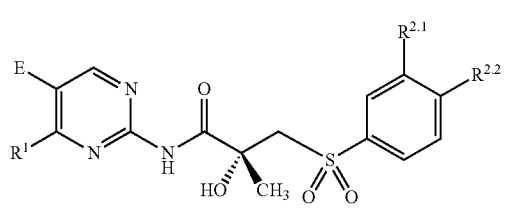

wherein E, R¹, R²·¹, and R²·² are as described herein, including in embodiments. The compound may be

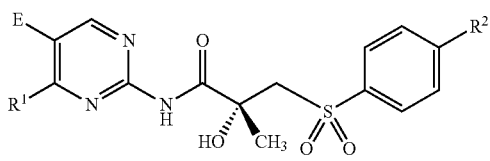

wherein E, R$^1$, and R$^2$ are as described herein, including in embodiments. The compound may be

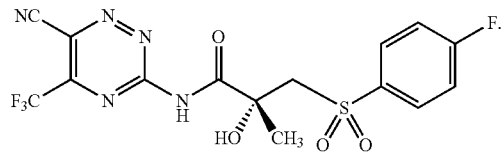 [SMILES: C[C@](O)(CS(=O)(=O)c1ccc(F)cc1)C(=O)Nc1nnc(C#N)c(C(F)(F)F)n1]

The compound may be

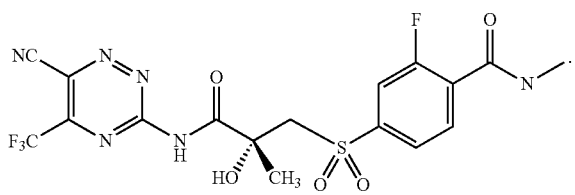 [SMILES: CNC(=O)c1ccc(S(=O)(=O)C[C@](C)(O)C(=O)Nc2nnc(C#N)c(C(F)(F)F)n2)cc1F]

The compound may be

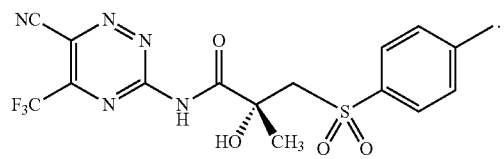

The compound may be

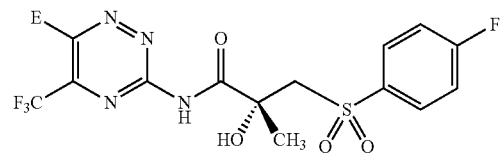

wherein is as described herein, including in embodiments. The compound may be

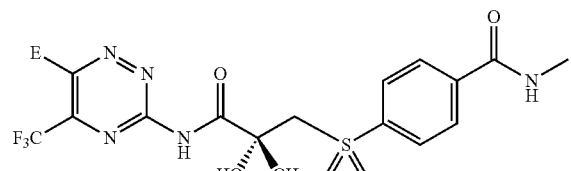

wherein E is as described herein, including in embodiments. The compound may be

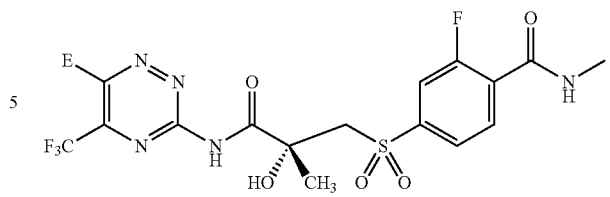

wherein E is as described herein, including in embodiments. The compound may be

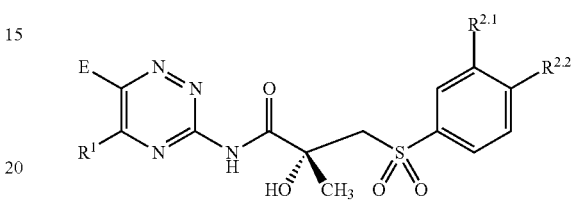

wherein E, R$^1$, R$^{2.1}$ and R$^{2.2}$ are as described herein, including in embodiments. The compound may be

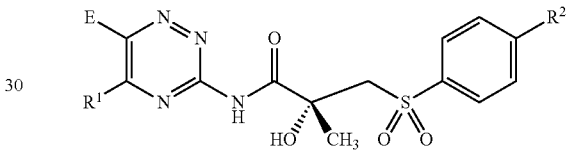

wherein E, R$^1$, and R$^2$ are as described herein, including in embodiments. The compound may be

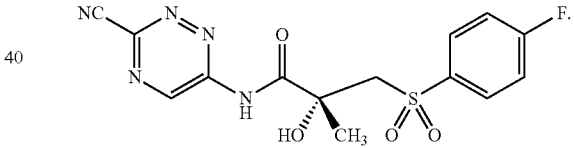

The compound may be

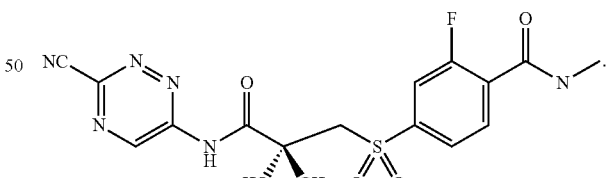

The compound may be

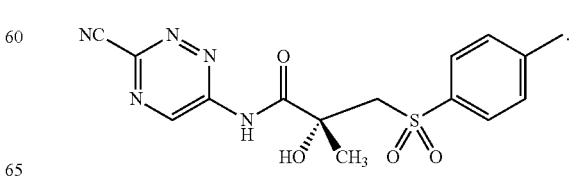

The compound may be

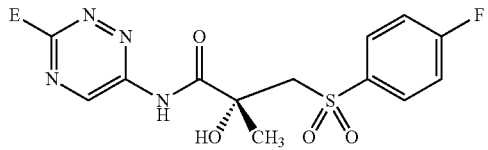

wherein E is as described herein, including in embodiments. The compound may be

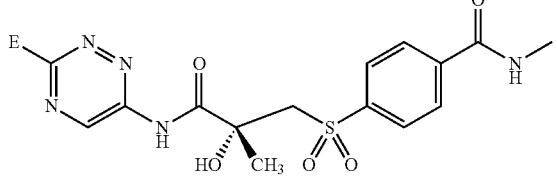

wherein E is as described herein, including in embodiments. The compound may be

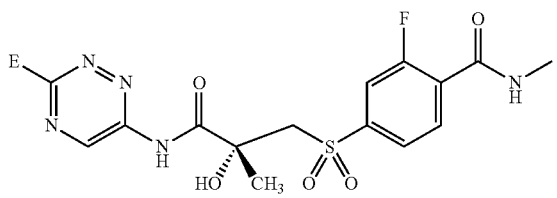

wherein E is as described herein, including in embodiments. The compound may be

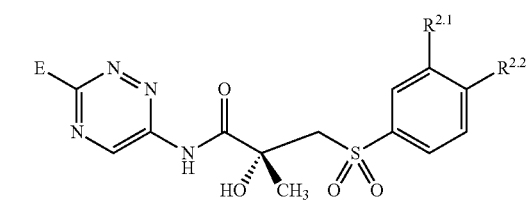

wherein E, $R^1$, $R^{2.1}$, and $R^{2.2}$ are as described herein, including in embodiments. The compound may be

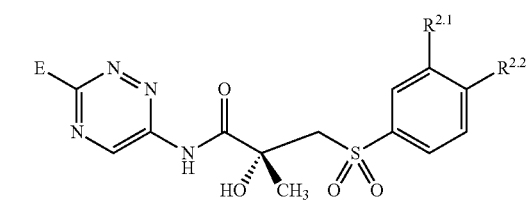

wherein E, $R^1$, and $R^2$ are as described herein, including in embodiments. The compound may be

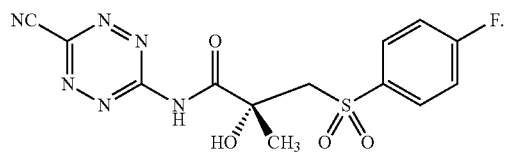 [SMILES: C[C@](O)(CS(=O)(=O)c1ccc(F)cc1)C(=O)Nc1nnc(C#N)nn1]

The compound may be

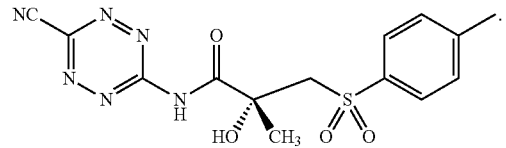 [SMILES: Cc1ccc(S(=O)(=O)C[C@](C)(O)C(=O)Nc2nnc(C#N)nn2)cc1]

The compound may be

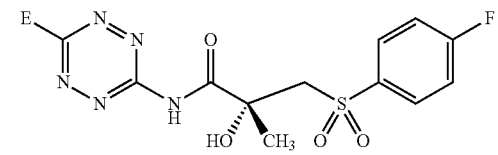

The compound may be

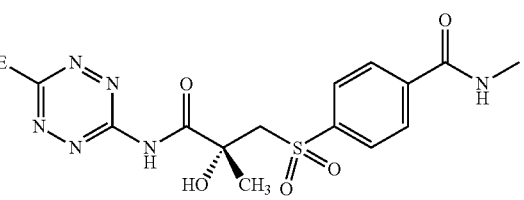

wherein E is as described herein, including in embodiments. The compound may be

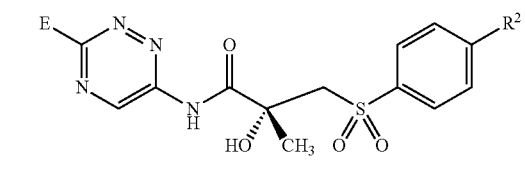

wherein E is as described herein, including in embodiments. The compound may be

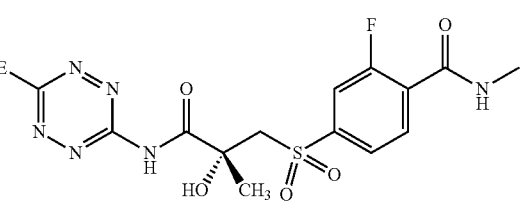

wherein E is as described herein, including in embodiments. The compound may be

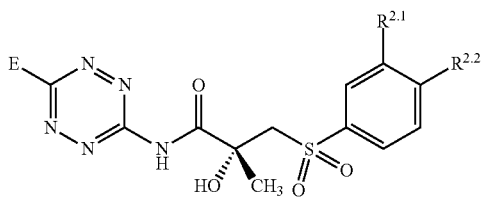

wherein E, R¹, R²·¹, and R²·² are as described herein, including in embodiments. The compound may be

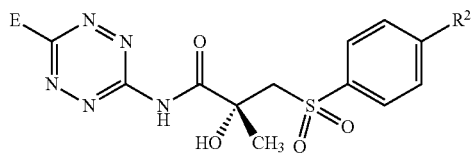

wherein E, R¹, and R² are as described herein, including in embodiments. In embodiments, the compound is a compound described herein, including in an aspect, embodiment, example, table, figure, or claim. The compound may be

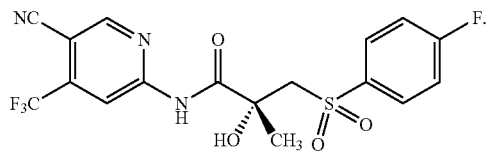 [SMILES: C[C@](O)(CS(=O)(=O)c1ccc(F)cc1)C(=O)Nc1cc(C(F)(F)F)c(C#N)cn1]

The compound may be

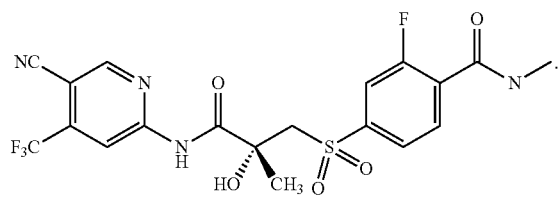 [SMILES: CNC(=O)c1ccc(S(=O)(=O)C[C@](C)(O)C(=O)Nc2cc(C(F)(F)F)c(C#N)cn2)cc1F]

The compound may be

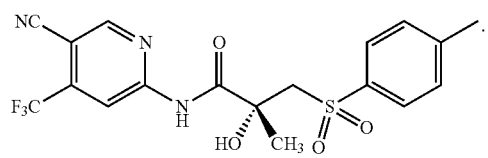 [SMILES: Cc1ccc(S(=O)(=O)C[C@](C)(O)C(=O)Nc2cc(C(F)(F)F)c(C#N)cn2)cc1]

The compound may be

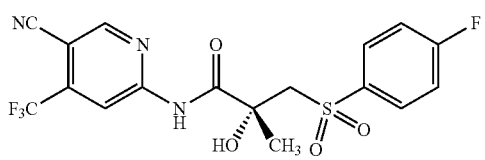

wherein E is as described herein, including in embodiments. The compound may be

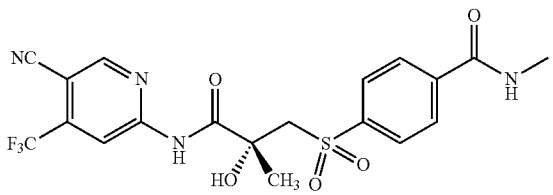

wherein E is as described herein, including in embodiments. The compound may be

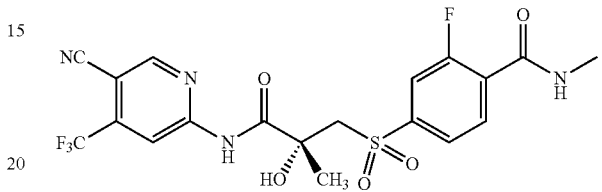

wherein E is as described herein, including in embodiments. The compound may be

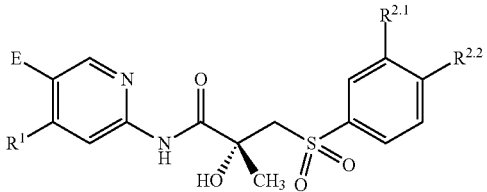

wherein E, R¹, R²·¹, and R²·² are as described herein, including in embodiments. The compound may be

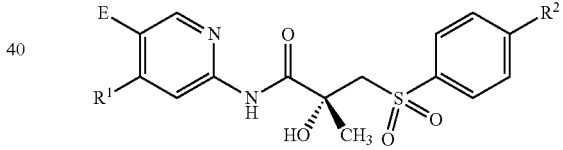

wherein E, R¹, and R² are as described herein, including in embodiments. The compound may be

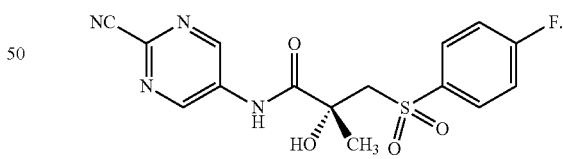

The compound may be

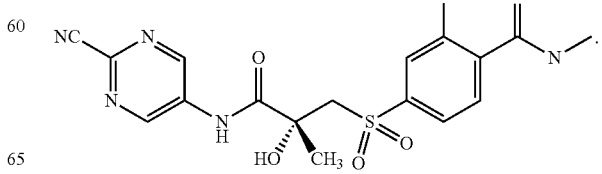

The compound may be

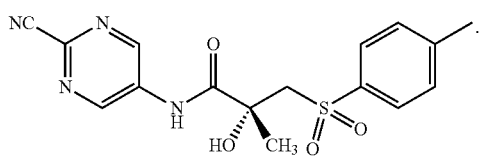 [SMILES: Cc1ccc(S(=O)(=O)C[C@](C)(O)C(=O)Nc2cnc(C#N)nc2)cc1]

The compound may be

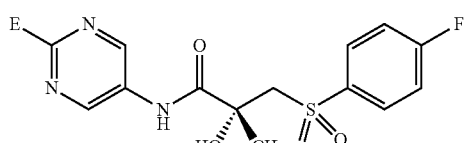

wherein E is as described herein, including in embodiments. The compound may be

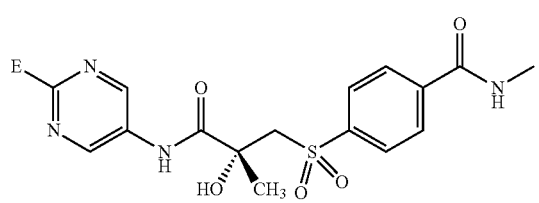

wherein E is as described herein, including in embodiments. The compound may be

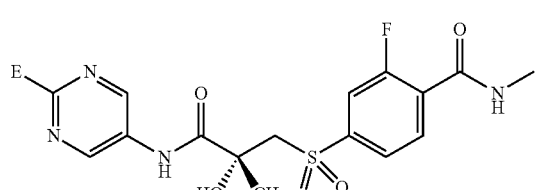

wherein E is as described herein, including in embodiments. The compound may be

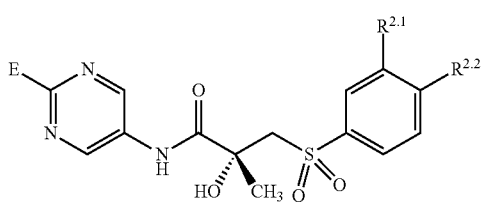

wherein E, $R^1$, $R^{2.1}$, and $R^{2.2}$ are as described herein, including in embodiments. The compound may be

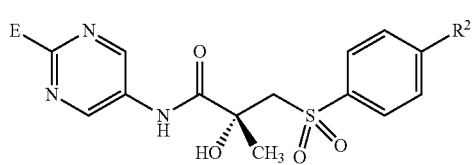

wherein E, $R^1$, and $R^2$ are as described herein, including in embodiments. The compound may be

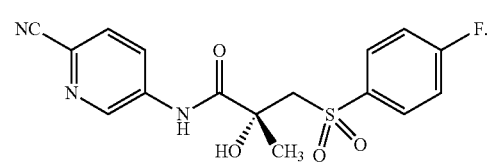 [SMILES: C[C@](O)(CS(=O)(=O)c1ccc(F)cc1)C(=O)Nc1ccc(C#N)nc1]

The compound may be

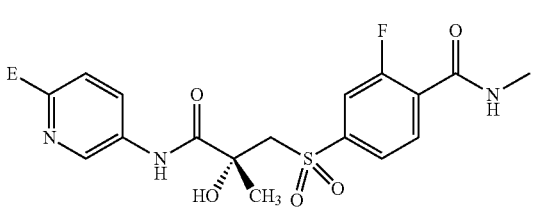

The compound may be

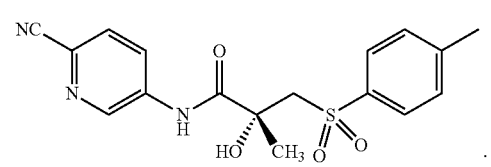 [SMILES: Cc1ccc(S(=O)(=O)C[C@](C)(O)C(=O)Nc2ccc(C#N)nc2)cc1]

The compound may be

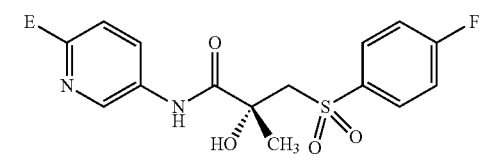

wherein E is as described herein, including in embodiments. The compound may be

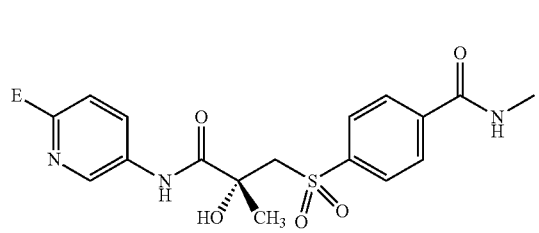

wherein E is as described herein, including in embodiments. The compound may be

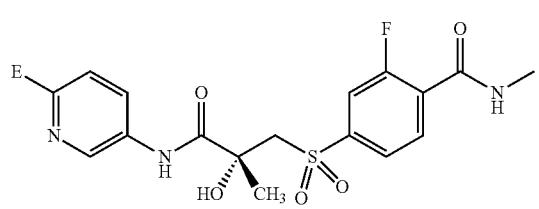

wherein E is as described herein, including in embodiments. The compound may be

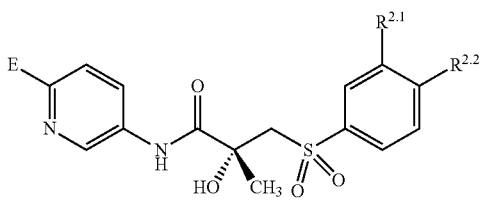

wherein E, $R^1$, and $R^{2.2}$ are as described herein, including in embodiments. The compound may be

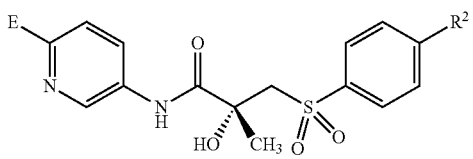

wherein E, $R^1$, and $R^2$ are as described herein, including in embodiments.

In embodiments, the compound is an antagonist of a nuclear receptor. In embodiments, the compound is an antagonist of an androgen receptor. In embodiments, the compound is an antagonist of a human androgen receptor. In embodiments, the compound is an antagonist of wildtype human androgen receptor. In embodiments, the compound is an antagonist of a mutant human androgen receptor. In embodiments, the compound is an antagonist of a drug-resistant human androgen receptor. In embodiments, the compound is an antagonist of a casodex-resistant human androgen receptor. In embodiments, the compound is an antagonist of a Flutamide-resistant human androgen receptor. In embodiments, the compound is an antagonist of an MDV3100-resistant human androgen receptor. In embodiments, the compound is an antagonist of an ARN-509-resistant human androgen receptor. In embodiments, the compound forms a covalent bond with a nuclear receptor. In embodiments, the compound forms a covalent bond with an androgen receptor. In embodiments, the covalent bond is reversible. In embodiments, the covalent bond is irreversible. In embodiments, the compound covalently (e.g., reversibly or irreversibly) bonds to Cys784 of human androgen receptor. In embodiments, the compound covalently (e.g., reversibly or irreversibly) bonds to the residue corresponding to Cys784 of human androgen receptor. In embodiments, the compound covalently (e.g., reversibly or irreversibly) bonds to a Cys residue of a nuclear receptor. In embodiments, the compound covalently (e.g., reversibly or irreversibly) bonds to a Cys residue of an androgen receptor. In embodiments, the compound covalently (e.g., reversibly or irreversibly) bonds to an Asp residue of a nuclear receptor. In embodiments, the compound covalently (e.g., reversibly or irreversibly) bonds to an Asp residue of an androgen receptor. In embodiments, the compound covalently (e.g., reversibly or irreversibly) bonds to a Glu residue of a nuclear receptor. In embodiments, the compound covalently (e.g., reversibly or irreversibly) bonds to a Glu residue of an androgen receptor. In embodiments, the compound covalently (e.g., reversibly or irreversibly) bonds to a Tyr residue of a nuclear receptor. In embodiments, the compound covalently (e.g., reversibly or irreversibly) bonds to a Tyr residue of an androgen receptor. In embodiments, the compound covalently (e.g., reversibly or irreversibly) bonds to a Ser residue of a nuclear receptor. In embodiments, the compound covalently (e.g., reversibly or irreversibly) bonds to a Ser residue of an androgen receptor. In embodiments, the compound covalently (e.g., reversibly or irreversibly) bonds to a Thr residue of a nuclear receptor. In embodiments, the compound covalently (e.g., reversibly or irreversibly) bonds to a Thr residue of an androgen receptor. In embodiments, the compound covalently (e.g., reversibly or irreversibly) bonds to a Lys residue of a nuclear receptor. In embodiments, the compound covalently (e.g., reversibly or irreversibly) bonds to a Lys residue of an androgen receptor.

In embodiments, the compound binds an androgen receptor with at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger affinity than flutamide. In embodiments, the compound binds an androgen receptor with at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger affinity than bicalutamide. In embodiments, the compound binds an androgen receptor with at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger affinity than nilutamide. In embodiments, the compound binds an androgen receptor with at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger affinity than enzalutamide. In embodiments, the compound binds an androgen receptor with at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-fold stronger affinity than ARN-509.

In embodiments, the compound inhibits an androgen receptor with an IC50 at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger (equivalent inhibition at a lower concentration of compound than the control) than flutamide. In embodiments, the compound inhibits an androgen receptor with an IC50 at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger than bicalutamide. In embodiments, the compound inhibits an androgen receptor with an IC50 at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger than nilutamide. In embodiments, the compound inhibits an androgen receptor with an IC50 at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger than enzalutamide. In embodiments, the compound inhibits an androgen receptor with an IC50 at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19. 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 100000-Fold stronger than ARN-509.

In some embodiments of the compounds provided herein, $R^1$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

$R^{20}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In embodiments, $R^{20}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In embodiments, $R^{20}$ is hydrogen. In embodiments, $R^{20}$ is halogen. In embodiments, $R^{20}$ is —$CF_3$. In embodiments, $R^{20}$ is —CN. In embodiments, $R^{20}$ is —OH. In embodiments, $R^{20}$ is —$NH_2$. In embodiments, $R^{20}$ is —COOH. In embodiments, $R^{20}$ is —$CONH_2$. In embodiments, $R^{20}$ is —$CH_3$. In embodiments, $R^{20}$ is unsubstituted alkyl.

$R^{21}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In some embodiments of the compounds provided herein, $R^2$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

$R^{23}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

$R^{24}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In some embodiments of the compounds provided herein, $R^7$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

$R^{38}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{39}$-substituted or unsubstituted alkyl, $R^{39}$-substituted or unsubstituted heteroalkyl, $R^{39}$-substituted or unsubstituted cycloalkyl, $R^{39}$ substituted or unsubstituted heterocycloalkyl, $R^{39}$-substituted or unsubstituted aryl, or $R^{39}$-substituted or unsubstituted heteroaryl.

$R^{39}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In some embodiments of the compounds provided herein, $R^8$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{41}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —S(O)$_2CHCH_2$, —NHS(O)$_2CHCH_2$, $R^{42}$-substituted or unsubstituted alkyl, $R^{42}$-substituted or unsubstituted heteroalkyl, $R^{42}$-substituted or unsubstituted cycloalkyl, $R^{42}$ substituted or unsubstituted heterocycloalkyl, $R^{42}$-substituted or unsubstituted aryl, or $R^{42}$-substituted or unsubstituted heteroaryl.

$R^{42}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —S(O)$_2CHCH_2$, —NHS(O)$_2CHCH_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

In some embodiments of the compounds provided herein, $R^9$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

$R^{44}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, $R^{45}$ substituted or unsubstituted heterocycloalkyl, $R^{45}$-substituted or unsubstituted aryl, or $R^{45}$-substituted or unsubstituted heteroaryl.

$R^{45}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl.

In some embodiments of the compounds provided herein, $R^{10}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl.

$R^{47}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{48}$-substituted or unsubstituted alkyl, $R^{48}$-substituted or unsubstituted heteroalkyl, $R^{48}$-substituted or unsubstituted cycloalkyl, $R^{48}$ substituted or unsubstituted heterocycloalkyl, $R^{48}$-substituted or unsubstituted aryl, or $R^{48}$-substituted or unsubstituted heteroaryl.

$R^{48}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

In some embodiments of the compounds provided herein, $R^{11}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl.

$R^{56}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{57}$-substituted or unsubstituted alkyl, $R^{57}$-substituted or unsubstituted heteroalkyl, $R^{57}$-substituted or unsubstituted cycloalkyl, $R^{57}$ substituted or unsubstituted heterocycloalkyl, $R^{57}$-substituted or unsubstituted aryl, or $R^{57}$-substituted or unsubstituted heteroaryl.

$R^{57}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl.

In embodiments of the compounds provided herein, $R^{12}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl.

$R^{59}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^{60}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

In embodiments of the compounds provided herein, $R^{13}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

$R^{62}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl.

$R^{63}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl.

In some embodiments of the compounds provided herein, $R^{14}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl.

$R^{65}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl.

$R^{66}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl.

In embodiments, $R^{15}$ is independently hydrogen, oxo, halogen, —$CX^{15}_3$, —$CHX^{15}_2$, —$OCH_2X^{15}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{15}_3$, —$OCHX^{15}_2$, $R^{72}$-substituted or unsubstituted alkyl, $R^{72}$-substituted or unsubstituted heteroalkyl, $R^{72}$-substituted or unsubstituted cycloalkyl, $R^{72}$-substituted or unsubstituted heterocycloalkyl, $R^{72}$-substituted or unsubstituted aryl, or $R^{72}$-substituted or unsubstituted heteroaryl. $X^{15}$ is halogen. In embodiments, $X^{15}$ is F.

$R^{72}$ is independently oxo, halogen, —$CX^{72}_3$, —$CHX^{72}_2$, —$OCH_2X^{72}$, —$OCHX^{72}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{72}_3$, —$OCHX^{72}_2$, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl. $X^{72}$ is halogen. In embodiments, $X^{72}$ is F.

$R^{73}$ is independently oxo, halogen, —$CX^{73}_3$, —$CHX^{73}_2$, —$OCH_2X^{73}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{73}_3$, —$OCHX^{73}_2$, $R^{74}$-substituted or unsubstituted alkyl, $R^{74}$-substituted or unsubstituted heteroalkyl, $R^{74}$-substituted or unsubstituted cycloalkyl, $R^{74}$-substituted or unsubstituted heterocycloalkyl, $R^{74}$-substituted or unsubstituted aryl, or $R^{74}$-substituted or unsubstituted heteroaryl. $X^{73}$ is halogen. In embodiments, $X^{73}$ is F.

In embodiments, $R^{16}$ is independently hydrogen, oxo, halogen, —$CX^{16}_3$, —$CHX^{16}_2$, —$OCH_2X^{16}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{16}_3$, —$OCHX^{16}_2$, $R^{75}$-substituted or unsubstituted alkyl, $R^{75}$-substituted or unsubstituted heteroalkyl, $R^{75}$-substituted or unsubstituted cycloalkyl, $R^{75}$-substituted or unsubstituted heterocycloalkyl, $R^{75}$-substituted or unsubstituted aryl, or $R^{75}$-substituted or unsubstituted heteroaryl. $X^{16}$ is halogen. In embodiments, $X^{16}$ is F.

$R^{75}$ is independently oxo, halogen, $-CX^{75}_3$, $-CHX^{75}_2$, $-OCH_2X^{75}$, $-OCHX^{75}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75}_3$, $-OCHX^{75}_2$, $R^{76}$-substituted or unsubstituted alkyl, $R^{76}$-substituted or unsubstituted heteroalkyl, $R^{76}$-substituted or unsubstituted cycloalkyl, $R^{76}$-substituted or unsubstituted heterocycloalkyl, $R^{76}$-substituted or unsubstituted aryl, or $R^{76}$-substituted or unsubstituted heteroaryl. $X^{75}$ is halogen. In embodiments, $X^{75}$ is F.

$R^{76}$ is independently oxo, halogen, $-CX^{76}_3$, $-CHX^{76}_2$, $-OCH_2X^{76}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76}_3$, $-OCHX^{76}_2$, $R^{77}$-substituted or unsubstituted alkyl, $R^{77}$-substituted or unsubstituted heteroalkyl, $R^{77}$-substituted or unsubstituted cycloalkyl, $R^{77}$-substituted or unsubstituted heterocycloalkyl, $R^{77}$-substituted or unsubstituted aryl, or $R^{77}$-substituted or unsubstituted heteroaryl. $X^{76}$ is halogen. In embodiments, $X^{76}$ is F.

In embodiments, $R^{17}$ is independently hydrogen, oxo, halogen, $-CX^{17}_3$, $-CHX^{17}_2$, $-OCH_2X^{17}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{17}_3$, $-OCHX^{17}_2$, $R^{78}$-substituted or unsubstituted alkyl, $R^{78}$-substituted or unsubstituted heteroalkyl, $R^{78}$-substituted or unsubstituted cycloalkyl, $R^{78}$-substituted or unsubstituted heterocycloalkyl, $R^{78}$-substituted or unsubstituted aryl, or $R^{78}$-substituted or unsubstituted heteroaryl. $X^{17}$ is halogen. In embodiments, $X^{17}$ is F.

$R^{78}$ is independently oxo, halogen, $-CX^{78}_3$, $-CHX^{78}_2$, $-OCH_2X^{78}$, $-OCHX^{78}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{78}_3$, $-OCHX^{78}_2$, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl. $X^{78}$ is halogen. In embodiments, $X^{78}$ is F.

$R^{79}$ is independently oxo, halogen, $-CX^{79}_3$, $-CHX^{79}_2$, $-OCH_2X^{79}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{79}_3$, $-OCHX^{79}_2$, $R^{80}$-substituted or unsubstituted alkyl, $R^{80}$-substituted or unsubstituted heteroalkyl, $R^{80}$-substituted or unsubstituted cycloalkyl, $R^{80}$-substituted or unsubstituted heterocycloalkyl, $R^{80}$-substituted or unsubstituted aryl, or $R^{80}$-substituted or unsubstituted heteroaryl. $X^{79}$ is halogen. In embodiments, $X^{79}$ is F.

In embodiments, $R^{18}$ is independently hydrogen, oxo, halogen, $-CX^{18}_3$, $-CHX^{18}_2$, $-OCH_2X^{18}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)$ $NHNH_2$, $-NHC=(O)NH_2$, $-NHSO_2H$, $-NHC=(O)H$, $-NHC(O)-OH$, $-NHOH$, $-OCX^{18}_3$, $-OCHX^{18}_2$, $R^{81}$-substituted or unsubstituted alkyl, $R^{81}$-substituted or unsubstituted heteroalkyl, $R^{81}$-substituted or unsubstituted cycloalkyl, $R^{81}$-substituted or unsubstituted heterocycloalkyl, $R^{81}$-substituted or unsubstituted aryl, or $R^{81}$-substituted or unsubstituted heteroaryl. $X^{18}$ is halogen. In embodiments, $X^{18}$ is F.

$R^{81}$ is independently oxo, halogen, $-CX^{81}_3$, $-CHX^{81}_2$, $-OCH_2X^{81}$, $-OCHX^{12}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{81}_3$, $-OCHX^{12}$, $R^{82}$-substituted or unsubstituted alkyl, $R^{82}$-substituted or unsubstituted heteroalkyl, $R^{82}$-substituted or unsubstituted cycloalkyl, $R^{82}$-substituted or unsubstituted heterocycloalkyl, $R^{82}$-substituted or unsubstituted aryl, or $R^{82}$-substituted or unsubstituted heteroaryl. $X^{81}$ is halogen. In embodiments, $X^{81}$ is F.

$R^{82}$ is independently oxo, halogen, $-CX^{82}_3$, $-CHX^{82}_2$, $-OCH_2X^{82}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{82}_3$, $-OCHX^{82}_2$, $R^{83}$-substituted or unsubstituted alkyl, $R^{83}$-substituted or unsubstituted heteroalkyl, $R^{83}$-substituted or unsubstituted cycloalkyl, $R^{83}$-substituted or unsubstituted aryl, or $R^{83}$-substituted or unsubstituted heteroaryl. $X^{82}$ is halogen. In embodiments, $X^{82}$ is F.

In embodiments, $R^{15A}$ is independently hydrogen, oxo, halogen, $-CX^{15A}_3$, $-CHX^{15A}_2$, $-OCH_2X^{15A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{15A}_3$, $-OCHX^{15A}_2$, $R^{72A}$-substituted or unsubstituted alkyl, $R^{72A}$-substituted or unsubstituted heteroalkyl, $R^{72A}$-substituted or unsubstituted cycloalkyl, $R^{72A}$-substituted or unsubstituted heterocycloalkyl, $R^{72A}$-substituted or unsubstituted aryl, or $R^{72A}$-substituted or unsubstituted heteroaryl. $X^{15A}$ is halogen. In embodiments, $X^{15A}$ is F.

$R^{72A}$ is independently oxo, halogen, $-CX^{72A}_3$, $-CHX^{72A}_2$, $-OCH_2X^{72A}$, $-OCHX^{72A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{72A}_3$, $-OCHX^{72A}_2$, $R^{73A}$-substituted or unsubstituted alkyl, $R^{73A}$-substituted or unsubstituted heteroalkyl, $R^{73A}$-substituted or unsubstituted cycloalkyl, $R^{73A}$-substituted or unsubstituted heterocycloalkyl, $R^{73A}$-substituted or unsubstituted aryl, or $R^{73A}$-substituted or unsubstituted heteroaryl. $X^{72A}$ is halogen. In embodiments, $X^{72A}$ is F.

$R^{73A}$ is independently oxo, halogen, $-CX^{73A}_3$, $-CHX^{73A}_2$, $-OCH_2X^{73A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{73A}_3$, $-OCHX^{73A}_2$, $R^{74A}$-substituted or unsubstituted alkyl, $R^{74A}$-substituted or unsubstituted heteroalkyl, $R^{74A}$-substituted or unsubstituted cycloalkyl, $R^{74A}$-substituted or unsubstituted heterocycloalkyl, $R^{74A}$-substituted or unsubstituted aryl, or $R^{74A}$-substituted or unsubstituted heteroaryl. $X^{73A}$ is halogen. In embodiments, $X^{73A}$ is F.

In embodiments, $R^{16A}$ is independently hydrogen, oxo, halogen, $-CX^{16A}_3$, $-CHX^{16A}_2$, $-OCH_2X^{16}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{16}_3$, $-OCHX^{16A}_2$, $R^{75A}$-substituted or unsubstituted alkyl, $R^{75A}$-substituted or unsubstituted heteroalkyl, $R^{75A}$-substituted or unsubstituted cycloalkyl, $R^{75A}$-substituted or unsubstituted heterocycloalkyl, $R^{75A}$-substituted or unsubstituted aryl, or $R^{75A}$-substituted or unsubstituted heteroaryl. $X^{16A}$ is halogen. In embodiments, $X^{16A}$ is F.

$R^{75A}$ is independently oxo, halogen, $-CX^{75A}_3$, $-CHX^{75A}_2$, $-OCH_2X^{75A}$, $-OCHX^{75A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75A}_3$, $-OCHX^{75A}_2$, $R^{76A}$ substituted or unsubstituted alkyl, $R^{76A}$-substituted or unsubstituted heteroalkyl, $R^{76A}$-substituted or unsubstituted cycloalkyl, $R^{76A}$-substituted or unsubstituted heterocycloalkyl, $R^{76A}$-substituted or unsubstituted aryl, or $R^{76A}$-substituted or unsubstituted heteroaryl. $X^{75A}$ is halogen. In embodiments, $X^{75A}$ is F.

$R^{76A}$ is independently oxo, halogen, $-CX^{76A}_3$, $-CHX^{76A}_2$, $-OCH_2X^{76A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76A}_3$, $-OCHX^{76A}_2$, $R^{77A}$-substituted or unsubstituted alkyl, $R^{77A}$-substituted or unsubstituted heteroalkyl, $R^{77A}$-substituted or unsubstituted cycloalkyl, $R^{77A}$-substituted or unsubstituted heterocycloalkyl, $R^{77A}$-substituted or unsubstituted aryl, or $R^{77A}$-substituted or unsubstituted heteroaryl. $X^{76A}$ is halogen. In embodiments, $X^{76A}$ is F.

In embodiments, $R^{17A}$ is independently hydrogen, oxo, halogen, $-CX^{17A}_3$, $-CHX^{17A}_2$, $-OCH_2X^{17A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{17A}_3$, $-OCHX^{17A}_2$, $R^{78A}$-substituted or unsubstituted alkyl, $R^{78A}$-substituted or unsubstituted heteroalkyl, $R^{78A}$-substituted or unsubstituted cycloalkyl, $R^{78A}$-substituted or unsubstituted heterocycloalkyl, $R^{78A}$-substituted or unsubstituted aryl, or $R^{78A}$-substituted or unsubstituted heteroaryl. $X^{17A}$ is halogen. In embodiments, $X^{17A}$ is F.

$R^{78A}$ is independently oxo, halogen, $-CX^{78A}_3$, $-CHX^{78A}_2$, $-OCH_2X^{78A}$, $-OCHX^{78A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{78A}_3$, $-OCHX^{78A}_2$, $R^{79A}$-substituted or unsubstituted alkyl, $R^{79A}$-substituted or unsubstituted heteroalkyl, $R^{79A}$-substituted or unsubstituted cycloalkyl, $R^{79A}$-substituted or unsubstituted heterocycloalkyl, $R^{79A}$-substituted or unsubstituted aryl, or $R^{79A}$-substituted or unsubstituted heteroaryl. $X^{78A}$ is halogen. In embodiments, $X^{78A}$ is F.

$R^{79A}$ is independently oxo, halogen, $-CX^{79A}_3$, $-CHX^{79A}_2$, $-OCH_2X^{79A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{79A}_3$, $-OCHX^{79A}_2$, $R^{80A}$-substituted or unsubstituted alkyl, $R^{80A}$-substituted or unsubstituted heteroalkyl, $R^{80A}$-substituted or unsubstituted cycloalkyl, $R^{80A}$-substituted or unsubstituted heterocycloalkyl, $R^{80A}$-substituted or unsubstituted aryl, or $R^{80A}$-substituted or unsubstituted heteroaryl. $X^{79A}$ is halogen. In embodiments, $X^{79A}$ is F.

In embodiments, $R^{18A}$ is independently hydrogen, oxo, halogen, $-CX^{18A}_3$, $-CHX^{18A}_2$, $-OCH_2X^{18A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{18A}_3$, $-OCHX^{18A}_2$, $R^{81A}$-substituted or unsubstituted alkyl, $R^{81A}$-substituted or unsubstituted heteroalkyl, $R^{81A}$-substituted or unsubstituted cycloalkyl, $R^{81A}$-substituted or unsubstituted heterocycloalkyl, $R^{81A}$-substituted or unsubstituted aryl, or $R^{81A}$-substituted or unsubstituted heteroaryl. $X^{18A}$ is halogen. In embodiments, $X^{18A}$ is F.

$R^{81A}$ is independently oxo, halogen, $-CX^{81A}_3$, $-CHX^{81A}_2$, $-OCH_2X^{81A}$, $-OCHX^{81A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{81A}_3$, $-OCHX^{81A}_2$, $R^{82A}$-substituted or unsubstituted alkyl, $R^{82A}$-substituted or unsubstituted heteroalkyl, $R^{82A}$-substituted or unsubstituted cycloalkyl, $R^{82A}$-substituted or unsubstituted heterocycloalkyl, $R^{82A}$-substituted or unsubstituted aryl, or $R^{82A}$-substituted or unsubstituted heteroaryl. $X^{81A}$ is halogen. In embodiments, $X^{81A}$ is F.

$R^{82A}$ is independently oxo, halogen, $-CX^{82A}_3$, $-CHX^{82A}_2$, $-OCH_2X^{82A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{82A}_3$, $-OCHX^{82A}_2$, $R^{83A}$-substituted or unsubstituted alkyl, $R^{83A}$-substituted or unsubstituted heteroalkyl, $R^{83A}$-substituted or unsubstituted cycloalkyl, $R^{83A}$-substituted or unsubstituted heterocycloalkyl, $R^{83A}$-substituted or unsubstituted aryl, or $R^{83A}$-substituted or unsubstituted heteroaryl. $X^{82A}$ is halogen. In embodiments, $X^{82A}$ is F.

In embodiments, $R^{15B}$ is independently hydrogen, oxo, halogen, $-CX^{15B}_3$, $-CHX^{15B}_2$, $-OCH_2X^{15B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{15B}_3$, $-OCHX^{15B}_2$, $R^{72B}$-substituted or unsubstituted alkyl, $R^{72B}$-substituted or unsubstituted heteroalkyl, $R^{72B}$-substituted or unsubstituted cycloalkyl, $R^{72B}$-substituted or unsubstituted heterocycloalkyl, $R^{72B}$-substituted or unsubstituted aryl, or $R^{72B}$-substituted or unsubstituted heteroaryl. $X^{15B}$ is halogen. In embodiments, $X^{15B}$ is F.

$R^{72B}$ is independently oxo, halogen, $-CX^{72B}_3$, $-CHX^{72B}_2$, $-OCH_2X^{72B}$, $-OCHX^{72B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{72B}_3$, $-OCHX^{72B}_2$, $R^{73B}$-substituted or unsubstituted alkyl, $R^{73B}$-substituted or unsubstituted heteroalkyl, $R^{73B}$-substituted or unsubstituted cycloalkyl, $R^{73B}$-substituted or unsubstituted heterocycloalkyl, $R^{73B}$-substituted or unsubstituted aryl, or $R^{73B}$-substituted or unsubstituted heteroaryl. $X^{72B}$ is halogen. In embodiments, $X^{72B}$ is F.

$R^{73B}$ is independently oxo, halogen, —$CX^{73B}_3$, —$CHX^{73B}_2$, —$OCH_2X^{73B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{73B}_3$, —$OCHX^{73B}_2$, $R^{74B}$-substituted or unsubstituted alkyl, $R^{74B}$-substituted or unsubstituted heteroalkyl, $R^{74B}$-substituted or unsubstituted cycloalkyl, $R^{74B}$-substituted or unsubstituted heterocycloalkyl, $R^{74B}$-substituted or unsubstituted aryl, or $R^{74B}$-substituted or unsubstituted heteroaryl. $X^{73B}$ is halogen. In embodiments, $X^{73B}$ is F.

In embodiments, $R^{16B}$ is independently hydrogen, oxo, halogen, —$CX^{16B}_3$, —$CHX^{16B}_2$, —$OCH_2X^{16B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{16B}_3$, —$OCHX^{16B}_2$, $R^{75B}$-substituted or unsubstituted alkyl, $R^{75B}$-substituted or unsubstituted heteroalkyl, $R^{75B}$-substituted or unsubstituted cycloalkyl, $R^{75B}$-substituted or unsubstituted heterocycloalkyl, $R^{75B}$-substituted or unsubstituted aryl, or $R^{75B}$-substituted or unsubstituted heteroaryl. $X^{16B}$ is halogen. In embodiments, $X^{16B}$ is F.

$R^{75B}$ is independently oxo, halogen, —$CX^{75B}_3$, —$CHX^{75B}_2$, —$OCH_2X^{75B}$, —$OCHX^{75B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{75B}_3$, —$OCHX^{75B}_2$, $R^{76B}$-substituted or unsubstituted alkyl, $R^{76B}$-substituted or unsubstituted heteroalkyl, $R^{76B}$-substituted or unsubstituted cycloalkyl, $R^{76B}$-substituted or unsubstituted heterocycloalkyl, $R^{76B}$-substituted or unsubstituted aryl, or $R^{76B}$-substituted or unsubstituted heteroaryl. $X^{75B}$ is halogen. In embodiments, $X^{75B}$ is F.

$R^{76B}$ is independently oxo, halogen, —$CX^{76B}_3$, —$CHX^{76B}_2$, —$OCH_2X^{76B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{76B}_3$, —$OCHX^{76B}_2$, $R^{77B}$-substituted or unsubstituted alkyl, $R^{77B}$-substituted or unsubstituted heteroalkyl, $R^{77B}$-substituted or unsubstituted cycloalkyl, $R^{77B}$-substituted or unsubstituted heterocycloalkyl, $R^{77B}$-substituted or unsubstituted aryl, or $R^{77B}$-substituted or unsubstituted heteroaryl. $X^{76B}$ is halogen. In embodiments, $X^{76B}$ is F.

In embodiments, $R^{17B}$ is independently hydrogen, oxo, halogen, —$CX^{17B}_3$, —$CHX^{17B}_2$, —$OCH_2X^{17B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{17B}_3$, —$OCHX^{17B}_2$, $R^{78B}$-substituted or unsubstituted alkyl, $R^{78B}$-substituted or unsubstituted heteroalkyl, $R^{78B}$-substituted or unsubstituted cycloalkyl, $R^{78B}$-substituted or unsubstituted heterocycloalkyl, $R^{78B}$-substituted or unsubstituted aryl, or $R^{78B}$-substituted or unsubstituted heteroaryl. $X^{17B}$ is halogen. In embodiments, $X^{17B}$ is F.

$R^{78B}$ is independently oxo, halogen, —$CX^{78B}_3$, —$CHX^{78B}_2$, —$OCH_2X^{78B}$, —$OCHX^{78B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —$OCX^{78B}_3$, —$OCHX^{78B}_2$, $R^{79B}$-substituted or unsubstituted alkyl, $R^{79B}$-substituted or unsubstituted heteroalkyl, $R^{79B}$-substituted or unsubstituted cycloalkyl, $R^{79B}$-substituted or unsubstituted heterocycloalkyl, $R^{79B}$-substituted or unsubstituted aryl, or $R^{79B}$-substituted or unsubstituted heteroaryl. $X^{78B}$ is halogen. In embodiments, $X^{78B}$ is F.

$R^{79B}$ is independently oxo, halogen, —$CX^{79B}_3$, —$CHX^{79B}_2$, —$OCH_2X^{79B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{79B}_3$, —$OCHX^{79B}_2$, $R^{80B}$-substituted or unsubstituted alkyl, $R^{80B}$-substituted or unsubstituted heteroalkyl, $R^{80B}$-substituted or unsubstituted cycloalkyl, $R^{80B}$-substituted or unsubstituted heterocycloalkyl, $R^{80B}$-substituted or unsubstituted aryl, or $R^{80B}$-substituted or unsubstituted heteroaryl. $X^{79B}$ is halogen. In embodiments, $X^{79B}$ is F.

In embodiments, $R^{18B}$ is independently hydrogen, oxo, halogen, —$CX^{18B}_3$, —$CHX^{18B}_2$, —$OCH_2X^{18B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{18B}_3$, —$OCHX^{18B}_2$, $R^{81B}$-substituted or unsubstituted alkyl, $R^{81B}$-substituted or unsubstituted heteroalkyl, $R^{81B}$-substituted or unsubstituted cycloalkyl, $R^{81B}$-substituted or unsubstituted heterocycloalkyl, $R^{81B}$-substituted or unsubstituted aryl, or $R^{81B}$-substituted or unsubstituted heteroaryl. $X^{18B}$ is halogen. In embodiments, $X^{18B}$ is F.

$R^{81B}$ is independently oxo, halogen, —$CX^{81B}_3$, —$CHX^{81B}_2$, —$OCH_2X^{81B}$, —$OCHX^{81B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{81B}_3$, —$OCHX^{81B}_2$, $R^{82B}$-substituted or unsubstituted alkyl, $R^{82B}$-substituted or unsubstituted heteroalkyl, $R^{82B}$-substituted or unsubstituted cycloalkyl, $R^{82B}$-substituted or unsubstituted heterocycloalkyl, $R^{82B}$-substituted or unsubstituted aryl, or $R^{82B}$-substituted or unsubstituted heteroaryl. $X^{81B}$ is halogen. In embodiments, $X^{81B}$ is F.

$R^{82B}$ is independently oxo, halogen, —$CX^{82B}_3$, —$CHX^{82B}_2$, —$OCH_2X^{82B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{82B}_3$, —$OCHX^{82B}_2$, $R^{83B}$-substituted or unsubstituted alkyl, $R^{83B}$-substituted or unsubstituted heteroalkyl, $R^{83B}$-substituted or unsubstituted cycloalkyl, $R^{83B}$-substituted or unsubstituted heterocycloalkyl, $R^{83B}$-substituted or unsubstituted aryl, or $R^{83B}$-substituted or unsubstituted heteroaryl. $X^{82B}$ is halogen. In embodiments, $X^{82B}$ is F.

In embodiments, $R^{15C}$ is independently hydrogen, oxo, halogen, —$CX^{15C}_3$, —$CHX^{15C}_2$, —$OCH_2X^{15C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{15C}_3$, —$OCHX^{15C}_2$, $R^{72C}$-substituted or unsubstituted alkyl, $R^{72C}$-substituted or unsubstituted heteroalkyl, $R^{72C}$-substituted or unsubstituted cycloalkyl, $R^{72C}$-substituted or unsubstituted heterocycloalkyl, $R^{72C}$-substituted or unsubstituted aryl, or $R^{72C}$-substituted or unsubstituted heteroaryl. $X^{15C}$ is halogen. In embodiments, $X^{15C}$ is F.

$R^{72C}$ is independently oxo, halogen, $-CX^{72C}_3$, $-CHX^{72C}_2$, $-OCH_2X^{72C}$, $-OCHX^{72C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{72C}_3$, $-OCHX^{72C}_2$, $R^{73C}$-substituted or unsubstituted alkyl, $R^{73C}$-substituted or unsubstituted heteroalkyl, $R^{73C}$-substituted or unsubstituted cycloalkyl, $R^{73C}$-substituted or unsubstituted heterocycloalkyl, $R^{73C}$-substituted or unsubstituted aryl, or $R^{73C}$-substituted or unsubstituted heteroaryl. $X^{72C}$ is halogen. In embodiments, $X^{72C}$ is F.

$R^{73C}$ is independently oxo, halogen, $-CX^{73C}_3$, $-CHX^{73C}_2$, $-OCH_2X^{73C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{73C}_3$, $-OCHX^{73C}_2$, $R^{74C}$-substituted or unsubstituted alkyl, $R^{74C}$-substituted or unsubstituted heteroalkyl, $R^{74C}$-substituted or unsubstituted cycloalkyl, $R^{74C}$-substituted or unsubstituted heterocycloalkyl, $R^{74C}$-substituted or unsubstituted aryl, or $R^{74C}$-substituted or unsubstituted heteroaryl. $X^{73C}$ is halogen. In embodiments, $X^{73C}$ is F.

In embodiments, $R^{16C}$ is independently hydrogen, oxo, halogen, $-CX^{16C}_3$, $-CHX^{16C}_2$, $-OCH_2X^{16C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{16C}_3$, $-OCHX^{16C}_2$, $R^{75C}$-substituted or unsubstituted alkyl, $R^{75C}$-substituted or unsubstituted heteroalkyl, $R^{75C}$-substituted or unsubstituted cycloalkyl, $R^{75C}$-substituted or unsubstituted heterocycloalkyl, $R^{75C}$-substituted or unsubstituted aryl, or $R^{75C}$-substituted or unsubstituted heteroaryl. $X^{16C}$ is halogen. In embodiments, $X^{16C}$ is F.

$R^{75C}$ is independently oxo, halogen, $-CX^{75C}_3$, $-CHX^{75C}_2$, $-OCH_2X^{75C}$, $-OCHX^{75C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75C}_3$, $-OCHX^{75C}_2$, $R^{76C}$-substituted or unsubstituted alkyl, $R^{76C}$-substituted or unsubstituted heteroalkyl, $R^{76C}$-substituted or unsubstituted cycloalkyl, $R^{76C}$-substituted or unsubstituted heterocycloalkyl, $R^{76C}$-substituted or unsubstituted aryl, or $R^{76C}$-substituted or unsubstituted heteroaryl. $X^{75C}$ is halogen. In embodiments, $X^{75C}$ is F.

$R^{76C}$ is independently oxo, halogen, $-CX^{76C}_3$, $-CHX^{76C}_2$, $-OCH_2X^{76C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76C}_3$, $-OCHX^{76C}_2$, $R^{77C}$-substituted or unsubstituted alkyl, $R^{77C}$-substituted or unsubstituted heteroalkyl, $R^{77C}$-substituted or unsubstituted cycloalkyl, $R^{77C}$-substituted or unsubstituted heterocycloalkyl, $R^{77C}$-substituted or unsubstituted aryl, or $R^{77C}$-substituted or unsubstituted heteroaryl. $X^{76C}$ is halogen. In embodiments, $X^{76C}$ is F.

In embodiments, $R^{17C}$ is independently hydrogen, oxo, halogen, $-CX^{17C}_3$, $-CHX^{17C}_2$, $-OCH_2X^{17C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{17C}_3$, $-OCHX^{17C}_2$, $R^{78C}$-substituted or unsubstituted alkyl, $R^{78C}$-substituted or unsubstituted heteroalkyl, $R^{78C}$-substituted or unsubstituted cycloalkyl, $R^{78C}$-substituted or unsubstituted heterocycloalkyl, $R^{78C}$-substituted or unsubstituted aryl, or $R^{78C}$-substituted or unsubstituted heteroaryl. $X^{17C}$ is halogen. In embodiments, $X^{17C}$ is F.

$R^{78C}$ is independently oxo, halogen, $-CX^{78C}_3$, $-CHX^{78C}_2$, $-OCH_2X^{78C}$, $-OCHX^{78C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{78C}_3$, $-OCHX^{78C}_2$, $R^{79C}$-substituted or unsubstituted alkyl, $R^{79C}$-substituted or unsubstituted heteroalkyl, $R^{79C}$-substituted or unsubstituted cycloalkyl, $R^{79C}$-substituted or unsubstituted heterocycloalkyl, $R^{79C}$-substituted or unsubstituted aryl, or $R^{79C}$-substituted or unsubstituted heteroaryl. $X^{78C}$ is halogen. In embodiments, $X^{78C}$ is F.

$R^{79C}$ is independently oxo, halogen, $-CX^{79C}_3$, $-CHX^{79C}_2$, $-OCH_2X^{79C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{79C}_3$, $-OCHX^{79C}_2$, $R^{80C}$-substituted or unsubstituted alkyl, $R^{80C}$-substituted or unsubstituted heteroalkyl, $R^{80C}$-substituted or unsubstituted cycloalkyl, $R^{80C}$-substituted or unsubstituted heterocycloalkyl, $R^{80C}$-substituted or unsubstituted aryl, or $R^{80C}$-substituted or unsubstituted heteroaryl. $X^{79C}$ is halogen. In embodiments, $X^{79C}$ is F.

In embodiments, $R^{18C}$ is independently hydrogen, oxo, halogen, $-CX^{18C}_3$, $-CHX^{18C}_2$, $-OCH_2X^{18C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{18C}_3$, $-OCHX^{18C}_2$, $R^{81C}$-substituted or unsubstituted alkyl, $R^{81C}$-substituted or unsubstituted heteroalkyl, $R^{81C}$-substituted or unsubstituted cycloalkyl, $R^{81C}$-substituted or unsubstituted heterocycloalkyl, $R^{81C}$-substituted or unsubstituted aryl, or $R^{81C}$-substituted or unsubstituted heteroaryl. $X^{18C}$ is halogen. In embodiments, $X^{18C}$ is F.

$R^{81C}$ is independently oxo, halogen, $-CX^{81C}_3$, $-CHX^{81C}_2$, $-OCH_2X^{81C}$, $-OCHX^{81C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{81C}_3$, $-OCHX^{81C}_2$, $R^{82C}$-substituted or unsubstituted alkyl, $R^{82C}$-substituted or unsubstituted heteroalkyl, $R^{82C}$-substituted or unsubstituted cycloalkyl, $R^{82C}$-substituted or unsubstituted heterocycloalkyl, $R^{82C}$-substituted or unsubstituted aryl, or $R^{82C}$-substituted or unsubstituted heteroaryl. $X^{81C}$ is halogen. In embodiments, $X^{81C}$ is F.

$R^{82C}$ is independently oxo, halogen, $-CX^{82C}_3$, $-CHX^{82C}_2$, $-OCH_2X^{82C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{82C}_3$, $-OCHX^{82C}_2$, $R^{83C}$-substituted or unsubstituted alkyl, $R^{83C}$-substituted or unsubstituted heteroalkyl, $R^{83C}$-substituted or unsubstituted cycloalkyl, $R^{83C}$-substituted or unsubstituted heterocycloalkyl, $R^{83C}$-substituted or unsubstituted aryl, or $R^{83C}$-substituted or unsubstituted heteroaryl. $X^{82C}$ is halogen. In embodiments, $X^{82C}$ is F.

In embodiments, $R^{15D}$ is independently hydrogen, oxo, halogen, $-CX^{15D}_3$, $-CHX^{15D}_2$, $-OCH_2X^{15D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{15D}_3$, $-OCHX^{15D}_2$, $R^{72D}$-substituted or unsubstituted alkyl, $R^{72D}$-substituted or unsubstituted heteroalkyl, $R^{72D}$-substituted or unsubstituted cycloalkyl, $R^{72D}$-substituted or unsubstituted heterocycloalkyl, $R^{72D}$-substituted or unsubstituted aryl, or $R^{72D}$-substituted or unsubstituted heteroaryl. $X^{15D}$ is halogen. In embodiments, $X^{15D}$ is F.

$R^{72D}$ is independently oxo, halogen, $-CX^{72D}_3$, $-CHX^{72D}_2$, $-OCH_2X^{72D}$, $-OCHX^{72D}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{72D}_3$, $-OCHX^{72D}_2$, $R^{73D}$-Substituted or unsubstituted alkyl, $R^{73D}$-substituted or unsubstituted heteroalkyl, $R^{73D}$-substituted or unsubstituted cycloalkyl, $R^{73D}$-substituted or unsubstituted heterocycloalkyl, $R^{73D}$-substituted or unsubstituted aryl, or $R^{73D}$-substituted or unsubstituted heteroaryl. $X^{72D}$ is halogen. In embodiments, $X^{72D}$ is F.

$R^{73D}$ is independently oxo, halogen, $-CX^{73D}_3$, $-CHX^{73D}_2$, $-OCH_2X^{73D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{73D}_3$, $-OCHX^{73D}_2$, $R^{74D}$-substituted or unsubstituted alkyl, $R^{74D}$-substituted or unsubstituted heteroalkyl, $R^{74D}$-substituted or unsubstituted cycloalkyl, $R^{74D}$-substituted or unsubstituted heterocycloalkyl, $R^{74D}$-substituted or unsubstituted aryl, or $R^{74D}$-substituted or unsubstituted heteroaryl. $X^{73D}$ is halogen. In embodiments, $X^{73D}$ is F.

In embodiments, $R^{16D}$ is independently hydrogen, oxo, halogen, $-CX^{16D}_3$, $-CHX^{16D}_2$, $-OCH_2X^{16D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{16D}_3$, $-OCHX^{16D}_2$, $R^{75D}$-substituted or unsubstituted alkyl, $R^{75D}$-substituted or unsubstituted heteroalkyl, $R^{75D}$-substituted or unsubstituted cycloalkyl, $R^{75D}$-substituted or unsubstituted heterocycloalkyl, $R^{75D}$-substituted or unsubstituted aryl, or $R^{75D}$-substituted or unsubstituted heteroaryl. $X^{16D}$ is halogen. In embodiments, $X^{16D}$ is F.

$R^{75D}$ is independently oxo, halogen, $-CX^{75D}_3$, $-CHX^{75D}_2$, $-OCH_2X^{75D}$, $-OCHX^{75D}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75D}_3$, $-OCHX^{75D}_2$, $R^{76D}$-substituted or unsubstituted alkyl, $R^{76D}$-substituted or unsubstituted heteroalkyl, $R^{76D}$-substituted or unsubstituted cycloalkyl, $R^{76D}$-substituted or unsubstituted heterocycloalkyl, $R^{76D}$-substituted or unsubstituted aryl, or $R^{76D}$-substituted or unsubstituted heteroaryl. $X^{75D}$ is halogen. In embodiments, $X^{75D}$ is F.

$R^{76D}$ is independently oxo, halogen, $-CX^{76D}_3$, $-CHX^{76D}_2$, $-OCH_2X^{76D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76D}_3$, $-OCHX^{76D}_2$, $R^{77D}$-substituted or unsubstituted alkyl, $R^{77D}$-substituted or unsubstituted heteroalkyl, $R^{77D}$-substituted or unsubstituted cycloalkyl, $R^{77D}$-substituted or unsubstituted heterocycloalkyl, $R^{77D}$-substituted or unsubstituted aryl, or $R^{77D}$-substituted or unsubstituted heteroaryl. $X^{76D}$ is halogen. In embodiments, $X^{76D}$ is F.

In embodiments, $R^{17D}$ is independently hydrogen, oxo, halogen, $-CX^{17D}_3$, $-CHX^{17D}_2$, $-OCH_2X^{17D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{17D}_3$, $-OCHX^{17D}_2$, $R^{78D}$-substituted or unsubstituted alkyl, $R^{78D}$-substituted or unsubstituted heteroalkyl, $R^{78D}$-substituted or unsubstituted cycloalkyl, $R^{78D}$-substituted or unsubstituted heterocycloalkyl, $R^{78D}$-substituted or unsubstituted aryl, or $R^{78D}$-substituted or unsubstituted heteroaryl. $X^{17D}$ is halogen. In embodiments, $X^{17D}$ is F.

$R^{78D}$ is independently oxo, halogen, $-CX^{78D}_3$, $-CHX^{78D}_2$, $-OCH_2X^{78D}$, $-OCHX^{78D}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{78D}_3$, $-OCHX^{78D}_2$, $R^{79D}$-substituted or unsubstituted alkyl, $R^{79D}$-substituted or unsubstituted heteroalkyl, $R^{79D}$-substituted or unsubstituted cycloalkyl, $R^{79D}$-substituted or unsubstituted heterocycloalkyl, $R^{79D}$-substituted or unsubstituted aryl, or $R^{79D}$-substituted or unsubstituted heteroaryl. $X^{78D}$ is halogen. In embodiments, $X^{78D}$ is F.

$R^{79D}$ is independently oxo, halogen, $-CX^{79D}_3$, $-CHX^{79D}_2$, $-OCH_2X^{79D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{79D}_3$, $-OCHX^{79D}_2$, $R^{80D}$-substituted or unsubstituted alkyl, $R^{80D}$-substituted or unsubstituted heteroalkyl, $R^{80D}$-substituted or unsubstituted cycloalkyl, $R^{80D}$-substituted or unsubstituted heterocycloalkyl, $R^{80D}$-substituted or unsubstituted aryl, or $R^{80D}$-substituted or unsubstituted heteroaryl. $X^{79D}$ is halogen. In embodiments, $X^{79D}$ is F.

In embodiments, $R^{18D}$ is independently hydrogen, oxo, halogen, $-CX^{18D}_3$, $-CHX^{18D}_2$, $-OCH_2X^{18D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{18D}_3$, $-OCHX^{18D}_2$, $R^{81D}$-substituted or unsubstituted alkyl, $R^{81D}$-substituted or unsubstituted heteroalkyl, $R^{81D}$-substituted or unsubstituted cycloalkyl, $R^{81D}$-substituted or unsubstituted heterocycloalkyl, $R^{81D}$-substituted or unsubstituted aryl, or $R^{81D}$-substituted or unsubstituted heteroaryl. $X^{18D}$ is halogen. In embodiments, $X^{18D}$ is F.

$R^{81D}$ is independently oxo, halogen, $-CX^{81D}_3$, $-CHX^{81D}_2$, $-OCH_2X^{81D}$, $-OCHX^{81D}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{81D}_3$, $-OCHX^{81D}_2$, $R^{82D}$-substituted or unsubstituted alkyl, $R^{82D}$-substituted or unsubstituted heteroalkyl, $R^{82D}$-substituted or unsubstituted cycloalkyl, $R^{82D}$-substituted or unsubstituted heterocycloalkyl, $R^{82D}$-substituted or unsubstituted aryl, or $R^{82D}$-substituted or unsubstituted heteroaryl. $X^{81D}$ is halogen. In embodiments, $X^{81D}$ is F.

$R^{82D}$ is independently oxo, halogen, $-CX^{82D}_3$, $-CHX^{82D}_2$, $-OCH_2X^{82D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{82D}_3$, $-OCHX^{82D}_2$, $R^{83D}$-substituted or unsubstituted alkyl, $R^{83D}$-substituted or unsubstituted heteroalkyl, $R^{83D}$-substituted or unsubstituted cycloalkyl, $R^{83D}$-substituted or unsubstituted heterocycloalkyl, $R^{83D}$-substituted or unsubstituted aryl, or $R^{83D}$-substituted or unsubstituted heteroaryl. $X^{82D}$ is halogen. In embodiments, $X^{82D}$ is F.

In embodiments, $L^1$ is a $R^{96}$-substituted or unsubstituted alkylene, $R^{96}$-substituted or unsubstituted heteroalkylene, $R^{96}$-substituted or unsubstituted cycloalkylene, $R^{96}$-substituted or unsubstituted heterocycloalkylene, $R^{96}$-substituted or unsubstituted arylene, or $R^{96}$-substituted or unsubstituted heteroarylene.

$R^{96}$ is independently oxo, halogen, $-CX^{96}_3$, $-CHX^{96}_2$, $-OCH_2X^{96}$, $-OCHX^{96}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}_3$, $-OCHX^{96}_2$, $R^{97}$-substituted or unsubstituted alkyl, $R^{97}$-substituted or unsubstituted heteroalkyl, $R^{97}$-substituted or unsubstituted cycloalkyl, $R^{97}$-substituted or unsubstituted heterocycloalkyl, $R^{97}$-substituted or unsubstituted aryl, or $R^{97}$-substituted or unsubstituted heteroaryl. $X^{96}$ is halogen. In embodiments, $X^{96}$ is F.

$R^{97}$ is independently oxo, halogen, $-CX^{97}_3$, $-CHX^{97}_2$, $-OCH_2X^{97}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{97}_3$, $-OCHX^{97}_2$, $R^{98}$-substituted or unsubstituted alkyl, $R^{98}$-substituted or unsubstituted heteroalkyl, $R^{98}$-substituted or unsubstituted cycloalkyl, $R^{98}$-substituted or unsubstituted heterocycloalkyl, $R^{98}$-substituted or unsubstituted aryl, or $R^{98}$-substituted or unsubstituted heteroaryl. $X^{97}$ is halogen. In embodiments, $X^{97}$ is F.

$R^{22}$, $R^{25}$, $R^{40}$, $R^{43}$, $R^{46}$, $R^{49}$, $R^{58}$, $R^{61}$, $R^{64}$, $R^{67}$, $R^{74}$, $R^{77}$, $R^{80}$, $R^{83}$, $R^{74A}$, $R^{77A}$, $R^{80A}$, $R^{83A}$, $R^{74B}$, $R^{77B}$, $R^{80B}$, $R^{83B}$, $R^{74C}$, $R^{77C}$, $R^{80C}$, $R^{83C}$, $R^{74D}$, $R^{77D}$, $R^{80D}$, $R^{83D}$, $R^{86}$, $R^{89}$, $R^{92}$, and $R^{98}$ are independently hydrogen, oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, a compound as described herein may include multiple instances of $R^1$, $R^2$, $R^7$, $R^8$, $R^9$, $R^{10}$, $R^{11}$, $R^{12}$, $R^{13}$, $R^{14}$, $X^a$, $X^b$, $X^c$, m1, n1, v1, m2, n2, v2, $R^{15}$, $R^{16}$, $R^{17}$, $R^{18}$, $X^{15}$, $X^{16}$, $X^{17}$, $X^{18}$, E, m15, n15, v15, m16, n16, v16, m17, n17, v17, m18, n18, v18, and/or other variables. In such embodiments, each variable may optional be different and be appropriately labeled to distinguish each group for greater clarity. For example, where each $R^1$, $R^2$, $R^7$, $R^8$, $R^9$, $R^{10}$, $R^{11}$, $R^{12}$, $R^{13}$, $R^{14}$, $X^a$, $X^b$, $X^c$, m1, n1, v1, m2, n2, v2, $R^{15}$, $R^{16}$, $R^{17}$, $R^{18}$, $X^{15}$., $X^{16}$., $X^{17}$., E, m15, n15, and/or v15, is different, they may be referred to, for example, as $R^{1.1}$, $R^{1.2}$, $R^{1.3}$, $R^{1.4}$, $R^{1.5}$, $R^{2.1}$, $R^{2.2}$, $R^{2.3}$, $R^{2.4}$, $R^{2.5}$, $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$, $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$, $R^{10.1}$, $R^{10.2}$, $R^{10.3}$, $R^{10.4}$, $R^{10.5}$, $R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$, $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$, $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$, $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$, $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$, $X^{a1}$, $X^{a2}$, $X^{a3}$, $X^{a4}$, $X^{a5}$, $X^{a6}$, $X^{a7}$, $X^{a8}$, $X^{a9}$, $X^{a10}$, $X^{a11}$, $X^{a12}$, $X^{a13}$, $X^{a14}$, $X^{a15}$, $X^{a16}$, $X^{a17}$, $X^{a18}$, $X^{a19}$, $X^{a20}$, $X^{a21}$, $X^{a22}$, $X^{a23}$, $X^{a24}$, $X^{a25}$, $X^{a26}$, $X^{a27}$, $X^{a28}$, $X^{a29}$, $X^{a30}$, $X^{a31}$, $X^{a32}$, $X^{a33}$, $X^{a34}$, $X^{a35}$, $X^{a36}$, $X^{a37}$, $X^{a38}$, $X^{a39}$, $X^{a40}$, $X^{a41}$, $X^{a42}$, $X^{b1}$, $X^{b2}$, $X^{b3}$, $X^{b4}$, $X^{b5}$, $X^{b6}$, $X^{b7}$, $X^{b8}$, $X^{b9}$, $X^{b10}$, $X^{b11}$, $X^{b12}$, $X^{b13}$, $X^{b14}$, $X^{b15}$, $X^{b16}$, $X^{b7}$, $X^{b8}$, $X^{b19}$, $X^{b20}$, $X^{b21}$, $X^{b22}$, $X^{b23}$, $X^{b24}$, $X^{b25}$, $X^{b26}$, $X^{b27}$, $X^{b28}$, $X^{b29}$, $X^{b30}$, $X^{b31}$, $X^{b32}$, $X^{b33}$, $X^{b34}$, $X^{b35}$, $X^{b36}$, $X^{b37}$, $X^{b38}$, $X^{b39}$, $X^{b40}$, $X^{b41}$, $X^{b42}$, $X^{c1}$, $X^{c2}$, $X^{c3}$, $X^{c4}$, $X^{c5}$, $X^{c6}$, $X^{c7}$, $X^{c8}$, $X^{c9}$, $X^{c10}$, $X^{c11}$, $X^{c12}$, $X^{c13}$, $X^{c14}$, $X^{c15}$, $X^{c16}$, $X^{c17}$, $X^{c18}$, $X^{c19}$, $X^{c20}$, $X^{c21}$, $X^{c22}$, $X^{c23}$, $X^{c24}$, $X^{c25}$, $X^{c26}$, $X^{c27}$, $X^{c28}$, $X^{c29}$, $X^{c30}$, $X^{c31}$, $X^{c32}$, $X^{c33}$, $X^{c34}$, $X^{c35}$, $X^{c36}$, $X^{c37}$, $X^{c38}$, $X^{c39}$, $X^{c40}$, $X^{c41}$, $X^{c42}$, $m1^1$, $m1^2$, $m1^3$, $m1^4$, $m1^5$, $m2^1$, $m2^2$, $m2^3$, $m2^4$, $m2^5$, $n1^1$, $n1^2$, $n1^3$, $n1^4$, $n1^5$, $n2^1$, $n2^2$, $n2^3$, $n2^4$, $n2^5$, $v1^1$, $v1^2$, $v1^3$, $v1^4$, $v1^5$, $v2^1$, $v2^2$, $v2^3$, $v2^4$, $v2^5$, $R^{15.1}$, $R^{15.2}$, $R^{15.3}$, $R^{15.4}$, $R^{15.5}$, $R^{15.6}$, $R^{15.7}$, $R^{15.8}$, $R^{15.9}$, $R^{15.10}$, $R^{15.11}$, $R^{15.12}$, $R^{15.13}$, $R^{15.14}$, $R^{15.15}$, $R^{15.16}$, $R^{15.17}$, $R^{15.18}$, $R^{15.19}$, $R^{15.20}$, $R^{15.21}$, $R^{15.22}$, $R^{15.23}$, $R^{15.24}$, $R^{15.25}$, $R^{15.26}$, $R^{15.27}$, $R^{15.28}$, $R^{15.29}$, $R^{15.30}$, $R^{15.31}$, $R^{15.32}$, $R^{15.33}$, $R^{15.34}$, $R^{15.35}$, $R^{15.36}$, $R^{15.37}$, $R^{15.38}$, $R^{15.39}$, $R^{15.40}$, $R^{15.41}$, $R^{15.42}$, $R^{16.1}$, $R^{16.2}$, $R^{16.3}$, $R^{16.4}$, $R^{16.5}$, $R^{16.6}$, $R^{16.7}$, $R^{16.8}$, $R^{16.9}$, $R^{16.10}$, $R^{16.11}$, $R^{16.12}$, $R^{16.13}$, $R^{16.14}$, $R^{16.15}$, $R^{16.16}$, $R^{16.17}$, $R^{16.18}$, $R^{16.19}$, $R^{16.20}$, $R^{16.21}$, $R^{16.22}$, $R^{16.23}$, $R^{16.24}$, $R^{16.25}$, $R^{16.26}$, $R^{16.27}$, $R^{16.28}$, $R^{16.29}$, $R^{16.30}$, $R^{16.31}$, $R^{16.32}$, $R^{16.33}$, $R^{16.34}$, $R^{16.35}$, $R^{16.36}$, $R^{16.37}$, $R^{16.38}$, $R^{16.39}$, $R^{16.40}$, $R^{16.41}$, $R^{16.42}$, $R^{17.1}$, $R^{17.2}$, $R^{17.3}$, $R^{17.4}$, $R^{17.5}$, $R^{17.6}$, $R^{17.7}$, $R^{17.8}$, $R^{17.9}$, $R^{17.10}$, $R^{17.11}$, $R^{17.12}$, $R^{17.13}$, $R^{17.14}$, $R^{17.15}$, $R^{17.16}$, $R^{17.17}$, $R^{17.18}$, $R^{17.19}$, $R^{17.20}$, $R^{17.21}$, $R^{17.22}$, $R^{17.23}$, $R^{17.24}$, $R^{17.25}$, $R^{17.26}$, $R^{17.27}$, $R^{17.28}$, $R^{17.29}$, $R^{17.30}$, $R^{17.31}$, $R^{17.32}$, $R^{17.33}$, $R^{17.34}$, $R^{17.35}$, $R^{17.36}$, $R^{17.37}$, $R^{17.38}$, $R^{17.39}$, $R^{17.40}$, $R^{17.41}$, $R^{17.42}$, $R^{18.1}$, $R^{18.2}, R^{18.3}, R^{18.4}, R^{18.5}, R^{18.6}, R^{18.7}, R^{18.8}, R^{18.9}, R^{18.10}, R^{18.11}, R^{18.12}, R^{18.13}, R^{18.14}, R^{18.15}, R^{18.16}, R^{18.17}, R^{18.18}, R^{18.19}, R^{18.20}, R^{18.21}, R^{18.22}, R^{18.23}, R^{18.24}, R^{18.25}, R^{18.26}, R^{18.27}, R^{18.28}, R^{18.29}, R^{18.30}, R^{18.31}, R^{18.32}, R^{18.33}, R^{18.34}, R^{18.35}, R^{18.36}, R^{18.37}, R^{18.38}, R^{18.39}, R^{18.40}, R^{18.41}, R^{18.42}; X^{15.1}, X^{15.2}, X^{15.3}, X^{15.4}, X^{15.5}, X^{15.6}, X^{15.7}, X^{15.8}, X^{15.9}, X^{15.10}, X^{15.11}, X^{15.12}, X^{15.13}, X^{15.14}, X^{15.15}, X^{15.16}, X^{15.17}, X^{15.18}, X^{15.19}, X^{15.20}, X^{15.21}, X^{15.22}, X^{15.23}, X^{15.24}, X^{15.25}, X^{15.26}, X^{15.27}, X^{15.28}, X^{15.29}, X^{15.30}, X^{15.31}, X^{15.32}, X^{15.33}, X^{15.34}, X^{15.35}, X^{15.36}, X^{15.37}, X^{15.38}, X^{15.39}, X^{15.40}, X^{15.41}, X^{15.42}, X^{16.1}, X^{16.2}, X^{16.3}, X^{16.4}, X^{16.5}, X^{16.6}, X^{16.7}, X^{16.8}, X^{16.9}, X^{16.10}, X^{16.11}, X^{16.12}, X^{16.13}, X^{16.14}, X^{16.15}, X^{16.16}, X^{16.17}, X^{16.18}, X^{16.19}, X^{16.20}, X^{16.21}, X^{16.22}, X^{16.23}, X^{16.24}, X^{16.25}, X^{16.26}, X^{16.27}, X^{16.28}, X^{16.29}, X^{16.30}, X^{16.31}, X^{16.32}, X^{16.33}, X^{16.34}, X^{16.35}, X^{16.36}, X^{16.37}, X^{16.38}, X^{16.39}, X^{16.40}, X^{16.41}, X^{16.42}, X^{17.1}, X^{17.2}, X^{17.3}, X^{17.4}, X^{17.5}, X^{17.6}, X^{17.7}, X^{17.8}, X^{17.9}, X^{17.10}, X^{17.11}, X^{17.12}, X^{17.13}, X^{17.14}, X^{17.15}, X^{17.16}, X^{17.17}, X^{17.18}, X^{17.19}, X^{17.20}, X^{17.21}, X^{17.22}, X^{17.23}, X^{17.24}, X^{17.25}, X^{17.26}, X^{17.27}, X^{17.28}, X^{17.29}, X^{17.30}, X^{17.31}, X^{17.32}, X^{17.33}, X^{17.34}, X^{17.35}, X^{17.36}, X^{17.37}, X^{17.38}, X^{17.39}, X^{17.40}, X^{17.41}, X^{17.42}, X^{18.1}, X^{18.2}, X^{18.3}, X^{18.4}, X^{18.5}, X^{18.6}, X^{18.7}, X^{18.8}, X^{18.9}, X^{18.10}, X^{18.11}, X^{18.12}, X^{18.13}, X^{18.14}, X^{18.15}, X^{18.16}, X^{18.17}, X^{18.18}, X^{18.19}, X^{18.20}, X^{18.21}, X^{18.22}, X^{18.23}, X^{18.24}, X^{18.25}, X^{18.26}, X^{18.27}, X^{18.28}, X^{18.29}, X^{18.30}, X^{18.31}, X^{18.32}, X^{18.33}, X^{18.34}, X^{18.35}, X^{18.36}, X^{18.37}, X^{18.38}, X^{18.39}, X^{18.40}, X^{18.41}, X^{18.42}, E^1, E^2, E^3, E^4, E^5, m15^1, m15^2, m15^3, m15^4, m15^5, n1^1, n1^2, n1^3, n1^4, n1^5, n15^1, n15^2, n15^3, n15^4, n15^5, v1^1, v1^2, v1^3, v1^4, v1^5, v15^1, v15^2, v15^3, v15^4, v15^5, m16^1, m16^2, m16^3, m16^4, m16^5, n16^1, n16^2, n16^3, n16^4, n16^5, v16^1, v16^2, v16^3, v16^4, v16^5, m17^1, m17^2, m17^3, m17^4, m17^5, n17^1, n17^2, n17^3, n17^4, n17^5, v17^1, v17^2, v17^3, v17^4, v17^5, m18^1, m18^2, m18^3, m18^4, m18^5, n18^1, n18^2, n18^3, n18^4, n18^5, v18^1, v18^2, v18^3, v18^4, v18^5$, respectively, wherein the definition of $R^1$ is assumed by $R^{1.1}, R^{1.2}, R^{1.3}, R^{1.4}, R^{1.5}$; $R^2$ is assumed by $R^{2.1}, R^{2.2}, R^{2.3}, R^{2.4}, R^{2.5}$; $R^7$ is assumed by $R^{7.1}, R^{7.2}, R^{7.3}, R^{7.4}, R^{7.5}, R^{7.6}, R^{7.7}, R^{7.8}, R^{7.9}, R^{7.10}, R^{7.11}, R^{7.12}, R^{7.13}, R^{7.14}, R^{7.15}, R^{7.16}, R^{7.17}, R^{7.18}, R^{7.19}, R^{7.20}, R^{7.21}, R^{7.22}, R^{7.23}, R^{7.24}, R^{7.25}, R^{7.26}, R^{7.27}, R^{7.28}, R^{7.29}, R^{7.30}, R^{7.31}, R^{7.32}, R^{7.33}, R^{7.34}, R^{7.35}, R^{7.36}, R^{7.37}, R^{7.38}, R^{7.39}, R^{7.40}, R^{7.41}, R^{7.42}$; $R^8$ is assumed by $R^{8.1}, R^{8.2}, R^{8.3}, R^{8.4}, R^{8.5}, R^{8.6}, R^{8.7}, R^{8.8}, R^{8.9}, R^{8.10}, R^{8.11}, R^{8.12}, R^{8.13}, R^{8.14}, R^{8.15}, R^{8.16}, R^{8.17}, R^{8.18}, R^{8.19}, R^{8.20}, R^{8.21}, R^{8.22}, R^{8.23}, R^{8.24}, R^{8.25}, R^{8.26}, R^{8.27}, R^{8.28}, R^{8.29}, R^{8.30}, R^{8.31}, R^{8.32}, R^{8.33}, R^{8.34}, R^{8.35}, R^{8.36}, R^{8.37}, R^{8.38}, R^{8.39}, R^{8.40}, R^{8.41}, R^{8.42}$; $R^9$ is assumed by $R^{9.1}, R^{9.2}, R^{9.3}, R^{9.4}, R^{9.5}, R^{9.6}, R^{9.7}, R^{9.8}, R^{9.9}, R^{9.10}, R^{9.11}, R^{9.12}, R^{9.13}, R^{9.14}, R^{9.15}, R^{9.16}, R^{9.17}, R^{9.18}, R^{9.19}, R^{9.20}, R^{9.21}, R^{9.22}, R^{9.23}, R^{9.24}, R^{9.25}, R^{9.26}, R^{9.27}, R^{9.28}, R^{9.29}, R^{9.30}, R^{9.31}, R^{9.32}, R^{9.33}, R^{9.34}, R^{9.35}, R^{9.36}, R^{9.37}, R^{9.38}, R^{9.39}, R^{9.40}, R^{9.41}, R^{9.42}$; $R^{10}$ is assumed by $R^{10.1}, R^{10.2}, R^{10.3}, R^{10.4}, R^{10.5}, R^{10.6}, R^{10.7}, R^{10.8}, R^{10.9}, R^{10.10}, R^{10.11}, R^{10.12}, R^{10.13}, R^{10.14}, R^{10.15}, R^{10.16}, R^{10.17}, R^{10.18}, R^{10.19}, R^{10.20}, R^{10.21}, R^{10.22}, R^{10.23}, R^{10.24}, R^{10.25}, R^{10.26}, R^{10.27}, R^{10.28}, R^{10.29}, R^{10.30}, R^{10.31}, R^{10.32}, R^{10.33}, R^{10.34}, R^{10.35}, R^{10.36}, R^{10.37}, R^{10.38}, R^{10.39}, R^{10.40}, R^{10.41}, R^{10.42}$; $R^{11}$ is assumed by $R^{11.1}, R^{11.2}, R^{11.3}, R^{11.4}, R^{11.5}, R^{11.6}, R^{11.7}, R^{11.8}, R^{11.9}, R^{11.10}, R^{11.11}, R^{11.12}, R^{11.13}, R^{11.14}, R^{11.15}, R^{11.16}, R^{11.17}, R^{11.18}, R^{11.19}, R^{11.20}, R^{11.21}, R^{11.22}, R^{11.23}, R^{11.24}, R^{11.25}, R^{11.26}, R^{11.27}, R^{11.28}, R^{11.29}, R^{11.30}, R^{11.31}, R^{11.32}, R^{11.33}, R^{11.34}, R^{11.35}, R^{11.36}, R^{11.37}, R^{11.38}, R^{11.39}, R^{11.40}, R^{11.41}, R^{11.42}$; $R^{12}$ is assumed by $R^{12.1}, R^{12.2}, R^{12.3}, R^{12.4}, R^{12.5}, R^{12.6}, R^{12.7}, R^{12.8}, R^{12.9}, R^{12.10}, R^{12.11}, R^{12.12}, R^{12.13}, R^{12.14}, R^{12.15}, R^{12.16}, R^{12.17}, R^{12.18}, R^{12.19}, R^{12.20}, R^{12.21}, R^{12.22}, R^{12.23}, R^{12.24}, R^{12.25}, R^{12.26}, R^{12.27}, R^{12.28}, R^{12.29}, R^{12.30}, R^{12.31}, R^{12.32}, R^{12.33}, R^{12.34}, R^{12.35}, R^{12.36}, R^{12.37}, R^{12.38}, R^{12.39}, R^{12.40}, R^{12.41}, R^{12.42}$; $R^{13}$ is assumed by $R^{13.1}, R^{13.2}, R^{13.3}, R^{13.4}, R^{13.5}, R^{13.6}, R^{13.7}, R^{13.8}, R^{13.9}, R^{13.10}, R^{13.11}, R^{13.12}, R^{13.13}, R^{13.14}, R^{13.15}, R^{13.16}, R^{13.17}, R^{13.18}, R^{13.19}, R^{13.20}, R^{13.21}, R^{13.22}, R^{13.23}, R^{13.24}, R^{13.25}, R^{13.26}, R^{13.27}, R^{13.28}, R^{13.29}, R^{13.30}, R^{13.31}, R^{13.32}, R^{13.33}, R^{13.34}, R^{13.35}, R^{13.36}, R^{13.37}, R^{13.38}, R^{13.39}, R^{13.40}, R^{13.41}, R^{13.42}$; $R^{14}$ is assumed by $R^{14.1}, R^{14.2}, R^{14.3}, R^{14.4}, R^{14.5}, R^{14.6}, R^{14.7}, R^{14.8}, R^{14.9}, R^{14.10}, R^{14.11}, R^{14.12}, R^{14.13}, R^{14.14}, R^{14.15}, R^{14.16}, R^{14.17}, R^{14.18}, R^{14.19}, R^{14.20}, R^{14.21}, R^{14.22}, R^{14.23}, R^{14.24}, R^{14.25}, R^{14.26}, R^{14.27}, R^{14.28}, R^{14.29}, R^{14.30}, R^{14.31}, R^{14.32}, R^{14.33}, R^{14.34}, R^{14.35}, R^{14.36}, R^{14.37}, R^{14.38}, R^{14.39}, R^{14.40}, R^{14.41}, R^{14.42}$; $X^a$ is assumed by $X^{a1}, X^{a2}, X^{a3}, X^{a4}, X^{a5}, X^{a6}, X^{a7}, X^{a8}, X^{a9}, X^{a10}, X^{a11}, X^{a12}, X^{a13}, X^{a14}, X^{a15}, X^{a16}, X^{a17}, X^{a18}, X^{a19}, X^{a20}, X^{a21}, X^{a22}, X^{a23}, X^{a24}, X^{a25}, X^{a26}, X^{a27}, X^{a28}, X^{a29}, X^{a30}, X^{a31}, X^{a32}, X^{a33}, X^{a34}, X^{a35}, X^{a36}, X^{a37}, X^{a38}, X^{a39}, X^{a40}, X^{a41}, X^{a42}$; $X^b$ is assumed by $X^{b1}, X^{b2}, X^{b3}, X^{b4}, X^{b5}, X^{b6}, X^{b7}, X^{b8}, X^{b9}, X^{b10}, X^{b11}, X^{b12}, X^{b13}, X^{b14}, X^{b15}, X^{b16}, X^{b17}, X^{b18}, X^{b19}, X^{b20}, X^{b21}, X^{b22}, X^{b23}, X^{b24}, X^{b25}, X^{b26}, X^{b27}, X^{b28}, X^{b29}, X^{b30}, X^{b31}, X^{b32}, X^{b33}, X^{b34}, X^{b35}, X^{b36}, X^{b37}, X^{b38}, X^{b39}, X^{b40}, X^{b41}, X^{b42}$; $X^c$ is assumed by $X^{c1}, X^{c2}, X^{c3}, X^{c4}, X^{c5}, X^{c6}, X^{c7}, X^{c8}, X^{c9}, X^{c10}, X^{c11}, X^{c12}, X^{c13}, X^{c14}, X^{c15}, X^{c16}, X^{c17}, X^{c18}, X^{c19}, X^{c20}, X^{c21}, X^{c22}, X^{c23}, X^{c24}, X^{c25}, X^{c26}, X^{c27}, X^{c28}, X^{c29}, X^{c30}, X^{c31}, X^{c32}, X^{c33}, X^{c34}, X^{c35}, X^{c36}, X^{c37}, X^{c38}, X^{c39}, X^{c40}, X^{c41}, X^{c42}$; m1 is assumed by $m1^1, m1^2, m1^3, m1^4, m1^5$; n1 is assumed by $n1^1, n1^2, n1^3, n1^4, n1^5$; v1 is assumed by $v1^1, v1^2, v1^3, v1^4, v1^5$; m2 is assumed by $m2^1, m2^2, m2^3, m2^4, m2^5$; n2 is assumed by $n2^1, n2^2, n2^3, n2^4, n2^5$; v2 is assumed by $v2^1, v2^2, v2^3, v2^4, v2^5$; $R^{15}$ is assumed by $R^{15.1}, R^{15.2}, R^{15.3}, R^{15.4}, R^{15.5}, R^{15.6}, R^{15.7}, R^{15.8}, R^{15.9}, R^{15.10}, R^{15.11}, R^{15.12}, R^{15.13}, R^{15.14}, R^{15.15}, R^{15.16}, R^{15.17}, R^{15.18}, R^{15.19}, R^{15.20}, R^{15.21}, R^{15.22}, R^{15.23}, R^{15.24}, R^{15.25}, R^{15.26}, R^{15.27}, R^{15.28}, R^{15.29}, R^{15.30}, R^{15.31}, R^{15.32}, R^{15.33}, R^{15.34}, R^{15.35}, R^{15.36}, R^{15.37}, R^{15.38}, R^{15.39}, R^{15.40}, R^{15.41}, R^{15.42}$; $R^{16}$ is assumed by $R^{16.1}, R^{16.2}, R^{16.3}, R^{16.4}, R^{16.5}, R^{16.6}, R^{16.7}, R^{16.8}, R^{16.9}, R^{16.10}, R^{16.11}, R^{16.12}, R^{16.13}, R^{16.14}, R^{16.15}, R^{16.16}, R^{16.17}, R^{16.18}, R^{16.19}, R^{16.20}, R^{16.21}, R^{16.22}, R^{16.23}, R^{16.24}, R^{16.25}, R^{16.26}, R^{16.27}, R^{16.28}, R^{16.29}, R^{16.30}, R^{16.31}, R^{16.32}, R^{16.33}, R^{16.34}, R^{16.35}, R^{16.36}, R^{16.37}, R^{16.38}, R^{16.39}, R^{16.40}, R^{16.41}, R^{16.42}$; $R^{17}$ is assumed by $R^{17.1}, R^{17.2}, R^{17.3}, R^{17.4}, R^{17.5}, R^{17.6}, R^{17.7}, R^{17.8}, R^{17.9}, R^{17.10}, R^{17.11}, R^{17.12}, R^{17.13}, R^{17.14}, R^{17.15}, R^{17.16}, R^{17.17}, R^{17.18}, R^{17.19}, R^{17.20}, R^{17.21}, R^{17.22}, R^{17.23}, R^{17.24}, R^{17.25}, R^{17.26}, R^{17.27}, R^{17.28}, R^{17.29}, R^{17.30}, R^{17.31}, R^{17.32}, R^{17.33}, R^{17.34}, R^{17.35}, R^{17.36}, R^{17.37}, R^{17.38}, R^{17.39}, R^{17.40}, R^{17.41}, R^{17.42}$; $R^{18}$ is assumed by $R^{18.1}, R^{18.2}, R^{18.3}, R^{18.4}, R^{18.5}, R^{18.6}, R^{18.7}, R^{18.8}, R^{18.9}, R^{18.10}, R^{18.11}, R^{18.12}, R^{18.13}, R^{18.14}, R^{18.15}, R^{18.16}, R^{18.17}, R^{18.18}, R^{18.19}, R^{18.20}, R^{18.21}, R^{18.22}, R^{18.23}, R^{18.24}, R^{18.25}, R^{18.26}, R^{18.27}, R^{18.28}, R^{18.29}, R^{18.30}, R^{18.31}, R^{18.32}, R^{18.33}, R^{18.34}, R^{18.35}, R^{18.36}, R^{18.37}, R^{18.38}, R^{18.39}, R^{18.40}, R^{18.41}, R^{18.42}$; $X^{15.}$ is assumed by $X^{15.1}, X^{15.2}, X^{15.3}, X^{15.4}, X^{15.5}, X^{15.6}, X^{15.7}, X^{15.8}, X^{15.9}, X^{15.10}, X^{15.11}, X^{15.12}, X^{15.13}, X^{15.14}, X^{15.15}, X^{15.16}, X^{15.17}, X^{15.18}, X^{15.19}, X^{15.20}, X^{15.21}, X^{15.22}, X^{15.23}, X^{15.24}, X^{15.25}, X^{15.26}, X^{15.27}, X^{15.28}, X^{15.29}, X^{15.30}, X^{15.31}, X^{15.32}, X^{15.33}, X^{15.34}, X^{15.35}, X^{15.36}, X^{15.37}, X^{15.38}, X^{15.39}, X^{15.40}, X^{15.41}, X^{15.42}$; $X^{16.}$ is assumed by $X^{16.1}, X^{16.2}, X^{16.3}, X^{16.4}, X^{16.5}, X^{16.6}, X^{16.7}, X^{16.8}, X^{16.9}, X^{16.10}, X^{16.11}, X^{16.12}, X^{16.13}, X^{16.14}, X^{16.15}, X^{16.16}, X^{16.17}, X^{16.18}, X^{16.19}, X^{16.20}, X^{16.21}, X^{16.22}, X^{16.23}, X^{16.24}, X^{16.25}, X^{16.26}, X^{16.27}, X^{16.28}, X^{16.29}, X^{16.30}, X^{16.31}, X^{16.32}, X^{16.33}, X^{16.34}, X^{16.35}, X^{16.36}, X^{16.37}, X^{16.38}, X^{16.39}, X^{16.40}, X^{16.41}, X^{16.42}$; $X^{17.}$ is assumed by $X^{17.1}, X^{17.2}, X^{17.3}, X^{17.4}, X^{17.5}, X^{17.6}, X^{17.7}, X^{17.8}, X^{17.9}, X^{17.10}, X^{17.11}, X^{17.12}, X^{17.13}, X^{17.14}, X^{17.15}, X^{17.16}, X^{17.17}, X^{17.18}, X^{17.19}, X^{17.20}, X^{17.21}, X^{17.22}, X^{17.23}, X^{17.24}, X^{17.25}, X^{17.26}, X^{17.27}, X^{17.28}, X^{17.29}, X^{17.30}, X^{17.31}, X^{17.32}, X^{17.33}, X^{17.34}, X^{17.35}, X^{17.36}, X^{17.37}, X^{17.38}, X^{17.39}, X^{17.40}, X^{17.41}, X^{17.42}$; $X^{18.}$ is assumed $X^{18.1}, X^{18.2}, X^{18.3}, X^{18.4}, X^{18.5}, X^{18.6}, X^{18.7}, X^{18.8}, X^{18.9}, X^{18.10}, X^{18.11}, X^{18.12}, X^{18.13}$ $X^{18.14}$, $X^{18.15}$, $X^{18.16}$, $X^{18.17}$, $X^{18.18}$, $X^{18.19}$, $X^{18.20}$, $X^{18.21}$, $X^{18.22}$, $X^{18.23}$, $X^{18.24}$, $X^{18.25}$, $X^{18.26}$, $X^{18.27}$, $X^{18.28}$, $X^{18.29}$, $X^{18.30}$, $X^{18.31}$, $X^{18.32}$, $X^{18.33}$, $X^{18.34}$, $X^{18.35}$, $X^{18.36}$, $X^{18.37}$, $X^{18.38}$, $X^{18.39}$, $X^{18.40}$, $X^{18.41}$, $X^{18.42}$; E is assumed by $E^1$, $E^2$, $E^3$, $E^4$, $E^5$; m15 is assumed by $m15^1$, $m15^2$, $m15^3$, $m15^4$, $m15^5$; n15 is assumed by $n15^1$, $n15^2$, $n15^3$, $n15^4$, $n15^5$; v15 is assumed by $v15^1$, $v15^2$, $v15^3$, $v15^4$, $v15^5$; m16 is assumed by $m16^1$, $m16^2$, $m16^3$, $m16^4$, $m16^5$; n16 is assumed by $n16^1$, $n16^2$, $n16^3$, $n16^4$, $n16^5$; v16 is assumed by $v16^1$, $v16^2$, $v16^3$, $v16^4$, $v16^5$; m17 is assumed by $m17^1$, $m17^2$, $m17^3$, $m17^4$, $m17^5$; n17 is assumed by $n17^1$, $n17^2$, $n17^3$, $n17^4$, $n17^5$; and/or v17 is assumed by $v17^1$, $v17^2$, $v17^3$, $v17^4$, $v17^5$; m18 is assumed by $m18^1$, $m18^2$, $m18^3$, $m18^4$, $m18^5$; n18 is assumed by $n18^1$, $n18^2$, $n18^3$, $n18^4$, $n18^5$; and/or v18 is assumed by $v18^1$, $v18^2$, $v18^3$, $v18^4$, $v18^5$. The variables used within a definition of $R^1$, $R^2$, $R^7$, $R^8$, $R^9$, $R^{10}$, $R^{11}$, $R^{12}$, $R^{13}$, $R^{14}$, $X^a$, $X^b$, $X^c$, m1, n1, v1, m2, n2, v2, $R^{15}$, $R^{16}$, $R^{17}$, $R^{18}$, $X^{15}$, $X^{16}$, $X^{17}$, $X^{18}$, E, m15, n15, v15, m16, n16, v16, m17, n17, v17, m18, n18, v18, and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

C. NUCLEAR RECEPTORS

In another aspect is provided a nuclear receptor protein covalently bonded to a compound (e.g., an inhibitor or an AR inhibitor), for example a compound as described herein.

In embodiments, the compound is covalently bonded to a cysteine residue of the nuclear receptor protein. In embodiments, the compound is covalently bonded to an aspartate residue of the nuclear receptor protein. In embodiments, the compound is covalently bonded to a glutamate residue of the nuclear receptor protein. In embodiments, the compound is covalently bonded to a tyrosine residue of the nuclear receptor protein. In embodiments, the compound is covalently bonded to a lysine residue of the nuclear receptor protein. In embodiments, the compound is covalently bonded to a serine residue of the nuclear receptor protein. In embodiments, the covalent bond is reversible. In embodiments, the covalent bond is irreversible. In embodiments, the nuclear receptor is a human receptor. In embodiments, the nuclear receptor is an androgen receptor. In embodiments, the androgen receptor is a human receptor. In embodiments, the compound is covalently bonded to Cys784. In embodiments, the compound is covalently bonded to a residue corresponding to Cys784 of human androgen receptor. In some embodiments, the covalently modified nuclear receptor (e.g., androgen receptor) has a modulated activity relative to a control. In embodiments, the nuclear receptor includes a mutation. In embodiments the mutation includes a residue that covalently bonds the compound. In embodiments, the covalently modified nuclear receptor protein (e.g., androgen receptor, human receptor, human androgen receptor) is in a subject. In embodiments, the covalently modified nuclear receptor protein (e.g., androgen receptor, human receptor, human androgen receptor) is in a sample extracted from a subject. In embodiments, the covalently modified nuclear receptor protein (e.g., androgen receptor, human receptor, human androgen receptor) is from a subject.

D. PHARMACEUTICAL COMPOSITIONS

In another aspect is provided a pharmaceutical composition including a pharmaceutically acceptable excipient and a compound, or pharmaceutically acceptable salt thereof, as described herein, including embodiments (e.g. compound of formula I or II, or any embodiment thereof; or in an example, table, figure, or claim).

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer (e.g. prostate cancer) or an aberrant level of androgen receptor activity or a disease associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism). In embodiments, the second agent is an anti-cancer agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at a site that does not include the hormone binding site. In embodiments, the second agent binds androgen receptor at a site that does is not the hormone binding site. In embodiments, the second agent does not bind the ligand binding domain. In embodiments, the second agent binds androgen receptor at a site that is different from the site bound by a compound described herein, including embodiments. In embodiments, the second agent binds androgen receptor at a site that does not overlap with the binding site of a compound described herein, including embodiments. In embodiments, the second agent is a luteinizing hormone-releasing hormone analogue (LHRH analogue or analog). In embodiments, the second agent is a luteinizing hormone-releasing hormone agonist. In embodiments, the second agent is a luteinizing hormone-releasing hormone analogue antagonist. In embodiments, the second agent is a gonadotropin-releasing hormone analogue (GnRH analogue or analog). In embodiments, the second agent is a gonadotropin-releasing hormone agonist. In embodiments, the second agent is a gonadotropin-releasing hormone analogue antagonist. In embodiments, the second agent is leuprolide, goserelin, triptorelin, hisrelin, degarelix, or abiraterone. A luteinizing hormone-releasing hormone analogue or gonadotropin-releasing hormone analogue is a composition (e.g., peptide) that interacts with (binds) the GnRH receptor and modulates the release of pituitary gonadotropins follicle-stimulating hormone and/or luteinizing hormone. In embodiments, the second agent is avorelin, buserelin, deslorelin, gonadorelin, goserelin, histrelin, leuprorelin, lutrelin, nafarelin, peforelin, or triptorelin. In embodiments, the second agent is abarelix, cetrorelix, degarelix, detirelix, ganirelix, iturelix, oxarelix, prazarelix, ramorelix, or teverelix.

E. METHODS OF TREATMENT

In another aspect is provided a method of treating a nuclear receptor activity-associated disease in a subject in need of such treatment, the method including administering a compound, or a pharmaceutically acceptable salt thereof, as described herein, including embodiments (e.g. compound of formula I or II, or any embodiment thereof; or in an example, table, figure, or claim).

In embodiments of the method, the compound, or pharmaceutically acceptable salt thereof, is included in an effective amount. In embodiments of the method, the compound, or pharmaceutically acceptable salt thereof, is included in a therapeutically effective amount. In embodiments of the method, the compound, or pharmaceutically acceptable salt thereof, is included in a prophylactically effective amount.

In embodiments, the method includes administering a second agent (e.g. therapeutic agent). In embodiments, the method includes administering a second agent (e.g. therapeutic agent) in a therapeutically effective amount. In embodiments of the methods, the second agent is an agent for treating cancer (e.g. prostate cancer) or an aberrant level of androgen receptor activity or a disease associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism). In embodiments, the second agent is an anti-cancer agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at a site that does not include the hormone binding site. In embodiments, the second agent binds androgen receptor at a site that does is not the hormone binding site. In embodiments, the second agent does not bind the ligand binding domain. In embodiments, the second agent binds androgen receptor at a site that is different from the site bound by a compound described herein, including embodiments. In embodiments, the second agent binds androgen receptor at a site that does not overlap with the binding site of a compound described herein, including embodiments. In embodiments, the second agent is a second agent described herein (e.g., in the pharmaceutical composition section above).

In embodiments, the nuclear receptor activity-associated disease is cancer. In embodiments, the nuclear receptor activity-associated disease is an androgen receptor activity-associated disease. In embodiments, the androgen receptor activity-associated disease is prostate cancer, benign prostatic hyperplasia, hypersexuality, acne, amenorrhea, seborrhea, hirsutism, androgenic alopecia, hidradenitis suppurativa, or hyperandrogenism. In embodiments, the disease is prostate cancer. In embodiments, the disease is hormone-sensitive prostate cancer. In embodiments, the disease is hormone-insensitive prostate cancer. In embodiments, the cancer is drug-resistant cancer. In embodiments, the prostate cancer is drug-resistant prostate cancer. In embodiments, the prostate cancer is casodex-resistant prostate cancer. In embodiments, the prostate cancer is Flutamide-resistant prostate cancer. In embodiments, the prostate cancer is MDV3100-resistant prostate cancer. In embodiments, the prostate cancer is ARN-509-resistant prostate cancer. In embodiments, the subject is resistant to casodex, flutamide, MDV3100, and/or ARN-509. In embodiments, the method of treatment includes a delay in drug resistance. In embodiments, the method of treatment includes a delay in drug resistance relative to the drug resistance that develops with treatment using Casodex (e.g., average time to resistance). In embodiments, the method of treatment includes a delay in drug resistance relative to the drug resistance that develops with treatment using enzalutimide (e.g., average time to resistance). In embodiments, the method of treatment includes a delay in drug resistance relative to the drug resistance that develops with treatment using ARN-509 (e.g., average time to resistance). In embodiments, the method of treatment includes a delay in drug resistance relative to the drug resistance that develops with treatment using flutamide (e.g., average time to resistance). In embodiments, the method of treatment includes a delay in drug resistance relative to the drug resistance that develops with treatment using MDV3100 (e.g., average time to resistance). In embodiments, the method of treatment does not result in drug resistance for at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 2000, or 3000 days (e.g., average time to resistance). In embodiments, the method of treatment does not result in drug resistance for about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 2000, or 3000 days (e.g., average time to resistance). In embodiments, the method of treatment does not result in drug resistance for 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 2000, or 3000 days (e.g., average time to resistance). In embodiments, the method of treatment does not result in drug resistance for at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or 600 weeks (e.g., average time to resistance). In embodiments, the method of treatment does not result in drug resistance for about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or 600 weeks (e.g., average time to resistance). In embodiments, the method of treatment does not result in drug resistance for 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or 600 weeks (e.g., average time to resistance). In embodiments, the method of treatment does not result in drug resistance for at least 1, 2, 3, 4, 5, 6, 7, 8, 9, or 10 years (e.g., average time to resistance). In embodiments, the method of treatment does not result in drug resistance for about 1, 2, 3, 4, 5, 6, 7, 8, 9, or 10 years (e.g., average time to resistance). In embodiments, the method of treatment does not result in drug resistance for 1, 2, 3, 4, 5, 6, 7, 8, 9, or 10 years (e.g., average time to resistance).

In embodiments, the method of treatment is a method of prevention. In embodiments, the compounds set forth herein are provided as pharmaceutical compositions including the compound and a pharmaceutically acceptable excipient.

In another aspect is provided a compound described herein, including embodiments (e.g. compound of formula I or II, or any embodiment thereof; or in an example, table, figure, or claim), for use in the treatment of a nuclear receptor activity-associated disease in a subject in need of such treatment. The use may include administering a compound, or a pharmaceutically acceptable salt thereof, as described herein, including embodiments (e.g. compound of formula I or II, or any embodiment thereof; or in an example, table, figure, or claim).

In another aspect is provided a compound described herein, including embodiments (e.g. compound of formula I or II, or any embodiment thereof; or in an example, table, figure, or claim), for use in the treatment of cancer. The use may include administering a compound, or a pharmaceutically acceptable salt thereof, as described herein, including embodiments (e.g. compound of formula I or II, or any embodiment thereof; or in an example, table, figure, or claim). In embodiments, the cancer is prostate cancer. In embodiments, the cancer is hormone-sensitive prostate cancer. In embodiments, the cancer is hormone-insensitive prostate cancer. In embodiments, the cancer is drug-resistant cancer. In embodiments, the prostate cancer is drug-resistant prostate cancer. In embodiments, the cancer is metastatic cancer. In embodiments, the cancer is metastatic prostate cancer. In embodiments, the cancer is castration-resistant prostate cancer.

In another aspect is provided a compound described herein, including embodiments (e.g. compound of formula I or II, or any embodiment thereof; or in an example, table, figure, or claim), for use as a medicament.

In another aspect is provided the use of a compound described herein, including embodiments (e.g. compound of formula I or II, or any embodiment thereof; or in an example, table, figure, or claim), in the manufacture of a medicament for the treatment of a nuclear receptor activity-associated disease in a subject in need of such treatment. The use may include administering a compound, or a pharmaceutically acceptable salt thereof, as described herein, including embodiments (e.g. compound of formula I or II, or any embodiment thereof; or in an example, table, figure, or claim).

In embodiments, the compound, or pharmaceutically acceptable salt thereof, is included in an effective amount. In embodiments, the compound, or pharmaceutically acceptable salt thereof, is included in a therapeutically effective amount. In embodiments, the compound, or pharmaceutically acceptable salt thereof, is included in a prophylactically effective amount.

In embodiments, the use includes a second agent (e.g. therapeutic agent). In embodiments, the use includes a second agent (e.g. therapeutic agent) in a therapeutically effective amount. In embodiments, the second agent is an agent for treating cancer (e.g. prostate cancer) or an aberrant level of androgen receptor activity or a disease associated with androgen receptor activity (e.g., prostate cancer, benign prostatic hyperplasia, hypersexuality, acne, amenorrhea, seborrhea, hirsutism, androgenic alopecia, hidradenitis suppurativa, or hyperandrogenism). In embodiments, the second agent is an anti-cancer agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at a site that does not include the hormone binding site. In embodiments, the second agent binds androgen receptor at a site that is not the hormone binding site. In embodiments, the second agent does not bind the ligand binding domain. In embodiments, the second agent binds androgen receptor at a site that is different from the site bound by a compound described herein, including embodiments. In embodiments, the second agent binds androgen receptor at a site that does not overlap with the binding site of a compound described herein, including embodiments. In embodiments, the second agent is a second agent described herein (e.g., in the pharmaceutical composition section above).

In embodiments, the nuclear receptor activity-associated disease is cancer. In embodiments, the nuclear receptor activity-associated disease is an androgen receptor activity-associated disease. In embodiments, the androgen receptor activity-associated disease is prostate cancer, benign prostatic hyperplasia, hypersexuality, acne, amenorrhea, seborrhea, hirsutism, androgenic alopecia, hidradenitis suppurativa, or hyperandrogenism. In embodiments, the disease is prostate cancer. In embodiments, the disease is hormone-sensitive prostate cancer. In embodiments, the disease is hormone-insensitive prostate cancer. In embodiments, the cancer is drug-resistant cancer. In embodiments, the prostate cancer is drug-resistant prostate cancer. In embodiments, the prostate cancer is casodex-resistant prostate cancer. In embodiments, the prostate cancer is Flutamide-resistant prostate cancer. In embodiments, the prostate cancer is MDV3100-resistant prostate cancer. In embodiments, the prostate cancer is ARN-509-resistant prostate cancer. In embodiments, the subject is resistant to casodex, flutamide, MDV3100, and/or ARN-509. In embodiments, the use includes a delay in drug resistance. In embodiments, the use includes a delay in drug resistance relative to the drug resistance that develops with treatment using Casodex (e.g., average time to resistance). In embodiments, the use includes a delay in drug resistance relative to the drug resistance that develops with treatment using enzalutimide (e.g., average time to resistance). In embodiments, the use includes a delay in drug resistance relative to the drug resistance that develops with treatment using ARN-509 (e.g., average time to resistance). In embodiments, the use includes a delay in drug resistance relative to the drug resistance that develops with treatment using flutamide (e.g., average time to resistance). In embodiments, the use includes a delay in drug resistance relative to the drug resistance that develops with treatment using MDV3100 (e.g., average time to resistance). In embodiments, the use does not result in drug resistance for at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 2000, or 3000 days (e.g., average time to resistance). In embodiments, the use does not result in drug resistance for about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 2000, or 3000 days (e.g., average time to resistance). In embodiments, the use does not result in drug resistance for 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 2000, or 3000 days (e.g., average time to resistance). In embodiments, the use does not result in drug resistance for at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or 600 weeks (e.g., average time to resistance). In embodiments, the use does not result in drug resistance for about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or 600 weeks (e.g., average time to resistance). In embodiments, the use does not result in drug resistance for 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or 600 weeks (e.g., average time to resistance). In embodiments, the use does not result in drug resistance for at least 1, 2, 3, 4, 5, 6, 7, 8, 9, or 10 years (e.g., average time to resistance). In embodiments, the use does not result in drug resistance for about 1, 2, 3, 4, 5, 6, 7, 8, 9, or 10 years (e.g., average time to resistance). In embodiments, the use does not result in drug resistance for 1, 2, 3, 4, 5, 6, 7, 8, 9, or 10 years (e.g., average time to resistance).

In embodiments, the treatment is prevention. In embodiments, the compounds set forth herein are provided as pharmaceutical compositions including the compound and a pharmaceutically acceptable excipient.

F. METHODS OF INHIBITING A NUCLEAR RECEPTOR

In another aspect is provided a method of inhibiting androgen receptor activity in a subject in need thereof, including administering to the subject an effective amount of a compound as described herein, or a pharmaceutically acceptable salt thereof.

In embodiments, the nuclear receptor is a human receptor. In embodiments, the nuclear receptor is an androgen receptor. In embodiments, the androgen receptor is a human receptor.

G. ADDITIONAL EMBODIMENTS

1p. A compound having the formula:

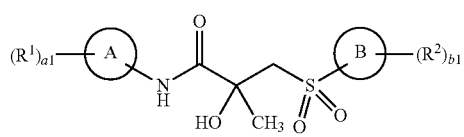

(I)

wherein Ring A is a heteroaryl; Ring B is a phenyl or heteroaryl; $R^1$ is independently a halogen, $-CX^a_3$, $-CN$, $-SO_2Cl$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^a_3$, $-OCHX^a_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; E is an electrophilic moiety; $R^2$ is independently a halogen, $-CX^b_3$, $-CN$, $-SO_2Cl$, $-SO_{n2}R^{14}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^b_3$, $-OCHX^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, $R^{10}$, $R^{11}$, $R^{12}$, $R^{13}$, and $R^{14}$ are independently hydrogen, halogen, $-CX^c_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^c_3$, $-OCHX^c_2$, $-CF_3$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; a1 is independently an integer from 0 to 4; b1 is independently an integer from 0 to 5; m1, m2, v1, and v2 are independently 1 or 2; n1 and n2 are independently an integer from 0 to 4; $X^a$, $X^b$, and $X^c$ are independently $-Cl$, $-Br$, $-I$, or $-F$.

2p. The compound of embodiment 1p, having the formula:

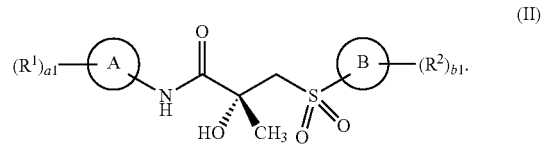

(II)

3p. The compound of one of embodiments 1p to 2p, wherein Ring A is a 6 membered heteroaryl.

4p. The compound of one of embodiments 1p to 2p, wherein Ring A is a 6 membered heteroaryl not comprising an ortho heteroatom.

5p. The compound of one of embodiments 1p to 2p, wherein Ring A is

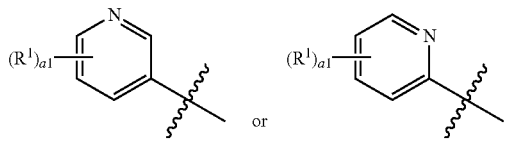

and a1 is an integer from 0 to 4; or

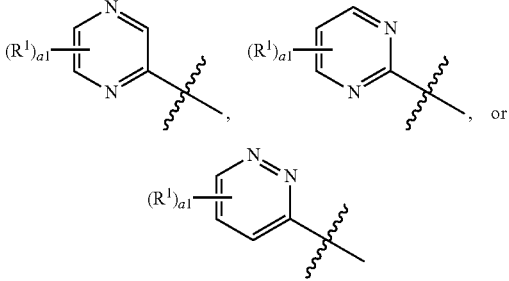

and a1 is an integer from 0 to 3.

6p. The compound of one of embodiments 1p to 2p, wherein Ring A is

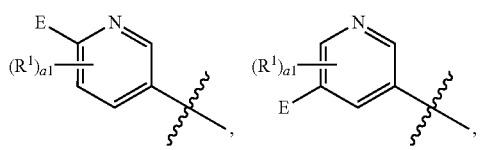

-continued

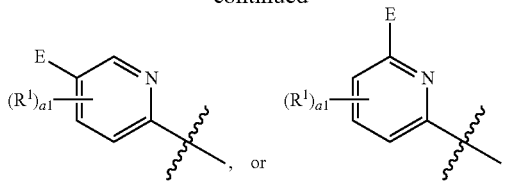

and a1 is an integer from 0 to 3; or

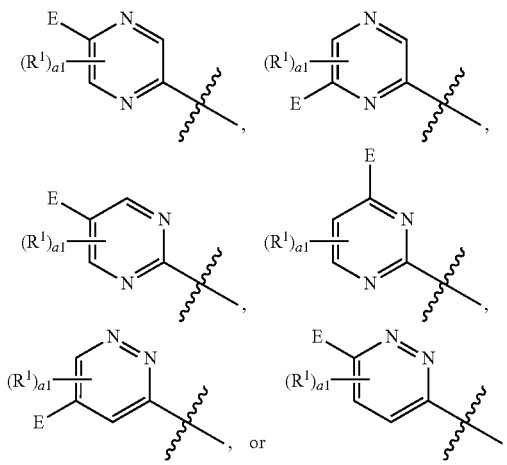

and a1 is an integer from 0 to 2.

7p. The compound of one of embodiments 1p to 2p, wherein Ring A is

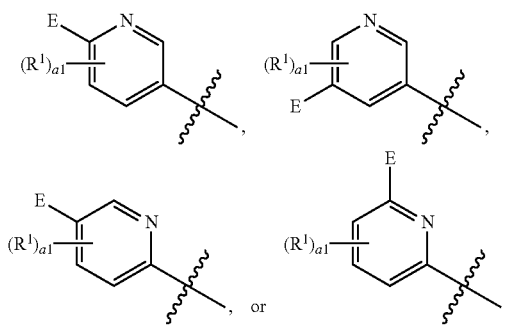

and a1 is an integer from 0 to 3.

8p. The compound of one of embodiments 1p to 2p, wherein Ring A is

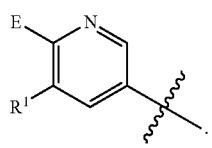

9p. The compound of one of embodiments 1p to 8p, wherein $R^1$ is a —Cl, —F, —Br, —I, —$CX^a_3$, —CN, —NHNH$_2$, —ONH$_2$, —NHC=(O)NHNH$_2$, —NHC=(O)NH$_2$, —NO$_2$, —NH$_2$, —C(O)H, —C(O)CH$_3$, —C(O)—OH, —C(O)—OCH$_3$, —C(O)NH$_2$, —OH, —NHC=(O)H, —NHC=(O)CH$_3$, —NHC(O)—OH, —NHC(O)OCH$_3$, —NHOH, —NHOCH$_3$. —$OCX^a_3$, —$OCHX^a_2$, substituted or unsubstituted $C_1$-$C_5$ alkyl, substituted or unsubstituted 2 to 5 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

10p. The compound of one of embodiments 1p to 9p, wherein $R^1$ is independently —Cl, —F, —Br, —Br, —I, —$CX^a_3$, —CN, —NO$_2$, —$OCX^a_3$, —$OCHX^a_2$,

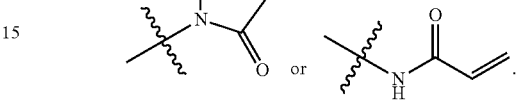

11p. The compound of one of embodiments 1p to 10p, wherein said electrophilic moiety is —CN, —NO$_2$,

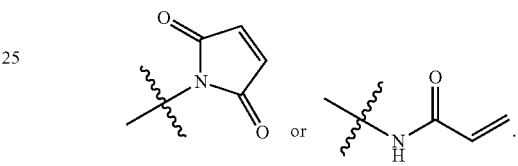

12p. The compound of one of embodiments 1p to 11p, wherein Ring B is a phenyl.
13p. The compound of one of embodiments 1p to 11p, wherein Ring B is a heteroaryl.
14p. The compound of one of embodiments 1p to 11p, wherein Ring B is a 6 membered heteroaryl.
15p. The compound of one of embodiments 1p to 14p, wherein $R^2$ is independently a halogen, —$CX^b_3$, —C(O)NHCH$_3$, substituted or unsubstituted $C_1$-$C_5$ alkyl, substituted or unsubstituted 2 to 5 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.
16p. The compound of embodiment 1p, wherein said compound is

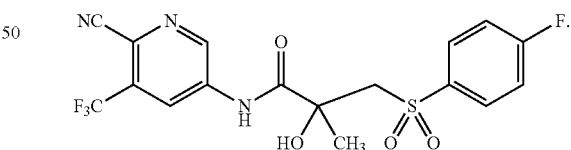

17p. The compound of embodiment 2p, wherein said compound is

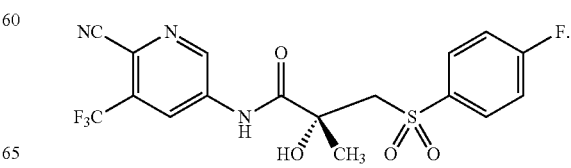

18p. The compound of one of embodiments 1p to 17p, wherein said compound is an antagonist of a nuclear receptor.

19p. The compound of one of embodiments 1p to 17p, wherein said compound is an antagonist of an androgen receptor.

20p. A pharmaceutical composition comprising a compound of one of embodiments 1p to 19p or a pharmaceutically acceptable salt thereof, and a pharmaceutically acceptable excipient.

21p. The pharmaceutical composition of embodiment 20p, comprising a therapeutically effective amount of said compound.

22p. An androgen receptor protein covalently bound to a compound of one of embodiments 1p to 19p, wherein said compound is covalently bound to a cysteine residue of said androgen receptor protein.

23p. A human androgen receptor protein covalently bound to a compound of one of embodiments 1p to 19p, wherein said compound is covalently bound to Cys784 of said human androgen receptor protein.

24p. A method of treating cancer in a subject in need thereof, comprising administering to said subject an effective amount of a compound of one of embodiments 1p to 19p, or a pharmaceutically acceptable salt thereof.

25p. The method of embodiment 23p, wherein said cancer is prostate cancer.

26p. The method of embodiment 23p, wherein said cancer is associated with androgen receptor activity.

27p. A method of inhibiting androgen receptor activity in a subject in need thereof, comprising administering to said subject an effective amount of a compound of one of embodiments 1p to 19p, or a pharmaceutically acceptable salt thereof.

1. A compound having the formula:

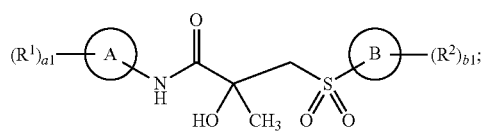

(I)

wherein; Ring A is a heteroaryl; Ring B is a phenyl or heteroaryl; $R^1$ is independently a halogen, $-CX^a_3$, $-CN$, $-SO_2Cl$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^a_3$, $-OCHX^a_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; E is an electrophilic moiety; $R^2$ is independently a halogen, $-CX^b_3$, $-CN$, $-SO_2Cl$, $-SO_{n2}R^{14}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^b_3$, $-OCHX^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, $R^{10}$, $R^{11}$, $R^{12}$, $R^{13}$, and $R^{14}$ are independently hydrogen, halogen, $-CX^c_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCX^c_3$, $-OCHX^c_2$, $-CF_3$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; a1 is independently an integer from 0 to 4; b1 is independently an integer from 0 to 5; m1, m2, v1, and v2 are independently 1 or 2; n1 and n2 are independently an integer from 0 to 4; $X^a$, $X^b$, and $X^c$ are independently $-Cl$, $-Br$, $-I$, or $-F$.

2. The compound of embodiment 1, having the formula:

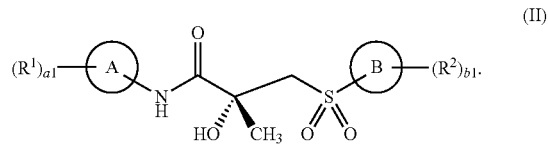

(II)

3. The compound of one of embodiments 1 to 2, wherein Ring A is a 6 membered heteroaryl.

4. The compound of one of embodiments 1 to 2, wherein Ring A is a 6 membered heteroaryl not comprising an ortho heteroatom.

5. The compound of one of embodiments 1 to 2, wherein Ring A is

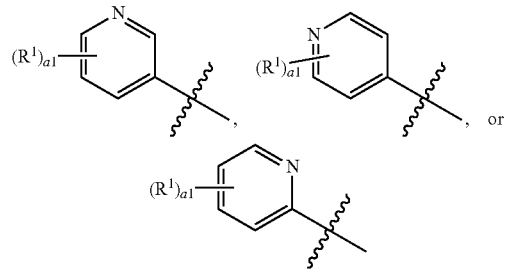

and a1 is an integer from 0 to 4; or

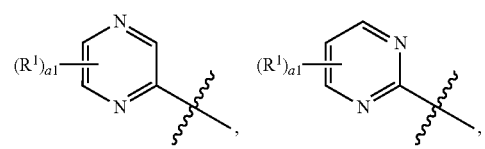

,

-continued
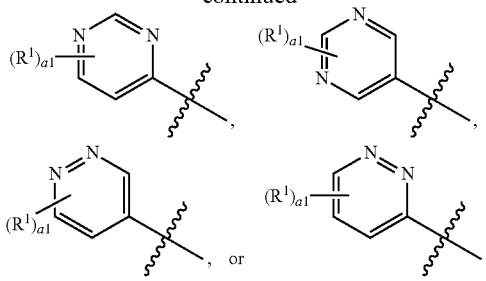
,
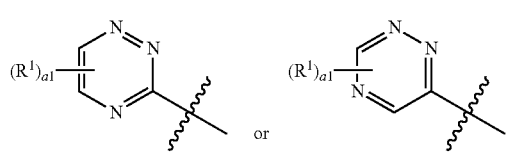
, or
and a1 is an integer from 0 to 3; or
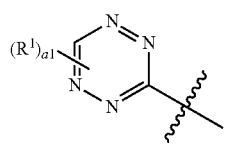
or
and a1 an integer from 0 to 2; or
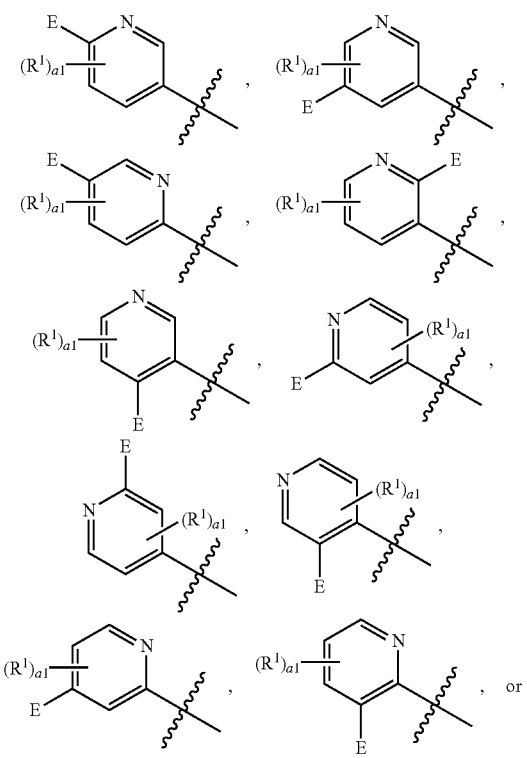
and a1 an integer from 0 to 1.
6. The compound of one of embodiments 1 to 2, wherein Ring A is
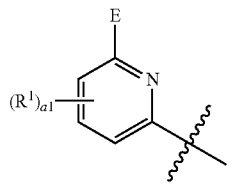
, or
-continued
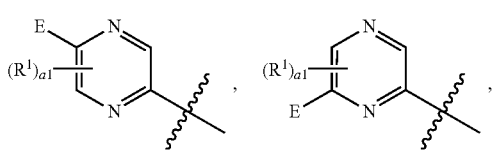
and a1 is an integer from 0 to 3; or
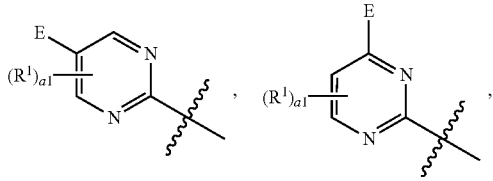
,
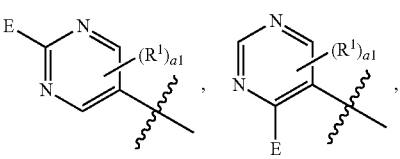
,
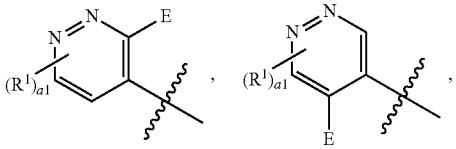
,
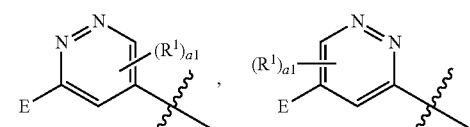
,
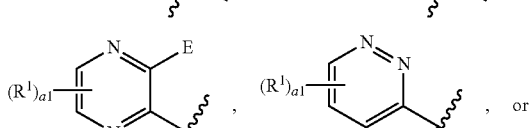
,
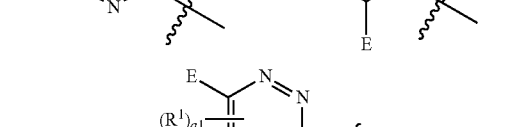
, or
and a1 is an integer from 0 to 2; or
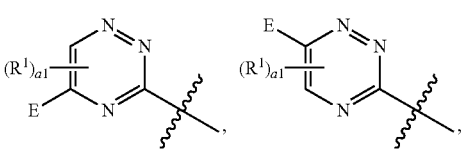
, -continued

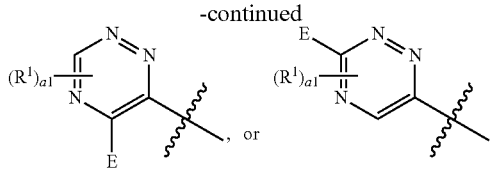

and a1 is an integer from 0 to 1; or

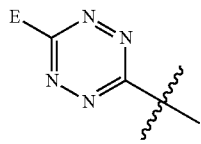

and a1 is 0.

7. The compound of one of embodiments 1 to 2, wherein Ring A is

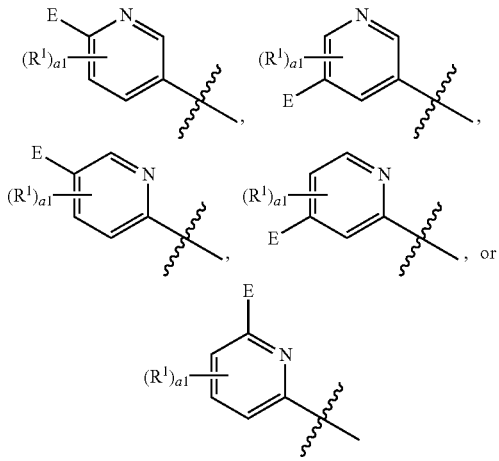

and a1 is an integer from 0 to 3.

8. The compound of one of embodiments 1 to 2, wherein Ring A is

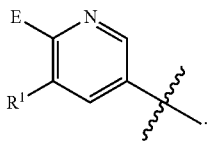

9. The compound of one of embodiments 1 to 8, wherein $R^1$ is a —Cl, —F, —Br, —I, —CX$^a{}_3$, —CN, —NHNH$_2$, —ONH$_2$, —NHC=(O)NHNH$_2$, —NHC=(O)NH$_2$, —NO$_2$, —NH$_2$, —C(O)H, —C(O)CH$_3$, —C(O)—OH, —C(O)—OCH$_3$, —C(O)NH$_2$, —OH, —NHC=(O)H, —NHC=(O)CH$_3$, —NHC(O)—OH, —NHC(O)OCH$_3$, —NHOH, —NHOCH$_3$. —OCX$^a{}_3$, —OCHX$^a{}_2$, substituted or unsubstituted C$_1$-C$_5$ alkyl, substituted or unsubstituted 2 to 5 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

10. The compound of one of embodiments 1 to 9, wherein $R^1$ is independently —CL, —F, —Br, —I, —CX$^a{}_3$, —CN, —NO$_2$, —OCX$^a{}_3$, —OCHX$^a{}_2$,

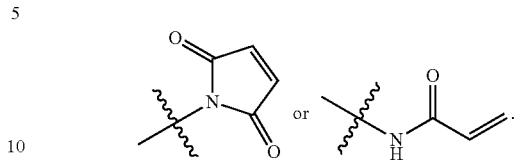

11. The compound of one of embodiments 1 to 10, wherein said electrophilic moiety is:

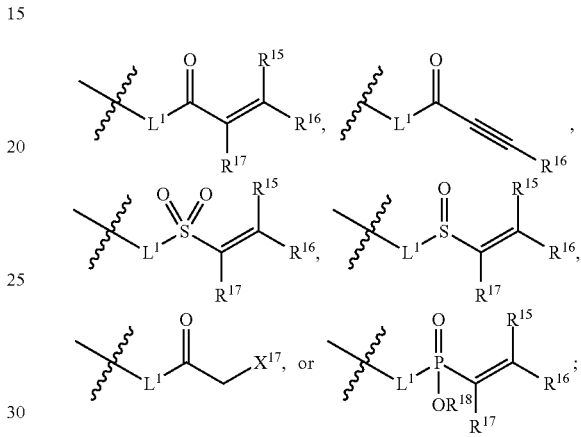

wherein $R^{15}$ is independently hydrogen, halogen, $CX^{15}{}_3$, —CHX$^{15}{}_2$, —CH$_2$X$^{15}$, —CN, —SO$_{n15}$R$^{15D}$, —SO$_{v15}$NR$^{15A}$R$^{15B}$, —NHNR$^{15A}$R$^{15B}$, —ONR$^{15A}$R$^{15B}$, —NHC=(O)NHNR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, —OCX$^{15}{}_3$, —OCHX$^{15}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16}$ is independently hydrogen, halogen, $CX^{16}{}_3$, —CHX$^{16}{}_2$, —CH$_2$X$^{16}$, —CN, —SO$_{n16}$R$^{16D}$, —SO$_{v16}$NR$^{16A}$R$^{16B}$, —NHNR$^{16A}$R$^{16B}$, —ONR$^{16A}$R$^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}{}_3$, —OCHX$^{16}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{17}$ is independently hydrogen, halogen, $CX^{17}{}_3$, —CHX$^{17}{}_2$, —CH$_2$X$^{17}$, —CN, —SO$_{n17}$R$^{17D}$, —SO$_{v17}$NR$^{17A}$R$^{17B}$, —NHNR$^{17A}$R$^{17B}$, —ONR$^{17A}$R$^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, —OCX$^{17}{}_3$, —OCHX$^{17}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{18}$ is independently hydrogen, $-CX^{18}_3$, $-CHX^{18}_2$, $-CH_2X^{18}$, $-C(O)R^{18C}$, $-C(O)OR^{18C}$, $-C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; each $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; each X, $X^{15}$, $X^{16}$, $X^{17}$ and $X^{18}$ is independently $-F$, $-Cl$, $-Br$, or $-I$; n15, n16, n17, v15, v16, and v17, are independently and integer from 0 to 4; m15, m16, and m17 are independently an integer between 1 and 2; $L^1$ is a bond, $-N(H)-$, $-N(CH_3)-$, or

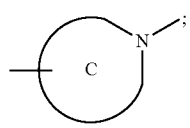

and Ring C is a substituted or unsubstituted heterocycloalkylene or substituted or unsubstituted heteroarylene.

12. The compound of embodiment 11, wherein E is:

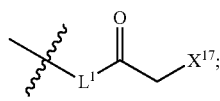

and $X^{17}$ is $-Cl$.

13. The compound of embodiment 11, wherein E is:

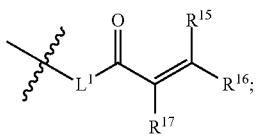

and $R^{15}$, $R^{16}$, and $R^{17}$ are independently hydrogen.

14. The compound of embodiment 11, wherein E is:

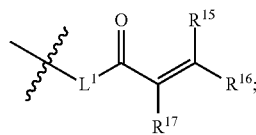

wherein $R^{15}$ is independently hydrogen; $R^{16}$ is independently hydrogen or $-CH_2NR^{16A}R^{16B}$; $R^{17}$ is independently hydrogen; and $R^{16A}$ and $R^{16B}$ are independently hydrogen or unsubstituted alkyl.

15. The compound of one of embodiments 1 to 10, wherein said electrophilic moiety is $-CN$, $-NO_2$,

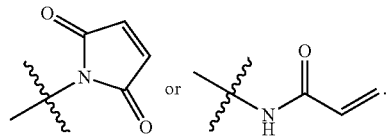

16. The compound of one of embodiments 1 to 15, wherein Ring B is a phenyl.
17. The compound of one of embodiments 1 to 15, wherein Ring B is a heteroaryl.
18. The compound of one of embodiments 1 to 15, wherein Ring B is a 6 membered heteroaryl.
19. The compound of one of embodiments 1 to 18, wherein $R^2$ is independently a halogen, $-CX^b_3$, $-C(O)NHCH_3$, substituted or unsubstituted $C_1$-$C_5$ alkyl, substituted or unsubstituted 2 to 5 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.
20. The compound of embodiment 1, wherein said compound is

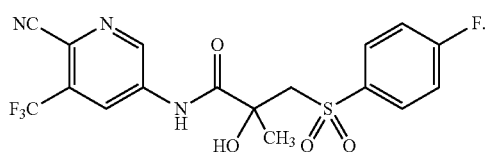 [SMILES: CC(O)(CS(=O)(=O)c1ccc(F)cc1)C(=O)Nc1cnc(C#N)c(C(F)(F)F)c1]

21. The compound of embodiment 2, wherein said compound is

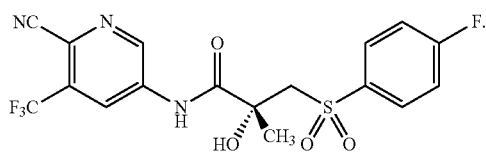 [SMILES: C[C@](O)(CS(=O)(=O)c1ccc(F)cc1)C(=O)Nc1cnc(C#N)c(C(F)(F)F)c1]

22. The compound of one of embodiments 1 to 21, wherein said compound is an antagonist of a nuclear receptor.
23. The compound of one of embodiments 1 to 21, wherein said compound is an antagonist of an androgen receptor.
24. A pharmaceutical composition comprising a compound of one of embodiments 1 to 23 or a pharmaceutically acceptable salt thereof, and a pharmaceutically acceptable excipient.

25. The pharmaceutical composition of embodiment 24, comprising a therapeutically effective amount of said compound.

26. An androgen receptor protein covalently bound to a compound of one of embodiments 1 to 23, wherein said compound is covalently bound to a cysteine residue of said androgen receptor protein.

27. A human androgen receptor protein covalently bound to a compound of one of embodiments 1 to 23, wherein said compound is covalently bound to Cys784 of said human androgen receptor protein.

28. A method of treating cancer in a subject in need thereof, comprising administering to said subject an effective amount of a compound of one of embodiments 1 to 23, or a pharmaceutically acceptable salt thereof.

29. The method of embodiment 28, wherein said cancer is prostate cancer.

30. The method of embodiment 29, wherein said prostate cancer is hormone sensitive prostate cancer.

31. The method of embodiment 29, wherein said prostate cancer is hormone refractory prostate cancer.

32. The method of embodiment 29, wherein said prostate cancer is resistant to casodex treatment.

33. The method of embodiment 29, wherein said prostate cancer is resistant to enzalutamide treatment.

34. The method of embodiment 29, wherein said prostate cancer is resistant to ARN-509 treatment.

35. The method of embodiment 28, wherein said cancer is associated with androgen receptor activity.

36. A method of inhibiting androgen receptor activity in a subject in need thereof, comprising administering to said subject an effective amount of a compound of one of embodiments 1 to 23, or a pharmaceutically acceptable salt thereof.

H. EXAMPLES

Example 1. Syntheses of Casodex Analogs

A New Strategy for Inhibiting Androgen Receptor Activation. The mainstay of current prostate cancer therapies are drugs that directly inhibit androgen receptor (AR) function by competitively inhibiting the binding of hormones (TES, DHT) to the receptor (e.g. Casodex, Flutamide, MDV3100, ARN-509). However, tumor cells often become resistant to antiandrogens within a few years of treatment and the progression of prostate cancer subsequently resumes. We hypothesize that the limited efficacy of antiandrogens is due in part to the fact that they bind AR with affinities weaker than or, at best, comparable to native hormones. This allows endogenous ligands to competitively activate the receptor, and selective pressure to drive escape mechanisms. Here we report the development of new antiandrogens, including one differing by two atoms (CH replaced by N) from Casodex that binds over 24-Fold more tightly to AR than the parent compound. The improved affinity of the new antiandrogen is attributed to a strategic substitution of a CH group by a N atom in the A-ring of Casodex, designed to alter the electronics of the molecule. Even higher affinity ligands can be produced by capitalizing on this strategy, as described herein.

TABLE 1

Antiandrogens. 1st generation. Casodex: 42-fold less potent than DHT.
2nd generation. RD162, MDV3100: changed B-ring of CDX,
improved affinity 8-fold. 3rd generation.
ARN-509: Added N to A-ring of RD162, increased affinity 2-fold.

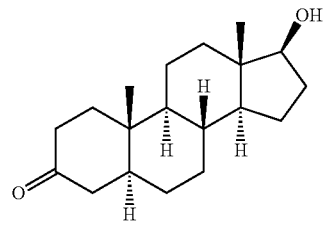

Dihydrotestosterone (DHT, $IC_{50}$ = 3.8 nM)

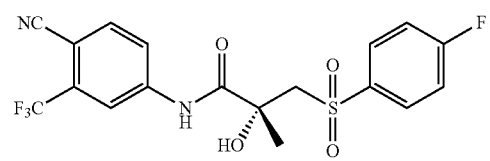 [SMILES: C[C@](O)(CS(=O)(=O)c1ccc(F)cc1)C(=O)Nc1ccc(C#N)c(C(F)(F)F)c1]

Casodex (CDX, $IC_{50}$ = 160 nM)

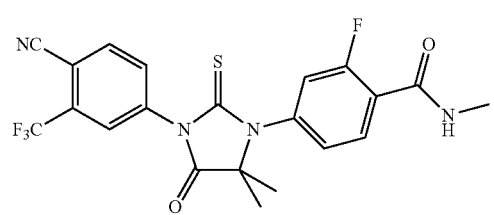 [SMILES: CNC(=O)c1ccc(N2C(=S)N(c3ccc(C#N)c(C(F)(F)F)c3)C(=O)C2(C)C)cc1F]

MDV3100 ($IC_{50}$ = 21.4 nM)

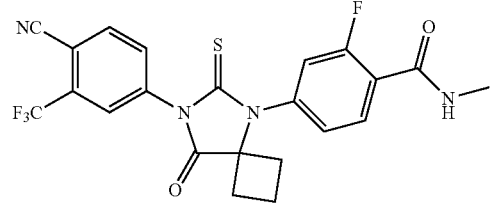 [SMILES: CNC(=O)c1ccc(N2C(=S)N(c3ccc(C#N)c(C(F)(F)F)c3)C(=O)C23CCC3)cc1F]

RD162 ($IC_{50}$ = 30.9 nM)

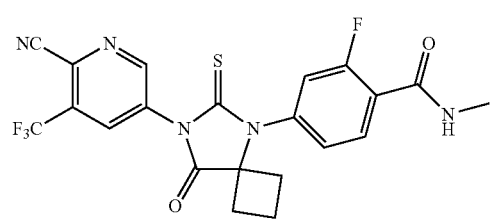 [SMILES: CNC(=O)c1ccc(N2C(=S)N(c3cnc(C#N)c(C(F)(F)F)c3)C(=O)C23CCC3)cc1F]

ARN-509 ($IC_{50}$ = 16.0 nM)

Casodex (bicalutamide) has been developed and utilized as chemotherapy for prostate cancer. Studies on bicalutamide show it is well tolerated with very few side effects. However, over time many current treatments are rendered ineffective. Tran and coworkers evaluated 200 thiohydantoin deriviatives and discovered MDV3100 and RD162 as lead compounds. Compared to casodex, MDV3100 and RD162 had 8-Fold and 5-Fold greater affinity, respectively. These compounds both contain the same A-ring as casodex but show drastic differences in the B-ring portion of the molecule and link between the A and B rings. Recently, the development of a novel antiandrogen, ARN-509, which displayed 7- to 10-Fold greater affinity than casodex was reported. It also shows greater efficacy in xenograft model of human prostate cancer than MDV3100 and RD162. Interestingly, an atomistic comparison of ARN-509 and RD162 shows that the two differ by the presence of a nitrogen in the A ring, which only leads to a 2-Fold increase in its affinity. Previously, it had been believed that increases in affinity largely come from changes in the B ring, while the A ring remained primarily the same.

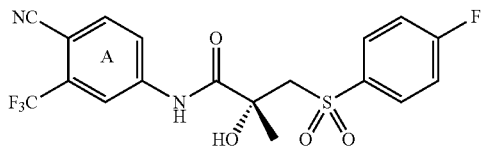

A-Ring Analogs

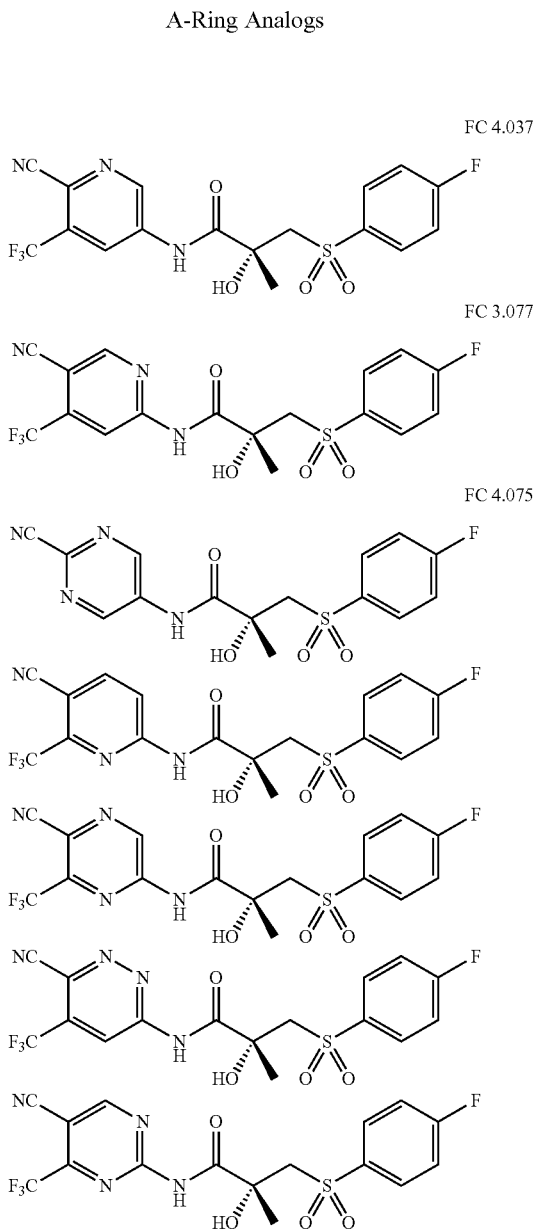

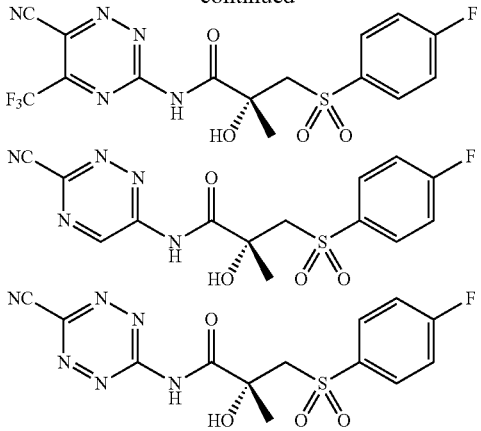

FIG. 1 displays an overlay of the crystal structures of wildtype AR bound to DHT (light gray) and AR mutant W741L bound to CDX (dark gray). The mutation W741 is hypothesized to be responsible for casodex withdrawal syndrome. A cysteine is located in the ligand binding pocket that may interact with the cyano group of casodex. It is known that a nitrile can form a reversible covalent bond with a relative (e.g., active site) cysteine and that this electrophilicity can be increased by the presence of an electron-withdrawing heterocycle. We hypothesized that the presence of a pyridinyl moiety in casodex would increase in affinity/efficacy of the compound due to reaction with Cys784 in the AR hormone binding pocket. To test this hypothesis, we synthesized multiple casodex analogs that contained a combination of the aryl nitrile and pyridine, and tested their activity through in vitro assays of transcription. If this hypothesis were true, it would expected that there would be an increase in affinity for the analog containing both a nitrile and pyridinyl moiety, while those lacking the aryl nitrile would exhibit little to no change.

A convergent approach was used in the synthesis of bicalutamide analogs by first synthesizing a carboxylic acid, based on the synthetic scheme found in Tucker and Chesterson, J Med Chem 1988, 31 (4), 885-887. D-proline was reacted with methacryloyl chloride and triethylamine to arrive at the acryamide. Reaction with NBS in dimethylformamide to form the bromolactone, followed by acid cleavage of the proline auxiliary led to chiral carboxylic acid. Displacement of the alkyl bromide with 4-Fluorothiophenol in sodium hydroxide and isopropanol gave a sulfide, which was followed by oxidation with peracetic acid to yield the desired carboxylic acid.

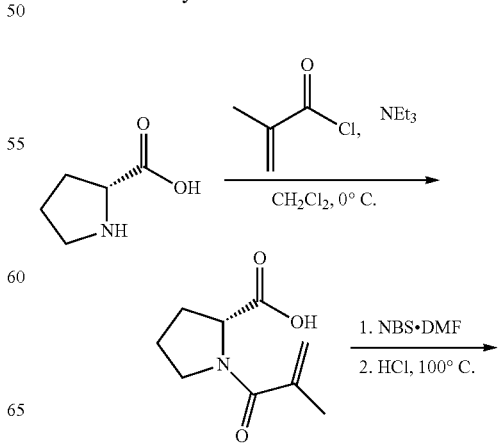

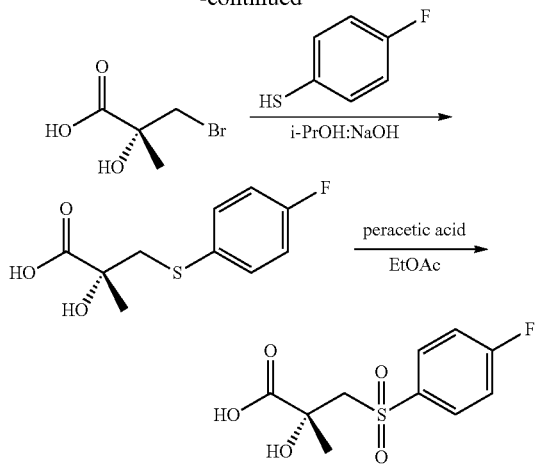

With synthesis of the B ring portion of casodex complete, it was necessary to prepare the A ring of the analogues. The anilides used were either purchased or synthesized according to literature precedent. Synthetic schemes for the anilides that were prepared in our lab are found below.

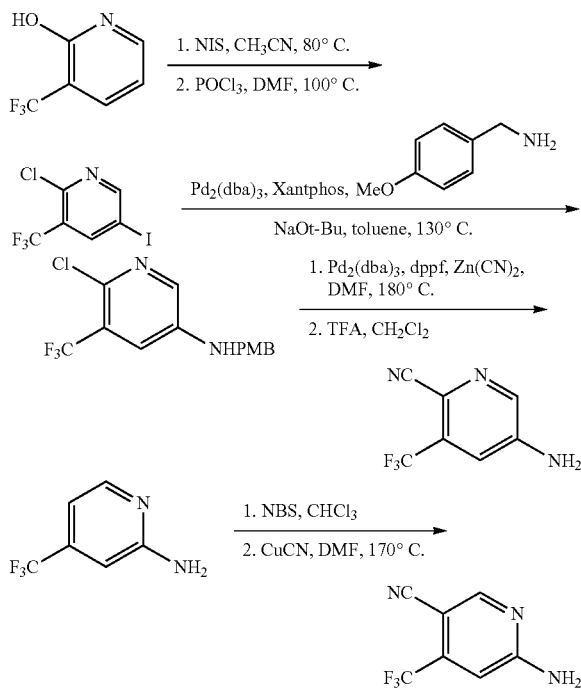

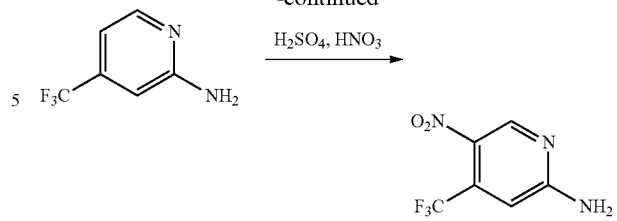

These anilides were then coupled with the late stage carboxylic acid through the reaction of the acid chloride formed by $SOCl_2$ in dimethylacetamide to give casodex and its analogues. The total list of analogues synthesized, along with their compound name, MW, ligand binding domain (LBD) $IC_{50}$, full length (FL) $IC_{50}$, and fold change (in relationship to the experimental casodex data) can be found in the tables below.

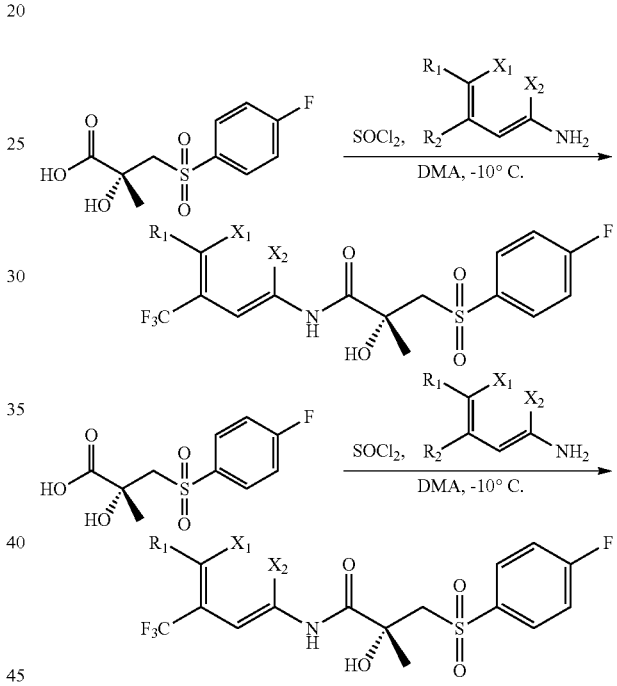

CDX $R_1$=—CN, $X_1$=CH, $X_2$=CH, 4.116 $R_1$=—H, $X_1$=CH, $X_2$=CH 4.127 $R_1$=—$NO_2$, $X_1$=CH, $X_2$=CH 4.037 $R_1$=—CN, $X_1$=N, $X_2$=CH, 4.126 $R_1$=—H, $X_1$=N, $X_2$=CH 4.129 $R_1$=—$NO_2$, $X_1$=CH, $X_2$=N 3.077 $R_1$=—CN, $X_1$=—CH, $X_2$=N, 4.125 $R_1$=—H, $X_1$=CH, $X_2$=N

TABLE 2

| Structure | Cmpd | MW (g/mol) | LBD $IC_{50}$ (µM) | FL $IC_{50}$ (µM) | LVCaP data | Fold chg (LBD) | Fold chg (FL) |
|---|---|---|---|---|---|---|---|
| (structure shown) | Casodex (CDX) | 430.37 g/mol | 0.36 ± 0.02 µM | 1.00 ± 0.24 µM | 0.35 ± 0.05 µM | 1.0 | 1.0 |

TABLE 2-continued

| Structure | Cmpd | MW (g/mol) | LBD IC$_{50}$ (μM) | FL IC$_{50}$ (μM) | LVCaP data | Fold chg (LBD) | Fold chg (FL) |
|---|---|---|---|---|---|---|---|
| 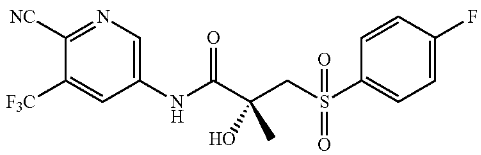 [SMILES: C[C@](O)(CS(=O)(=O)c1ccc(F)cc1)C(=O)Nc1cnc(C#N)c(C(F)(F)F)c1] | FC 4.037 (N-CDX) | 431.06 g/mol | 0.015 ± 0.001 μM | 0.19 ± 0.06 μM | 0.14 ± 0.10 μM | 24.0 | 5.3 |
| 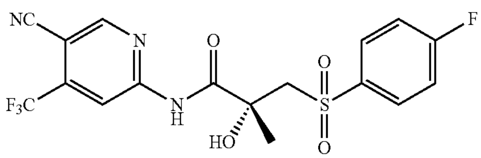 [SMILES: C[C@](O)(CS(=O)(=O)c1ccc(F)cc1)C(=O)Nc1cc(C(F)(F)F)c(C#N)cn1] | FC 3.077 | 431.06 g/mol | 0.49 ± 0.06 μM | N/A | Not tested | 0.74 | 0.33 |
| 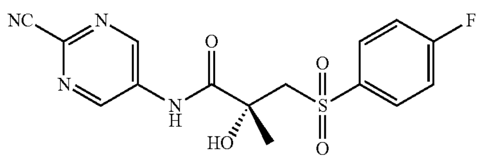 [SMILES: C[C@](O)(CS(=O)(=O)c1ccc(F)cc1)C(=O)Nc1cnc(C#N)nc1] | FC 4.075 | 364.06 g/mol | N/A | N/A | Not tested | — | — |
| 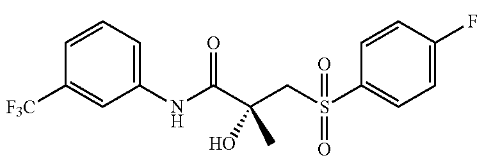 [SMILES: C[C@](O)(CS(=O)(=O)c1ccc(F)cc1)C(=O)Nc1cccc(C(F)(F)F)c1] | FC 4.116 | 405.07 g/mol | 2.53 ± 1.16 μM | 71.7 ± 512 μM | 0.53 ± 0.27 μM | 0.14 | 0.014 |
| 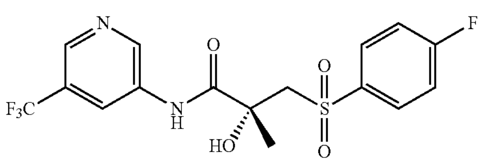 [SMILES: C[C@](O)(CS(=O)(=O)c1ccc(F)cc1)C(=O)Nc1cncc(C(F)(F)F)c1] | FC 4.126 | 406.06 g/mol | 1.55 ± 0.41 μM | 12.4 ± 14.2 μM | 0.11 ± 0.02 μM | 0.23 | 0.08 |
| 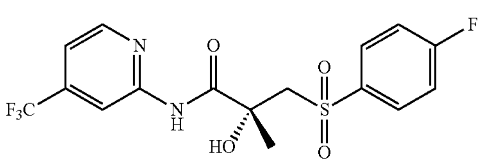 [SMILES: C[C@](O)(CS(=O)(=O)c1ccc(F)cc1)C(=O)Nc1cc(C(F)(F)F)ccn1] | FC 4.125 | 406.06 g/mol | 22.4 ± 41.8 μM | N/A | Not tested | 0.016 | — |
| 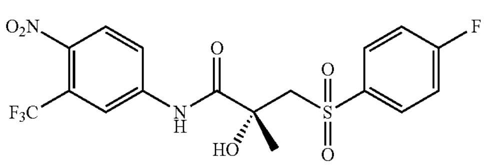 [SMILES: C[C@](O)(CS(=O)(=O)c1ccc(F)cc1)C(=O)Nc1ccc([N+](=O)[O-])c(C(F)(F)F)c1] | FC 4.127 | 450.05 g/mol | 7.26 ± 10.7 μM | 8.74 ± 15.8 μM | Not tested | 0.050 | 0.11 |
| 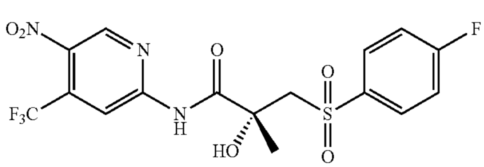 [SMILES: C[C@](O)(CS(=O)(=O)c1ccc(F)cc1)C(=O)Nc1cc(C(F)(F)F)c([N+](=O)[O-])cn1] | FC 4.129 | 451.05 g/mol | 1.94 ± 0.43 μM | 8.61 ± 5.96 μM | Not tested | 0.19 | 0.12 |
| 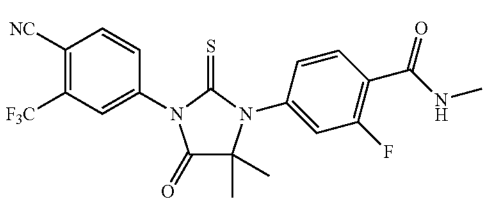 [SMILES: CNC(=O)c1ccc(N2C(=S)N(c3ccc(C#N)c(C(F)(F)F)c3)C(=O)C2(C)C)cc1F] | MDV3100 | 464.09 g/mol | 3.28 ± 0.79 μM | 19.5 ± 30.9 μM | 0.10 ± 0.01 μM | 0.14 | 0.05 |

TABLE 2-continued

| Structure | Cmpd | MW (g/mol) | LBD IC$_{50}$ (μM) | FL IC$_{50}$ (μM) | LVCaP data | Fold chg (LBD) | Fold chg (FL) |
|---|---|---|---|---|---|---|---|
| 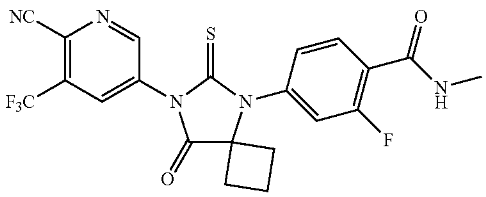 [SMILES: CNC(=O)c1ccc(N2C(=S)N(c3cnc(C#N)c(C(F)(F)F)c3)C(=O)C23CCC3)cc1F] | ARN-509 | 477.09 g/mol | 3.11 ± 0.64 μM | N/A | 0.12 ± 0.02 μM | 0.30 | |

**N/A means the compound was tested but IC$_{50}$ could not be calculated.

Example 2. IC$_{50}$ Data and Quantum Mechanics Calculations

Density functional calculations to determine the electrophilicity of the nitriles in our synthetic compounds were performed as in Oballa et al. Bioorg Med Chem Lett 2007, 17 (4), 998-1002, discussing a method for assessing nitrile electrophilicity. Briefly, the free energy of thioimidate formation from the reaction of the desired nitrile and methanethiol was calculated. The geometry of both reagents and the thioimidate was optimized in the gas phase with B3LYP/6-311G(d,p) level of theory, followed by a single point calculation with the PCM method in water, to avoid overestimation of intramolecular H-bonds. Finally the equation E(adduct)−E(nitrile)−E(methanethiol) is used to find the reactivity in kcal/mol, listed in the tables below. Calculations were also performed to determine the charge on the electronegative atom at the R1 position that is thought to interact with Arg752. There is an obvious increase in electrophilicity going from Casodex to Enzlutamide to ARN-509 as well as a similar increase in 4.037. Compound 4.075 has the highest electrophilicity, yet lacking a —CF3 group, which has been determined to be essential to binding.

TABLE 3

Electrophilicity and point charge calculations

| Structure | Name | Electrophilicity of —CN (kcal/mol) | R$_1$ Point charge |
|---|---|---|---|
| 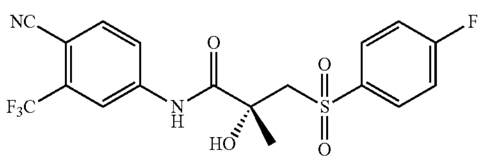 [SMILES: C[C@](O)(CS(=O)(=O)c1ccc(F)cc1)C(=O)Nc1ccc(C#N)c(C(F)(F)F)c1] | Casodex (CDX) | −5.647 | −0.562 |
| 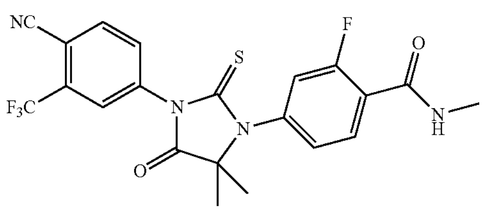 [SMILES: CNC(=O)c1ccc(N2C(=S)N(c3ccc(C#N)c(C(F)(F)F)c3)C(=O)C2(C)C)cc1F] | Enzalutamide | −7.160 | −0.534 |
| 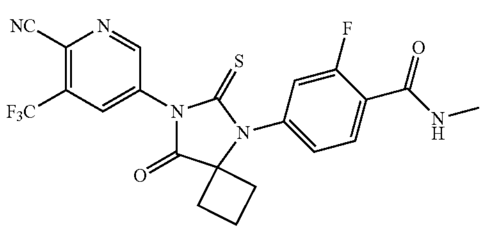 [SMILES: CNC(=O)c1ccc(N2C(=S)N(c3cnc(C#N)c(C(F)(F)F)c3)C(=O)C23CCC3)cc1F] | ARN-509 | −9.120 | −0.459 |
| 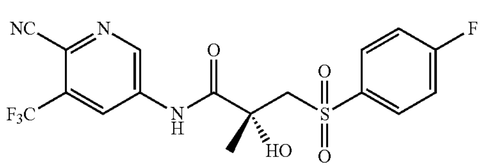 [SMILES: C[C@](O)(CS(=O)(=O)c1ccc(F)cc1)C(=O)Nc1cnc(C#N)c(C(F)(F)F)c1] | FC 4.037 | −7.641 | −0.486 |

TABLE 3-continued

Electrophilicity and point charge calculations

| Structure | Name | Electrophilicity of —CN (kcal/mol) | R₁ Point charge |
|---|---|---|---|
| (structure) | FC 3.077 | −7.114 | −0.533 |
| (structure) | FC 4.075 | −12.422 | −0.460 |
| (structure) | FC 4.116 | n/a | n/a |
| (structure) | FC 4.126 | n/a | n/a |
| (structure) | FC 4.125 | n/a | n/a |
| (structure) | FC 4.127 | n/a | −0.461, −0.479 |
| (structure) | FC 4.129 | n/a | −0.456, −0.471 |

TABLE 4

Compound characterization.

A.

![Structure A]

| Cmpd | $R_1$ | $X_1$ | $X_2$ | Experimental $IC_{50}$ (μM) | Fold change* | $R_1$ point charge | Electrophilicity (kcal/mol) |
|---|---|---|---|---|---|---|---|
| CDX | —CN | CH | CH | 0.36 ± 0.02 | 1.0 | −0.56 | −5.65 |
| 4.037 | —CN | N | CH | 0.015 ± 0.001 | 24.0 | −0.49 | −7.61 |
| 3.077 | —CN | CH | N | 0.49 ± 0.06 | 0.74 | −0.53 | −7.11 |
| 4.116 | —H | CH | CH | 2.53 ± 1.16 | 0.14 | — | — |
| 4.126 | —H | N | CH | 1.55 ± 0.41 | 0.23 | — | — |
| 4.125 | —H | CH | N | 22.4 ± 41.8 | 0.016 | — | — |
| 4.127 | —NO$_2$ | CH | CH | 7.26 ± 10.7 | 0.05 | −0.46, −0.48 | — |
| 4.129 | —NO$_2$ | CH | N | 1.94 ± 0.43 | 0.19 | −0.46, −0.47 | — |

Example 3. Characterization of Antiandrogens and Mechanism of Action

Addition of nitrogen ortho to —CN increases affinity 24-Fold, while addition of N in CDX analogs lacking —CN has no effect. It was noted that placing the nitrogen meta to the R1 caused a decrease in affinity. One explanation for this result can be found in the work by Tucker et al. J Med Chem 1988, 31 (5), 954-959. Physiochemical studies show that the dominant configuration places the amide hydrogen coplanar to the hydroxyl group. This allows for the hydroxyl group to form an intramolecular H-bond and increase the proton donor ability of the hydroxyl proton. As supported by Yin et al. Mol Pharmacol 2003, 63 (1), 211-223, replacing the hydroxyl group with an acetyl moiety obliterates the efficacy of this class of compounds. It is possible that having a nitrogen meta to the aryl nitrile allows for the tautomeric equilibrium of the amide to become perturbed. This weakens the influence of the internal H-bond on the hydroxyl proton donor ability, lowering the affinity.

Nitrogen meta to —CN decreases affinity, likely due to conformational change.

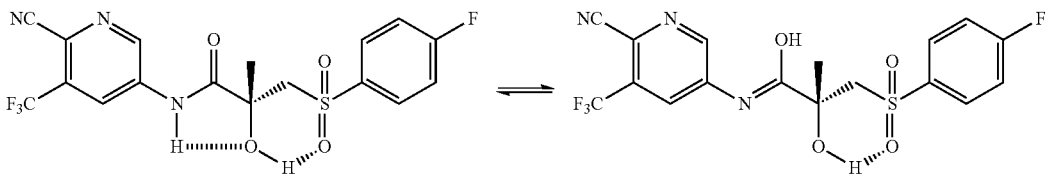

Amide hydrogen increases proton donor ability. Conformation change decreases proton donor ability

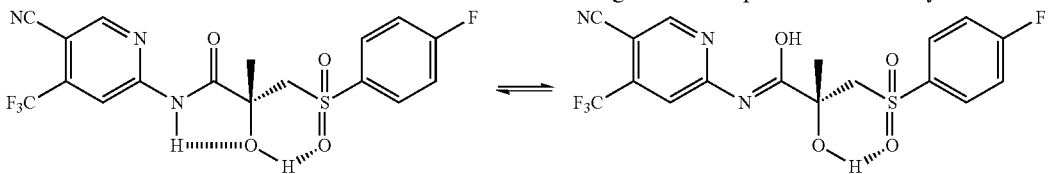

Conformation change decreases proton donor ability

Example 4. Additional Syntheses and Characterization of Compounds

Demonstrate cysteine-nitrile interaction through irreversible bond formation with electrophilic CDX analogs. We are also making covalent analogs of casodex to show the interaction of Cys784 with the R1 position. Synthetically, 4-nitro-3-(trifluoromethyl)aniline is coupled with carboxylic acid followed by oxidation to the sulfoxide. Reduction of the nitro group with SnCl$_2$ followed by reaction with the electrophilic moiety precursor leades to four different electrophilic casodex analogs. Their structures and IC$_{50}$ data can be found in the table below.

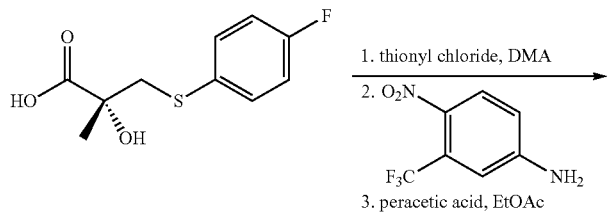

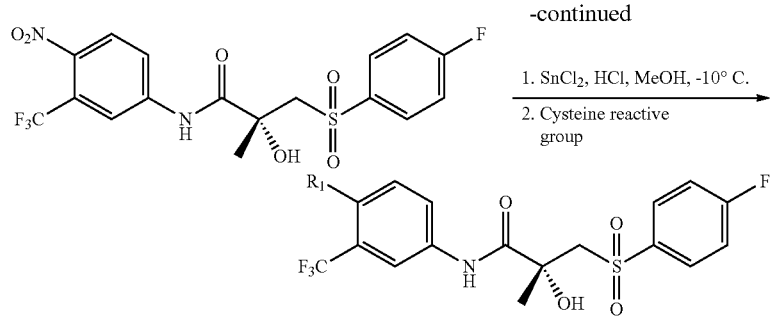
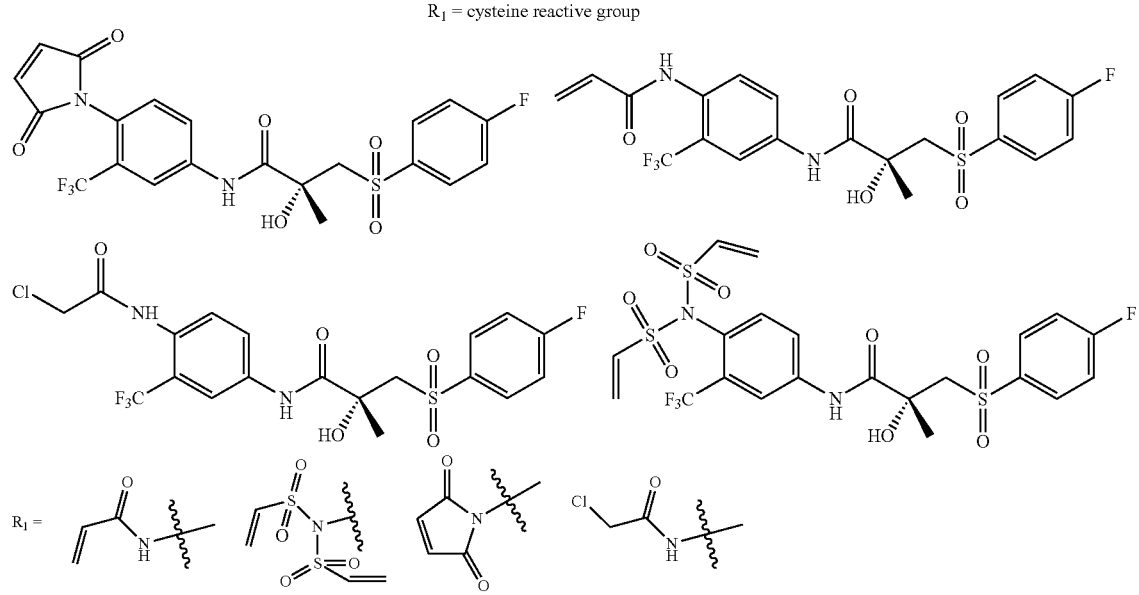
| Structure | Cmpd | MW (g/mol) | LBD IC$_{50}$ (μM) | FL IC$_{50}$ (μM) | Fold chg (LBD) | Fold chg (FL) |
|---|---|---|---|---|---|---|
| 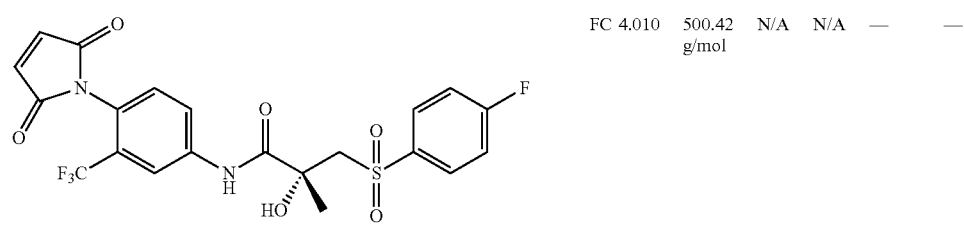 | Casodex (CDX) | 430.37 g/mol | 0.36 ± 0.02 μM | 1.00 ± 0.24 μM | | |
| 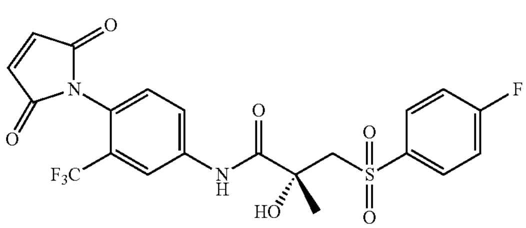 [SMILES: C[C@](O)(CS(=O)(=O)c1ccc(F)cc1)C(=O)Nc1ccc(N2C(=O)C=CC2=O)c(C(F)(F)F)c1] | FC 4.010 | 500.42 g/mol | N/A | N/A | — | — |

-continued

| Structure | Cmpd | MW (g/mol) | LBD IC$_{50}$ (µM) | FL IC$_{50}$ (µM) | Fold chg (LBD) | Fold chg (FL) |
|---|---|---|---|---|---|---|
| 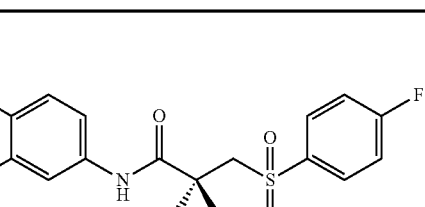 | FC 4.039 | 474.43 g/mol | 0.75 ± 0.26 µM | N/A | 0.48 | — |
| 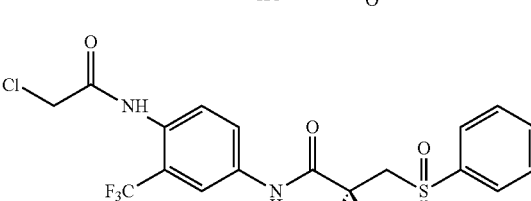 | FC 4.015 | 496.86 g/mol | N/A | N/A | — | — |
| 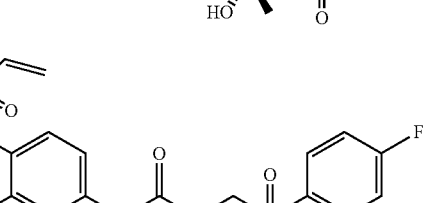 | FC 4.025 | 600.58 g/mol | 0.58 ± 0.11 µM | 1.29 ± 1.29 µM | 0.62 | 0.78 |

**N/A means the compound was tested but IC$_{50}$ could not be calculated.

Show reversible cysteine-nitrile formation through IR experiments.

Example 5. Modulation of AR LBD

In order to test the effect of ligands on the AR ligand-binding domain (AR LBD), a Gal4-luciferase reporter assay was used. Briefly, the AR LBD is expressed as a fusion with the Gal4 transcription factor, which binds to the Gal4 reporter DNA. Upon activation with agonist hormone (DHT), the Gal-AR LBD binds to the Gal4 reporter gene, which in turn drives the transcription (and subsequently translation) of the reporter luciferase. The effect of antiandrogens (competitive antagonists) on this process is measured by quantifying the amount of luciferase activity after 24 hours in the presence of varying concentrations of antiandrogens. From these values, an IC50 for each antagonist is calculated. Experimentally, Hela cells were maintained in Dulbecco's modified Eagle's medium H-21 4.5 g/L glucose, containing 10% steroid depleted fetal bovine serum, 50 units/mL penicillin. For transfection, (1×10$^5$) cells per well were plated and incubated overnight. A mixture of typically 200 ng of Gal4 responsive luciferase reporter plasmid, 10 ng of β-actin-β-galactosidase internal control, 10 ng of GAL-AR LBD or empty vector control, and 10-100 ng of β-catenin or empty vector control were mixed with 0.5 µL of transfection reagent from BioRad and incubated for 20 min and then plated in 24 well plate triplicates. Cells were induced with 1 nM DHT and 0.1 nM-30 uM test compounds after 3 hr and then incubated over night. Cells were collected, and pellets were lysed in 100 µL of 100 mM Tris-HCl (pH 7.5) containing 0.1% Triton X-100. Luciferase and β-galactosidase activities were measured using the Luciferase Assay System (Promega) and Galacto-Light Plus-galactosidase reporter gene assay system (Applied Biosystems), according to the manufacturer's instructions.

Example 6. Modulation of Full Length AR

In order to test the effect of antiandrogens on full length AR, a mmTV-luciferase reporter assay was used. An AR-response element is contained within the mmTV sequence and drives the expression of luciferase. The effect of antiandrogens (competitive antagonists) on this process is measured by quantifying the amount of luciferase activity after 24 hours in the presence of varying concentrations of antiandrogens. From these values, an IC50 for each antagonist is calculated. Experimentally, HeLa cells were maintained in Dulbecco's modified Eagle's medium H-21 4.5 g/L glucose, containing 10% steroid depleted fetal bovine serum, 50 units/mL penicillin. For transfection, (1×10$^5$) cells per well were plated and incubated overnight. A mixture of typically 200 ng of mmTV responsive luciferase reporter plasmid, 10 ng of β-actin-β-galactosidase internal control, 10 ng of AR full length CMV expression vector or empty vector control, and 10-100 ng of β-catenin or empty vector control were mixed with 0.5 µL of transfection reagent from BioRad and incubated for 20 min and then plated in 24 well plate triplicates. Cells were induced with 1 nM DHT and 0.1 nM-30 uM compounds after 3 hrs and then incubated overnight. Cells were collected, and pellets were lysed in 100 µL of 100 mM Tris-HCl (pH 7.5) containing 0.1% Triton X-100. Luciferase and β-galactosidase activities were measured using the Luciferase Assay System (Promega) and Galacto-Light Plus-galactosidase reporter gene assay system (Applied Biosystems), according to the manufacturer's instructions.

Example 7. Modulation of Endogenous AR

In order to test the effect of antiandrogens on endogenous full length AR activity, LNCaP cells were used along with the mmTV-luciferase reporter plasmid/assay. LNCaP cells were maintained in Dulbecco's modified Eagle's medium H-21 4.5 g/L glucose, containing 10% steroid depleted fetal bovine serum, 50 units/mL penicillin. For transfection, ($1\times10^5$) cells per well were plated and incubated overnight. A mixture of typically 200 ng of mmTV responsive luciferase reporter plasmid and 10 ng of β-actin-β-galactosidase internal control were mixed with 0.5 μL of transfection reagent from BioRad and incubated for 20 min. They were then plated in 24 well plate triplicates. Cells were induced with 10 nM DHT and 0.03 nM-10 μM compounds after 3 h and then incubated over night. Cells were collected, and pellets were lysed in 100 μL of 100 mM Tris-HCl (pH 7.5) containing 0.1% Triton X-100. Luciferase and β-galactosidase activities were measured using the Luciferase Assay System (Promega) and Galacto-Light Plus-galactosidase reporter gene assay system (Applied Biosystems), according to the manufacturer's instructions.

Example 8. Modulation of AR Active Site

We are developing antiandrogens designed to form a covalent bond with cysteine 784 (C784) located in the AR hormone binding pocket. To assess the importance of cysteine 784 (C784) on AR translation and/or function, we mutated this residue to Ala (A), Phe (F), His (H), Leu (L), Ser (S), and Val (V) and evaluated the level of AR-driven, DHT-induced luciferase activity using expression of the Gal4-AR LBD construct in HeLa cells and the Gal4-luciferase reporter assay (as described in other sections). We found that none of the mutants drive the expression of luciferase. To determine if this effect is the result of poor translation (no AR is made) or non-functional protein (AR is made, but is non-functional), we carried out western blot assays on each of the mutants. In all cases, the mutant protein is observed, demonstrating that the AR is expressed, but is not functional when Cys784 is mutated. Experimentally, HeLa cells in 6 well dishes were transfected with 100 μg Gal4 empty vector or Gal-AR LBD expression vector and treated with DHT and antiandrogens for 20 hrs. They were then chilled on ice and washed with cold PBS, incubated with Lysis Buffer for 10 mins, and scraped and centrifuged at 4° C. for 10 minutes. Protein concentration in cell extract was measured by standard methods. 50 μg of proteins were loaded on SDS-PAGE gel. Proteins were transferred to a wet Immuno-Blot membrane at 400 mA for 2 hrs. The membrane was then incubated in 5% non-fat milk in TBS-T (20 mM Tris, 500 mM NaCl pH 7.5, 0.1% Tween-20) for 15 mins, washed twice with TBS-T at RT. The primary Gal4/NTD antibody was diluted 1:500/1:1500 in TBS-T and incubated with protein membrane overnight, followed with 3 washes at 15 minutes each. Then, it was incubated with secondary anti-mouse IgG (1:3000 dilution), followed by 3 washes at 15 mins each. The membrane was developed with an ECL kit and exposed to X-ray film.

Example 9. Modulation of AR Expression Levels

To determine if the effect of our antiandrogens on AR expression levels, we carried out Western blot experiments in the presence of our antiandrogens and previously reported antiandrogens ARN-509 and MDV3100. We found that none of these compounds have a strong effect on DHT-induced AR expression, suggesting they all bind specifically to the AR FL, and not in a non-specific manner that would lead to degradation of the protein. Experimentally, HeLa cells in 6 well dishes were transfected with 100 μg CMV empty vector or pCMV AR FL expression vector and treated with DHT and compounds for 20 hrs. They were then chilled on ice and washed with cold PBS, incubated with Lysis Buffer for 10 mins, and scraped and centrifuged at 4° C. for 10 minutes. Protein concentration in cell extract was measured by standard methods. 50 μg of proteins were loaded on SDS-PAGE gel. Proteins were transferred to a wet Immuno-Blot membrane at 400 mA for 2 hrs. The membrane was then incubated in 5% non-fat milk in TBS-T (20 mM Tris, 500 mM NaCl pH 7.5, 0.1% Tween-20) for 15 mins, washed twice with TBS-T at RT. The primary antibody was diluted 1:500/1:1500 in TBS-T and incubated with protein membrane overnight, followed with 3 washes at 15 minutes each. Then, it was incubated with secondary anti-mouse IgG (1:3000 dilution), followed by 3 washes at 15 mins each. The membrane was developed with an ECL kit and exposed to X-ray film.

REFERENCES

Blackledge, G. R. P., Eur Urol 1996, 29, 96-104. Feldman, B. J.; Feldman, D., Nat Rev Cancer 2001, 1 (1), 34-45. Tran, C.; et al., Science 2009, 324 (5928), 787-90. Clegg, N. J.; et al. Cancer Res 2012, 72 (6), 1494-1503. Hara, T.; et al. Cancer Res 2003, 63 (1), 149-53. Oballa, R. M.; et al. Bioorg Med Chem Lett 2007, 17 (4), 998-1002. Tucker, H.; Chesterson, G. J., J Med Chem 1988, 31 (4), 885-887. Tucker, H.; et al., J Med Chem 1988, 31 (5), 954-959. Yin, D. et al. Mol Pharmacol 2003, 63 (1), 211-223.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

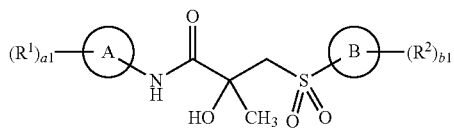

(I)

wherein

Ring A is a 6 membered heteroaryl;

Ring B is a phenyl or heteroaryl;

$R^1$ is independently a halogen, —$CX^a_3$, —CN, —$SO_2Cl$, —$SO_{n1}R^{10}$, —$SO_{v1}NR^7R^8$, —$NHNH_2$, —$ONR^7R^8$, —NHC=(O)NHNH$_2$, —NHC=(O)NR$^7$R$^8$, —N(O)$_{m1}$, —NR$^7$R$^8$, —C(O)R$^9$, —C(O)—OR$^9$, —C(O)NR$^7$R$^8$, —NR$^7$SO$_2$R$^{10}$, —NR$^7$C=(O)R$^9$, —NR$^7$C(O)—OR$^9$, —NR$^7$OR$^9$, —OCX$^a_3$, —OCHX$^a_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

E is independently —CN, —NO$_2$,

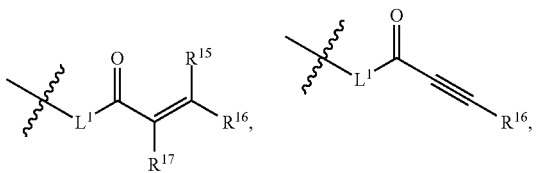

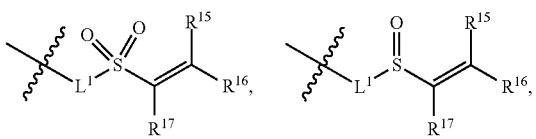

-continued

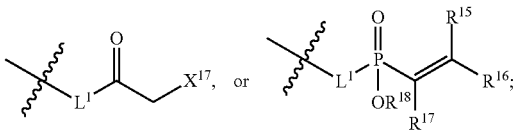

$L^1$ is independently a bond, —O—, —C(O)—, —S—, —SO—, —S(O)$_2$—, —N(H)—, —NHC(O)—, —C(O)NH—, —SO$_2$NH—, —NHSO$_2$—, —OC(O)NH—, —NHC(O)O—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{15}$ is independently hydrogen, halogen, $CX^{15}_3$, —$CHX^{15}_2$, —$CH_2X^{15}$, —CN, —SO$_{n15}$R$^{15D}$, —SO$_{v15}$NR$^{15A}$R$^{15B}$, —NHNR$^{15A}$R$^{15B}$, —ONR$^{15A}$R$^{15B}$, —NHC=(O)NHNR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, —OCX$^{15}_3$—, —OCHX$^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is independently hydrogen, halogen, $CX^{16}_3$, —$CHX^{16}_2$, —$CH_2X^{16}$, —CN, —SO$_{n16}$R$^{16D}$, —SO$_{v16}$NR$^{16A}$R$^{16B}$, —NHNR$^{16A}$R$^{16B}$, —ONR$^{16A}$R$^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}_3$, —OCHX$^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, $CX^{17}_3$, —$CHX^{17}_2$, —$CH_2X^{17}$, —CN, —SO$_{n17}$R$^{17D}$, —SO$_{v17}$NR$^{17A}$R$^{17B}$, —NHNR$^{17A}$R$^{17B}$, —ONR$^{17A}$R$^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)

OR$^{17C}$, —NR$^{17A}$OR$^{17C}$, —OCX$^{17}_3$, —OCHX$^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{18}$ is independently hydrogen, —CX$^{18}_3$, —CHX$^{18}_2$, —CH$_2$X$^{18}$, —C(O)R$^{18C}$, —C(O)OR$^{18C}$, —C(O)NR$^{18A}$R$^{18B}$, substituted or substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

Each R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$, R$^{18D}$, is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15A}$ and R$^{15B}$ substituents bonded to the same nitrogen atom may optionally be joined to form a substituted or unsubstituted heterocycloalkyl or substituted or unsubstituted heteroaryl; R$^{16A}$ and R$^{16B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl;

each X, X$^{15}$, X$^{16}$, X$^{17}$, and X$^{18}$, is independently —F, —Cl, —Br, or —I;

n15, n16, n17, v15, v16, and v17, are independently and integer from 0 to 4;

m15, m16, and m17 are independently 1 or 2;

R$^2$ is independently a halogen, —CX$^b_3$, —CN, —SO$_2$Cl, —SO$_{n2}$R$^{14}$, —SO$_{v2}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m2}$, —NR$^{11}$R$^{12}$, —C(O)R$^{13}$, —C(O)—OR$^{13}$, —C(O)NR$^{11}$R$^{12}$, —OR$^{14}$, —NR$^{11}$SO$_2$R$^{14}$, —NR$^{11}$C=(O)R$^{13}$, —NR$^{11}$C(O)—OR$^{13}$, —NR$^{11}$OR$^{13}$, —OCX$^b_3$, —OCHX$^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl;

R$^7$, R$^8$, R$^9$, R$^{10}$, R$^{11}$, R$^{12}$, R$^{13}$, and R$^{14}$ are independently hydrogen, halogen, —CX$^c_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^c_3$, —OCHX$^c_2$, —CF$_3$, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl;

a1 is independently an integer from 0 to 4;
b1 is independently an integer from 0 to 5;
m1, m2, v1, and v2 are independently 1 or 2;
n1 and n2 are independently an integer from 0 to 4;
X$^a$, X$^b$, and X$^c$ are independently —Cl, —Br, —I, or —F.

2. The compound of claim 1, having the formula:

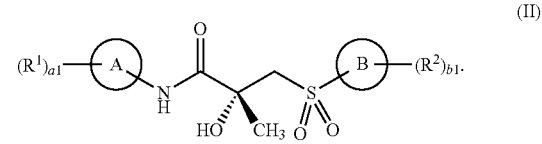

(II)

3. The compound of claim 2, wherein Ring A is

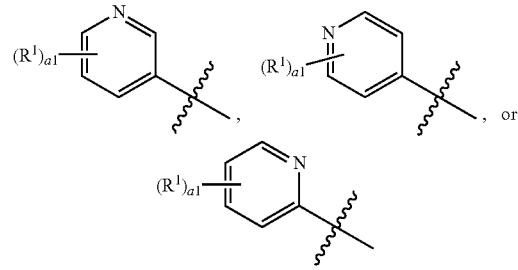

and a1 is an integer from 0 to 4; or

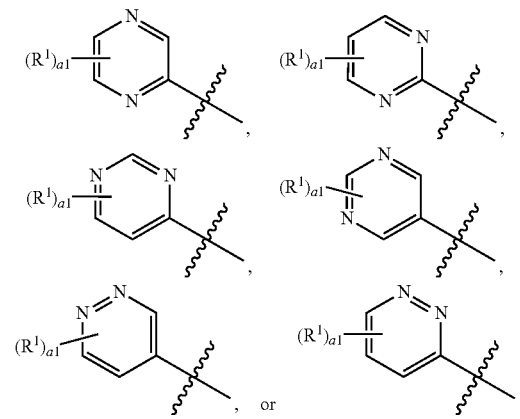

and a1 is an integer from 0 to 3; or

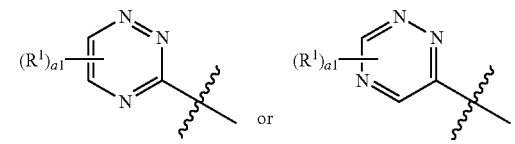

or and a1 an integer from 0 to 2; or

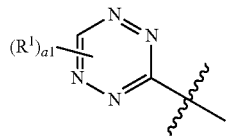

and a1 an integer from 0 to 1.

4. The compound of claim 2, wherein
R¹ is independently a halogen, —CX$^a_3$, —CN, —SO$_2$Cl, —SO$_{n1}$R$^{10}$, —SO$_{v1}$NR$^7$R$^8$, —NHNH$_2$, —ONR$^7$R$^8$, —NHC=(O)NHNH$_2$, —NHC=(O)NR$^7$R$^8$, —N(O)$_{m1}$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C=(O)R$^9$, —NR$^7$C(O)—OR$^9$, —NR$^7$OR$^9$, —OCX$^a_3$, —OCHX$^a_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R¹ substituents may optionally be joined to form a substituted or unsubstituted cycloalkyl, substituted or unsubstituted heterocycloalkyl, substituted or unsubstituted aryl, or substituted or unsubstituted heteroaryl;

Ring A is

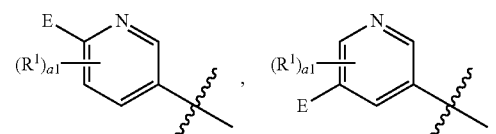

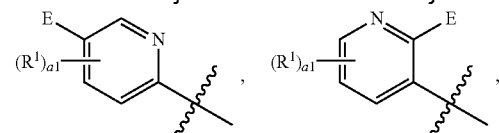

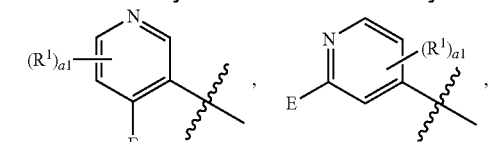

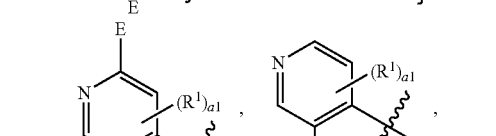

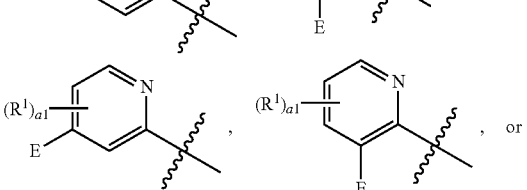

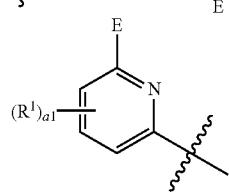, and a1 is an integer from 0 to 3; or

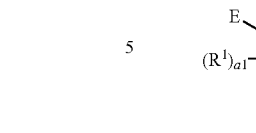

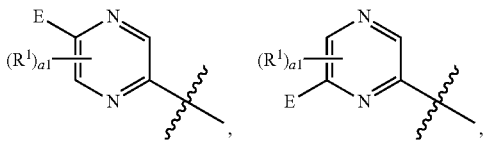

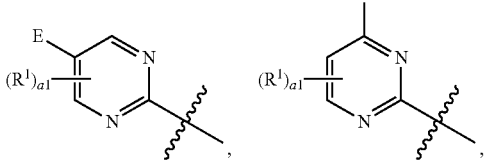

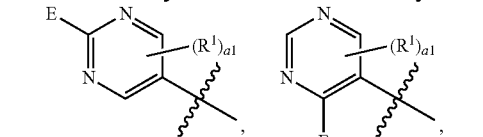

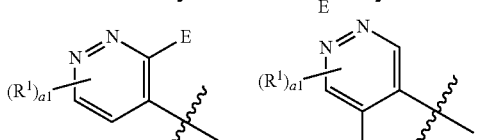

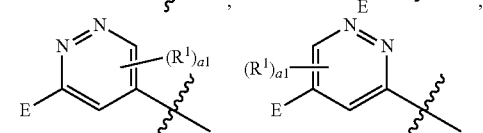

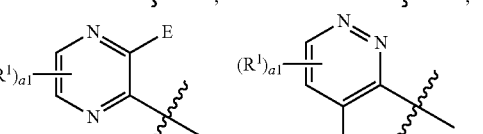, or

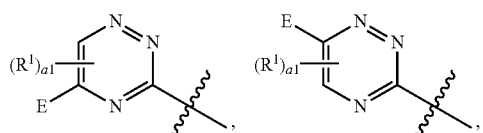

and a1 is an integer from 0 to 2; or

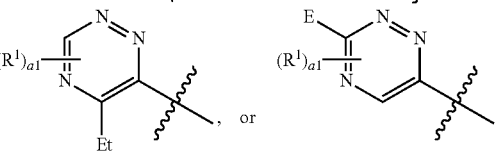

and a1 is an integer from 0 to 1; or

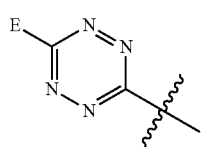

and a1 is 0.

5. The compound of claim 4, wherein Ring A is

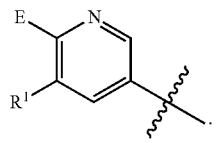

6. The compound of claim 2, wherein $R^1$ is a —Cl, —F, —Br, —I, —$CX^a_3$, —CN, —NHNH$_2$, —ONH$_2$, —NHC=(O)NHNH$_2$,
—NHC=(O)NH$_2$, —NO$_2$, —NH$_2$, —C(O)H, —C(O)CH$_3$, —C(O)—OH, —C(O)—OCH$_3$, —C(O)NH$_2$, —OH, —NHC=(O)H, —NHC=(O)CH$_3$, —NHC(O)—OH, —NHC(O)OCH$_3$, —NHOH, —NHOCH$_3$, —OCX$^a_3$, —OCHX$^a_2$, substituted or unsubstituted $C_1$-$C_5$ alkyl, substituted or unsubstituted 2 to 5 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

7. The compound of claim 2, wherein $R^1$ is independently —Cl, —F, —Br, —I, —$CX^a_3$, —CN, —NO$_2$, —OCX$^a_3$, —OCHX$^a_2$,

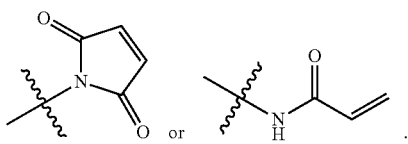

8. The compound of claim 2, wherein Ring B is a phenyl.

9. The compound of claim 2, wherein Ring B is a heteroaryl.

10. The compound of claim 2, wherein $R^2$ is independently a halogen, —$CX^b_3$, —C(O)NHCH$_3$, substituted or unsubstituted $C_1$-$C_5$ alkyl, substituted or unsubstituted 2 to 5 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

11. The compound of claim 1, wherein said compound is

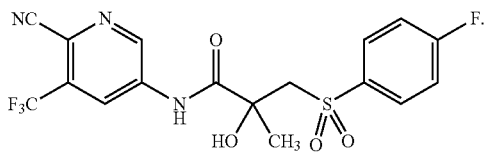 [SMILES: CC(O)(CS(=O)(=O)c1ccc(F)cc1)C(=O)Nc1cnc(C#N)c(C(F)(F)F)c1]

12. The compound of claim 2, wherein said compound is

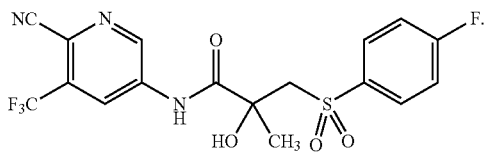

13. The compound of claim 2, wherein said compound is

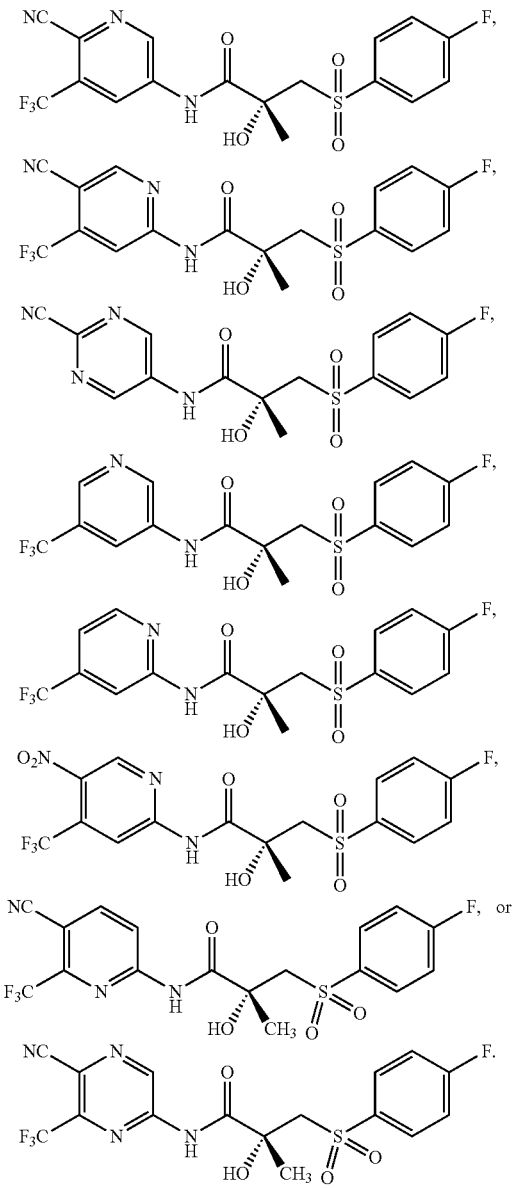

14. A pharmaceutical composition comprising a compound of claim 1, or a pharmaceutically acceptable salt thereof, and a pharmaceutically acceptable excipient.

15. An androgen receptor protein covalently bound to an androgen receptor inhibitor, wherein said androgen receptor inhibitor is a compound of claim 1 and said compound is covalently bound to a cysteine residue of said androgen receptor protein.

16. A method of treating cancer in a subject in need thereof, wherein the cancer is prostate cancer, comprising administering to said subject an effective amount of a compound of claim 1, or a pharmaceutically acceptable salt thereof.

17. The method of claim 16, wherein said cancer is hormone sensitive prostate cancer.

18. The method of claim 16, wherein said cancer is hormone refractory prostate cancer.

19. A method of inhibiting androgen receptor activity in a subject in need thereof, comprising administering to said subject an effective amount of a compound of claim 1, or a pharmaceutically acceptable salt thereof.

* * * * *